United States Patent
Lee et al.

(10) Patent No.: US 10,505,122 B2
(45) Date of Patent: *Dec. 10, 2019

(54) HETERO RING COMPOUND AND ORGANIC LIGHT EMITTING DIODE COMPRISING SAME

(71) Applicant: LG CHEM, LTD., Seoul (KR)

(72) Inventors: Sangbin Lee, Daejeon (KR); Dong Hoon Lee, Daejeon (KR); Jungoh Huh, Daejeon (KR); Dong Uk Heo, Daejeon (KR); Miyeon Han, Daejeon (KR); Boonjae Jang, Daejeon (KR); Minyoung Kang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 215 days.

This patent is subject to a terminal disclaimer.

(21) Appl. No.: 14/392,199

(22) PCT Filed: Jun. 26, 2014

(86) PCT No.: PCT/KR2014/005670
§ 371 (c)(1),
(2) Date: Dec. 23, 2015

(87) PCT Pub. No.: WO2014/209028
PCT Pub. Date: Dec. 31, 2014

(65) Prior Publication Data
US 2016/0172598 A1  Jun. 16, 2016

(30) Foreign Application Priority Data

Jun. 28, 2013 (KR) .................. 10-2013-0075662

(51) Int. Cl.
*H01L 51/00* (2006.01)
*C07D 403/10* (2006.01)
(Continued)

(52) U.S. Cl.
CPC ........ *H01L 51/0067* (2013.01); *C07D 251/24* (2013.01); *C07D 401/10* (2013.01);
(Continued)

(58) Field of Classification Search
USPC ....... 428/690, 691, 917, 411.4, 336; 427/58, 427/66; 313/500–512; 257/40, 88–104,
(Continued)

(56) References Cited

U.S. PATENT DOCUMENTS 6,057,048 A    5/2000  Hu et al.
9,199,966 B2  12/2015  Kim et al.
(Continued)

FOREIGN PATENT DOCUMENTS

CN    102532000 A    7/2012
CN    102593374 A    7/2012
(Continued)

OTHER PUBLICATIONS

International Search Report from PCT/KR2014/005670, dated Oct. 31, 2014.
(Continued)

*Primary Examiner* — Jennifer A Chriss
*Assistant Examiner* — Sean M DeGuire
(74) *Attorney, Agent, or Firm* — Dentons US LLP

(57) ABSTRACT

The present specification provides a novel compound capable of significantly improving lifespan, efficiency, electrochemical stability and thermal stability of an organic light emitting device, and an organic light emitting device containing the compound in an organic compound layer.

14 Claims, 1 Drawing Sheet

(51) Int. Cl.
*C09K 11/06* (2006.01)
*C07D 251/24* (2006.01)
*C07D 401/10* (2006.01)
*C09K 11/02* (2006.01)
*H01L 51/50* (2006.01)

(52) U.S. Cl.
CPC .......... *C07D 403/10* (2013.01); *C09K 11/025* (2013.01); *C09K 11/06* (2013.01); *H01L 51/0052* (2013.01); *H01L 51/0058* (2013.01); *H01L 51/0072* (2013.01); *H01L 51/5012* (2013.01); *H01L 51/5056* (2013.01); *H01L 51/5072* (2013.01); *H01L 51/5088* (2013.01); *H01L 51/5092* (2013.01)

(58) Field of Classification Search
USPC ........ 257/E51, E51.052; 252/301.16–301.35
See application file for complete search history.

(56) References Cited

U.S. PATENT DOCUMENTS

| | | | |
|---|---|---|---|
| 9,406,891 B2 | 8/2016 | Jung et al. | |
| 9,614,161 B2* | 4/2017 | Park | C07D 405/14 |
| 9,882,145 B2* | 1/2018 | Lee | C07D 403/10 |
| 2007/0190355 A1* | 8/2007 | Ikeda | C07D 239/26 |
| | | | 428/690 |
| 2008/0111473 A1 | 5/2008 | Kawamura et al. | |
| 2009/0174312 A1 | 7/2009 | Kim et al. | |
| 2009/0281311 A1* | 11/2009 | Yamakawa | C07D 401/10 |
| | | | 544/180 |
| 2011/0156014 A1 | 6/2011 | Kim et al. | |
| 2011/0240983 A1 | 10/2011 | Sekiguchi et al. | |
| 2012/0104941 A1 | 5/2012 | Jung et al. | |
| 2012/0273771 A1 | 11/2012 | Jung et al. | |
| 2012/0280613 A1 | 11/2012 | Kang et al. | |
| 2012/0286249 A1 | 11/2012 | Lee et al. | |
| 2013/0153863 A1 | 6/2013 | Wong et al. | |
| 2013/0248830 A1* | 9/2013 | Welsh | H01L 51/0067 |
| | | | 257/40 |
| 2014/0158999 A1 | 6/2014 | Jung et al. | |
| 2014/0203272 A1* | 7/2014 | Hong | H01L 51/0052 |
| | | | 257/40 |
| 2014/0367645 A1* | 12/2014 | Seo | H01L 51/0072 |
| | | | 257/40 |
| 2014/0367654 A1 | 12/2014 | Kim et al. | |
| 2015/0340620 A1* | 11/2015 | Park | C07D 405/14 |
| | | | 257/40 |
| 2016/0141514 A1* | 5/2016 | Lee | C07D 403/10 |
| | | | 257/40 |
| 2017/0012221 A1 | 1/2017 | Buesing et al. | |

FOREIGN PATENT DOCUMENTS

| | | | |
|---|---|---|---|
| JP | 2010-138121 A | | 6/2010 |
| JP | 2012-501091 A | | 1/2012 |
| JP | 2012-28524 A | | 2/2012 |
| JP | 2012-513987 A | | 6/2012 |
| JP | 2013-518069 A | | 5/2013 |
| JP | 2014-118410 A | | 6/2014 |
| KR | 10-2007-0088728 A | | 8/2007 |
| KR | 10-2008-0016007 A | | 2/2008 |
| KR | 10-2011-0079197 A | | 7/2011 |
| KR | 10-2011-0111093 A | | 10/2011 |
| KR | 10-2012-0127683 A | | 11/2012 |
| KR | 20130060157 A | | 6/2013 |
| KR | 10-2013-0134471 A | | 12/2013 |
| KR | 20140094408 A | * | 7/2014 |
| TW | 201402565 A | | 1/2014 |
| WO | 2007/105884 A1 | | 9/2007 |
| WO | 2013-129835 A1 | | 9/2013 |

OTHER PUBLICATIONS

Written Opinion of the ISA from PCT/KR2014/005670, dated Jul. 21, 2015.
Written Opinion of the ISA from PCT/KR2013/010079, dated Jul. 21, 2015.
Office Action of Korean Patent Office in Appl'n No. 10-2013-0134471 dated Sep. 18, 2014.
Decision of Rejection of Korean Patent Office in Appl'n No. 10-2013-0134471, dated Jan. 15, 2015.
Office Action of Korean Patent Office in Appl'n No. 10-2014-0078411, dated Nov. 21, 2014.
Office Action of Korean Patent Office in Appl'n No. 10-2014-0078411, dated May 21, 2015.
Office Action of Taiwanese Patent Office in Appl'n No. 102140663, dated Sep. 25, 2014.
Office Action of Taiwanese Patent Office in Appl'n No. 103122044, dated Apr. 14, 2015.

* cited by examiner

[FIG. 1]
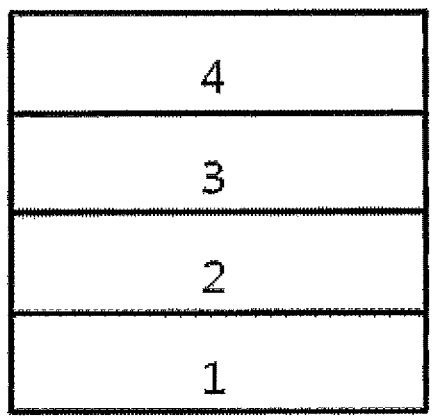
[FIG. 2]
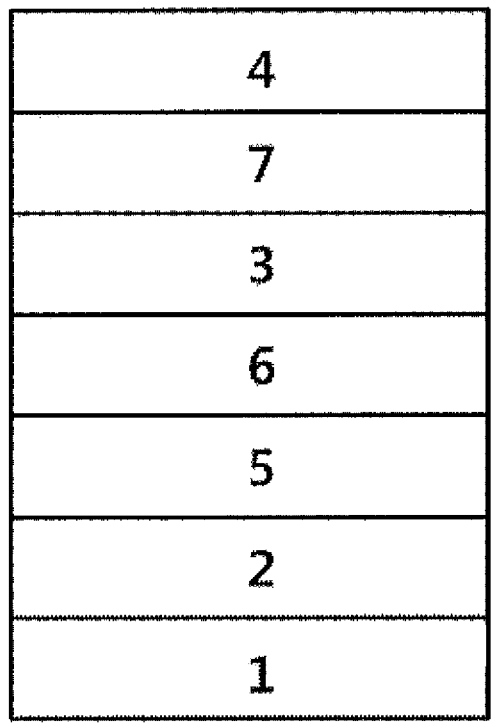

HETERO RING COMPOUND AND ORGANIC LIGHT EMITTING DIODE COMPRISING SAME

TECHNICAL FIELD

This application is a National Stage Application of International Application No. PCT/KR2014/005670, filed on Jun. 26, 2014, which claims the benefit of Korean Patent Application No. KR 10-2013-0075662, filed on Jun. 28, 2013, all of which are hereby incorporated by reference in their entirety for all purposes as if fully set forth herein.

The present disclosure relates to a novel hetero-cyclic compound and an organic light emitting device including the same.

BACKGROUND ART

An organic light emission phenomenon generally refers to a phenomenon that converts electric energy to light energy using an organic material. An organic light emitting device using an organic light emission phenomenon typically has a structure that includes an anode, a cathode, and an organic material layer therebetween. Herein, the organic material layer is usually formed as a multilayer structure formed with different materials in order to improve the efficiency and the stability of an organic light emitting device, and for example, may be formed with a hole injection layer, a hole transfer layer, a light emitting layer, an electron transfer layer, an electron injection layer, and the like. In the structure of such an organic light emitting device, holes from an anode and electrons from a cathode flow into an organic material layer when voltage is applied between the two electrodes, excitons form when the injected electrons and holes meet, and light emits when these excitons fall back to the ground state.

There have been continuous demands for the development of new materials for organic light emitting devices such as above.

DISCLOSURE

Technical Problem

In view of the above, an objective of the present application is to provide a hetero-cyclic compound having a chemical structure capable of performing various roles required in an organic light emitting device depending on substituents, and to provide an organic light emitting device including the hetero-cyclic compound.

Technical Solution

The present specification provides a hetero-cyclic compound represented by the following Chemical Formula 1.

[Chemical Formula 1]

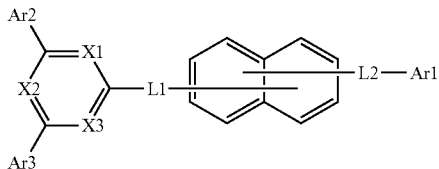

In Chemical Formula 1,

L1 and L2 are the same as or different from each other, and each independently a direct bond; a substituted or unsubstituted arylene group; or a substituted or unsubstituted alkenylene group, X1 to X3 are the same as or different from each other, and each independently a trivalent heteroatom or CH, and at least one of X1 to X3 is a trivalent heteroatom, Ar2 and Ar3 are the same as or different from each other and each independently a substituted or unsubstituted aryl group; or a substituted or unsubstituted heteroring group, Ar1 is represented by any one of the following Chemical Formula 2 to Chemical Formula 4,

[Chemical Formula 2]

[Chemical Formula 3]

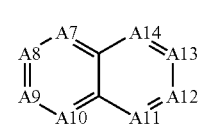

[Chemical Formula 4]

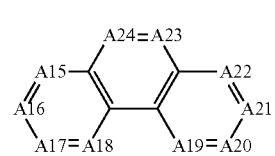

in Chemical Formulae 2 to 4, one of A1 to A6 is N, another is a carbon atom linking to L2, and the rest is CR, at least one of A7 to A14 is N, another is a carbon atom linking to L2, and the rest is CR, at least one of A15 to A24 is N, another is a carbon atom linking to L2, and the rest is CR, CRs that are not N or a carbon atom linking to L2 among A1 to A24 are the same as or different from each other, R is hydrogen; a substituted or unsubstituted aryl group; or a substituted or unsubstituted heteroring group, and

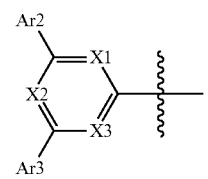

and Ar1 are different from each other.

In addition, the present specification provides an organic light emitting device including a first electrode; a second electrode provided opposite to the first electrode; and one or more organic material layers provided between the first electrode and the second electrode, wherein one or more layers of the organic material layers include the hetero-cyclic compound represented by Chemical Formula 1.

Advantageous Effects

A novel compound according to the present specification can be used as the material of an organic material layer of an organic light emitting device, and by using the compound, an improvement of efficiency, a low driving voltage and/or an improvement of lifespan characteristics are possible.

DESCRIPTION OF DRAWINGS

FIG. 1 shows an example of an organic electronic device in which a substrate (1), an anode (2), a light emitting layer (3) and a cathode (4) are laminated in consecutive order.

FIG. 2 shows an example of an organic electronic device in which a substrate (1), an anode (2), a hole injection layer (5), a hole transfer layer (6), a light emitting layer (3), an electron transfer layer (7) and a cathode (4) are laminated in consecutive order.

REFERENCE NUMERALS

1: Substrate
2: Anode
3: Light Emitting Layer
4: Cathode
5: Hole Injection Layer
6: Hole Transfer Layer
7: Electron Transfer Layer

MODE FOR DISCLOSURE

Hereinafter, the present specification will be described in detail.

The present specification provides a compound represented by Chemical Formula 1.

A hetero-cyclic compound according to one embodiment of the present specification uses a divalent naphthalene group as a linker of

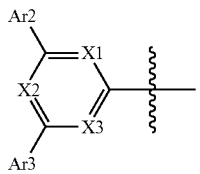

and Ar1. A divalent naphthalene group has wider LUMO orbital distribution compared to a monocyclic aromatic hydrocarbon ring group such as phenyl thereby lowers an LUMO energy level. Accordingly, the hetero-cyclic compound according to one embodiment of the present specification has excellent electron transfer and injection abilities, and may provide devices having low voltage and/or high efficiency.

In addition, the naphthyl group has abundant pi-conjugated electrons, and is capable of increasing charge mobility of materials.

In one embodiment of the present specification,

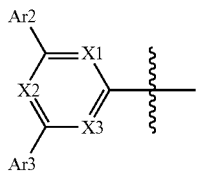

and Ar1 in Chemical Formula 1 are different from each other. In this case, a uniform thin film may be formed in a deposition process of a device compared to a case in which

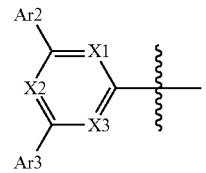

and Ar1 are the same as each other due to low crystallization properties. Accordingly, a device including the hetero-cyclic compound according to one embodiment of the present specification has excellent charge mobility.

In addition, a hetero-cyclic compound according to one embodiment of the present specification has a high dipole moment value due to electrophysical asymmetry. The hetero-cyclic compound according to one embodiment having a high dipole moment value may play a role to improve high electron transfer abilities in a device.

In one embodiment of the present specification, the

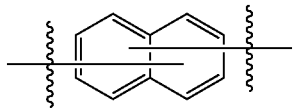

in Chemical Formula 1 may be selected from among the following structures.

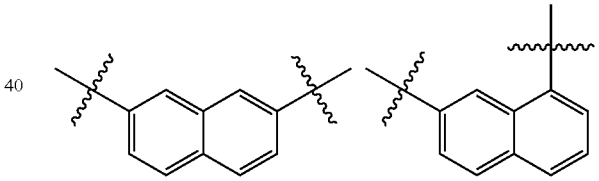

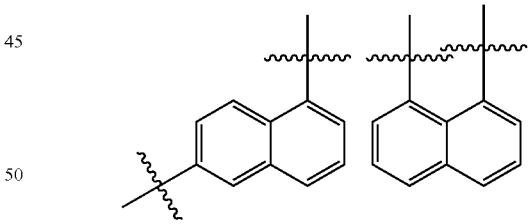

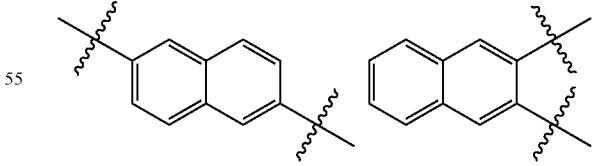

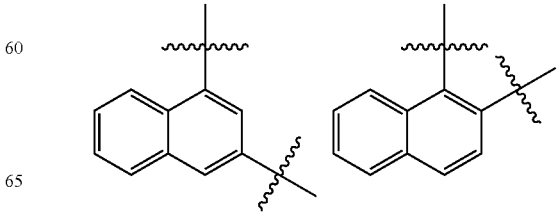

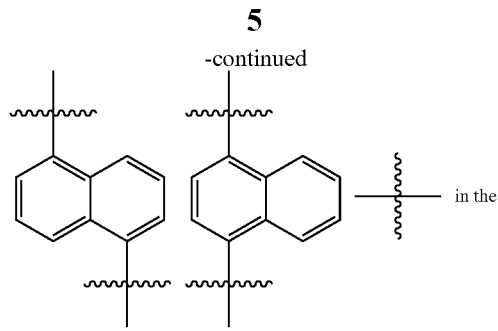

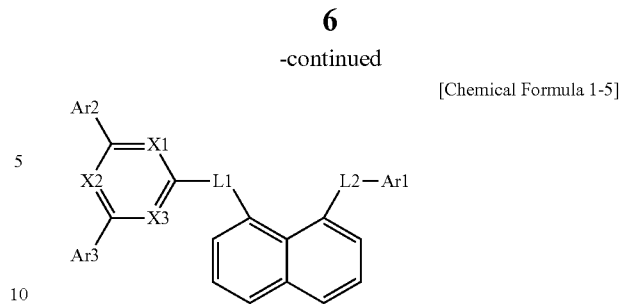
[Chemical Formula 1-5]

in the

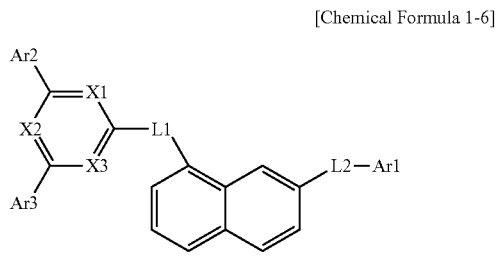
[Chemical Formula 1-6]

means linking to L1 or L2 of Chemical Formula 1.

In one embodiment of the present specification, the hetero-cyclic compound represented by Chemical Formula 1 may be represented by any one of the following Chemical Formulae 1-1 to 1-8.

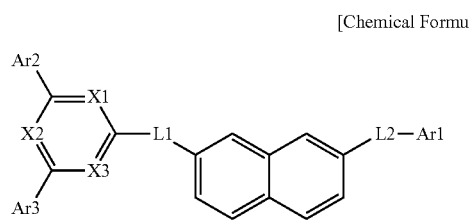
[Chemical Formula 1-1]

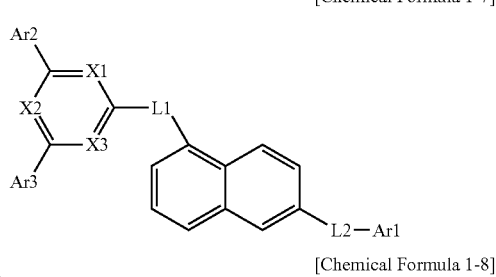
[Chemical Formula 1-7]

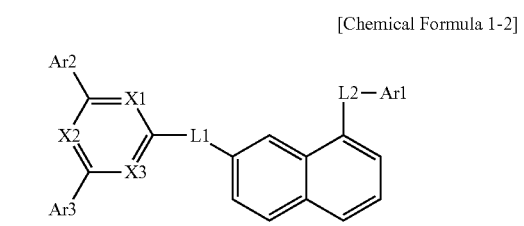
[Chemical Formula 1-2]

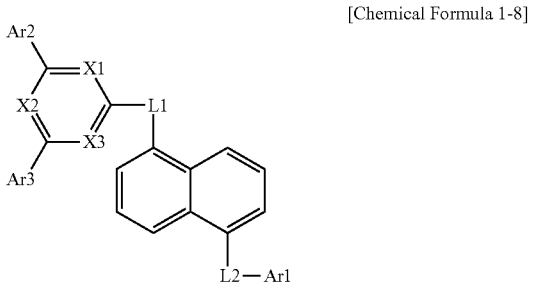
[Chemical Formula 1-8]

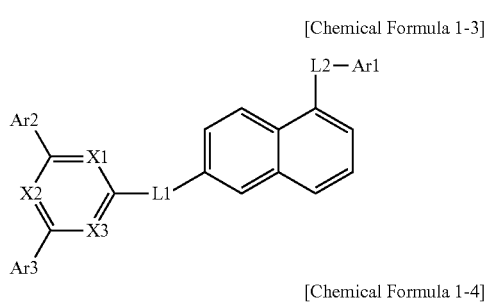
[Chemical Formula 1-3]

In Chemical Formulae 1-1 to 1-8, Ar1, Ar2, Ar3, X1 to X3, and L1 and L2 are the same as those defined in Chemical Formula 1.

In one embodiment of the present specification, the hetero-cyclic compound represented by Chemical Formula 1 is represented by any one of the following Chemical Formulae 1-9 to 1-14.

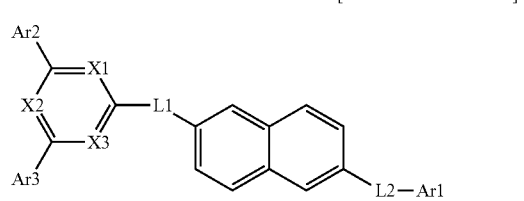
[Chemical Formula 1-4]

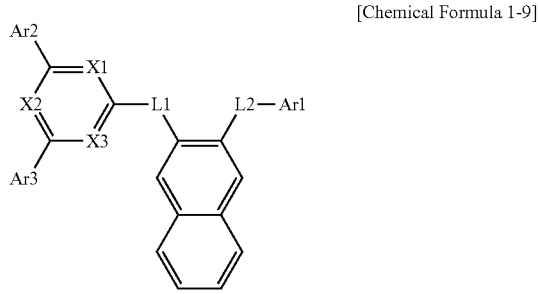
[Chemical Formula 1-9]

[Chemical Formula 1-10]

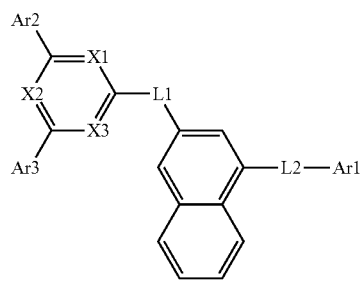

[Chemical Formula 1-11]

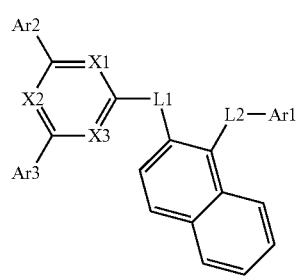

[Chemical Formula 1-12]

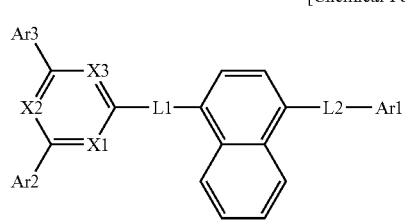

[Chemical Formula 1-13]

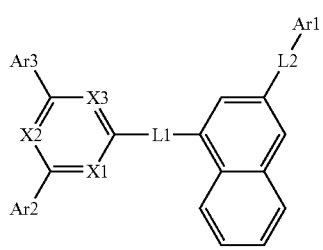

[Chemical Formula 1-14]

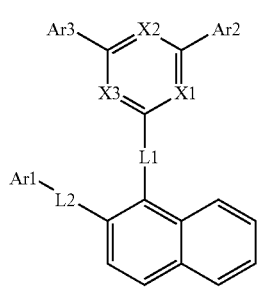

In Chemical Formulae 1-9 to 1-14, Ar1, Ar2, Ar3, X1 to X3, and L1 and L2 are the same as those defined in Chemical Formula 1.

Examples of the substituents are described below, however, the substituents are not limited thereto.

In the present specification,

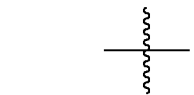

means a site linking to other substituents.

In the present specification, the term "substituted or unsubstituted" means being substituted with one or more substituents selected from the group consisting of deuterium; a halogen group; a nitrile group; a nitro group; an imide group; an amide group; a hydroxyl group; a thiol group; an alkyl group; an alkenyl group; an alkoxy group; a cycloalkyl group; a silyl group; an arylalkenyl group; an aryloxy group; an alkylthioxy group; an arylthioxy group; an alkylsulfoxy group; an arylsulfoxy group; a silyl group; a boron group; an alkylamine group; an aralkylamine group; an arylamine group; an aryl group; an arylalkyl group; an arylalkenyl group; and a heteroring group, or having no substituents.

The term "substitution" means a hydrogen atom bonded to a carbon atom of a compound being replaced by another substituent, and the position of substitution is not limited as long as it is a position that a hydrogen atom is substituted, that is, a position that a substituent may substitute, and when 2 or more substituents substitute, the 2 or more substituents may be the same as or different from each other.

In the present specification, examples of the halogen group include fluorine, chlorine, bromine or iodine.

In the present specification, the number of carbon atoms of the imide group is not particularly limited, but is preferably 1 to 25. Specifically, compounds having the following structures may be included, but the compound is not limited thereto.

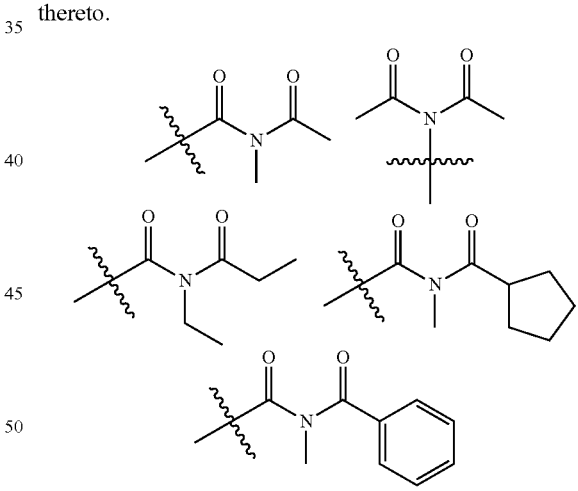

In the present specification, in the amide group, the nitrogen of the amide group may be once or twice substituted with hydrogen, a linear, branched or cyclic alkyl group having 1 to 25 carbon atoms, or an aryl group having 6 to 25 carbon atoms. Specifically, compounds having the following structures may be included, but the compound is not limited thereto.

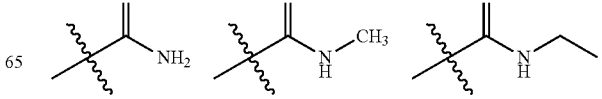

-continued

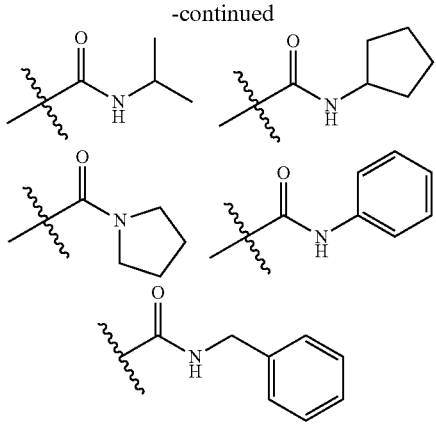

In the present specification, the alkyl group may be linear or branched, and the number of carbon atoms is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 60 atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the alkenyl group may be linear or branched, and although not particularly limited, the number of carbon atoms is preferably 2 to 40. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the aryl group may be a monocyclic aryl group or a multicyclic aryl group, and includes a case in which an alkyl group having 1 to 25 carbon atoms or an alkoxy group having 1 to 25 carbon atoms is substituted. In addition, the aryl group in the present specification may mean an aromatic ring.

When the aryl group is a monocyclic aryl group, although not particularly limited, the number of carbon atoms is preferably 6 to 25. Specific examples of the monocyclic aryl group may include a phenyl group, a biphenyl group, a terphenyl group and the like, but are not limited thereto.

When the aryl group is a multicyclic aryl group, although not particularly limited, the number of carbon atoms is preferably 10 to 24. Specific example of the multicyclic aryl group may include a naphthyl group, an anthracenyl group, a phenanthryl group, a pyrenyl group, a perylenyl group, a crycenyl group, a fluorenyl group and the like, but are not limited thereto.

In the present specification, the fluorenyl group may be substituted, and adjacent substituents may bind to each other to form a ring.

When the fluorenyl group is substituted,

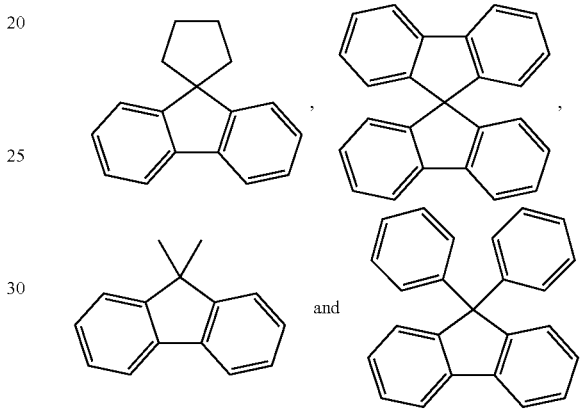

and may be included. However, the structure is not limited thereto.

In the present specification, the heteroring group includes one or more non-carbon atoms, that is, heteroatoms, and specifically, the heteroatom may include one or more atoms selected from the group consisting of O, N, S and the like. The number of carbon atoms of the heteroring group is not particularly limited, but is preferably 2 to 60. Examples of the heteroring group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group and the like, but are not limited thereto.

The heteroring group may be monocyclic or multicyclic, and may be aromatic, aliphatic, or a fused ring of aromatic and aliphatic.

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present specification, the number of carbon atoms of the amine group is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include a monocyclic aryl group, a multicyclic aryl group, or a monocyclic aryl group and a multicyclic aryl group at the same time.

Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, and a triphenylamine group, and the like, but are not limited thereto.

In the present specification, the heteroaryl group in the heteroarylamine group may be selected from among the examples of the heteroring group described above.

In the present specification, the aryl group in the aryloxy group, the arylthioxy group, the arylsulfoxy group and the aralkylamine group is the same as the aryl group examples described above. Specific examples of the aryloxy group include phenoxy, p-tolyloxy, m-tolyloxy, 3,5-dimethyl-phenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, 9-phenanthryloxy and the like, examples of the arylthioxy group include a phenylthioxy group, a 2-methylphenylthioxy group, a 4-tert-butylphenylthioxy group and the like, and examples of the arylsulfoxy group include a benzenesulfoxy group, a p-toluenesulfoxy group and the like, but the examples are not limited thereto.

In the present specification, the alkyl group in the alkylthioxy group and the alkylsulfoxy group is the same as the alkyl group examples described above. Specific examples of the alkylthioxy group include a methylthioxy group, an ethylthioxy group, a tert-butylthioxy group, a hexylthioxy group, an octylthioxy group and the like, and examples of the alkylsulfoxy group include a mesyl group, an ethylsulfoxy group, a propylsulfoxy group, a butylsulfoxy group and the like, but the examples are not limited thereto.

In the present specification, the arylene group and the alkenylene group mean having two binding sites in an aryl group and an alkenyl group, respectively, which mean, in other words, a divalent group. Descriptions on the aryl group and the alkenyl group may be applied, respectively, except that the arylene group and the alkenylene group are divalent groups.

In one embodiment of the present specification, the carbon atom binding to L2, and N are provided at an ortho position in Chemical Formula 2.

In another embodiment, the carbon atom binding to L2, and N are provided at a meta position in Chemical Formula 2.

In still another embodiment, the carbon atom binding to L2, and N are provided at a para position in Chemical Formula 2.

In one embodiment of the present specification, A1 is carbon binding to L2.

In another embodiment, A1 is carbon binding to L2, A2 is N, and A3 to A6 are CR.

In another embodiment, A1 is carbon binding to L2, A3 is N, and A2 and A4 to A6 are CR.

In another embodiment, A1 is carbon binding to L2, A4 is N, and A2, A3, A5 and A6 are CR.

Among the CRs of each A1 to A6, Rs, which are substituents of carbon, are the same as or different from each other.

In one embodiment of the present specification, Ar1 represented by Chemical Formula 2 is any one of the following structures.

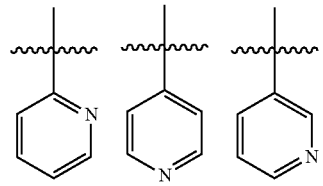

The above structure is unsubstituted or substituted with one, two or more substituents selected from the group consisting of a substituted or unsubstituted aryl group; and a substituted or unsubstituted heteroring group.

In one embodiment of the present specification, at least one of A7 to A14 is N, another is a carbon atom linking to L2, and the rest is CR.

Specifically, one or two of A7 to A14 are N, and one is a carbon atom linking to L2.

In one embodiment of the present specification, A7 is carbon binding to L2.

In one embodiment of the present specification, A7 is carbon binding to L2, A14 is N, and A8 to A13 are CR.

In another embodiment, A8 is carbon binding to L2.

In another embodiment, A8 is carbon binding to L2, A10 is N, and A7, A9 and A11 to A14 are CR.

Among the CRs of each A7 to A14, Rs, which are substituents of carbon, are the same as or different from each other.

In one embodiment of the present specification, Ar1 represented by Chemical Formula 3 is any one of the following structures.

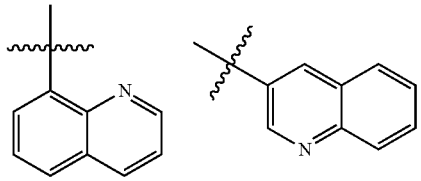 [SMILES: *c1cccc2cccnc12 ; *c1cnc2ccccc2c1]

The above structure is unsubstituted or substituted with one, two or more substituents selected from the group consisting of a substituted or unsubstituted aryl group; and a substituted or unsubstituted heteroring group.

In one embodiment of the present specification, at least one of A15 to A24 is N, another is a carbon atom linking to L2, and the rest is CR.

Specifically, one of A15 to A24 is N, one is a carbon atom linking to L2, and the rest is CR.

In one embodiment of the present specification, A23 is carbon binding to L2.

In one embodiment of the present specification, A23 is carbon binding to L2, A24 is N, and A15 to A22 are CR.

Among the CRs of each A15 to A24, Rs, which are substituents of carbon, are the same as or different from each other.

In one embodiment of the present specification, Ar1 represented by Chemical Formula 4 is the following structure.

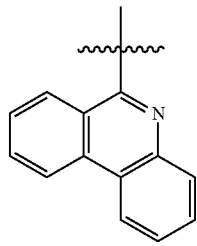 [SMILES: *c1nc2ccccc2c2ccccc12]

The above structure is unsubstituted or substituted with one, two or more substituents selected from the group consisting of a substituted or unsubstituted aryl group; and a substituted or unsubstituted heteroring group.

Specifically, carbon atoms of the above structure may be unsubstituted or substituted with one, two or more substituents selected from the group consisting of a substituted or unsubstituted aryl group; and a substituted or unsubstituted heteroring group.

In one embodiment of the present specification, at least one of L1 and L2 is an arylene group.

In one embodiment of the present specification, when at least one of L1 and L2 is an arylene group, the LUMO energy level becoming too low due to the short distance between Ar1 and

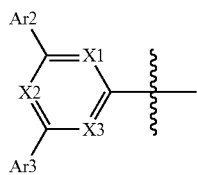

may be prevented. In this case, efficiency may be improved by lowering the energy barrier between an electron transfer layer and a light emitting layer.

In one embodiment of the present specification, L1 and L2 are the same as or different from each other, and each independently a substituted or unsubstituted arylene group.

In another embodiment, L1 and L2 are the same as or different from each other, and each independently a substituted or unsubstituted phenylene group.

In one embodiment, L1 and L2 are the same as each other, and are phenylene groups.

In one embodiment of the present specification, any one of L1 and L2 is a direct bond, and the other is a substituted or unsubstituted arylene group.

In another embodiment, any one of L1 and L2 is a direct bond, and the other is a substituted or unsubstituted phenylene group.

In one embodiment of the present specification, L1 is a direct bond.

In one embodiment of the present specification, L1 is a substituted or unsubstituted arylene group.

In one embodiment of the present specification, L1 is a substituted or unsubstituted phenylene group.

In one embodiment of the present specification, L1 is a phenylene group.

In one embodiment of the present specification, L1 is a phenylene group, and the phenylene group is

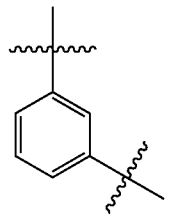

In another embodiment, L1 is a phenylene group, and the phenylene group is

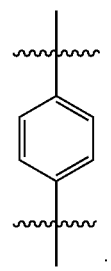

of L1 means linking to

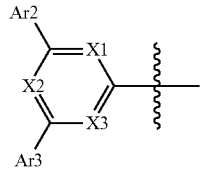

or a naphthyl group in Chemical Formula 1.

In one embodiment of the present specification, L2 is a substituted or unsubstituted arylene group.

In one embodiment of the present specification, L2 is a substituted or unsubstituted phenylene group.

In one embodiment of the present specification, L2 is a phenylene group.

In one embodiment of the present specification, L2 is a phenylene group, and the phenylene group is

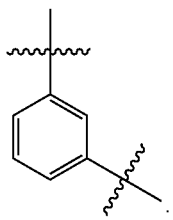 [SMILES: *c1cccc(*)c1]

In another embodiment, L2 is a phenylene group, and the phenylene group is

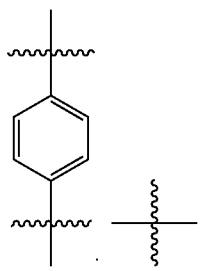

of L2 means linking to Ar1 or a naphthyl group in Chemical Formula 1.

In one embodiment, L1 is a direct bond, and L2 is a phenylene group.

In one embodiment of the present specification, Ar1 is Chemical Formula 2.

In one embodiment of the present specification, Ar1 is Chemical Formula 3.

In one embodiment of the present specification, A1 is Chemical Formula 4.

In the present specification, the trivalent heteroatom includes N, P or the like, but is not limited thereto.

In one embodiment of the present specification, the trivalent heteroatom is N.

In one embodiment of the present specification, X1 to X3 are the same as or different from each other, and each independently N or CH, and at least one of X1 to X3 is N.

In one embodiment of the present specification, Ar2 and Ar3 are the same as or different from each other, and each independently a substituted or unsubstituted phenyl group; a substituted or unsubstituted biphenyl group; or a substituted or unsubstituted naphthyl group.

In one embodiment, at least any one of X1 to X3 in Chemical Formula 1 may be a trivalent heteroatom.

In one embodiment of the present specification, two of X1 to X3 are trivalent heteroatoms.

In another embodiment, three of X1 to X3 are trivalent heteroatoms.

Specifically, at least any one of X1 to X3 is N or P.

In one embodiment of the present specification, X1 to X3 may be all N.

In one embodiment of the present specification, X1 is N, and X2 and X3 may be CH.

In one embodiment of the present specification, X2 is N, and X1 and X3 may be CH.

In one embodiment of the present specification, X3 is N, and X1 and X2 may be CH.

In one embodiment of the present specification, X1 and X2 may be N. In this case, X3 is CH.

In one embodiment of the present specification, X1 and X3 may be N. In this case, X2 is CH.

In one embodiment of the present specification, X2 and X3 may be N. In this case, X1 is CH.

In one embodiment of the present specification, Ar2 and Ar3 in Chemical Formula 1 are the same as or different from each other, and each independently a substituted or unsubstituted aryl group.

In one embodiment of the present specification, Ar2 is a phenyl group.

In one embodiment of the present specification, Ar3 is a phenyl group.

In one embodiment of the present specification, R is hydrogen or an aryl group.

In one embodiment of the present specification, R is hydrogen or a phenyl group.

In another embodiment, R is hydrogen.

In another embodiment, R is a substituted or unsubstituted aryl group.

In another embodiment, R is a substituted or unsubstituted phenyl group.

In one embodiment, R is a phenyl group.

In one embodiment of the present specification, Ar1 is any one of the following structures.

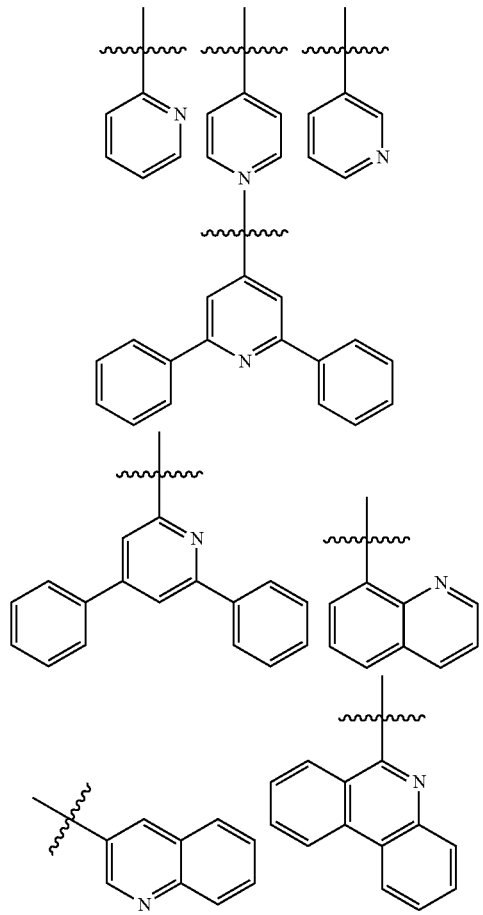

In one embodiment of the present specification, Ar1 is Chemical Formula 2, and the hetero-cyclic compound having a structure of Chemical Formula 1-1 is represented by any one of the following Formulae 2-1-1 to 2-1-5.

[formula 2-1-1]
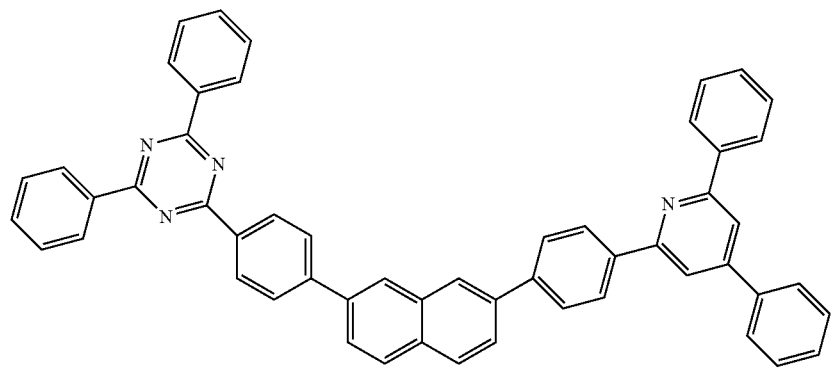
[formula 2-1-2]
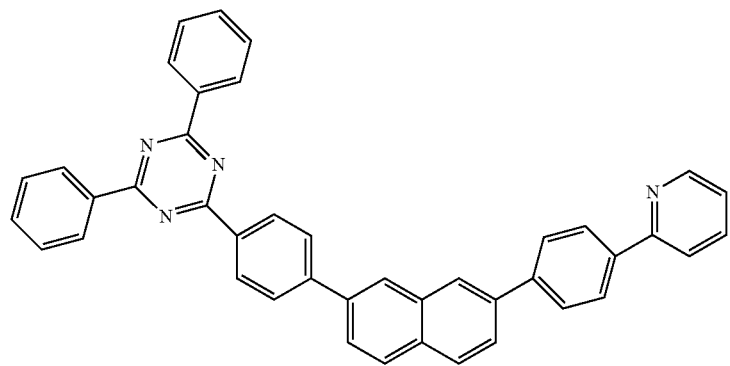
[formula 2-1-3]
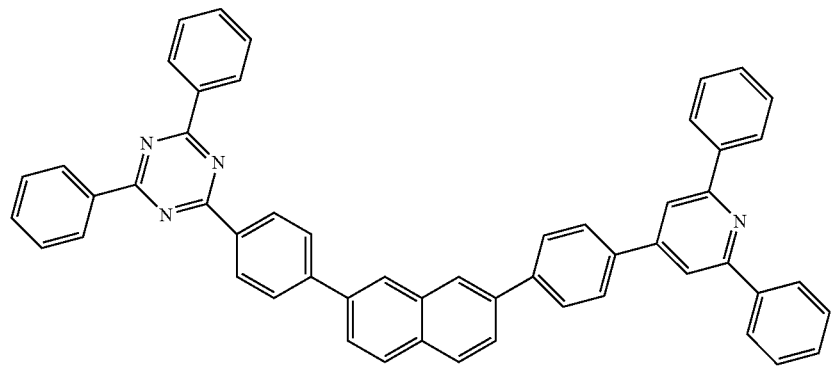
[formula 2-1-4]      [formula 2-1-5]
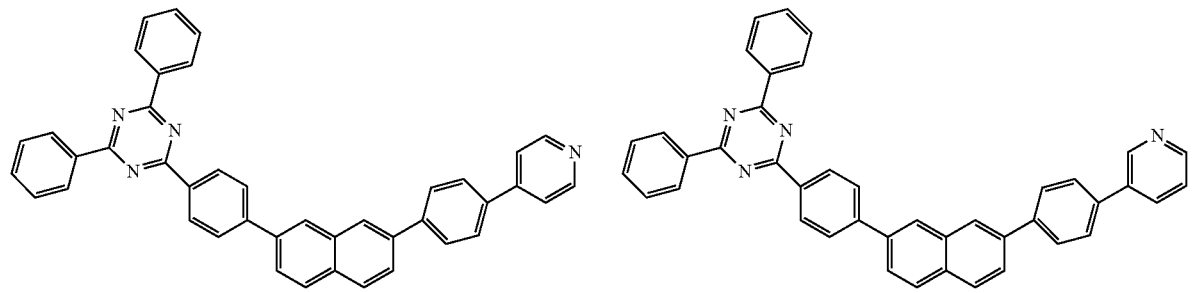
In one embodiment of the present specification, Ar1 is Chemical Formula 2, and the hetero-cyclic compound having a structure of Chemical Formula 1-2 is represented by any one of the following Formulae 2-2-1 to 2-2-5.

[formula 2-2-1]
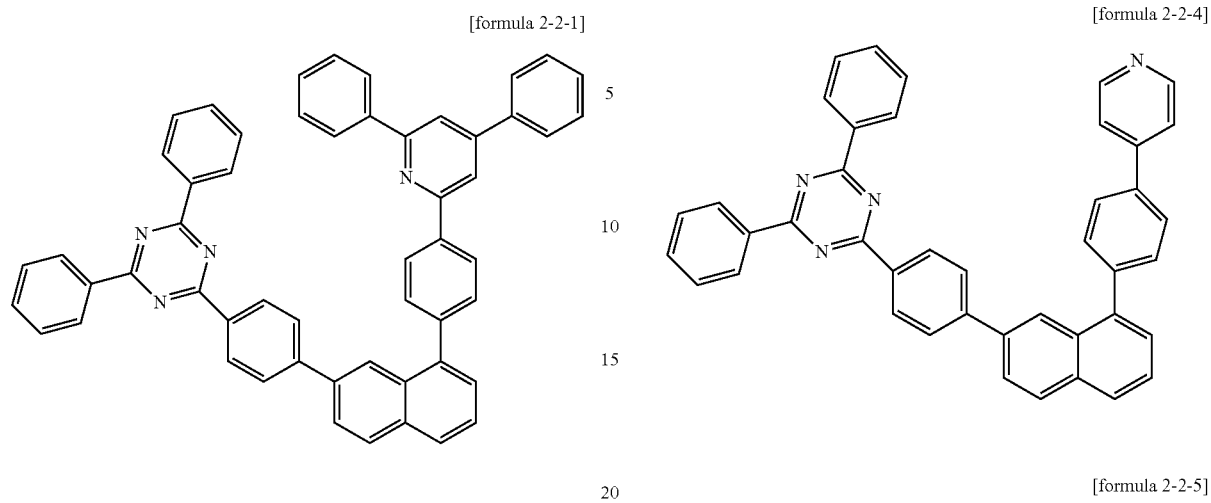
[formula 2-2-2]
[formula 2-2-3]
[formula 2-2-4]
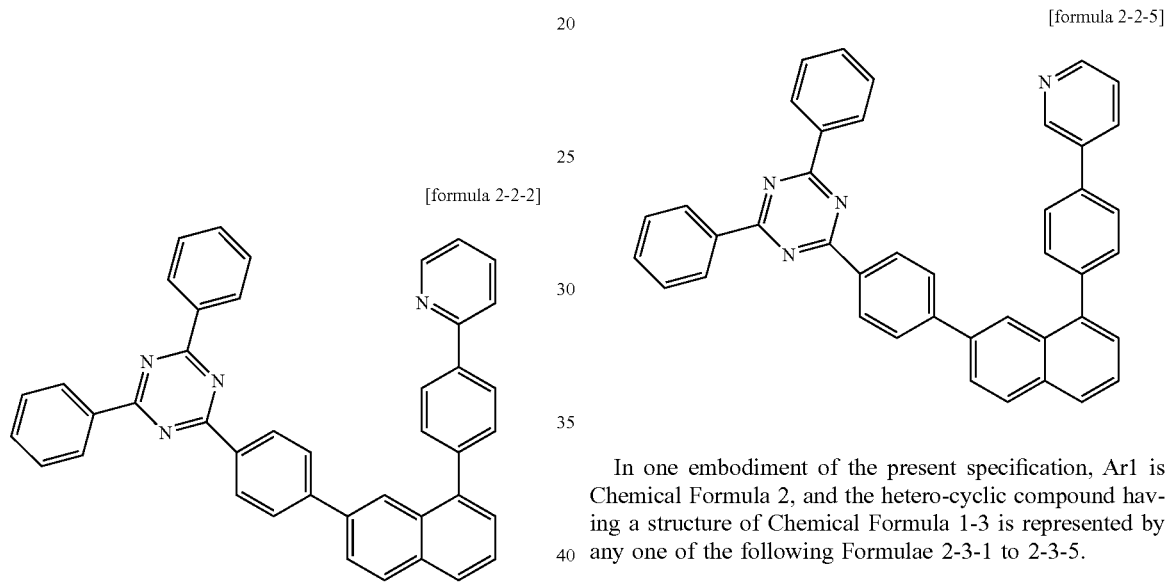
[formula 2-2-5]
In one embodiment of the present specification, Ar1 is Chemical Formula 2, and the hetero-cyclic compound having a structure of Chemical Formula 1-3 is represented by any one of the following Formulae 2-3-1 to 2-3-5.
[formula 2-3-1]
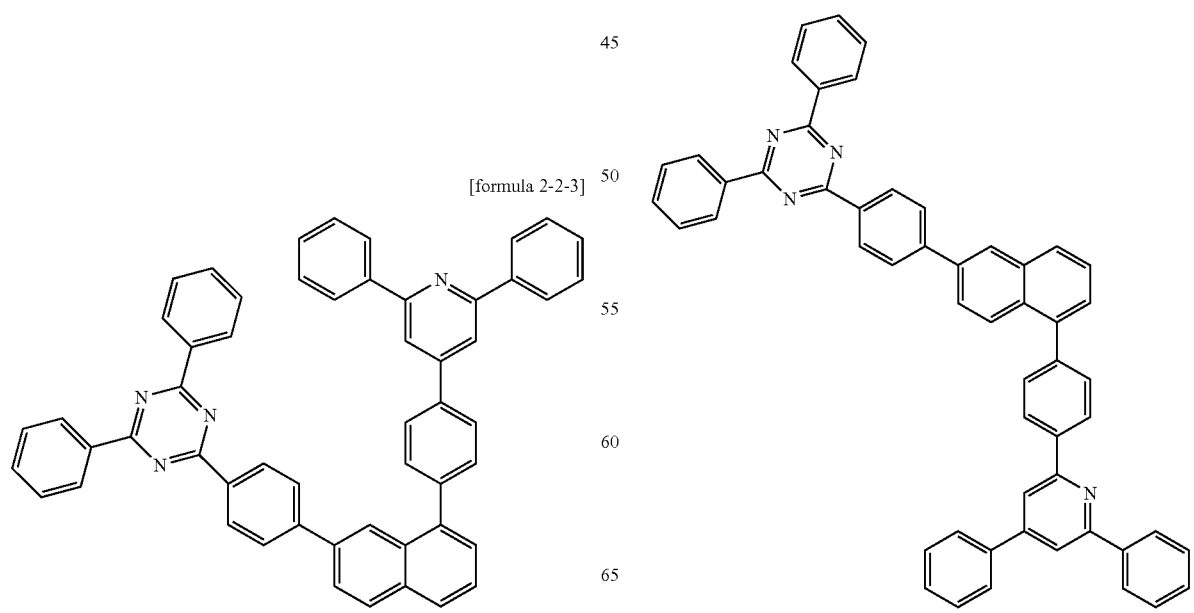

[formula 2-3-2]
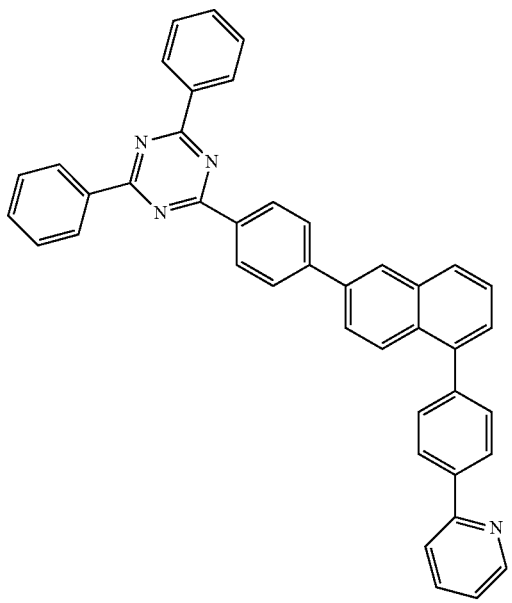
[formula 2-3-4]
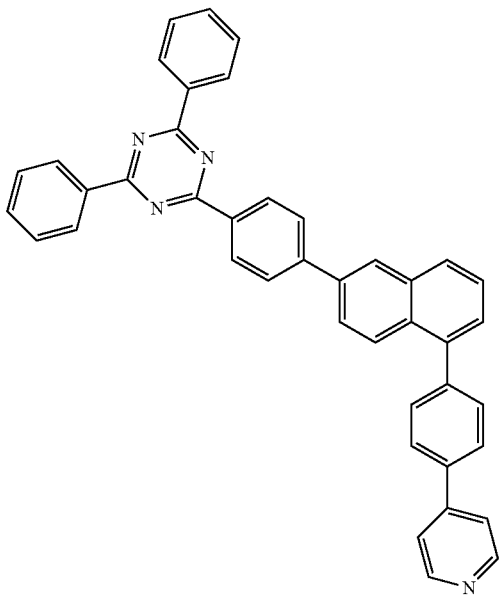
[formula 2-3-3]
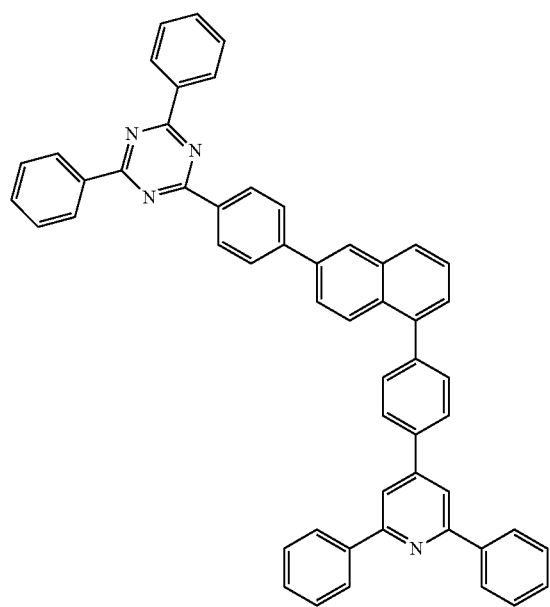
[formula 2-3-5]
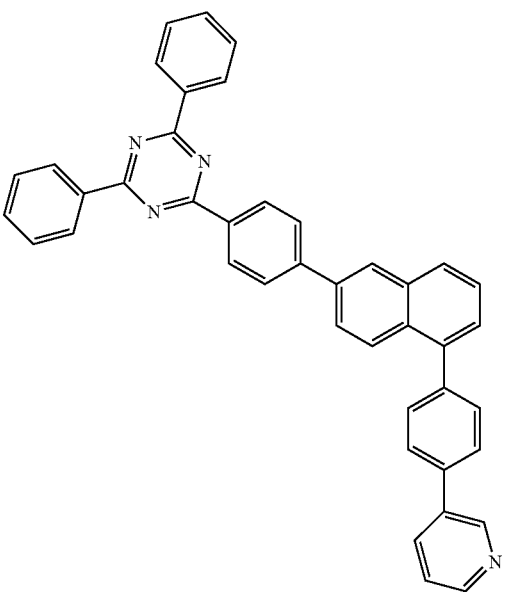
In one embodiment of the present specification, Ar1 is Chemical Formula 2, and the hetero-cyclic compound having structure of Chemical Formula 1-4 is represented by any one of the following Formulae 2-4-1 to 2-4-5.

[formula 2-4-1]
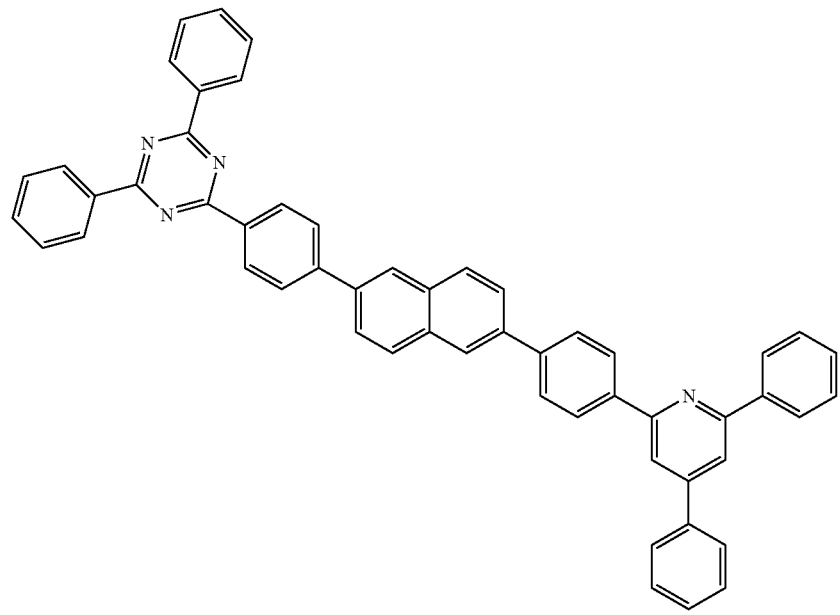
[formula 2-4-2]
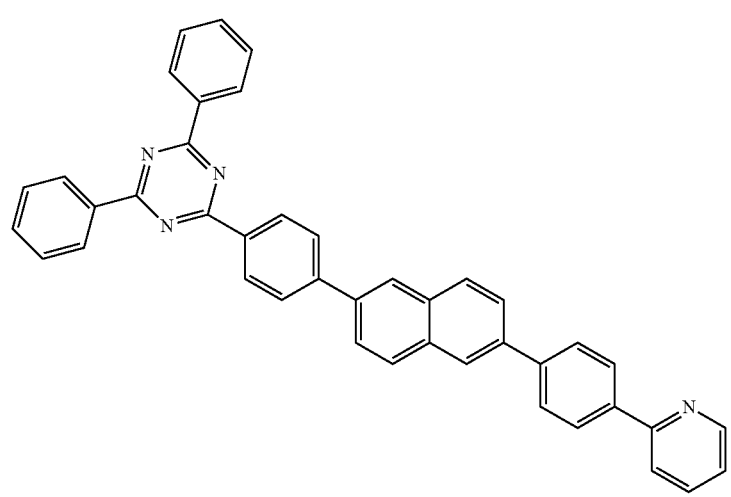

[formula 2-4-3]
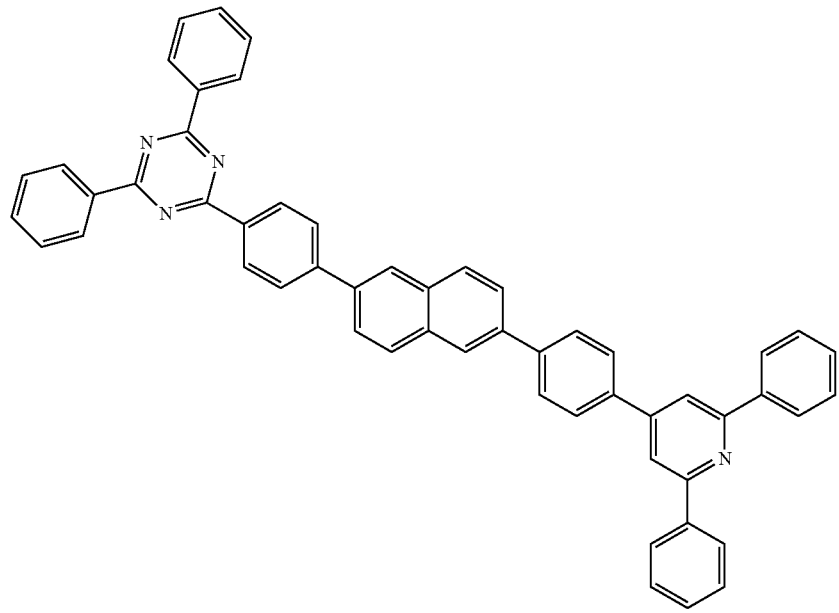
[formula 2-4-4]
[formula 2-4-5]
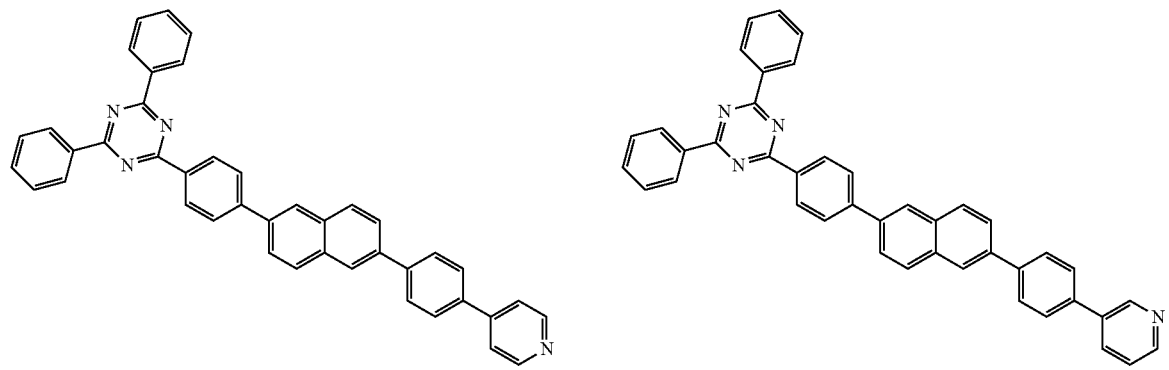
In one embodiment of the present specification, Ar1 is Chemical Formula 2, and the hetero-cyclic compound having a structure of Chemical Formula 1-5 is represented by any one of the following Formulae 2-5-1 to 2-5-5.
[formula 2-5-1]
[formula 2-5-2]
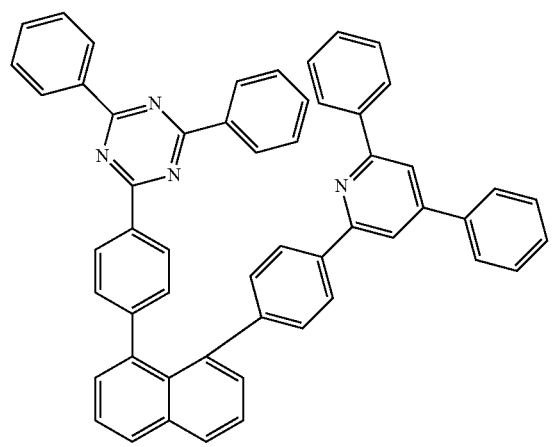
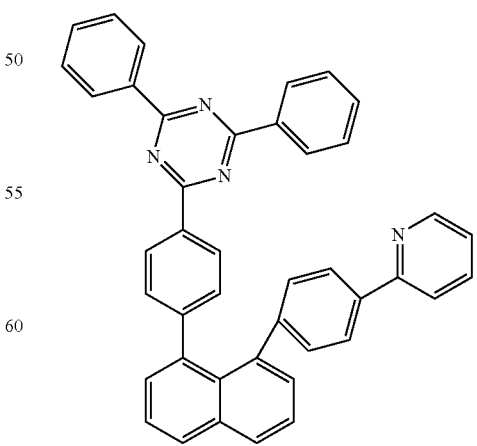

[formula 2-5-3]
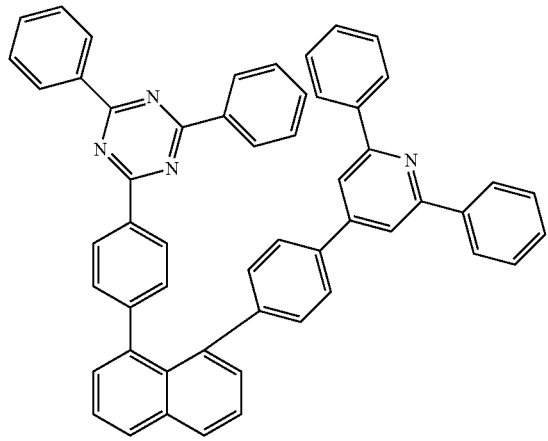
[formula 2-6-1]
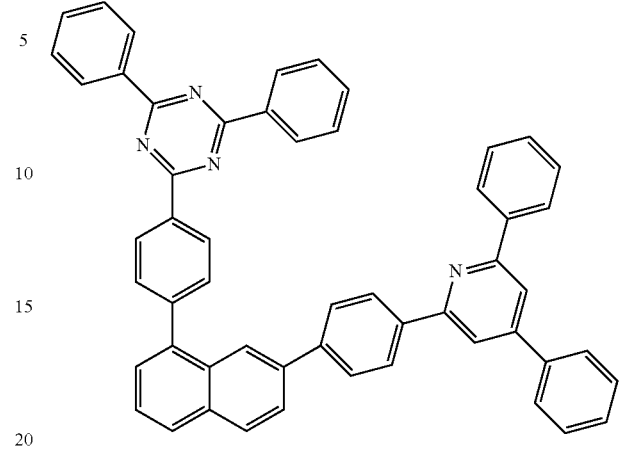
[formula 2-5-4]
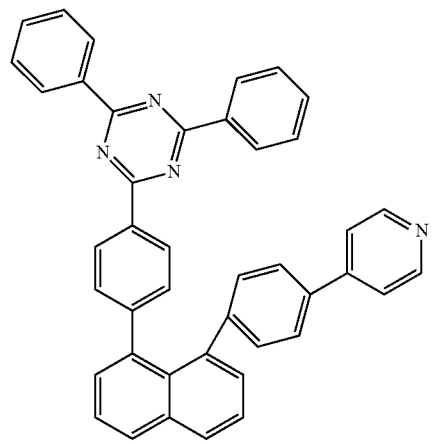
[formula 2-6-2]
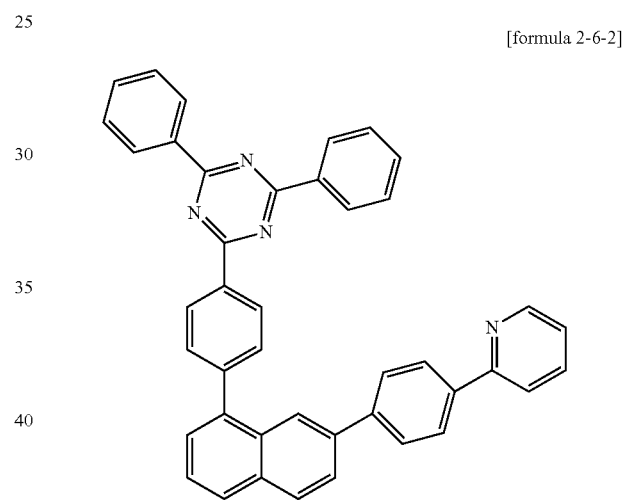
[formula 2-5-5]
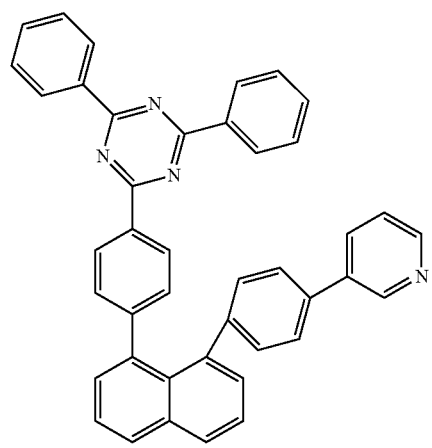
[formula 2-6-3]
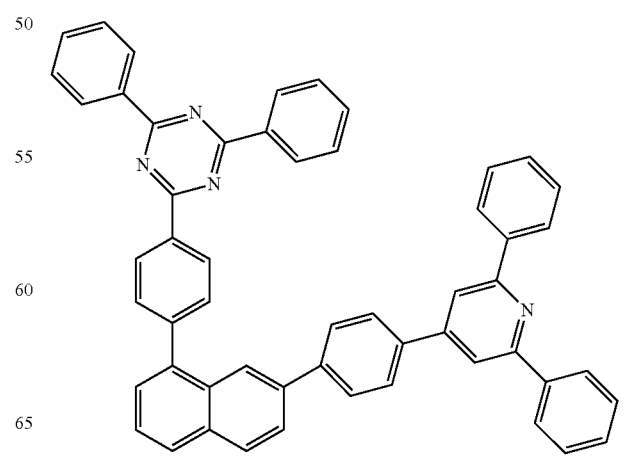
In one embodiment of the present specification, Ar1 is Chemical Formula 2, and the hetero-cyclic compound having a structure of Chemical Formula 1-6 is represented by any one of the following Formulae 2-6-1 to 2-6-5.

[formula 2-6-4]
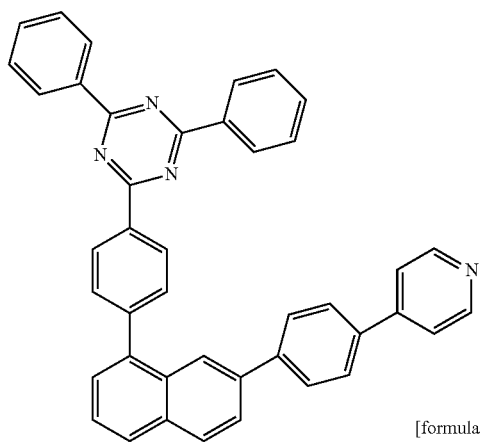
[formula 2-6-5]
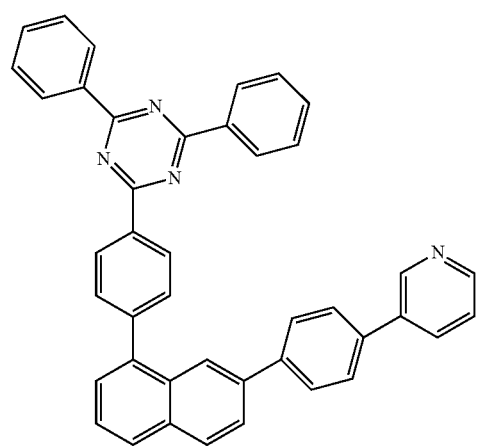
[formula 2-7-2]
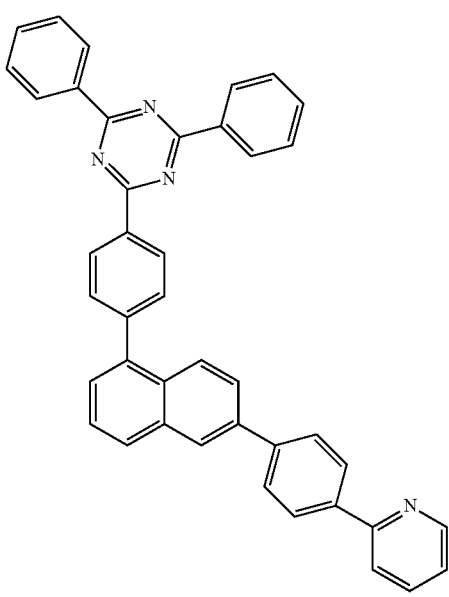
In one embodiment of the present specification, Ar1 is Chemical Formula 2, and the hetero-cyclic compound having structure of Chemical Formula 1-7 is represented by any one of the following Formulae 2-7-1 to 2-7-5.
[formula 2-7-1]
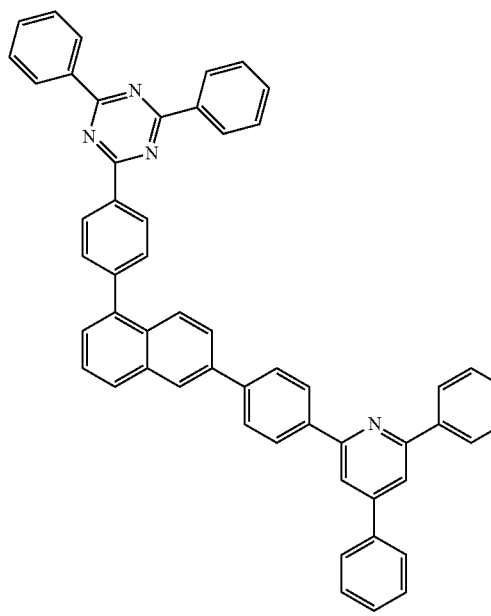
[formula 2-7-3]
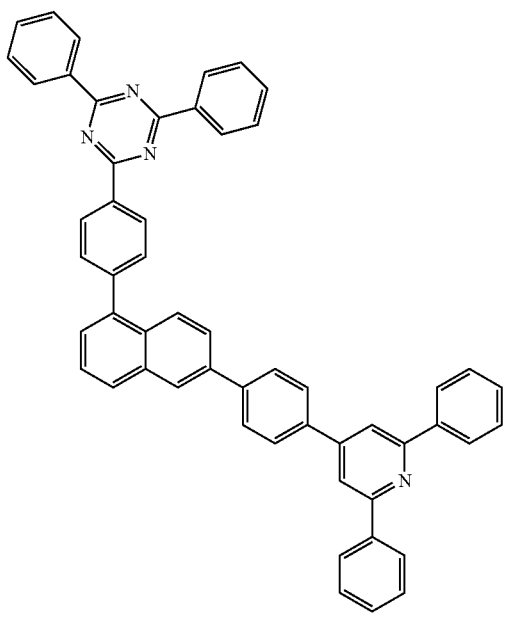

[formula 2-7-4]
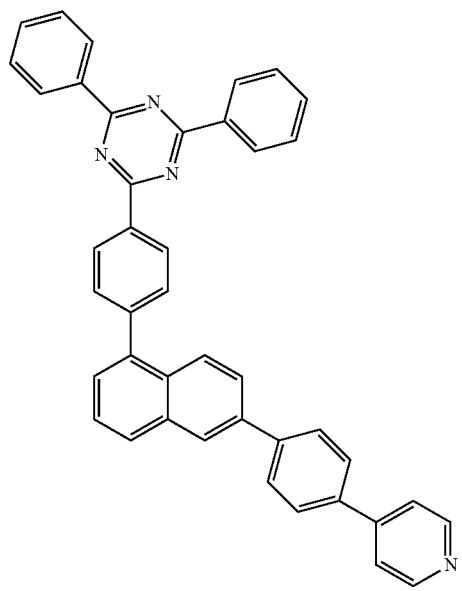
[formula 2-8-1]
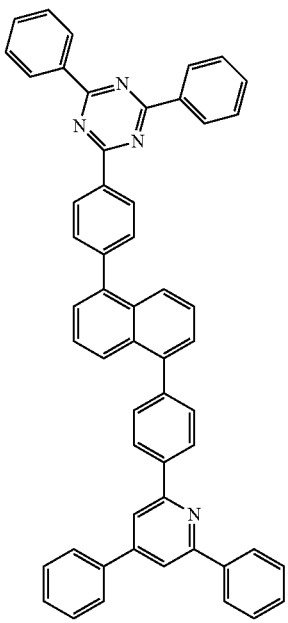
[formula 2-7-5]
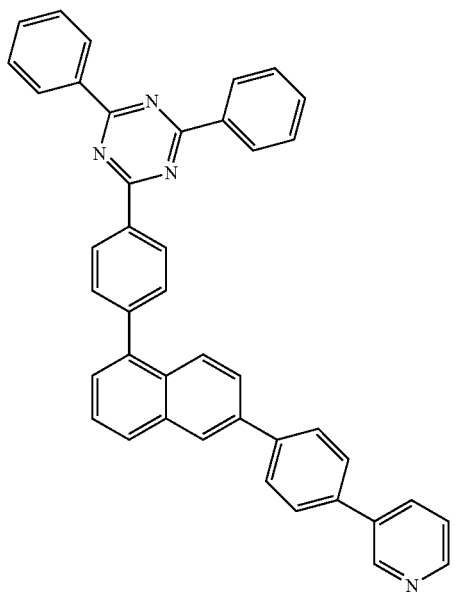
[formula 2-8-2]
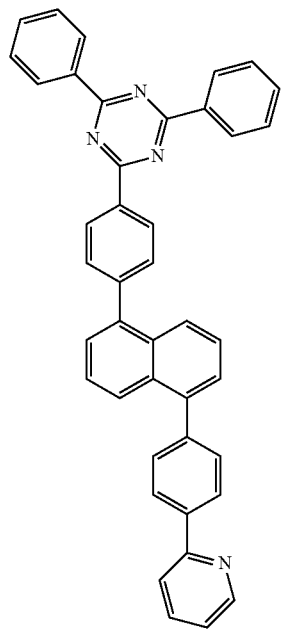
In one embodiment of the present specification, Ar1 is Chemical Formula 2, and the hetero-cyclic compound having a structure of Chemical Formula 1-8 is represented by any one of the following Formulae 2-8-1 to 2-8-5.

[formula 2-8-3]
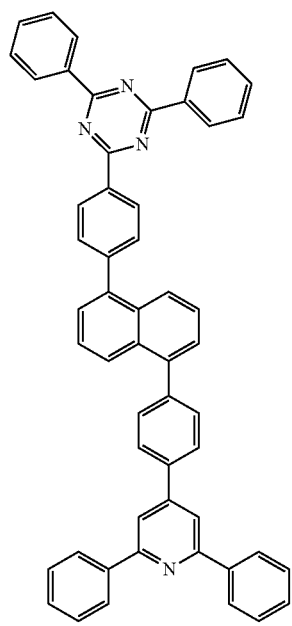
[formula 2-8-5]
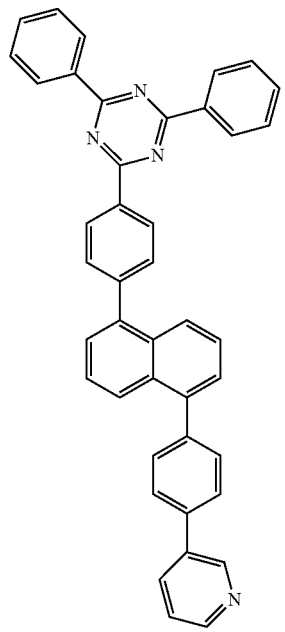
In one embodiment of the present specification, Ar1 is Chemical Formula 2, and the hetero-cyclic compound having a structure of Chemical Formula 1-9 is represented by any one of the following Formulae 2-9-1 to 2-9-5.
[formula 2-8-4]
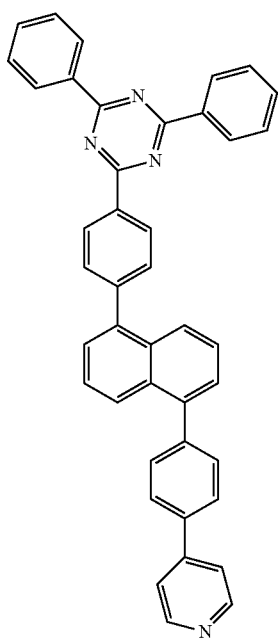
[formula 2-9-1]
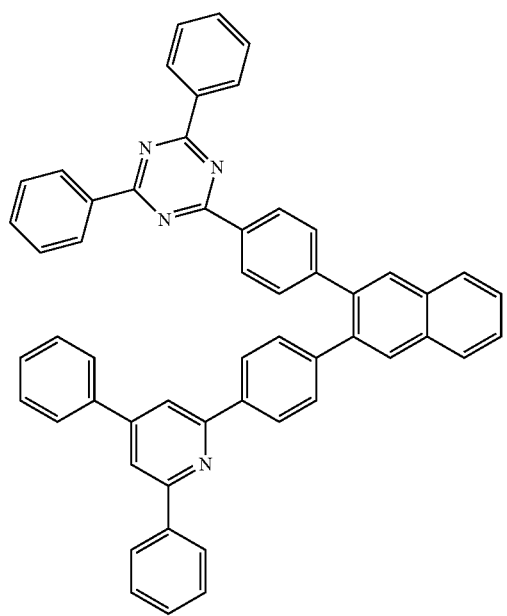

[formula 2-9-2]
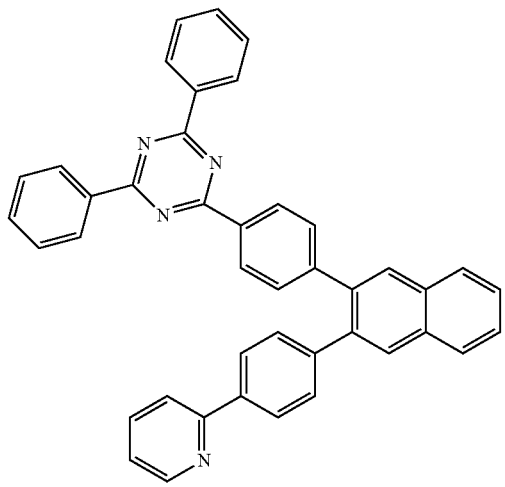
[formula 2-9-3]
[formula 2-9-4]
[formula 2-9-5]
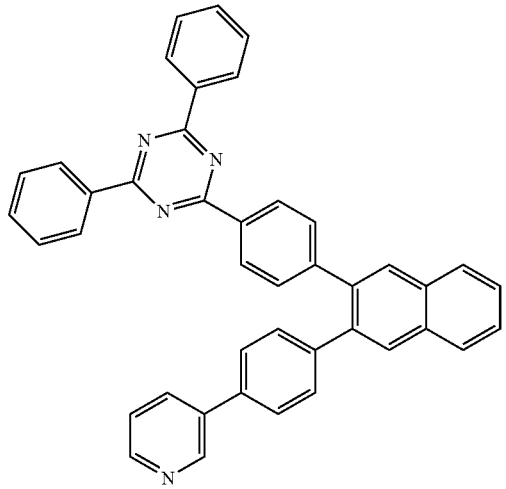
In one embodiment of the present specification, Ar1 is Chemical Formula 2, and the hetero-cyclic compound having a structure of Chemical Formula 1-10 is represented by any one of the following Formulae 2-10-1 to 2-10-5.
[formula 2-10-1]
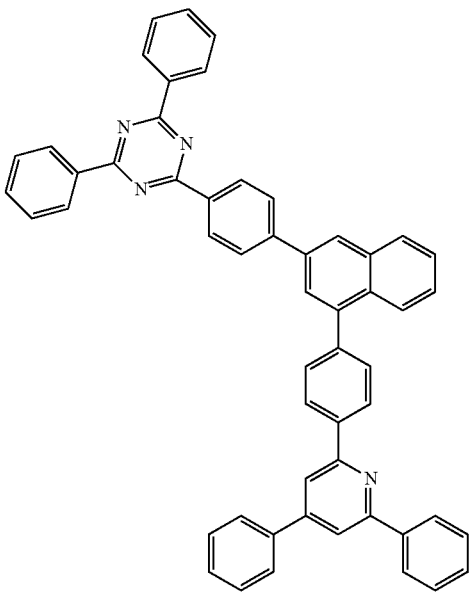

[formula 2-10-2]
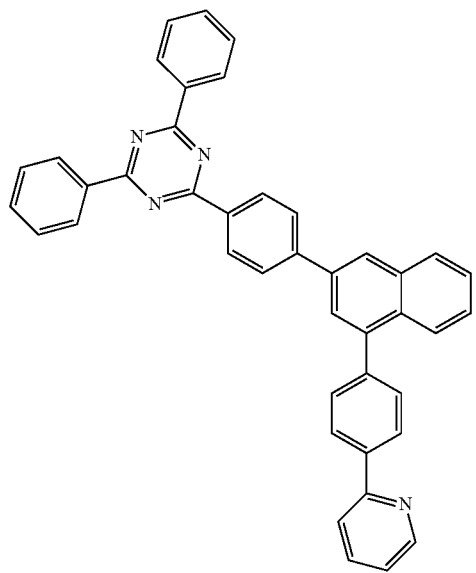
[formula 2-10-4]
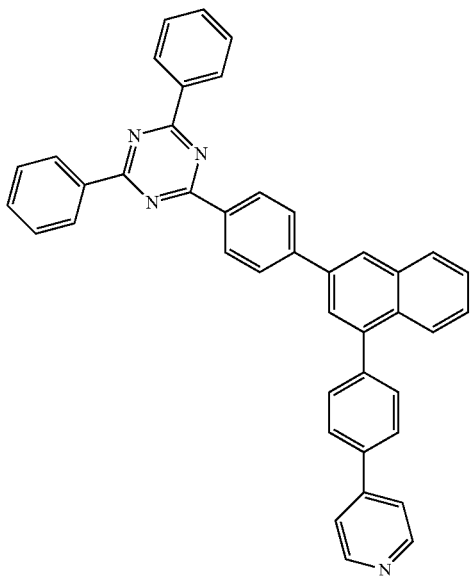
[formula 2-10-3]
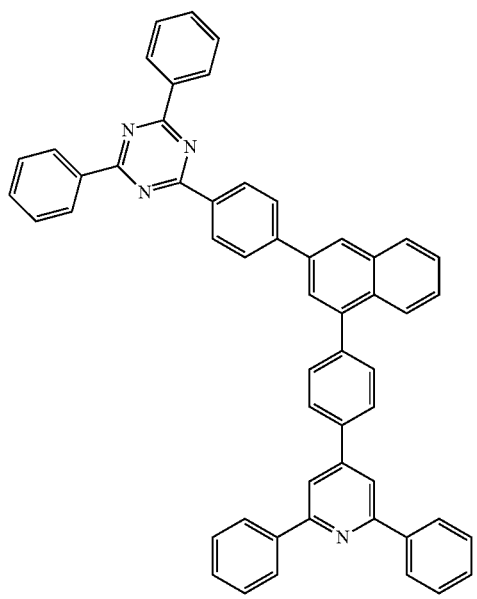
[formula 2-10-5]
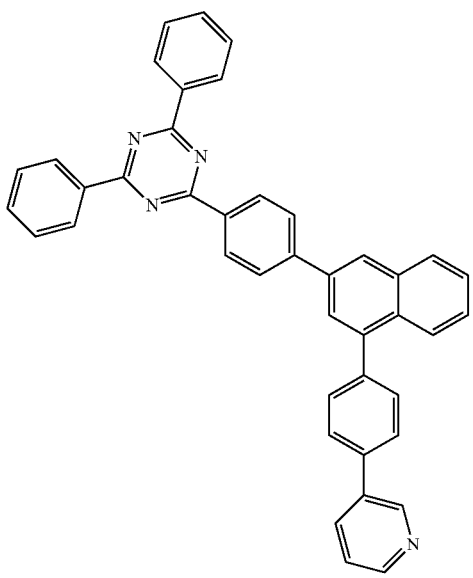
In one embodiment of the present specification, Ar1 is Chemical Formula 2, and the hetero-cyclic compound having a structure of Chemical Formula 1-11 is represented by any one of the following Formulae 2-11-1 to 2-11-5.

[formula 2-11-1]
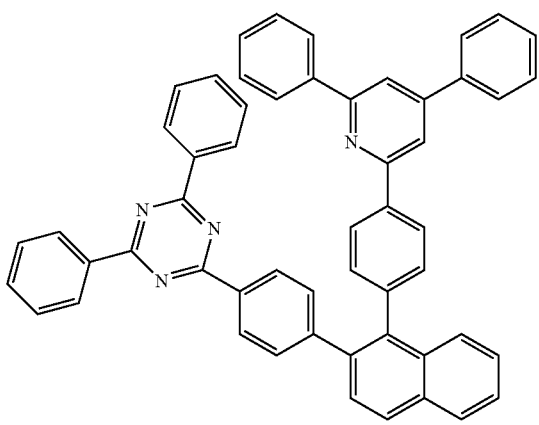
[formula 2-11-2]
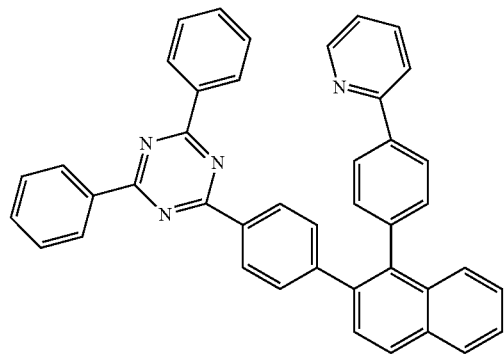
[formula 2-11-3]
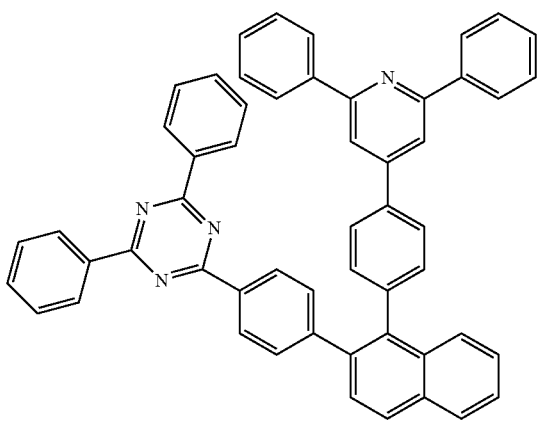
[formula 2-11-4]
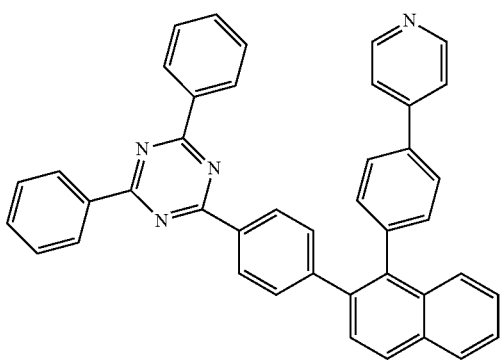
[formula 2-11-5]
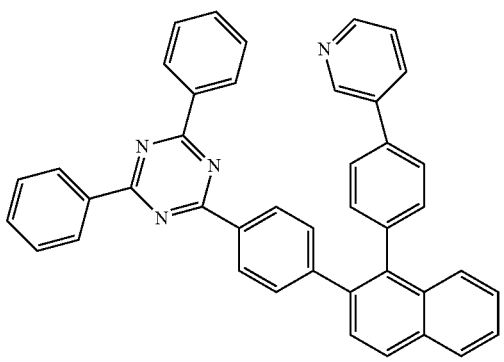
In one embodiment of the present specification, Ar1 is Chemical Formula 2, and the hetero-cyclic compound having a structure of Chemical Formula 1-12 is represented by any one of the following Formulae 2-12-1 to 2-12-5.
[formula 2-12-1]
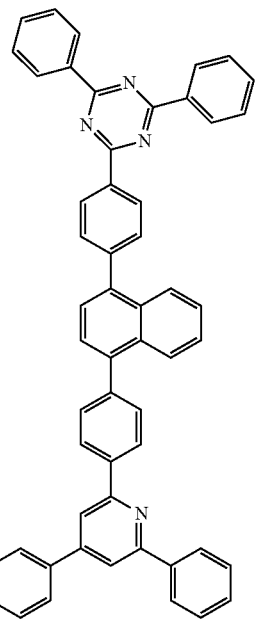

[formula 2-12-2]
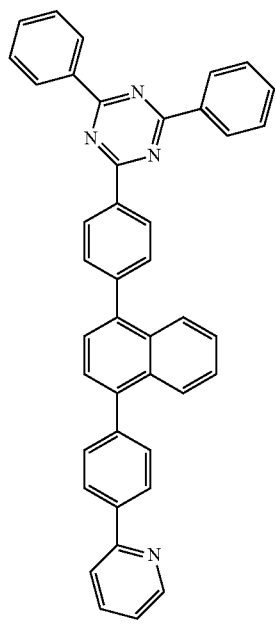
[formula 2-12-3]
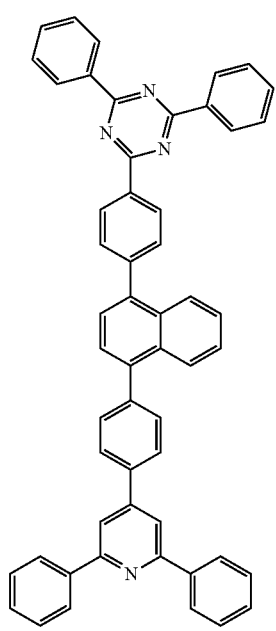
[formula 2-12-4]
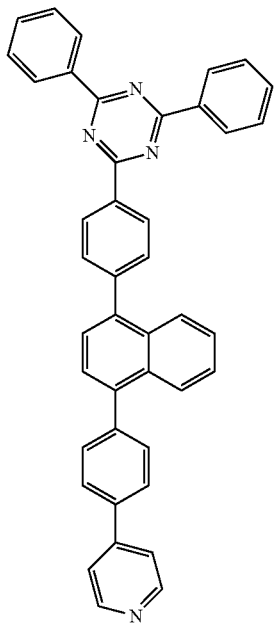
[formula 2-12-5]
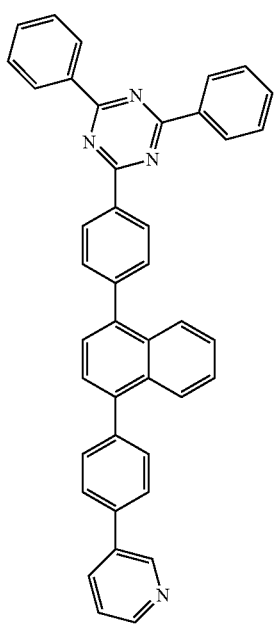
In one embodiment of the present specification, Ar1 is Chemical Formula 2, and the hetero-cyclic compound having a structure of Chemical Formula 1-13 is represented by any one of the following Formulae 2-13-1 to 2-13-5.

[formula 2-13-1]
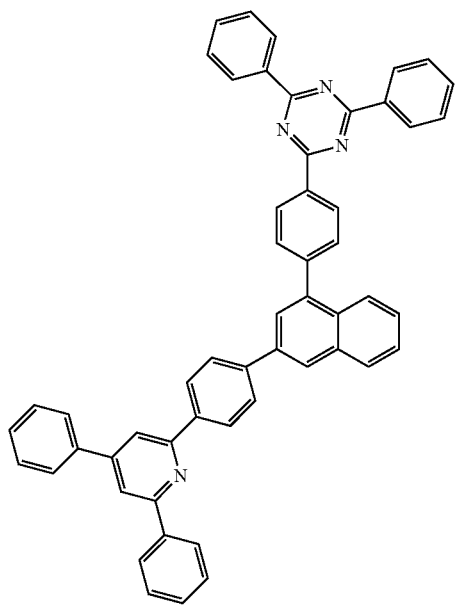
[formula 2-13-2]
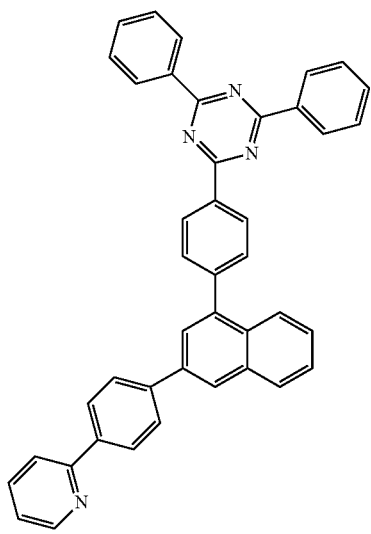
[formula 2-13-3]
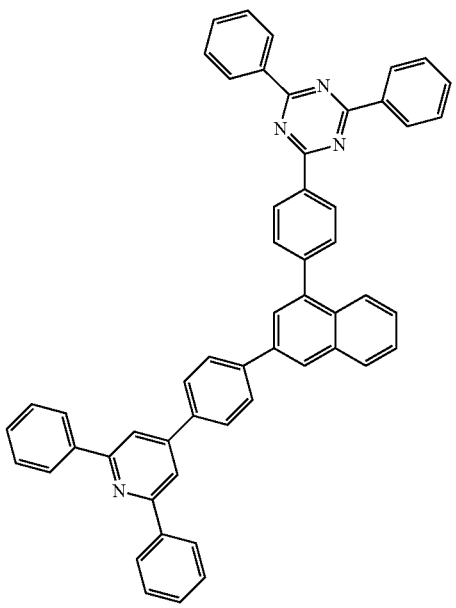
[formula 2-13-4]
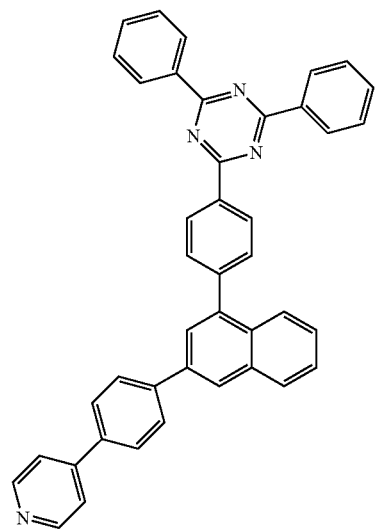

[formula 2-13-5]

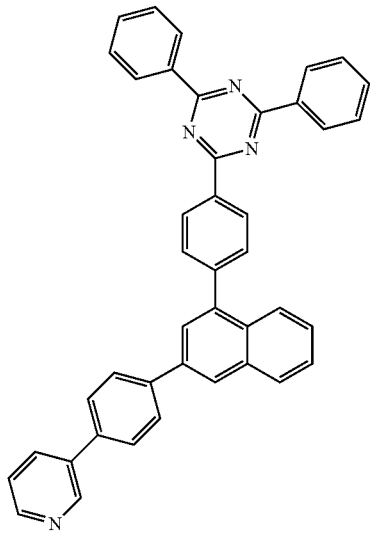

In one embodiment of the present specification, Ar1 is Chemical Formula 2, and the hetero-cyclic compound having a structure of Chemical Formula 1-14 is represented by any one of the following Formulae 2-14-1 to 2-14-5.

[formula 2-14-1]

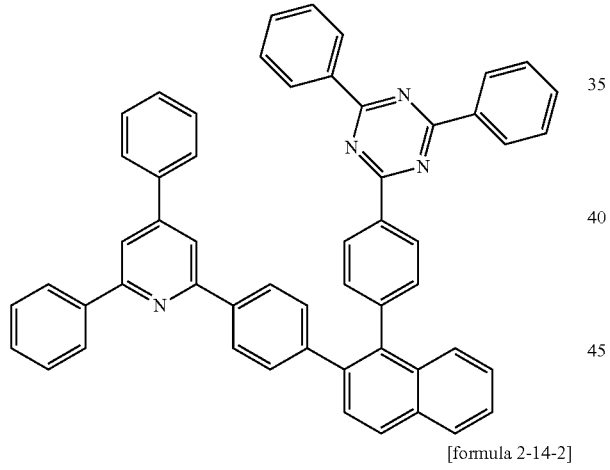

[formula 2-14-2]

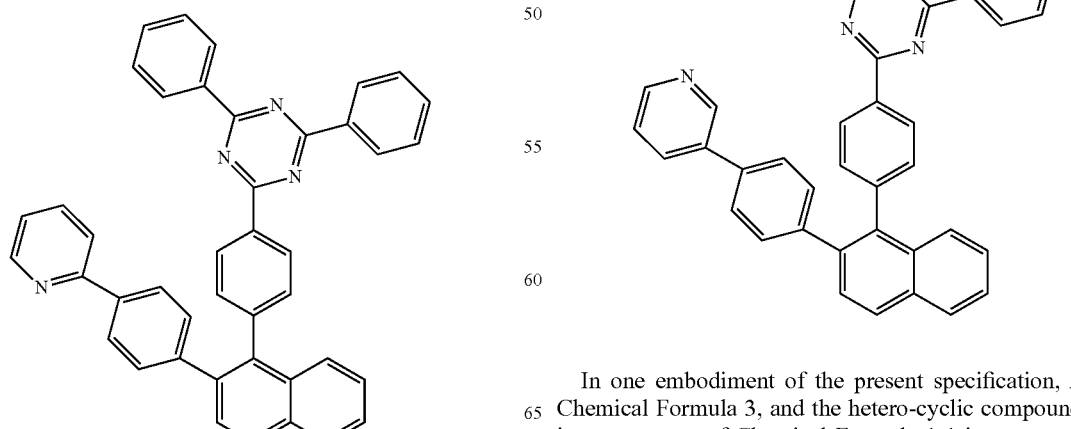

[formula 2-14-3]

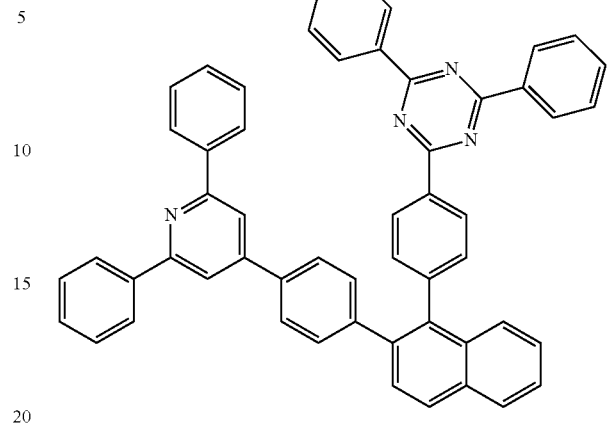

[formula 2-14-4]

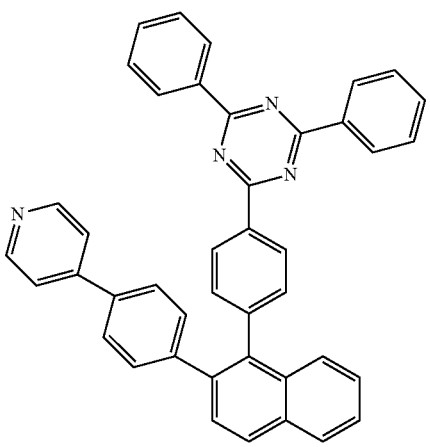

[formula 2-14-5]

In one embodiment of the present specification, Ar1 is Chemical Formula 3, and the hetero-cyclic compound having a structure of Chemical Formula 1-1 is represented by any one of the following Formulae 3-1-1 to 3-1-6.

[formula 3-1-1]
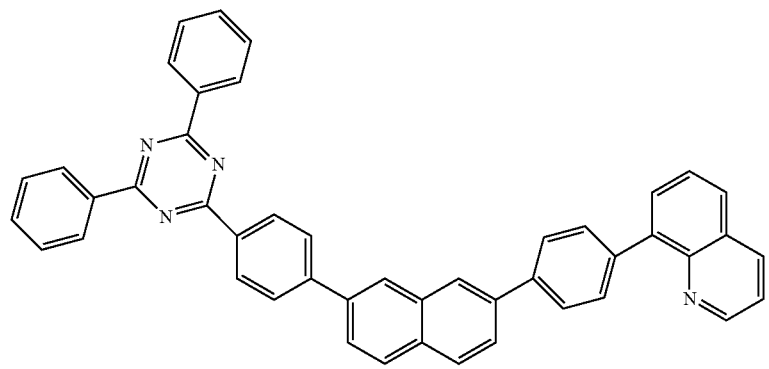
[formula 3-1-2]
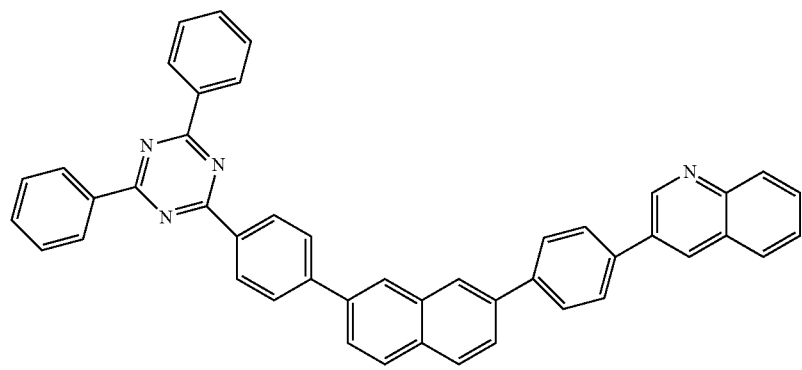
[formula 3-1-3]
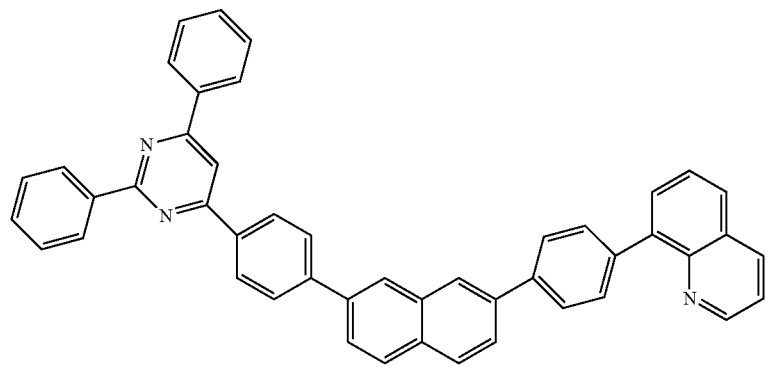
[formula 3-1-4]
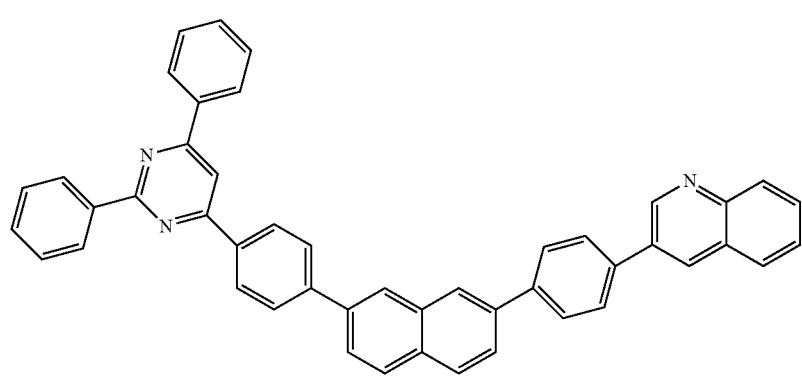

[formula 3-1-5]
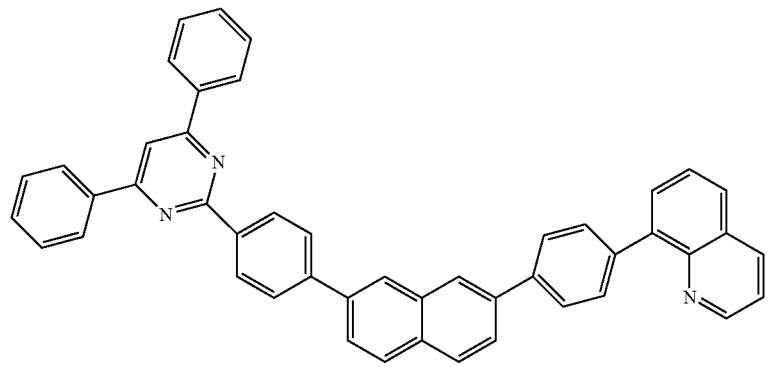
[formula 3-1-6]
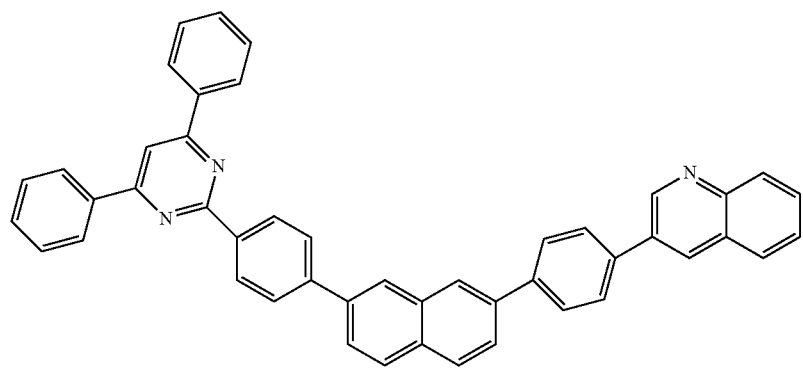
In one embodiment of the present specification, Ar1 is Chemical Formula 3, and the hetero-cyclic compound having a structure of Chemical Formula 1-2 is represented by any one of the following Formulae 3-2-1 to 3-2-6.
[formula 3-2-1]
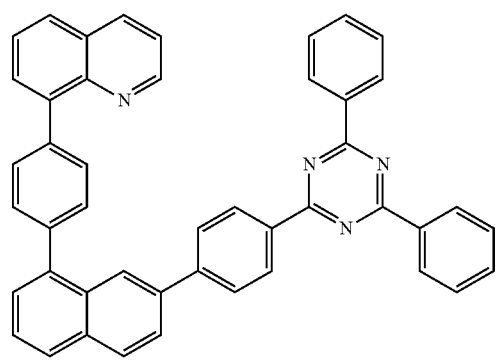
[formula 3-2-2]
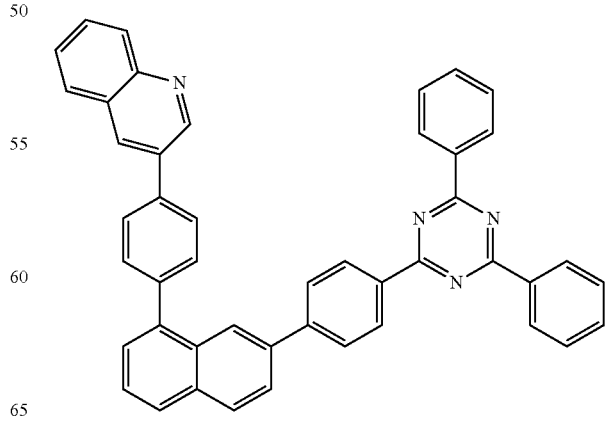

-continued
[formula 3-2-3]
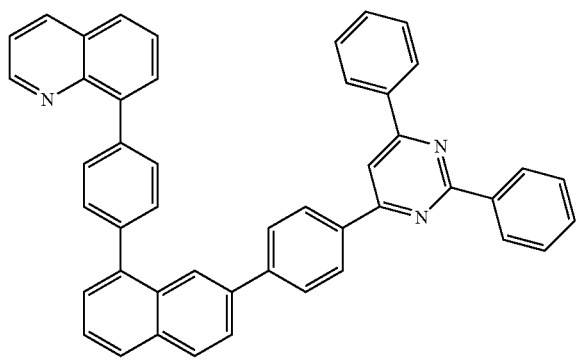
[formula 3-2-4]
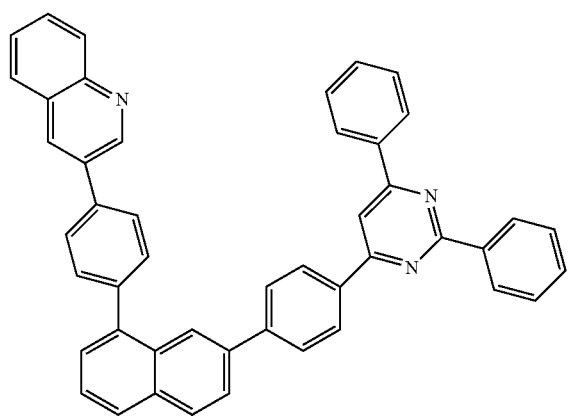
[formula 3-2-5]
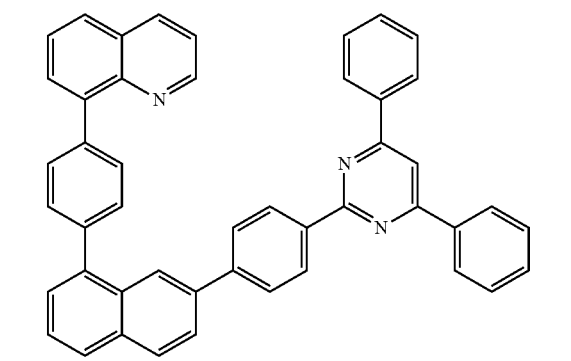
[formula 3-2-6]
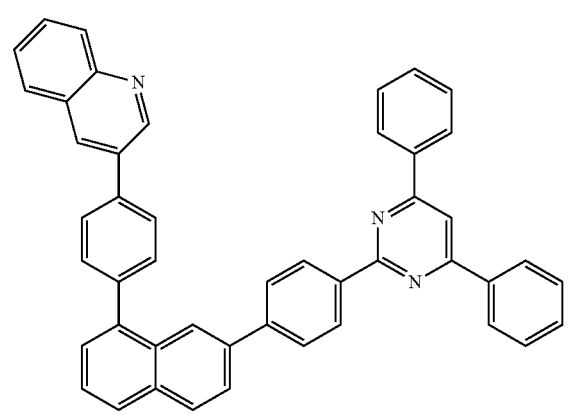
In one embodiment of the present specification, Ar1 is Chemical Formula 3, and the hetero-cyclic compound having a structure of Chemical Formula 1-3 is represented by any one of the following Formulae 3-3-1 to 3-3-6.
[formula 3-3-1]
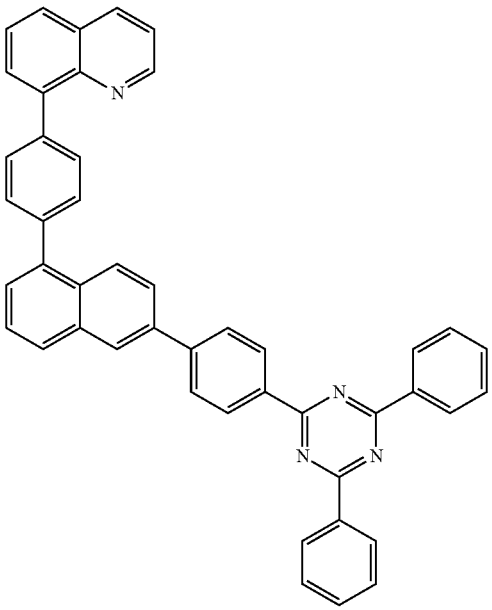
[formula 3-3-2]
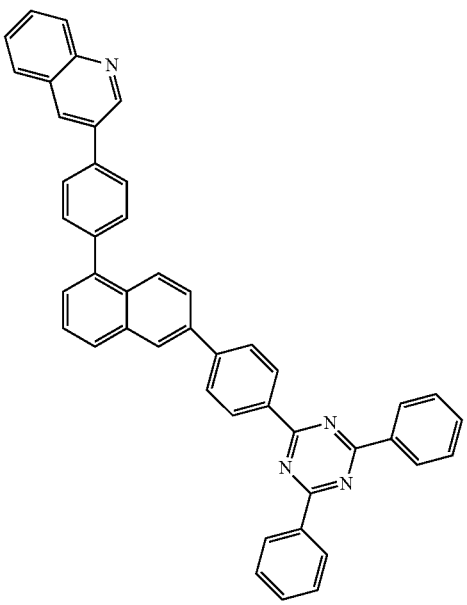

[formula 3-3-3]
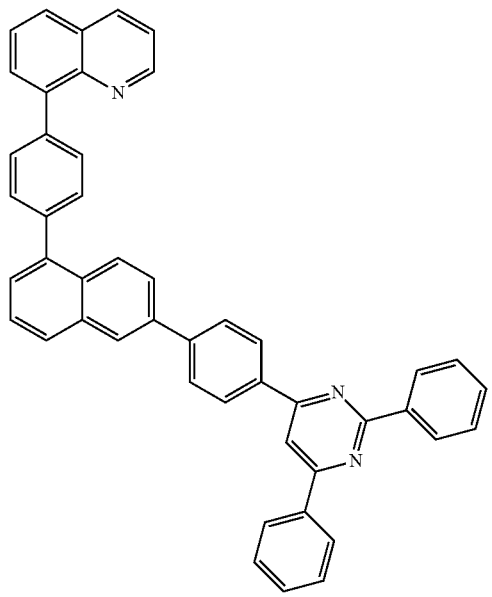
[formula 3-3-5]
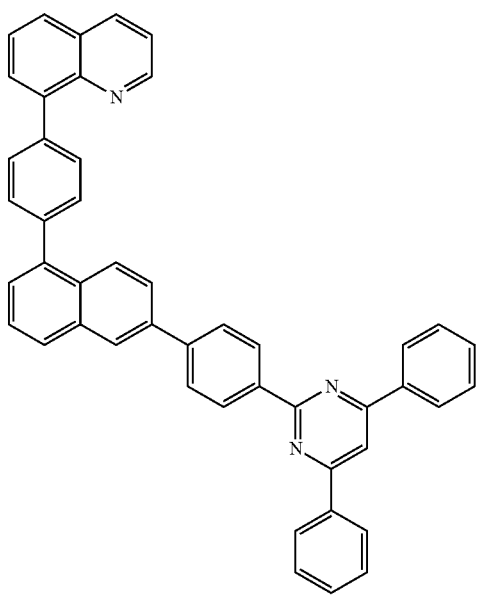
[formula 3-3-4]
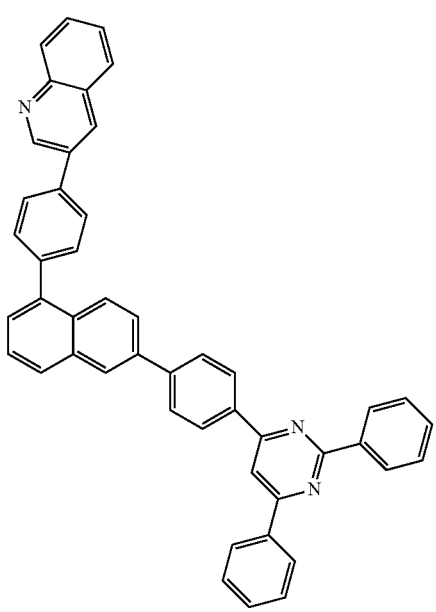
[formula 3-3-6]
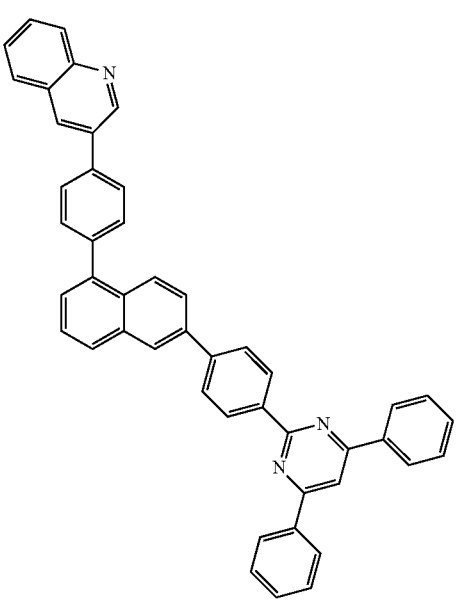
In one embodiment of the present specification, Ar1 is Chemical Formula 3, and the hetero-cyclic compound having a structure of Chemical Formula 1-4 is represented by any one of the following Formulae 3-4-1 to 3-4-6.

[formula 3-4-1]
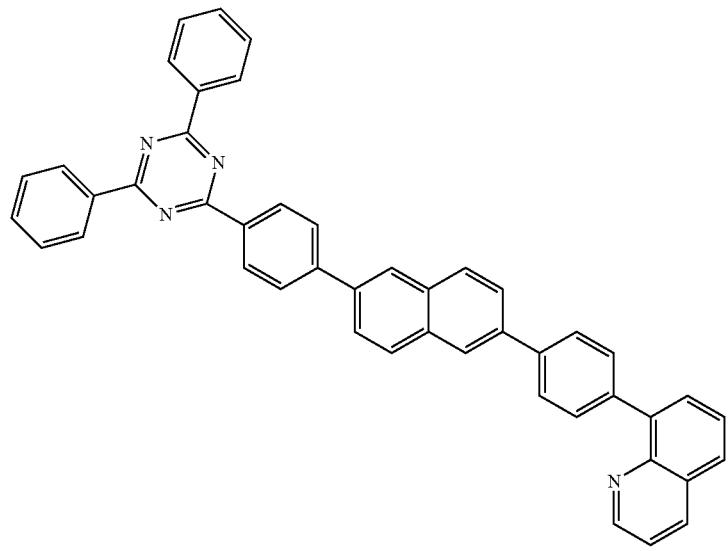
[formula 3-4-1]
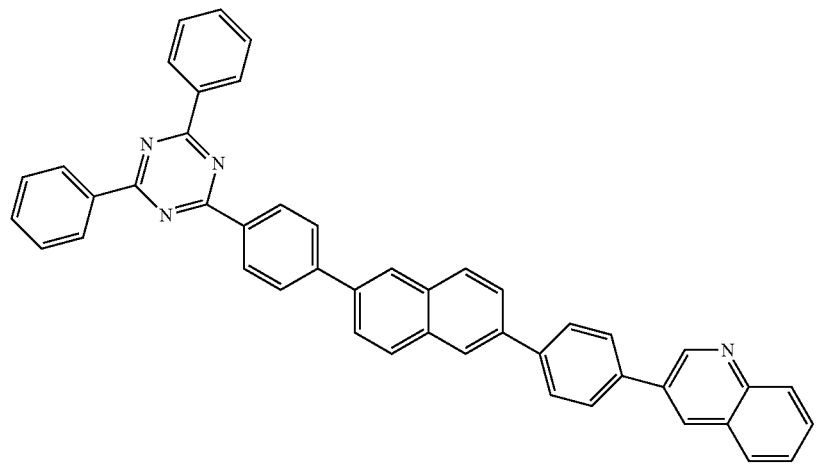
[formula 3-4-3]
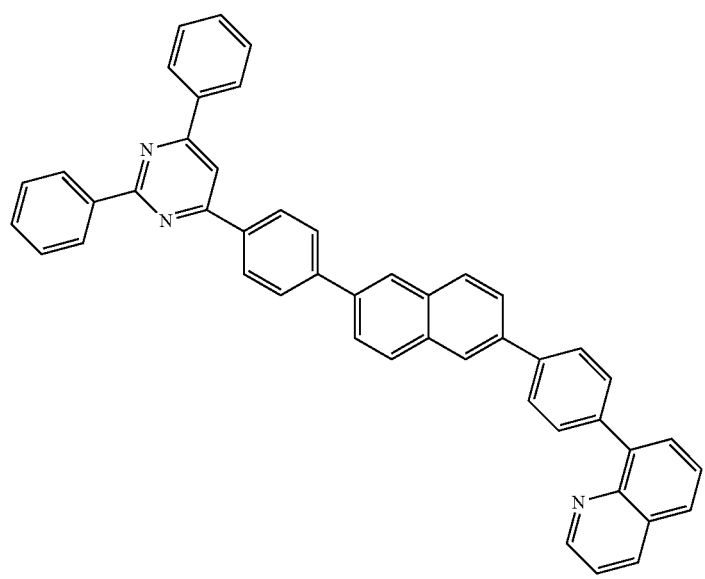

[formula 3-4-4]
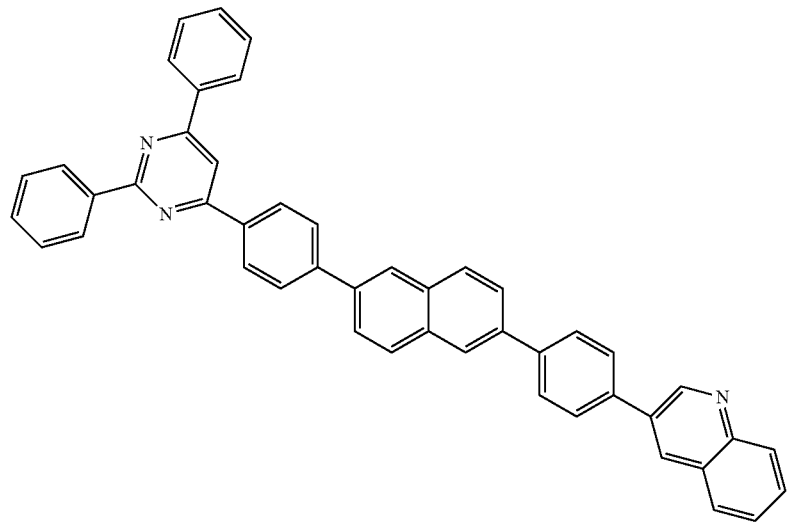
[formula 3-4-5]
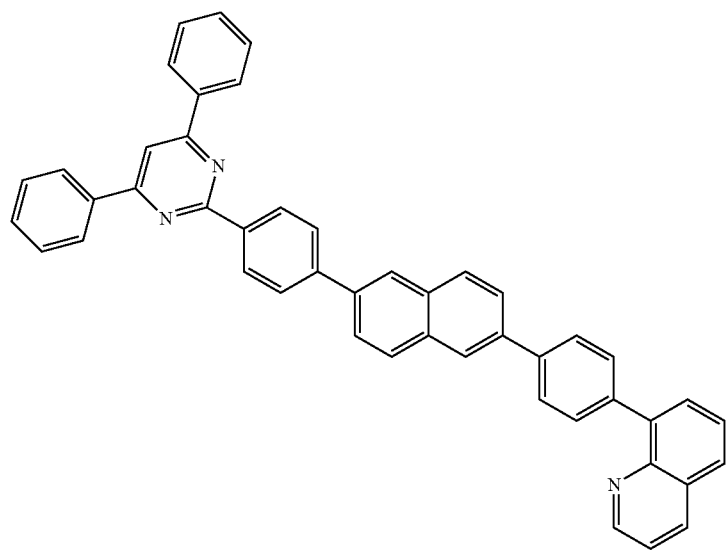
[formula 3-4-6]
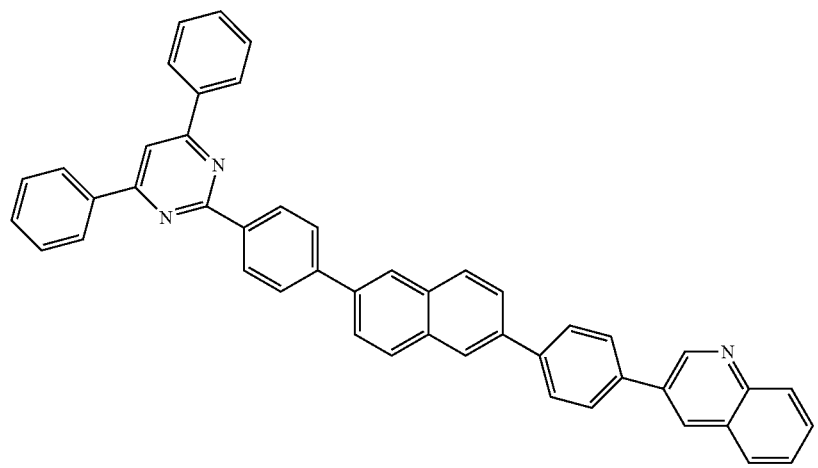
In one embodiment of the present specification, Ar1 is Chemical Formula 3, and the hetero-cyclic compound having a structure of Chemical Formula 1-5 is represented by any one of the following Formulae 3-5-1 to 3-5-6.

[formula 3-5-1]
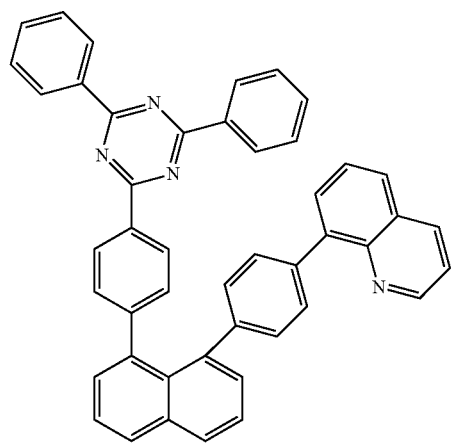
[formula 3-5-2]
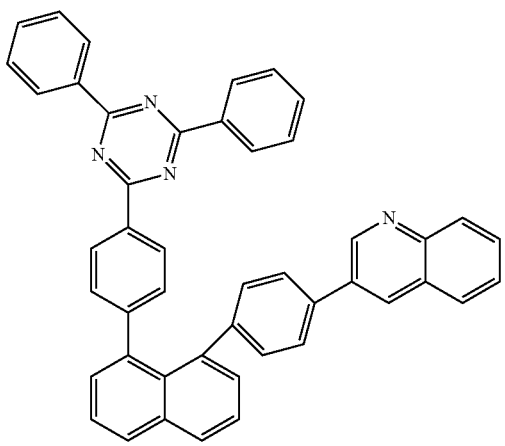
[formula 3-5-3]
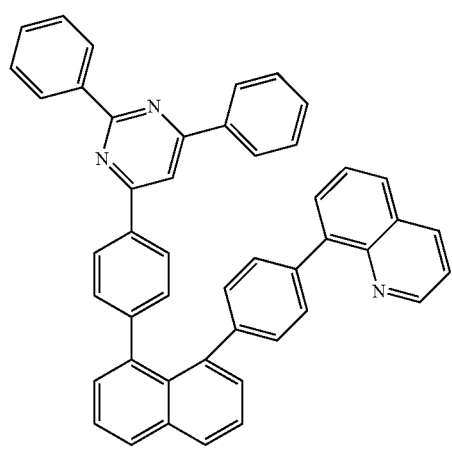
[formula 3-5-4]
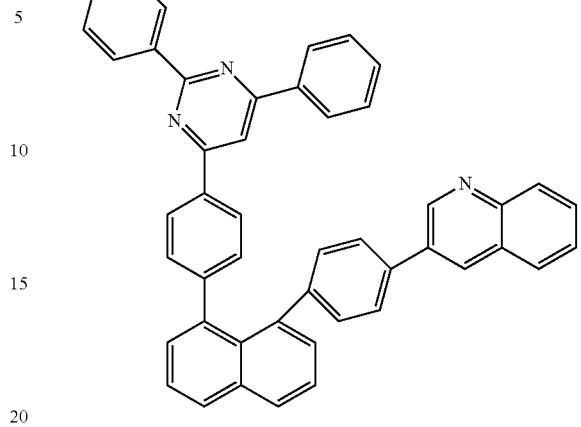
[formula 3-5-5]
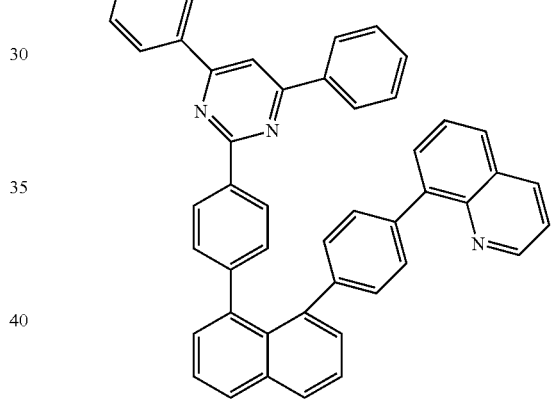
[formula 3-5-6]
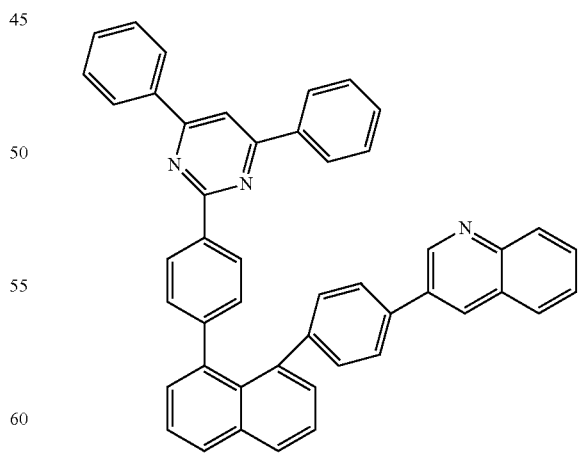
In one embodiment of the present specification, Ar1 is Chemical Formula 3, and the hetero-cyclic compound having a structure of Chemical Formula 1-6 is represented by any one of the following Formulae 3-6-1 to 3-6-6.

[formula 3-6-1]
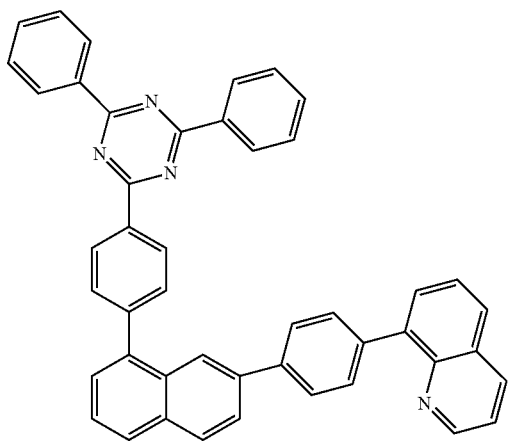
[formula 3-6-4]
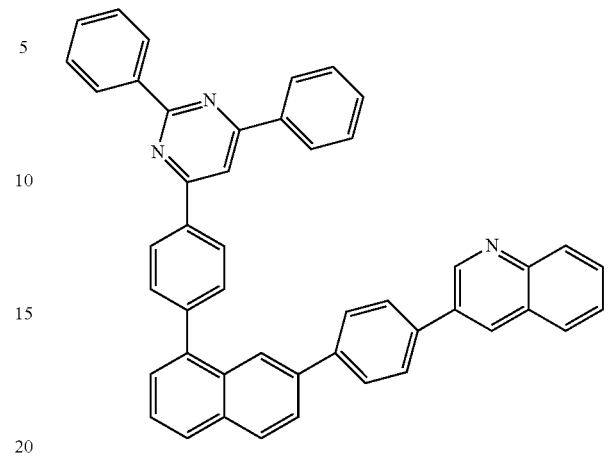
[formula 3-6-2]
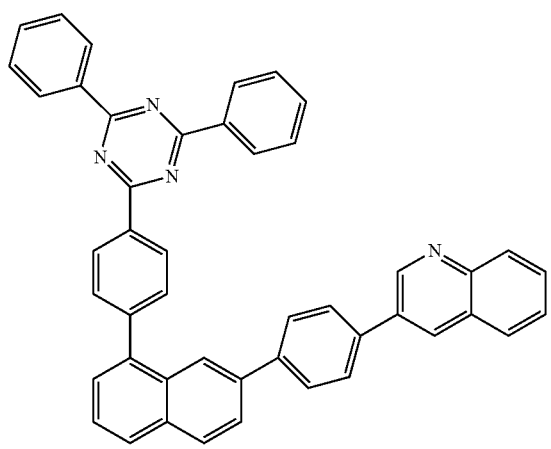
[formula 3-6-5]
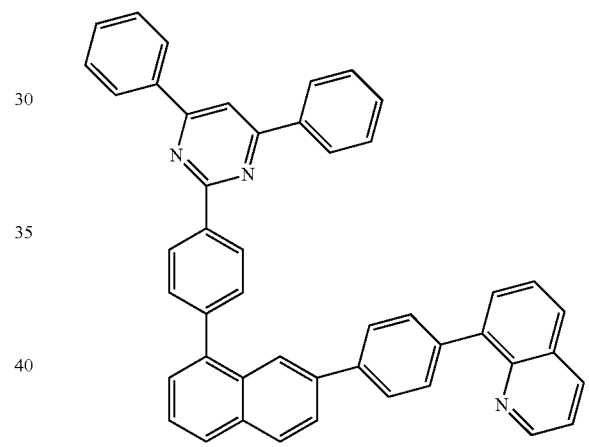
[formula 3-6-3]
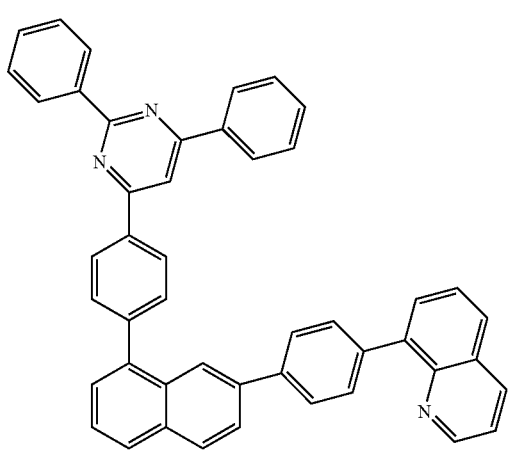
[formula 3-6-6]
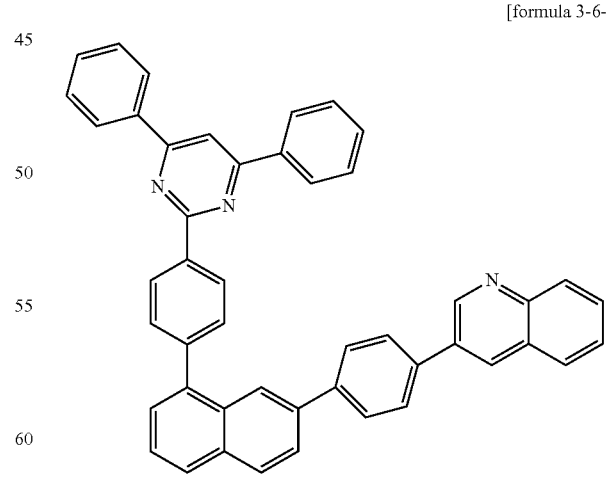
In one embodiment of the present specification, Ar1 is Chemical Formula 3, and the hetero-cyclic compound having a structure of Chemical Formula 1-7 is represented by any one of the following Formulae 3-7-1 to 3-7-6.

[formula 3-7-1]
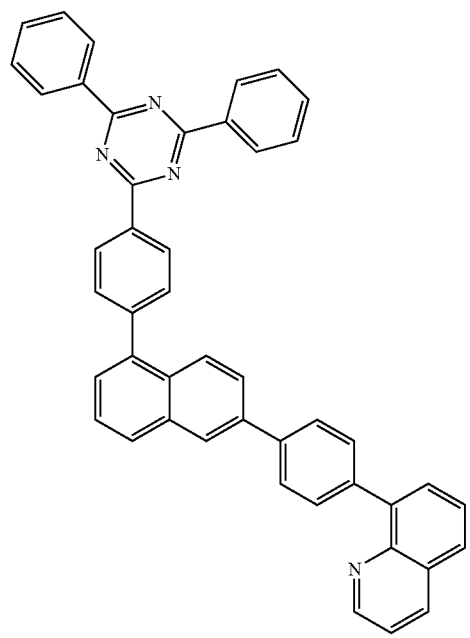
[formula 3-7-2]
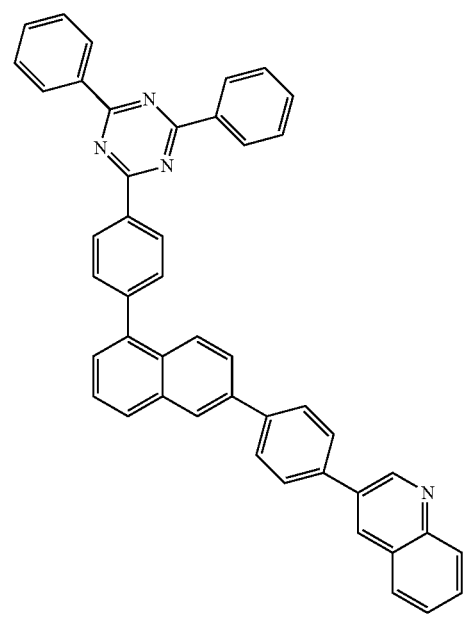
[formula 3-7-3]
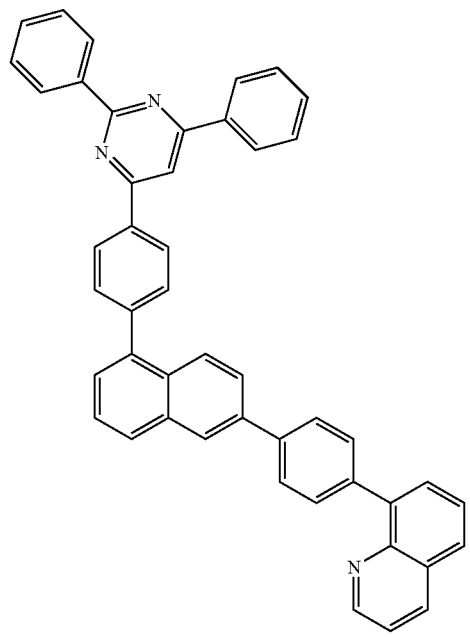
[formula 3-7-4]
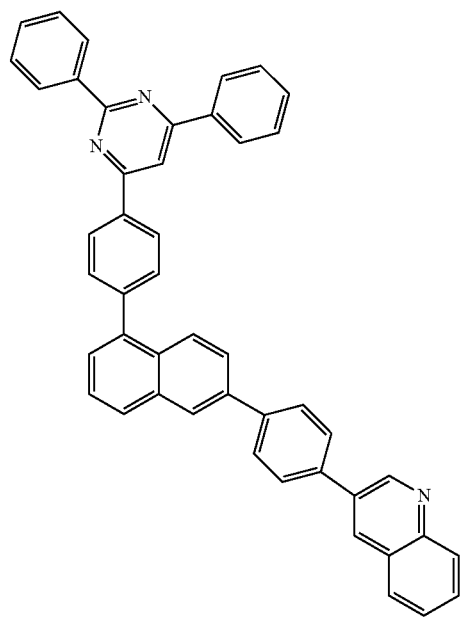

[formula 3-7-5]
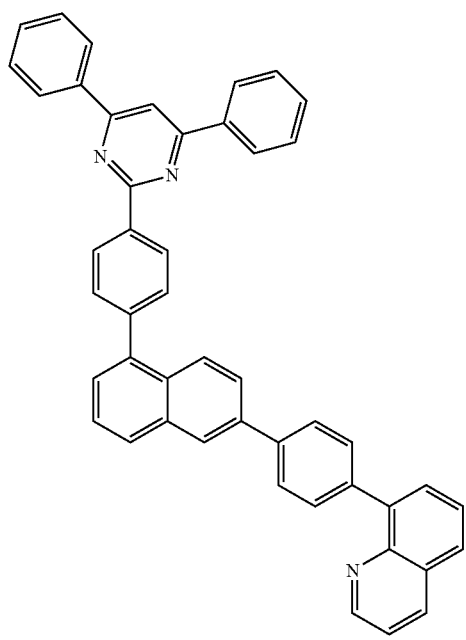
[formula 3-7-6]
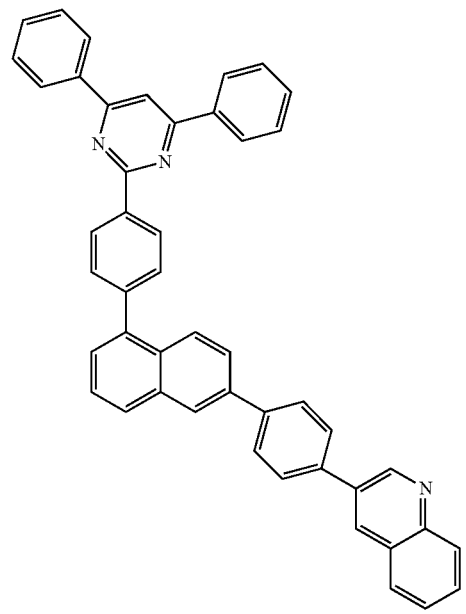
[formula 3-8-1]
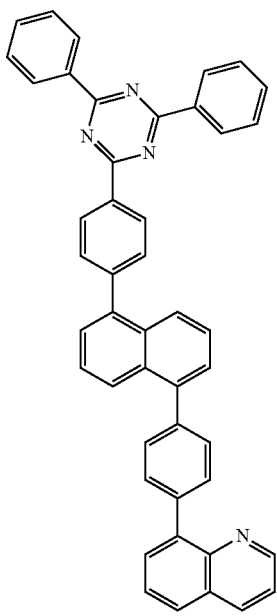
[formula 3-8-2]
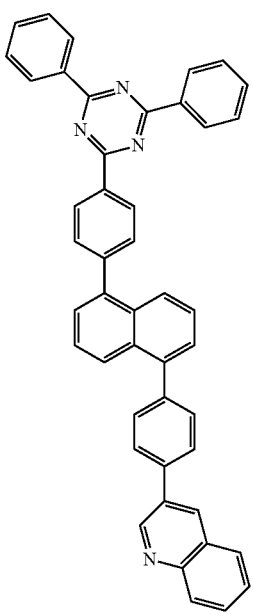
In one embodiment of the present specification, Ar1 is Chemical Formula 3, and the hetero-cyclic compound having a structure of Chemical Formula 1-8 is represented by any one of the following Formulae 3-8-1 to 3-8-6.

[formula 3-8-3]
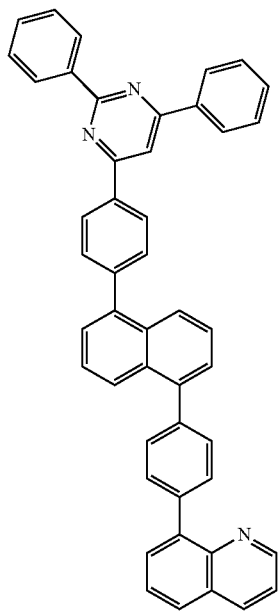
[formula 3-8-5]
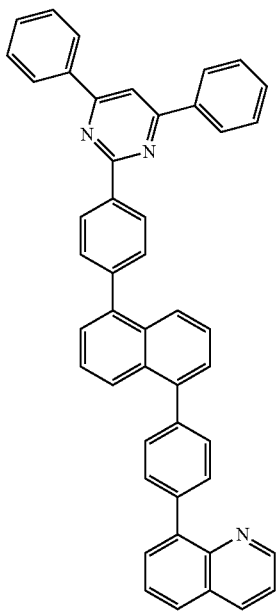
[formula 3-8-4]
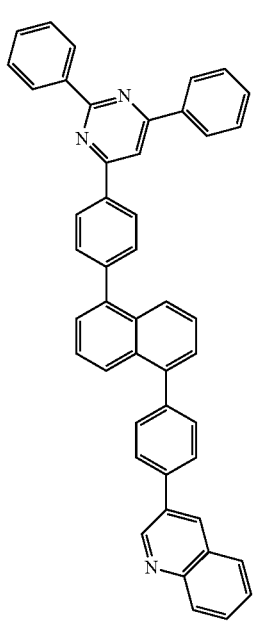
[formula 3-8-6]
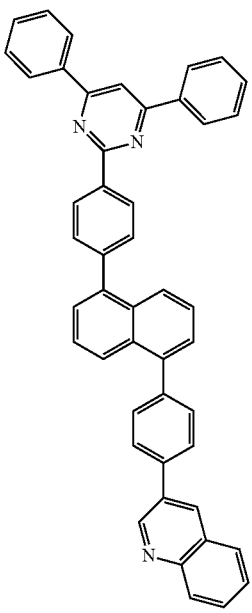
In one embodiment of the present specification, Ar1 is Chemical Formula 3, and the hetero-cyclic compound having a structure of Chemical Formula 1-9 is represented by any one of the following Formulae 3-9-1 to 3-9-6.

[formula 3-9-1]
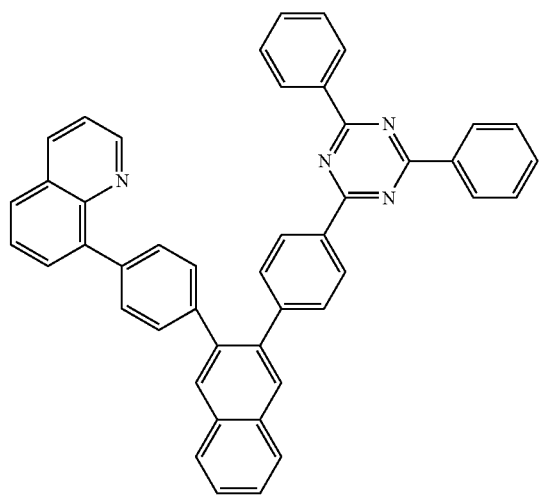
[formula 3-9-2]
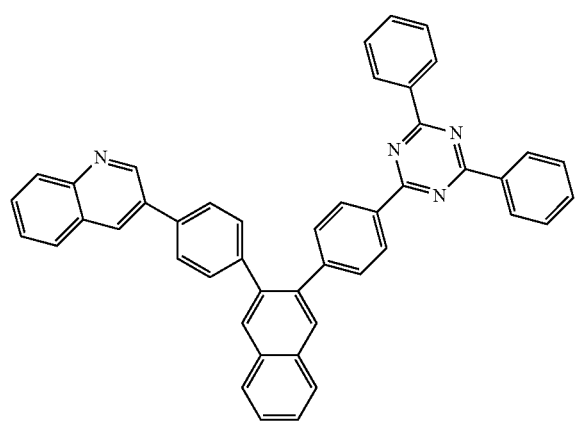
[formula 3-9-3]
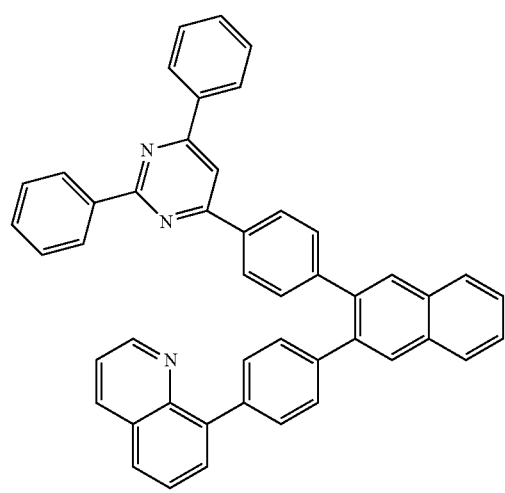
[formula 3-9-4]
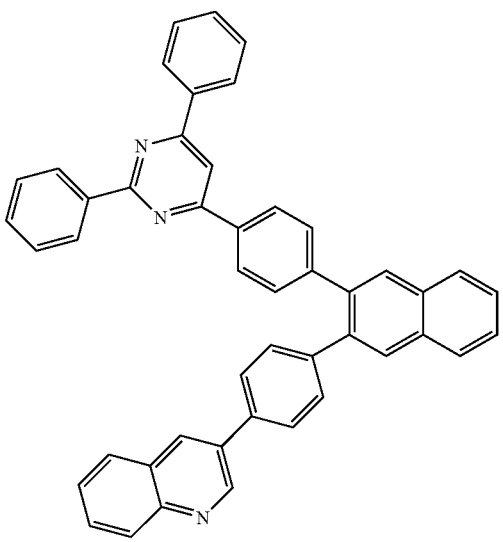
[formula 3-9-5]
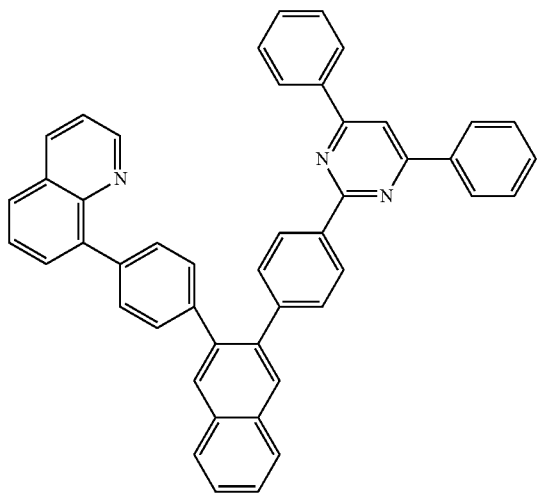
[formula 3-9-6]
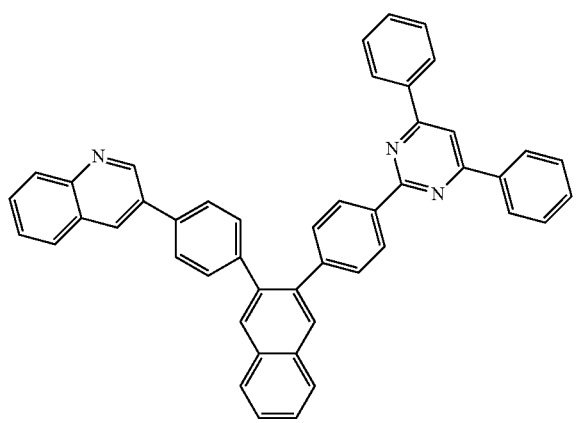
In one embodiment of the present specification, Ar1 is Chemical Formula 3, and the hetero-cyclic compound having a structure of Chemical Formula 1-10 is represented by any one of the following Formulae 3-10-1 to 3-10-6.

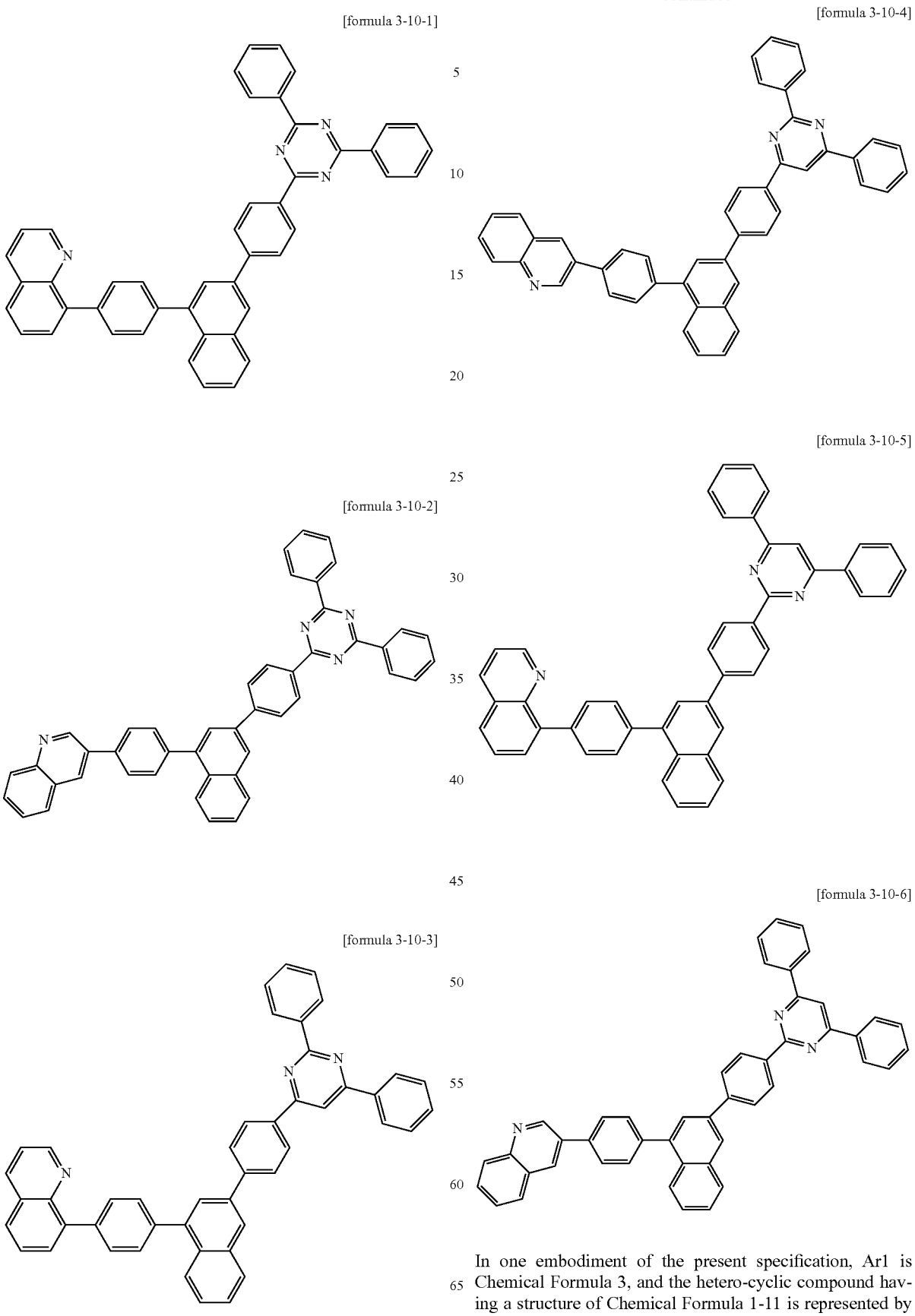
In one embodiment of the present specification, Ar1 is Chemical Formula 3, and the hetero-cyclic compound having a structure of Chemical Formula 1-11 is represented by any one of the following Formulae 3-11-1 to 3-11-6.

[formula 3-11-1]
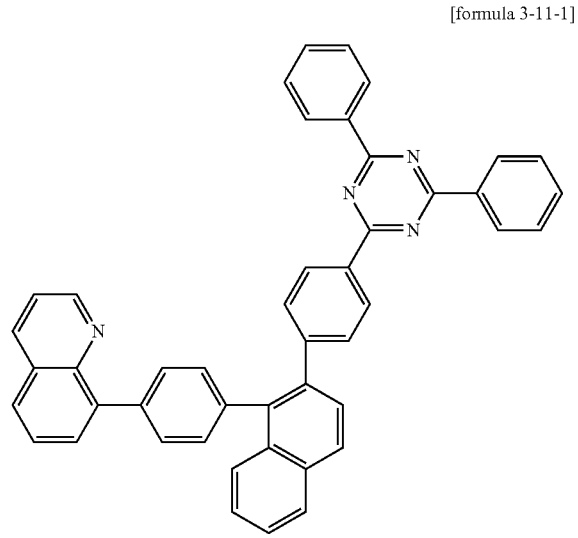
[formula 3-11-2]
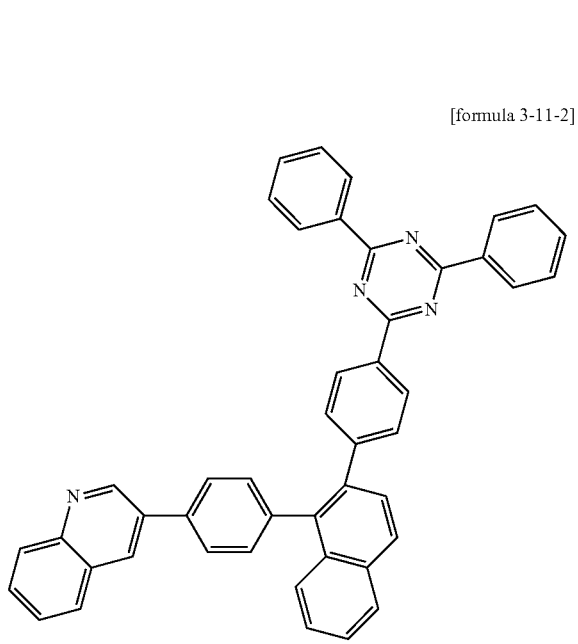
[formula 3-11-3]
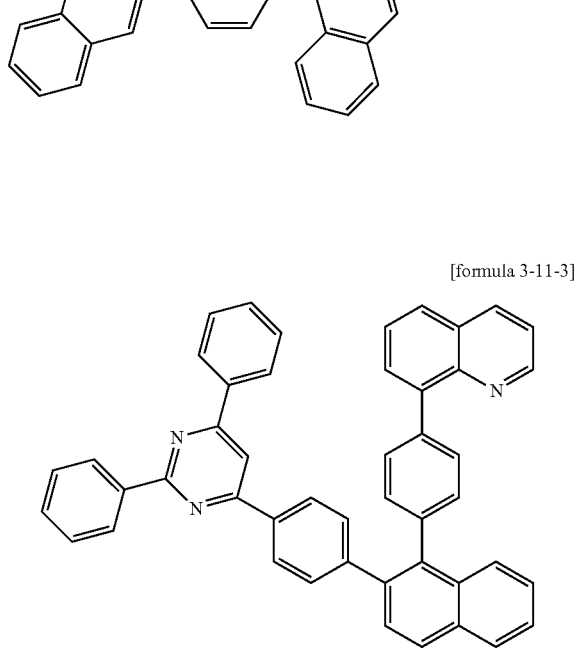
[formula 3-11-4]
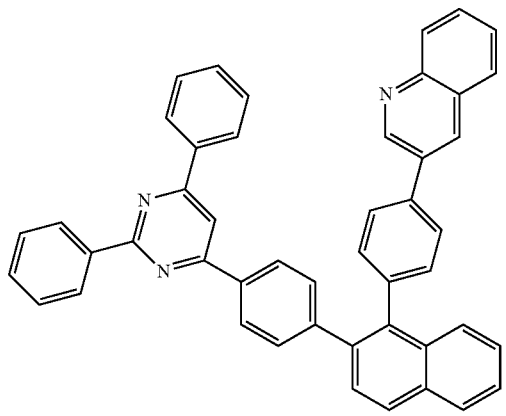
[formula 3-11-5]
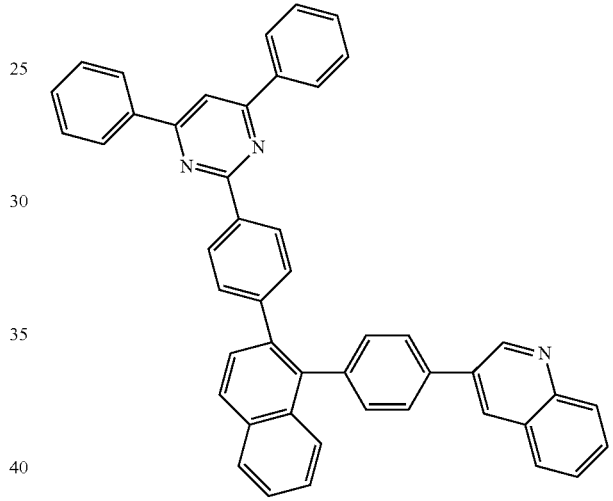
[formula 3-11-6]
In one embodiment of the present specification, Ar1 is Chemical Formula 3, and the hetero-cyclic compound having a structure of Chemical Formula 1-12 is represented by any one of the following Formulae 3-12-1 to 3-12-6.

[formula 3-12-1]
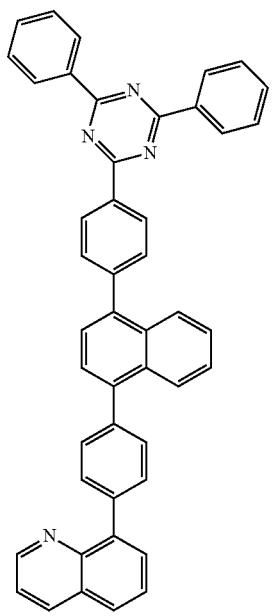
[formula 3-12-2]
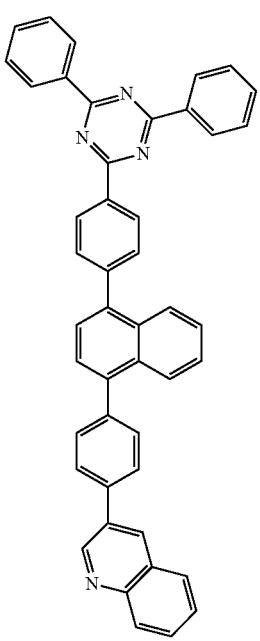
[formula 3-12-3]
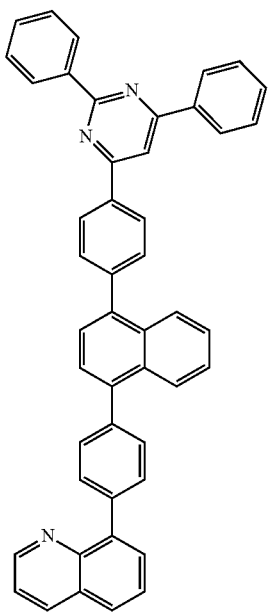
[formula 3-12-4]
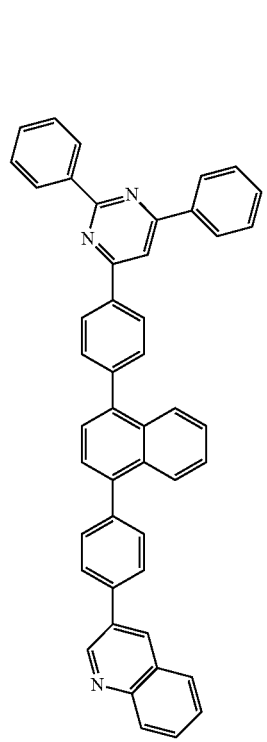

[formula 3-12-5]
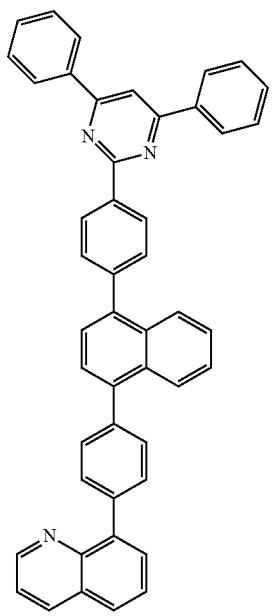
[formula 3-13-1]
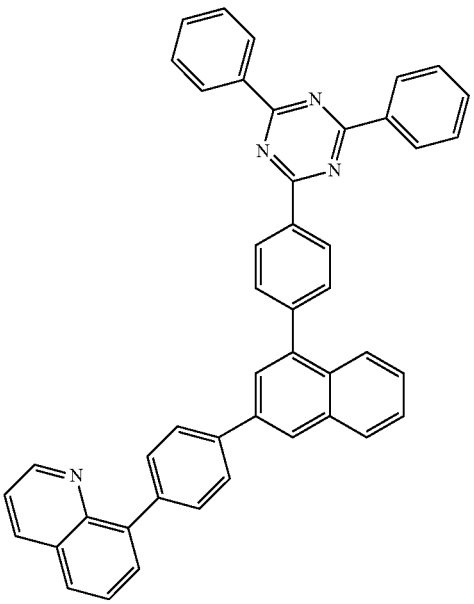
[formula 3-12-6]
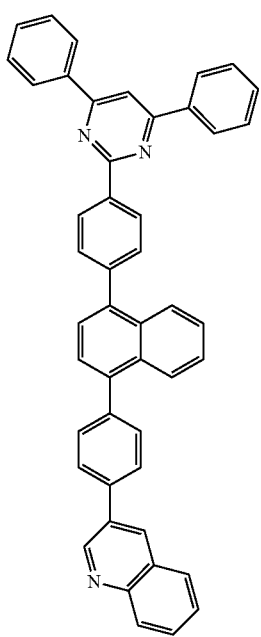
[formula 3-13-2]
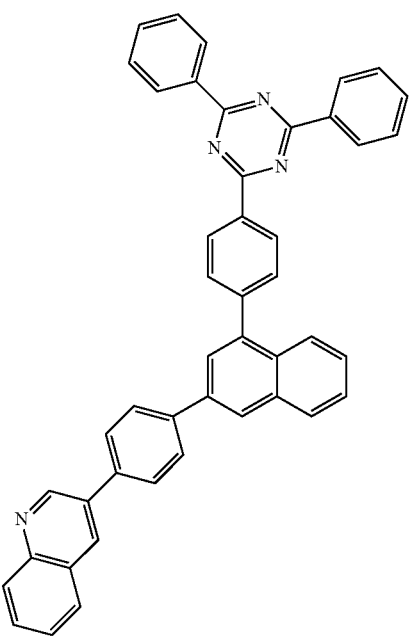
In one embodiment of the present specification, Ar1 is Chemical Formula 3, and the hetero-cyclic compound having a structure of Chemical Formula 1-13 is represented by any one of the following Formulae 3-13-1 to 3-13-6.

-continued
[formula 3-13-3]
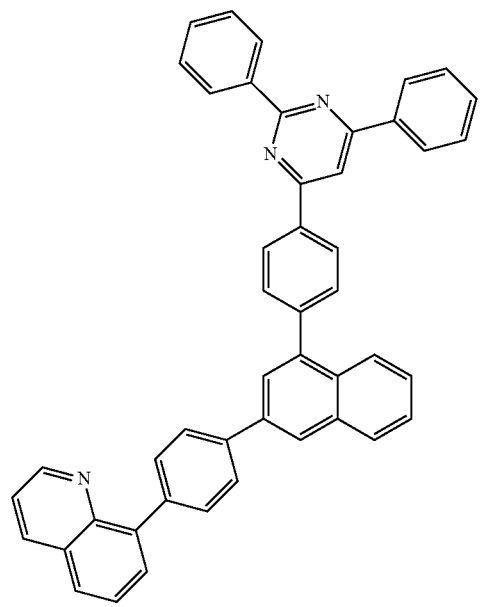
[formula 3-13-4]
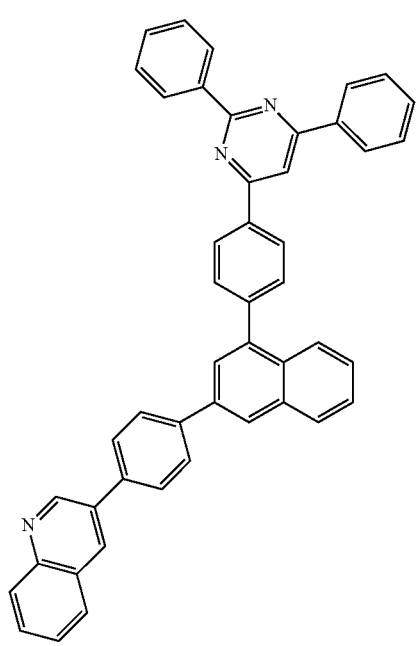
-continued
[formula 3-13-5]
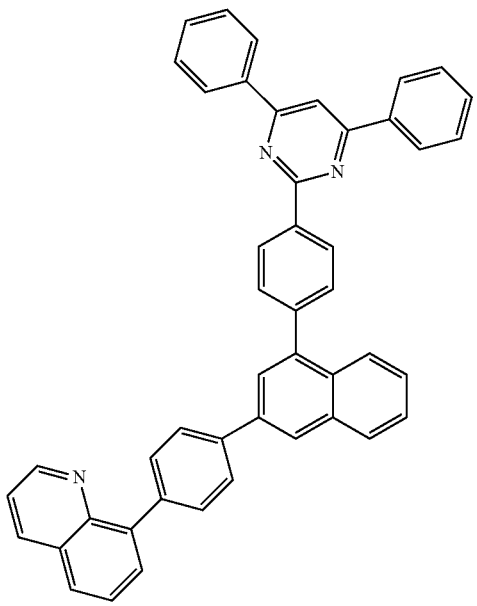
[formula 3-13-6]
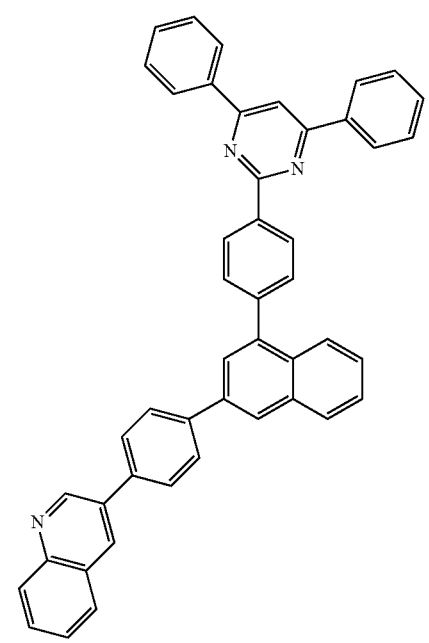
In one embodiment of the present specification, Ar1 is Chemical Formula 3, and the hetero-cyclic compound having a structure of Chemical Formula 1-14 is represented by any one of the following Formulae 3-14-1 to 3-14-6.

[formula 3-14-1]
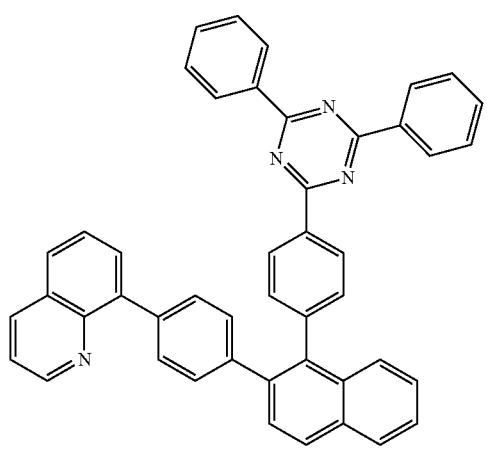
[formula 3-14-4]
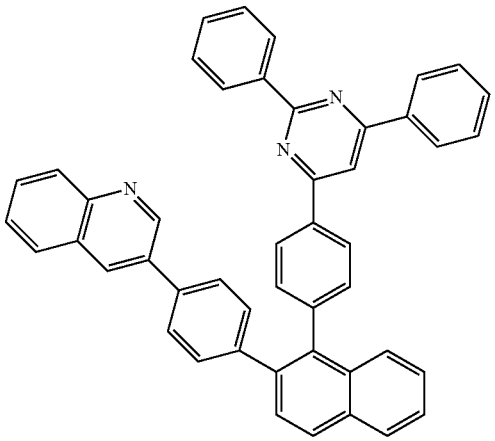
[formula 3-14-2]
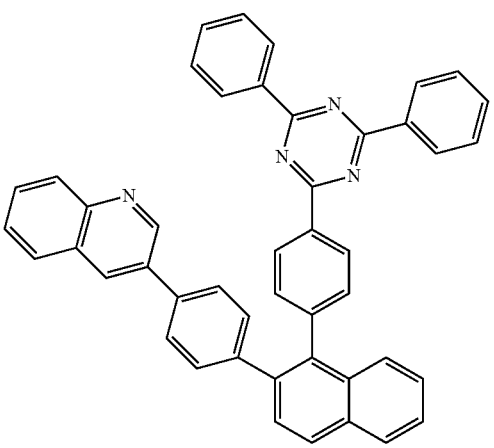
[formula 3-14-5]
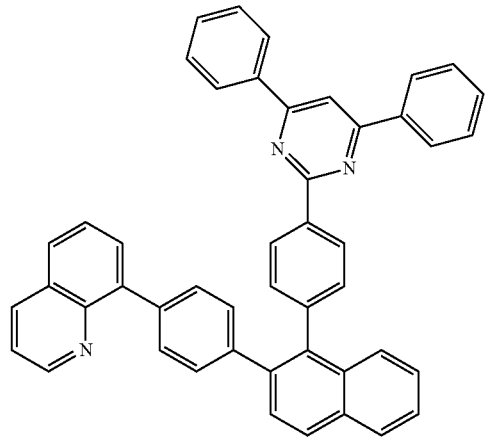
[formula 3-14-3]
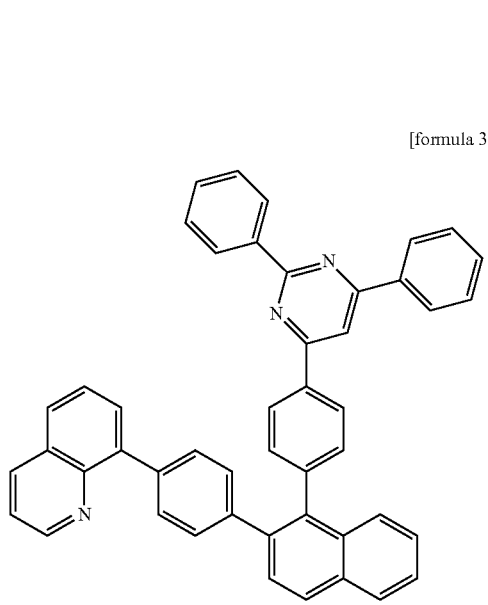
[formula 3-14-6]
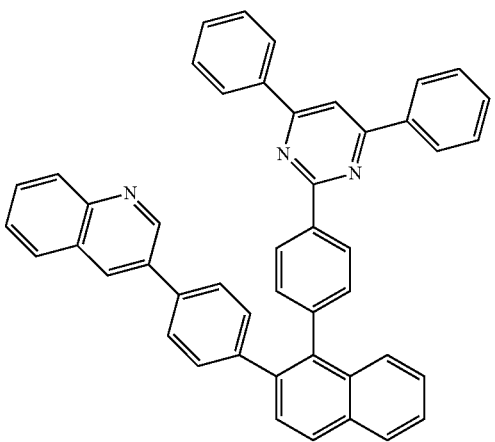
In one embodiment of the present specification, Ar1 is Chemical Formula 4, the hetero-cyclic compound having structures of Chemical Formulae 1-1 to 1-14 is represented by any one of the following Formula 4-1-1 to Formula 4-14-1.

[formula 4-1-1]
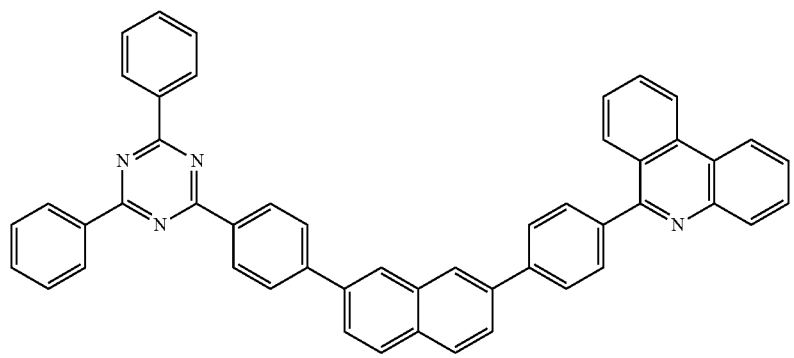
[formula 4-2-1]
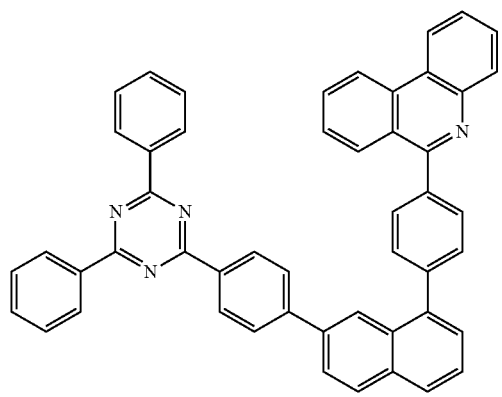
[formula 4-3-1]
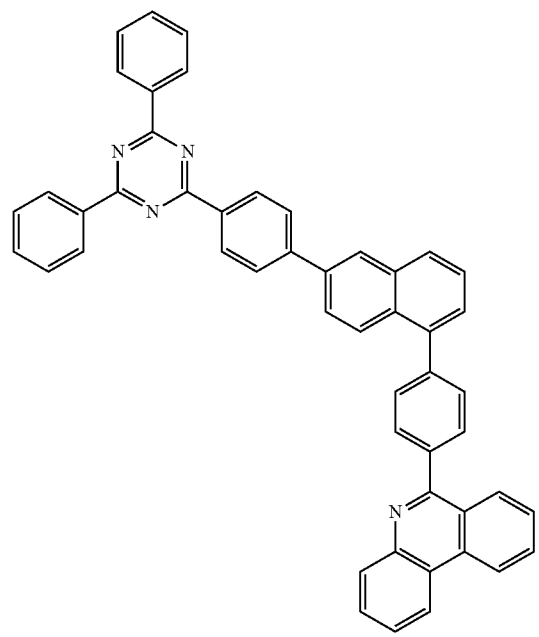
[formula 4-4-1]
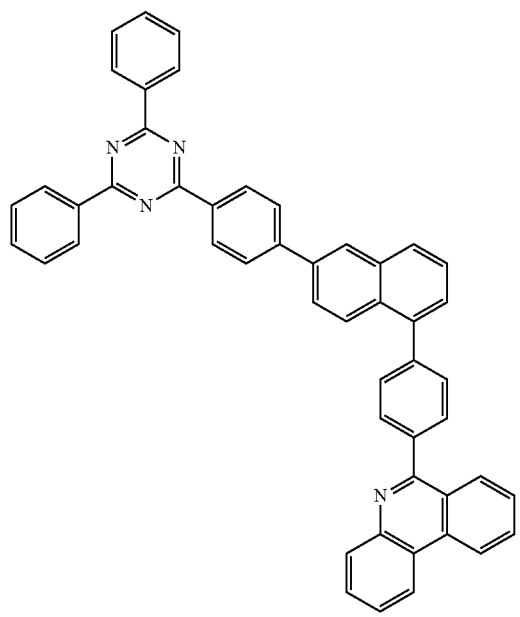
[formula 4-5-1]
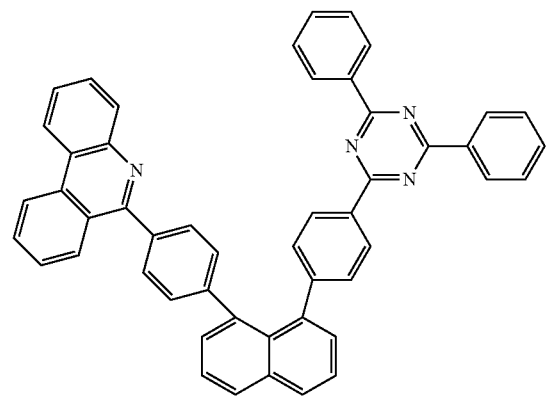

-continued
[formula 4-6-1]
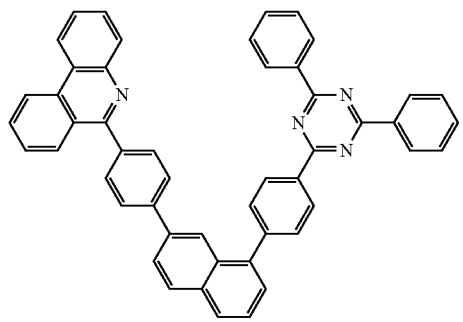
[formula 4-7-1]
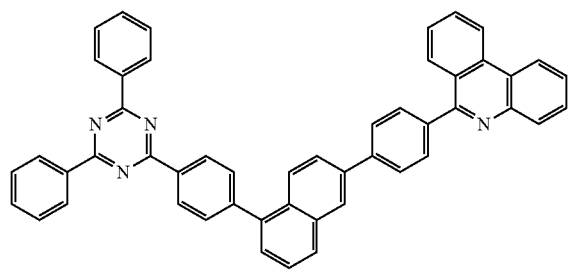
[formula 4-8-1]
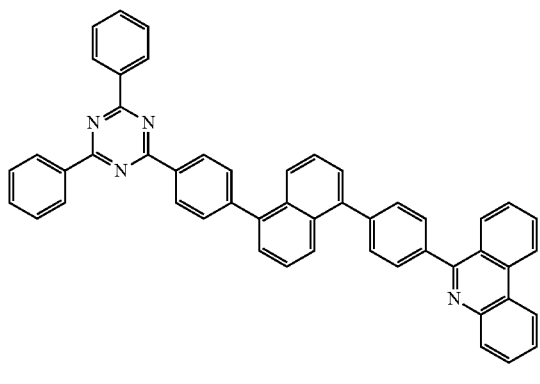
[formula 4-9-1]
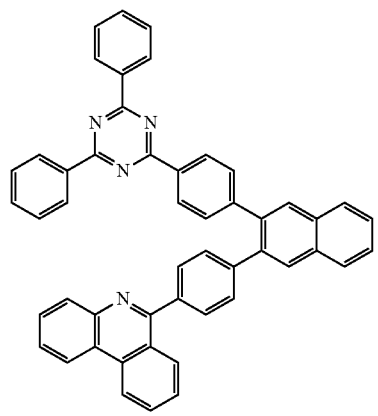
[formula 4-10-1]
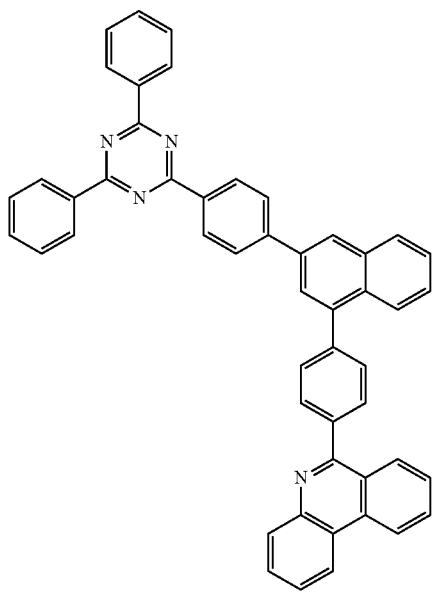
[formula 4-11-1]
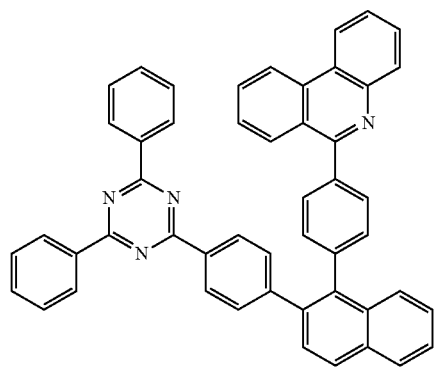

[formula 4-12-1]
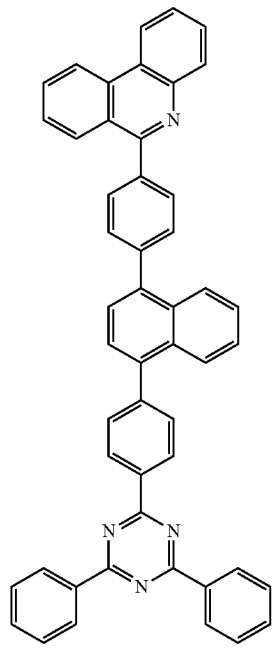
[formula 4-13-1]
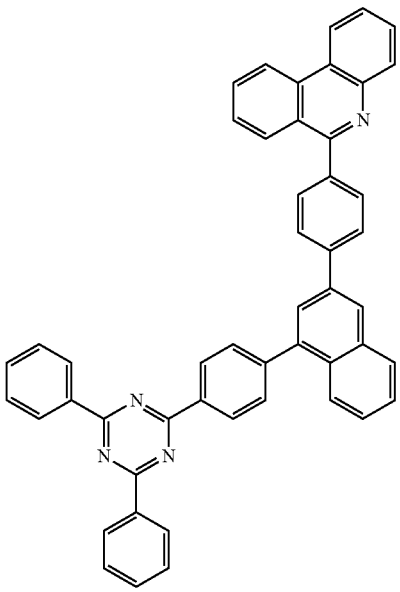
[formula 4-14-1]
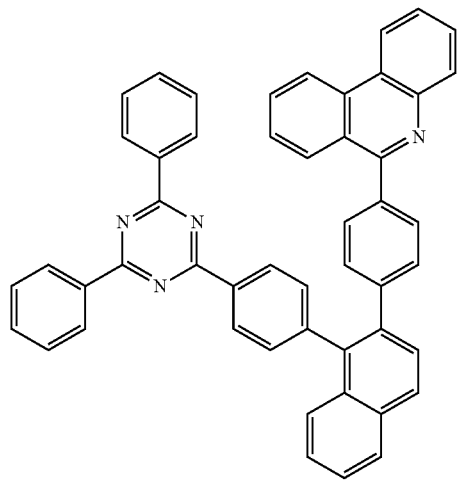
In one embodiment of the present specification, Ar1 is Chemical Formula 2, and the hetero-cyclic compound having a structure of Chemical Formula 1-1 is represented by any one of the following Formulae 5-1-1 to 5-1-5.
[formula 5-1-1]
[formula 5-1-2]
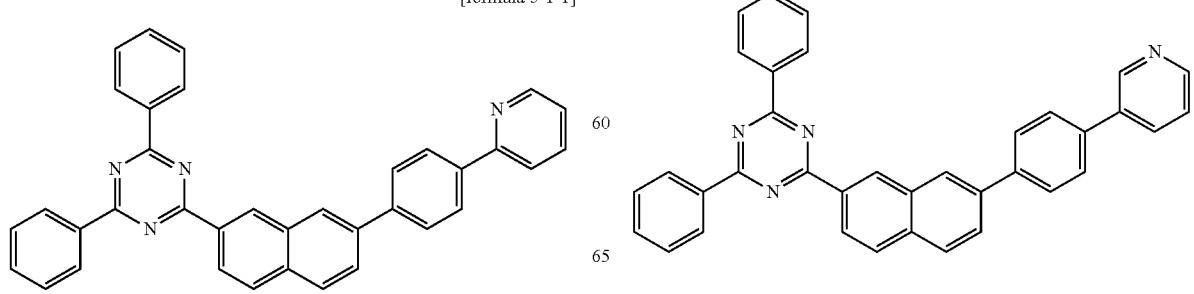
-continued

[formula 5-1-3]

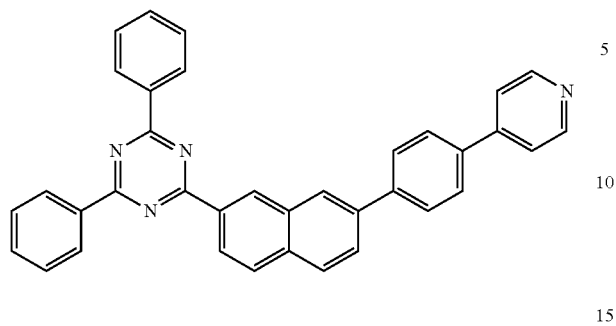

[formula 5-1-4]

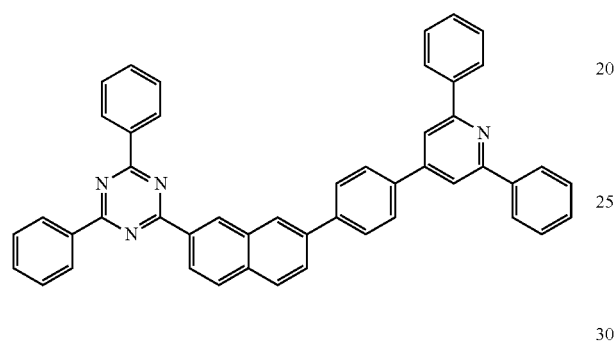

[formula 5-1-5]

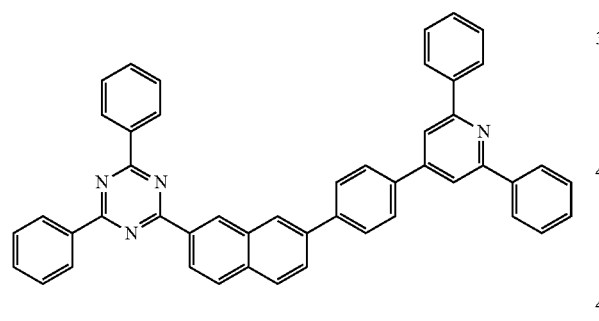

In one embodiment of the present specification, Ar1 is Chemical Formula 2, and the hetero-cyclic compound having a structure of Chemical Formula 1-2 is represented by any one of the following Formulae 5-2-1 to 5-2-5.

[formula 5-2-1]

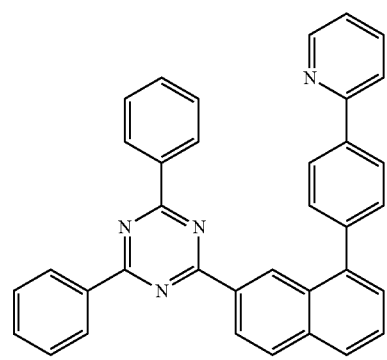

[formula 5-2-2]

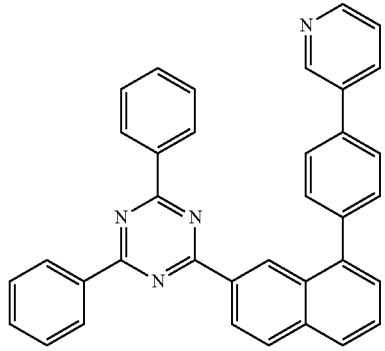

[formula 5-2-3]

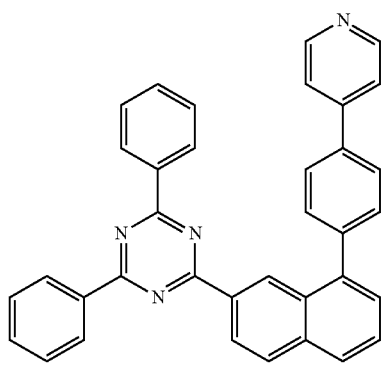

[formula 5-2-4]

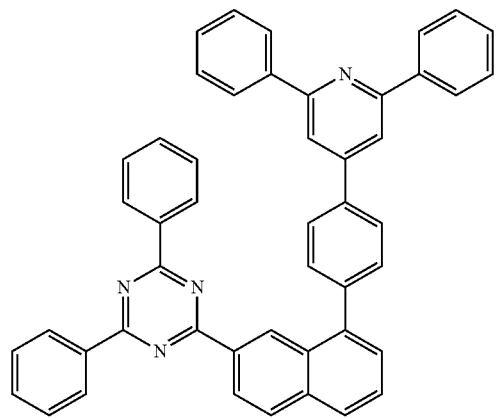

[formula 5-2-5]

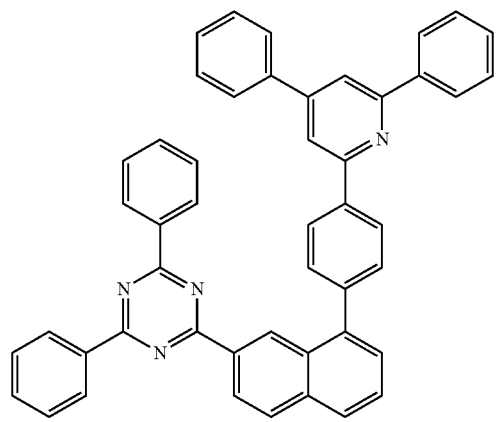

In one embodiment of the present specification, Ar1 is Chemical Formula 2, and the hetero-cyclic compound having a structure of Chemical Formula 1-3 is represented by any one of the following Formulae 5-3-1 to 5-3-5.
[formula 5-3-1]
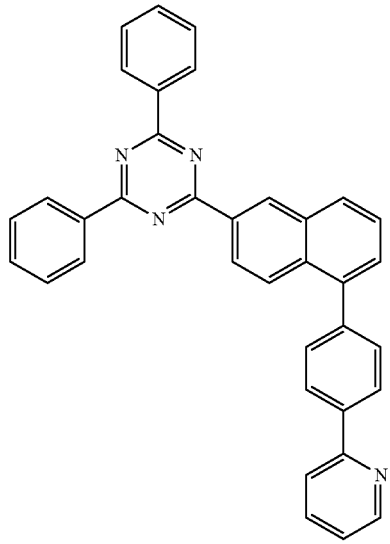
[formula 5-3-2]
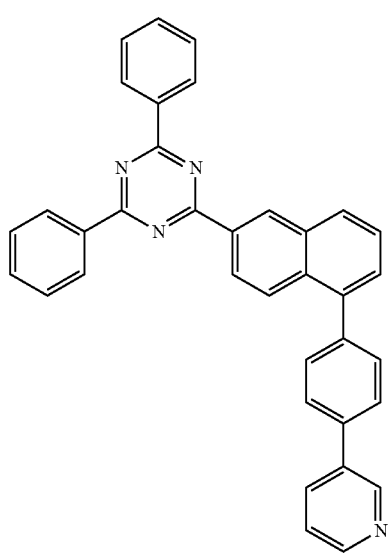
[formula 5-3-3]
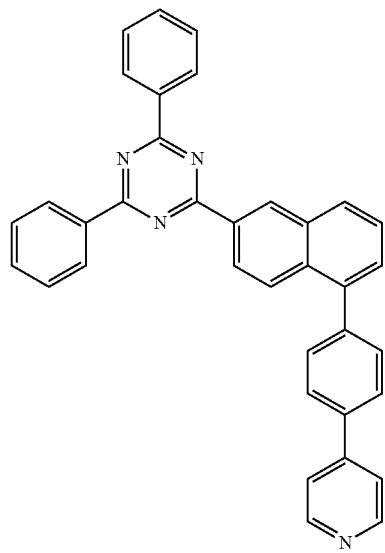
[formula 5-3-4]
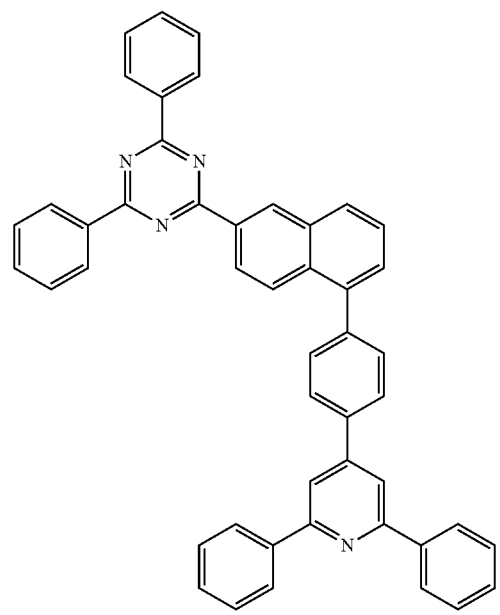

[formula 5-3-5]

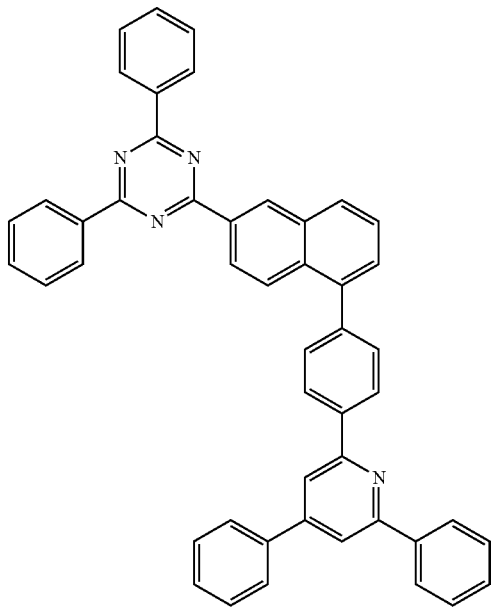

In one embodiment of the present specification, Ar1 is Chemical Formula 2, and the hetero-cyclic compound having a structure of Chemical Formula 1-4 is represented by any one of the following Formulae 5-4-1 to 5-4-5.

[formula 5-4-1]

[formula 5-4-2]

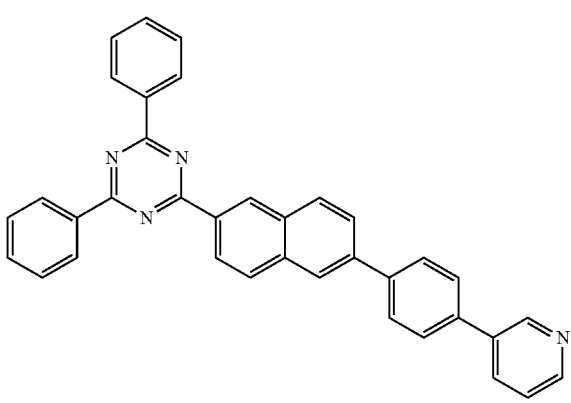

[formula 5-4-3]

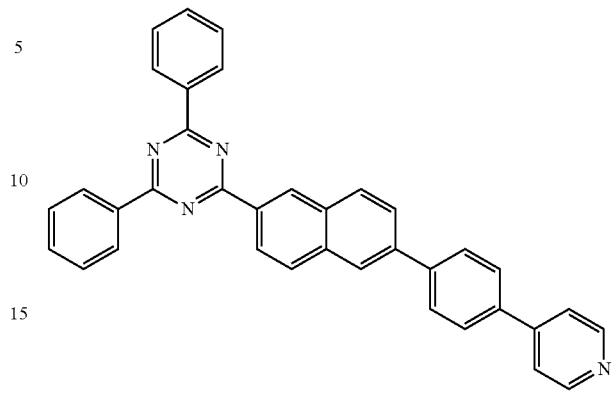

[formula 5-4-4]

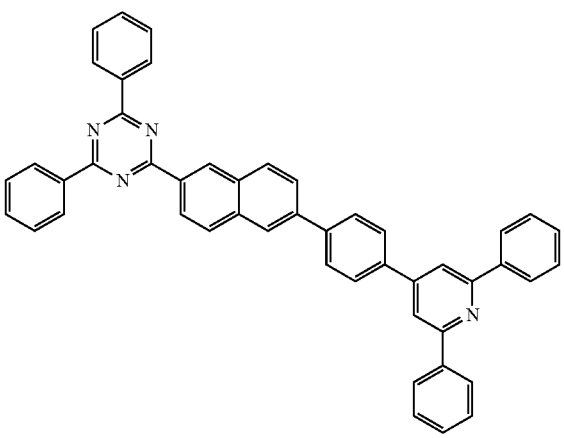

[formula 5-4-5]

In one embodiment of the present specification, Ar1 is Chemical Formula 2, and the hetero-cyclic compound having a structure of Chemical Formula 1-5 is represented by any one of the following Formulae 5-5-1 to 5-5-5.

[formula 5-5-1]
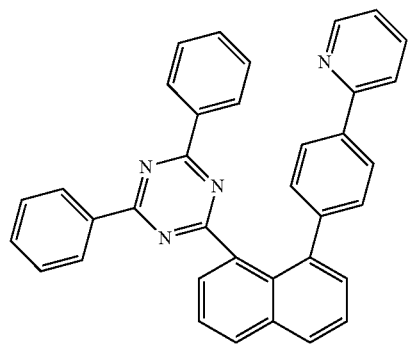
[formula 5-5-2]
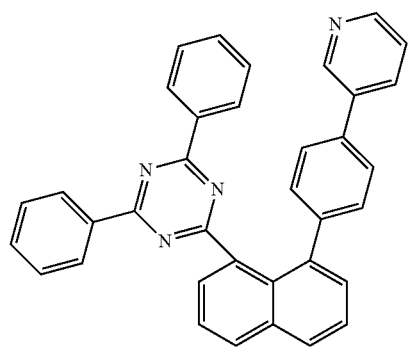
[formula 5-5-3]
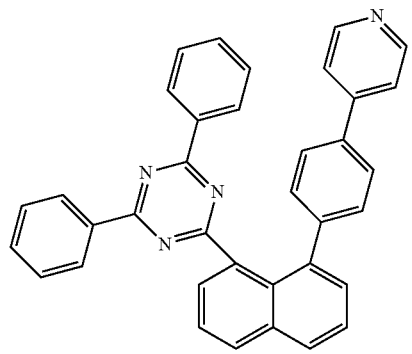
[formula 5-5-4]
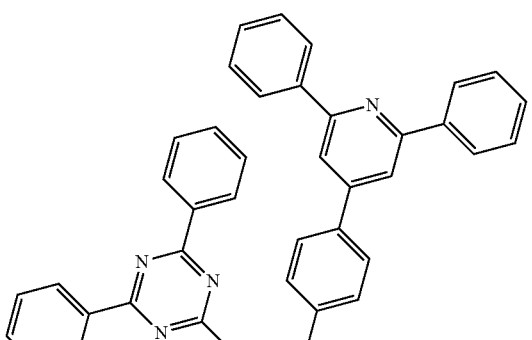
[formula 5-5-5]
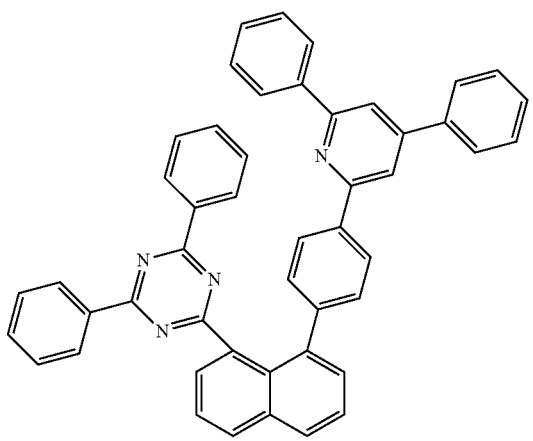
In one embodiment of the present specification, Ar1 is Chemical Formula 2, and the hetero-cyclic compound having a structure of Chemical Formula 1-6 is represented by any one of the following Formulae 5-6-1 to 5-6-5.
[formula 5-6-1]
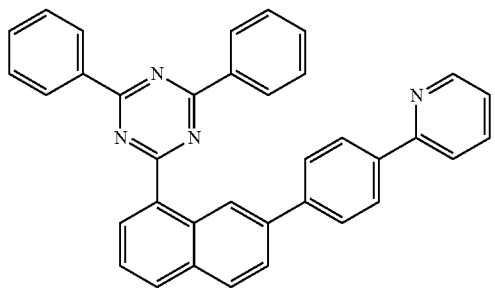
[formula 5-6-2]
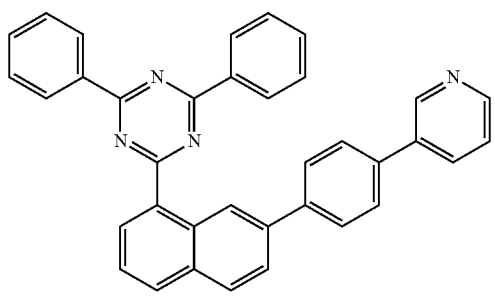
[formula 5-6-3]
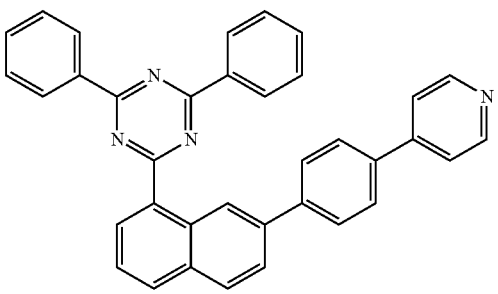

[formula 5-6-4]
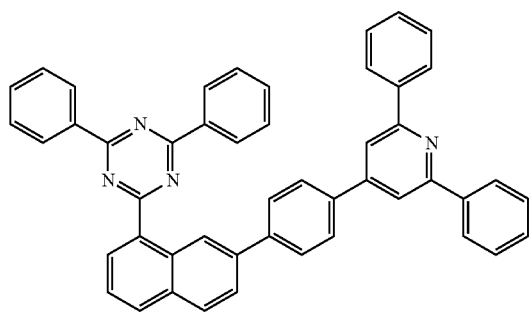
[formula 5-6-5]
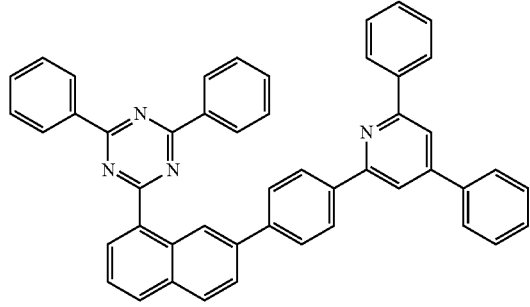
In one embodiment of the present specification, Ar1 is Chemical Formula 2, and the hetero-cyclic compound having a structure of Chemical Formula 1-7 is represented by any one of the following Formulae 5-7-1 to 5-7-5.
[formula 5-7-1]
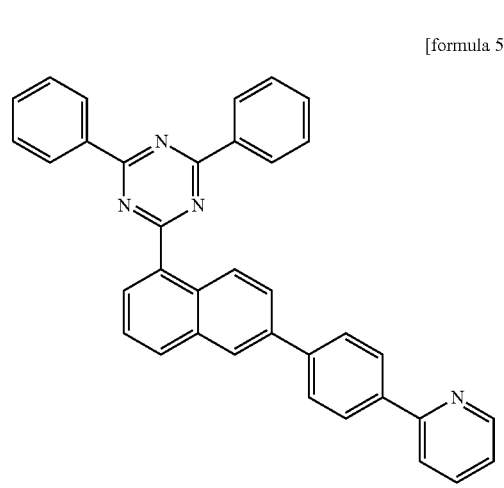
[formula 5-7-2]
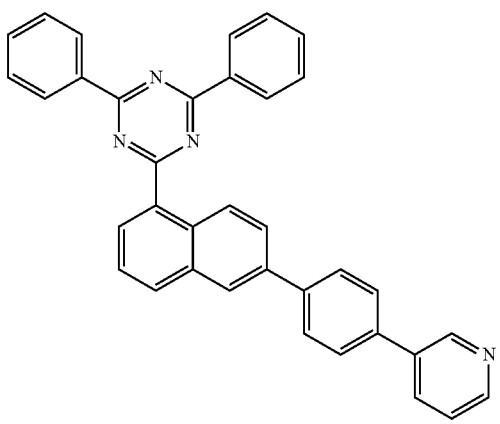
[formula 5-7-3]
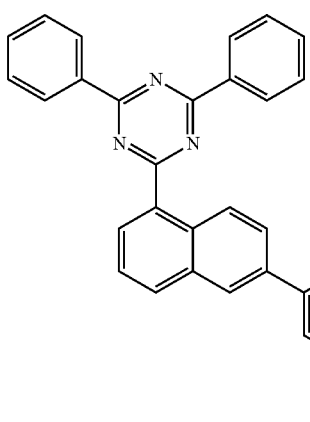
[formula 5-7-4]
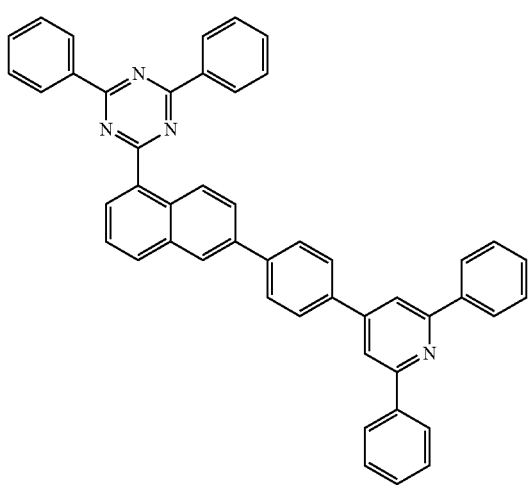

[formula 5-7-5]
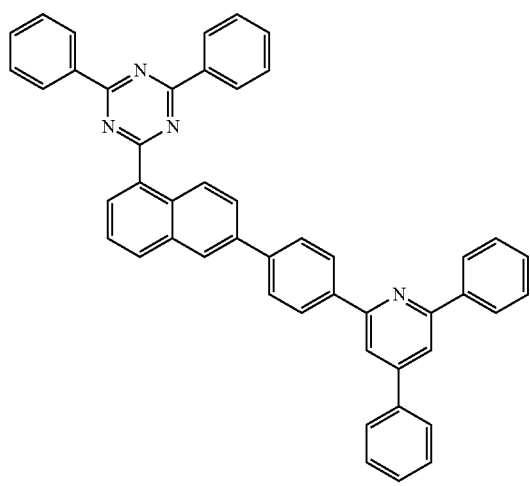
[formula 5-8-2]
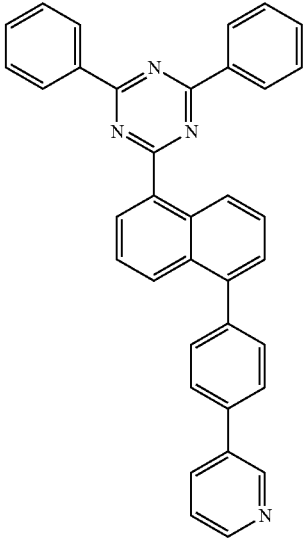
In one embodiment of the present specification, Ar1 is Chemical Formula 2, and the hetero-cyclic compound having a structure of Chemical Formula 1-8 is represented by any one of the following Formulae 5-8-1 to 5-8-5.
[formula 5-8-1]
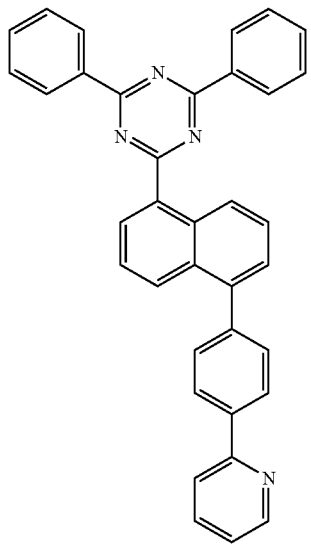
[formula 5-8-3]
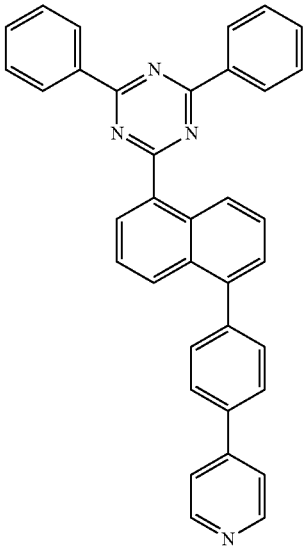

-continued
[formula 5-8-4]
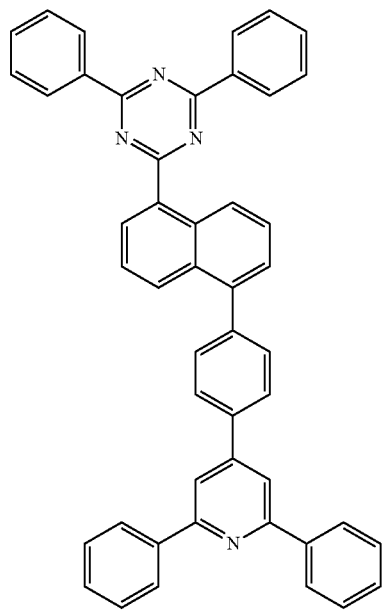
[formula 5-8-5]
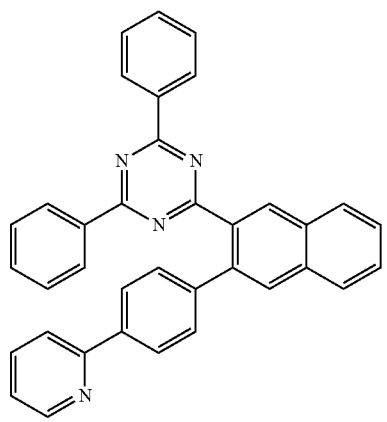
In one embodiment of the present specification, Ar1 is Chemical Formula 2, and the hetero-cyclic compound having a structure of Chemical Formula 1-9 is represented by any one of the following Formulae 5-9-1 to 5-9-5.
[formula 5-9-1]
-continued
[formula 5-9-2]
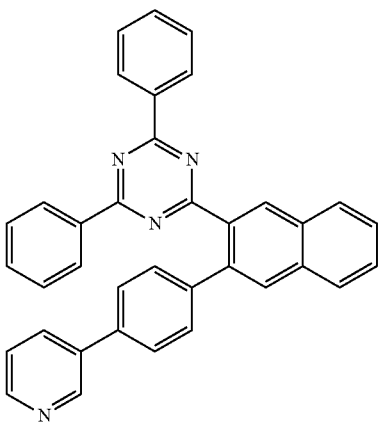
[formula 5-9-3]
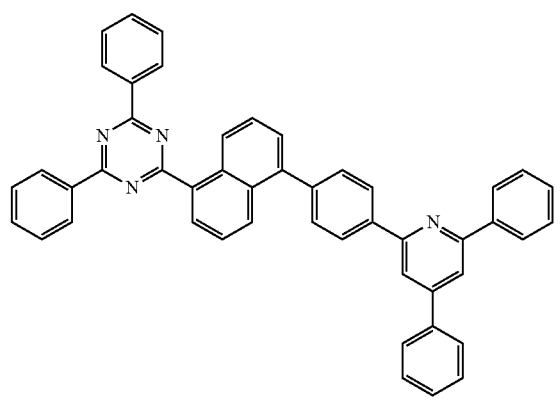
[formula 5-9-4]
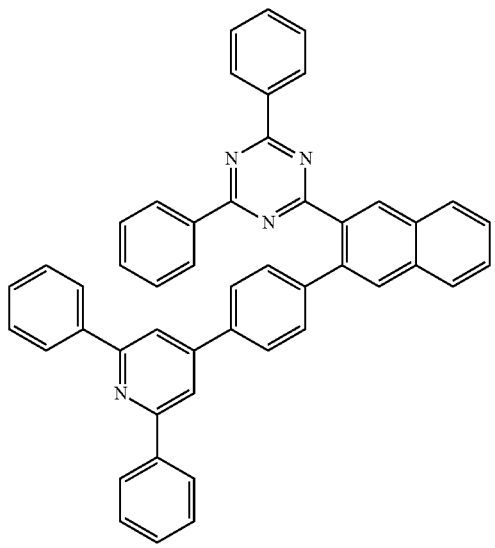

-continued
[formula 5-9-5]
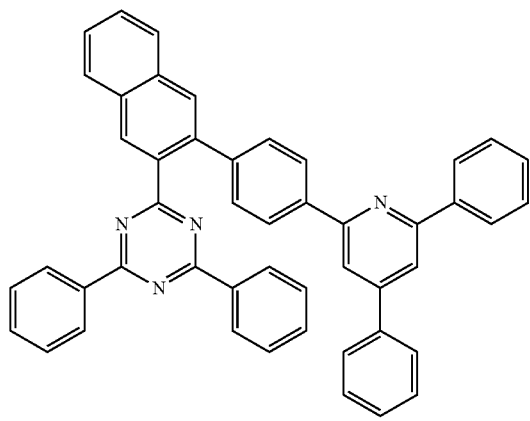
In one embodiment of the present specification, Ar1 is Chemical Formula 2, and the hetero-cyclic compound having a structure of Chemical Formula 1-10 is represented by any one of the following Formulae 5-10-1 to 5-10-5.
[formula 5-10-1]
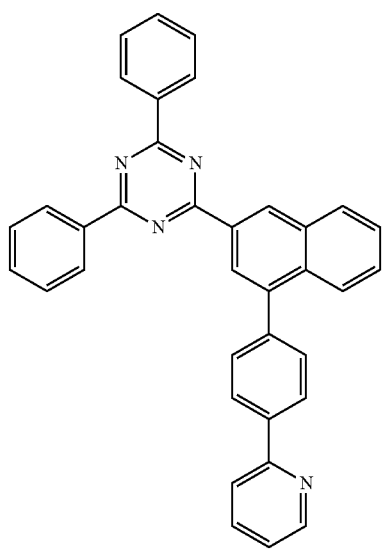
[formula 5-10-2]
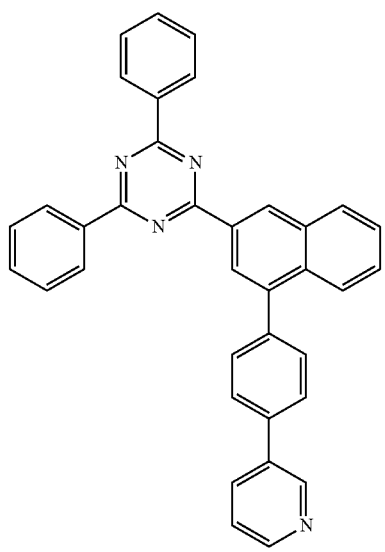
-continued
[formula 5-10-3]
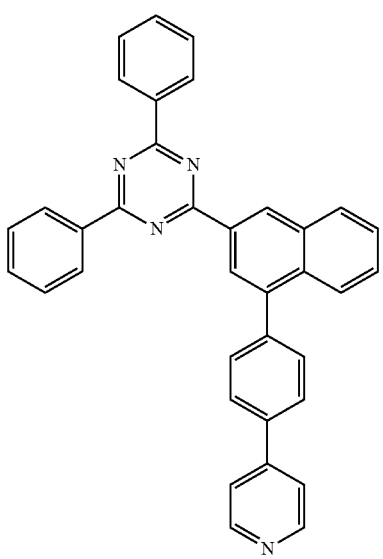
[formula 5-10-4]
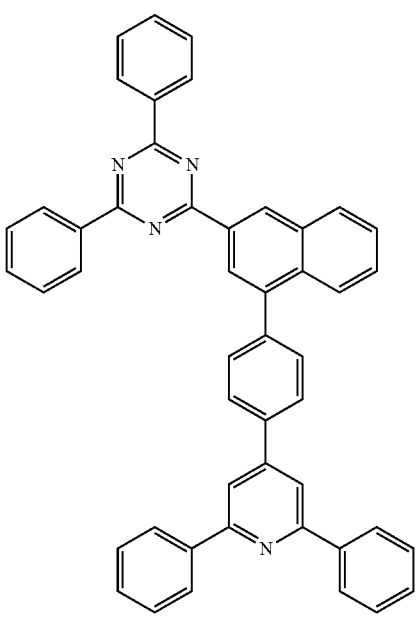

[formula 5-10-5]

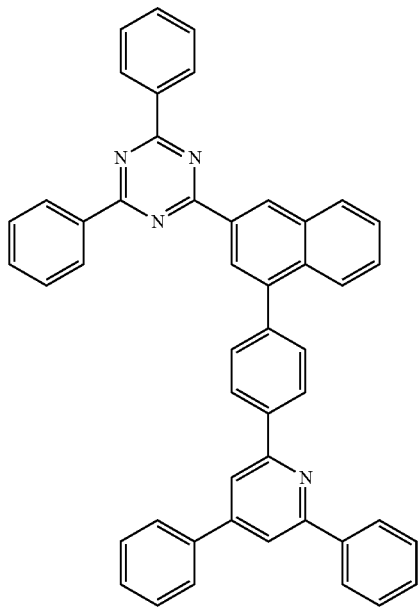

In one embodiment of the present specification, Ar1 is Chemical Formula 2, and the hetero-cyclic compound having a structure of Chemical Formula 1-11 is represented by any one of the following Formulae 5-11-1 to 5-11-5.

[formula 5-11-1]

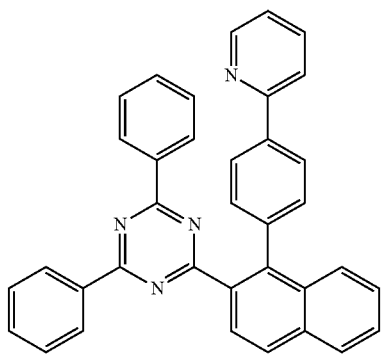

[formula 5-11-2]

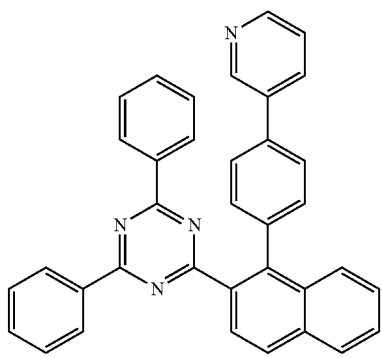

[formula 5-11-3]

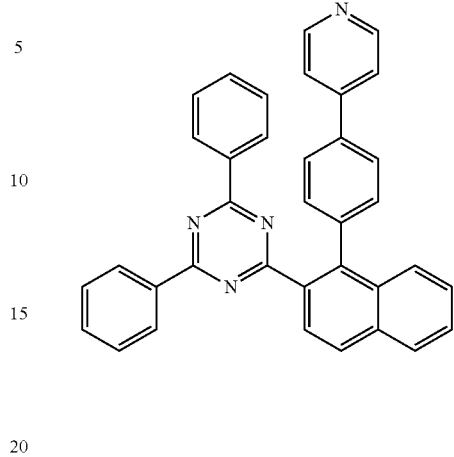

[formula 5-11-4]

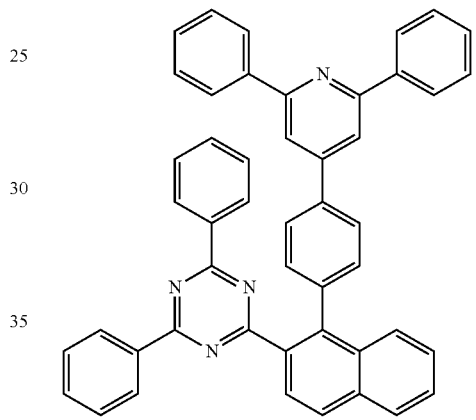

[formula 5-11-5]

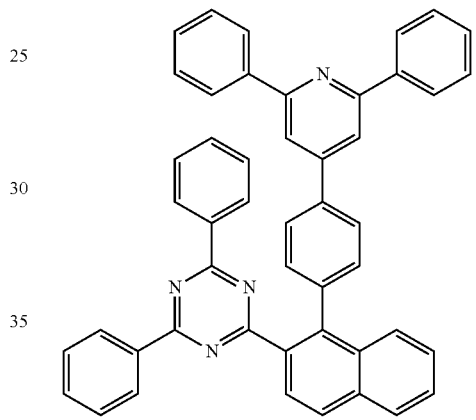

In one embodiment of the present specification, Ar1 is Chemical Formula 2, and the hetero-cyclic compound having a structure of Chemical Formula 1-12 is represented by any one of the following Formulae 5-12-1 to 5-12-5.

[formula 5-12-1]
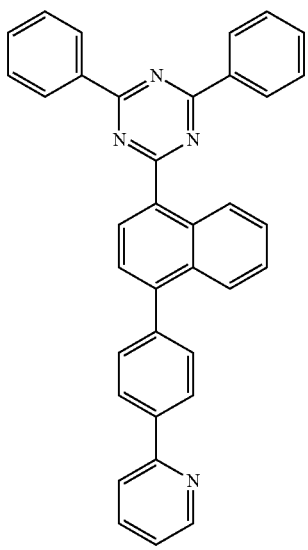
[formula 5-12-2]
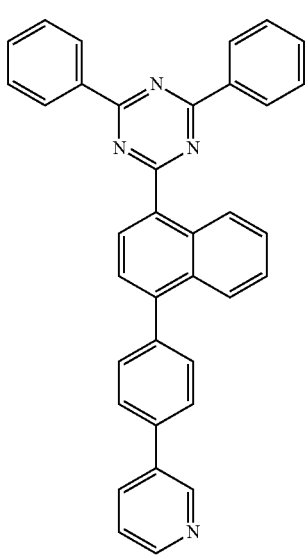
[formula 5-12-3]
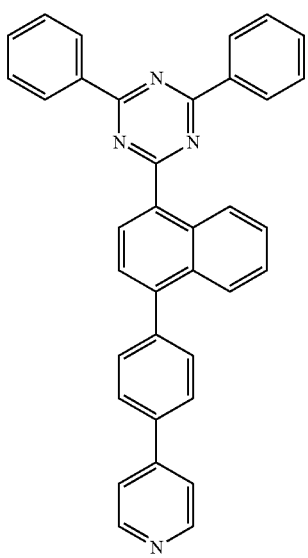
[formula 5-12-4]
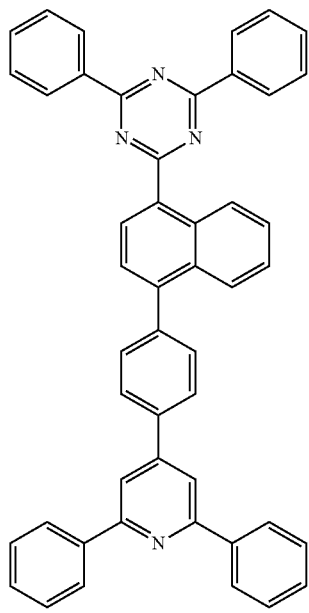
[formula 5-12-5]
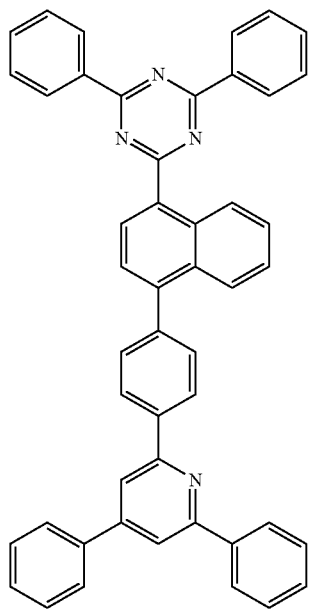
In one embodiment of the present specification, Ar1 is Chemical Formula 2, and the hetero-cyclic compound having a structure of Chemical Formula 1-13 is represented by any one of the following Formulae 5-13-1 to 5-13-5.

[formula 5-13-1]
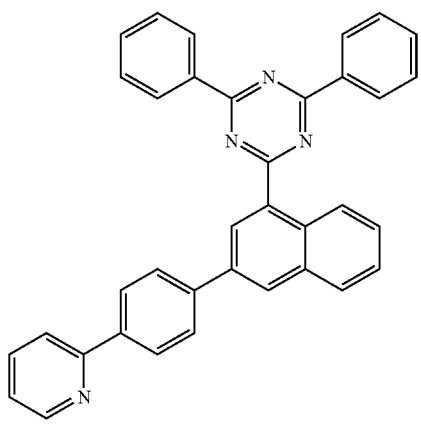
[formula 5-13-2]
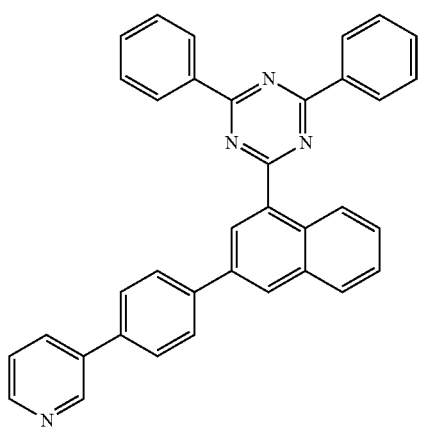
[formula 5-13-3]
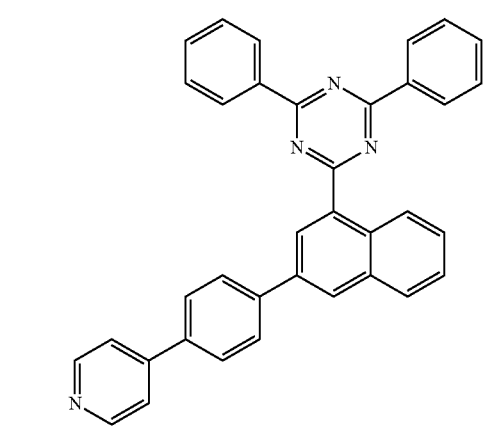
[formula 5-13-4]
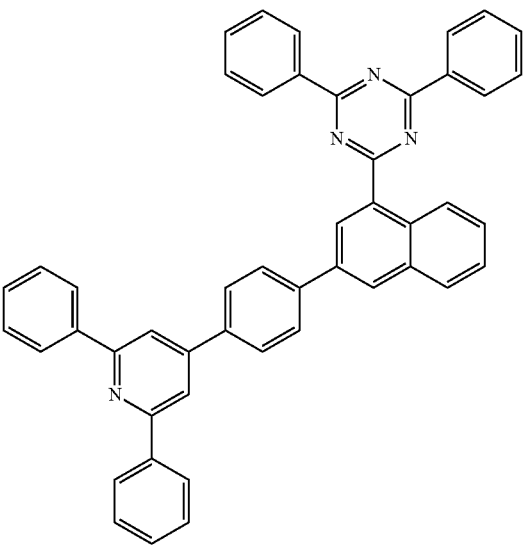
[formula 5-13-5]
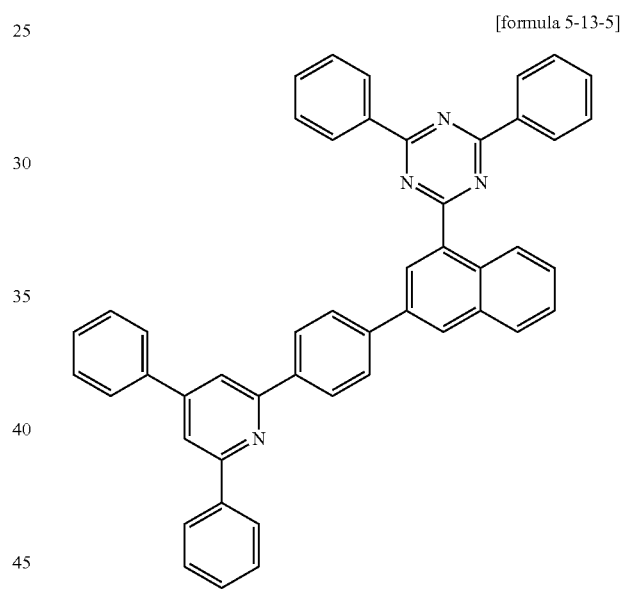
In one embodiment of the present specification, Ar1 is Chemical Formula 2, and the hetero-cyclic compound having a structure of Chemical Formula 1-14 is represented by any one of the following Formulae 5-14-1 to 5-14-5.
[formula 5-14-1]
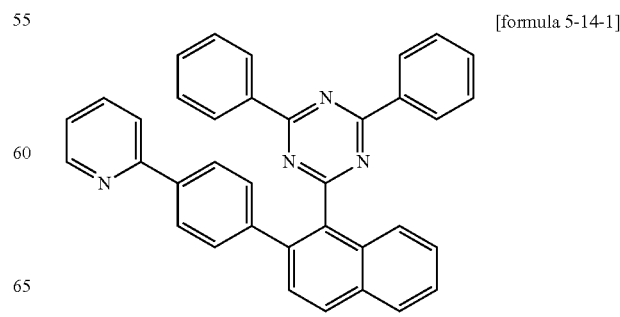

[formula 5-14-2]
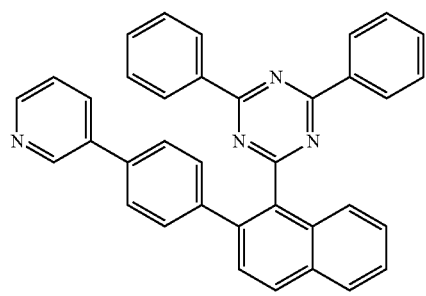
[formula 6-1-1]
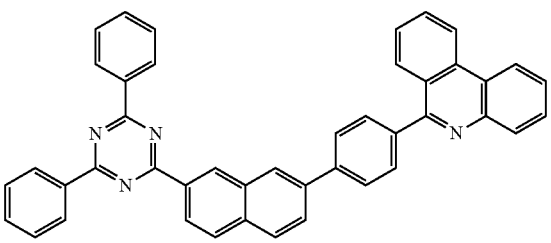
[formula 5-14-3]
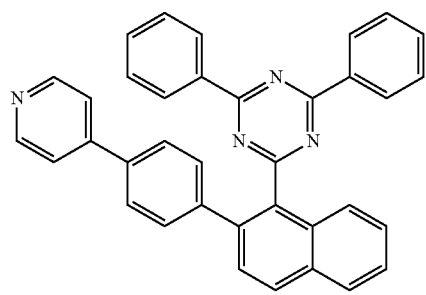
[formula 6-2-1]
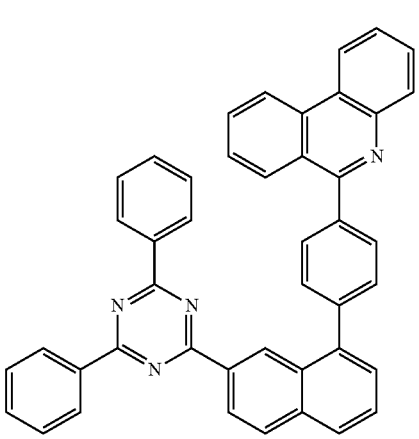
[formula 5-14-4]
[formula 5-14-5]
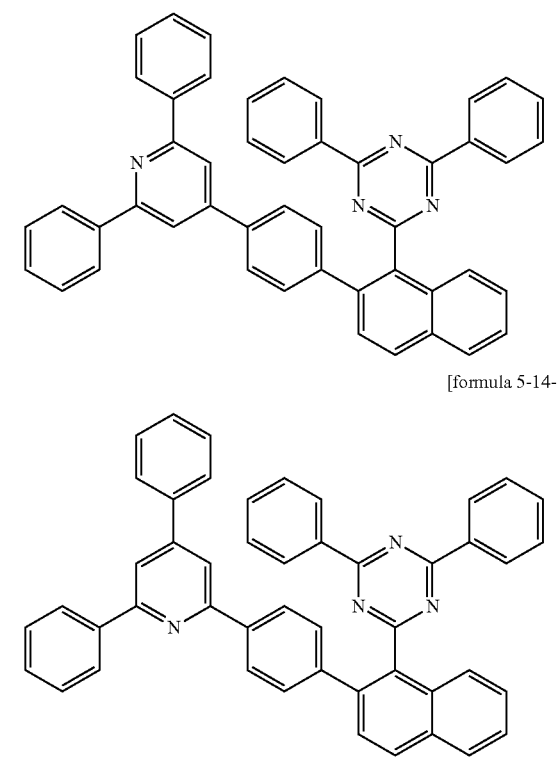
[formula 6-3-1]
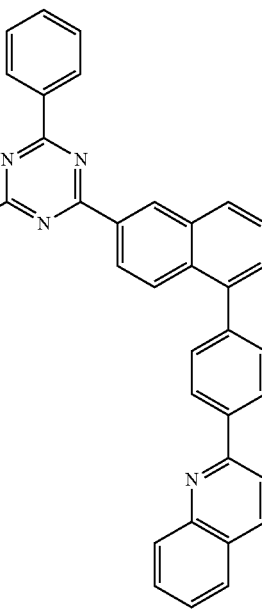
In one embodiment of the present specification, Ar1 is Chemical Formula 4, and the hetero-cyclic compound having structures of Chemical Formulae 1-1 to 1-14 is represented by any one of the following Formula 6-1-1 to Formula 6-14-1.

[formula 6-4-1]
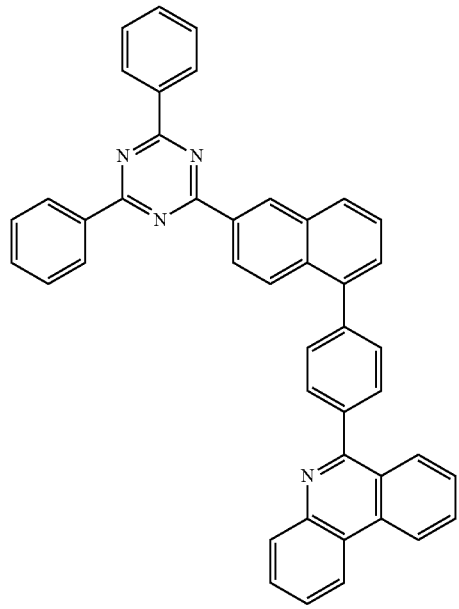
[formula 6-5-1]
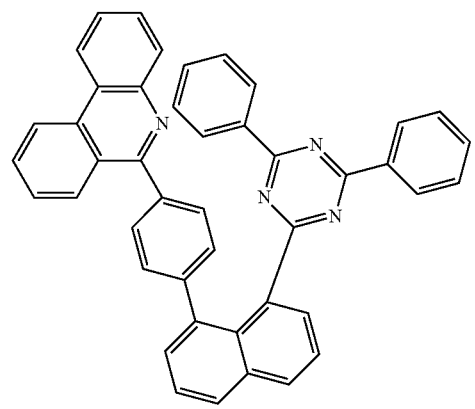
[formula 6-6-1]
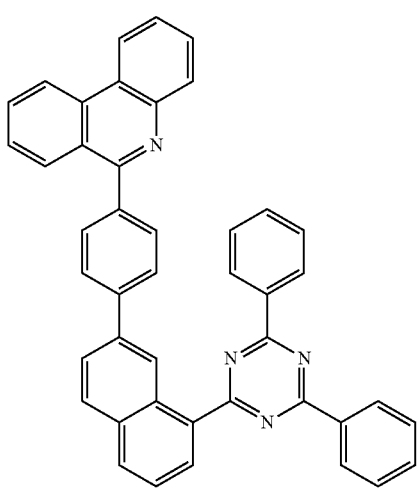
[formula 6-7-1]
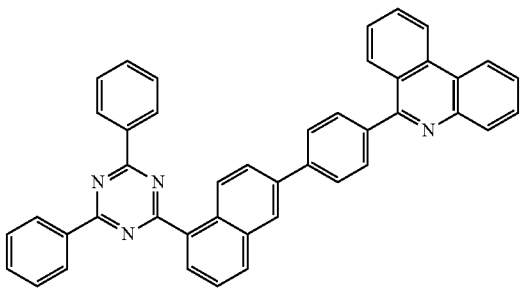
[formula 6-8-1]
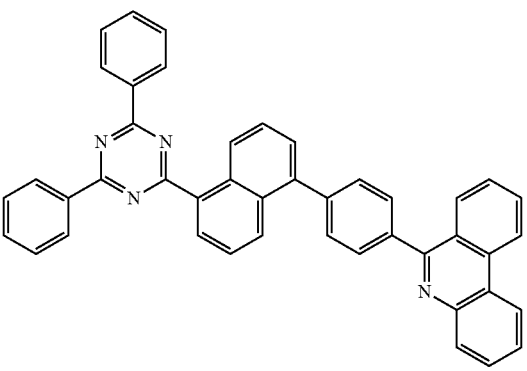
[formula 6-9-1]
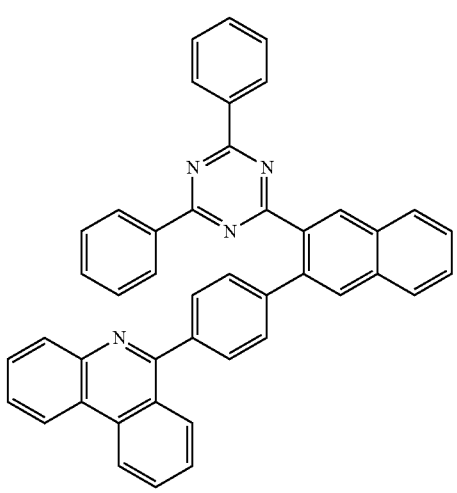

[formula 6-10-1]
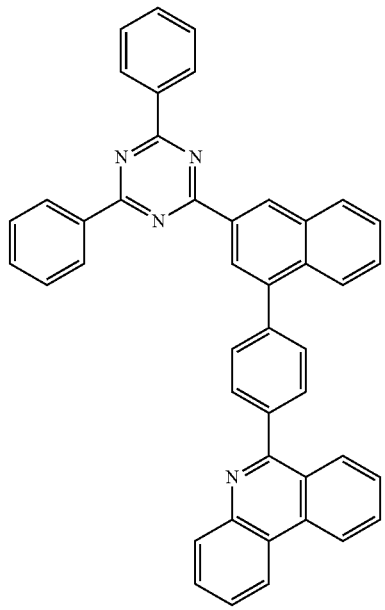
[formula 6-12-1]
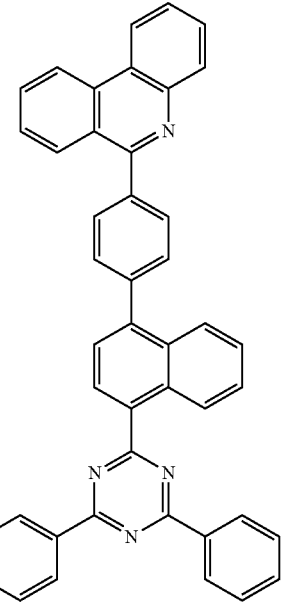
[formula 6-11-1]
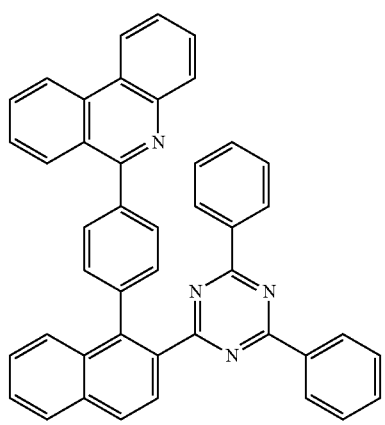
[formula 6-13-1]
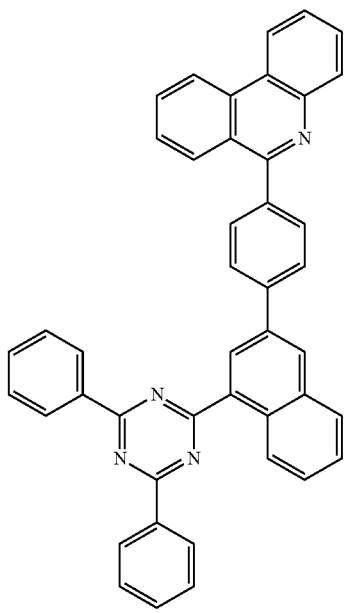

[formula 6-14-1]

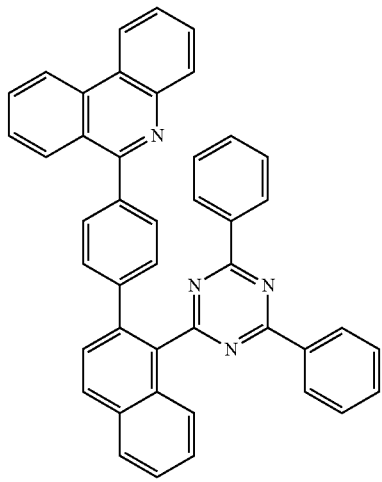

In one embodiment of the present specification, the hetero-cyclic compound represented by Chemical Formula 1 is represented by any one of the Chemical Formulae shown above.

The compound of Chemical Formula 1 may have suitable properties to be used as an organic material layer used in an organic light emitting device, by introducing substituents having different heterorings on both sides with a naphthalene group at the center, as shown in Chemical Formula 1.

The compound represented by Chemical Formula 1 includes a hetero-cyclic compound including X1 to X3. Therefore, the compound represented by Chemical Formula 1 has a suitable energy level as an electron injection and/or an electron transfer material in an organic light emitting device, since the compound includes a hetero-cyclic structure. In addition, an organic light emitting device having low driving voltage and high light efficiency may be obtained by selecting compounds having suitable energy levels depending on the substituents from among the compounds represented by Chemical Formula 1 in the present specification, and using them in the device.

In addition, by introducing various substituents to the core structure, the energy band gap may be finely adjusted, and meanwhile, properties at the interface between organic materials are improved. Therefore, applications of the material may be diverse.

Meanwhile, the compound of Chemical Formula 1 has a high glass transition temperature (Tg) thereby has excellent thermal stability. Such a thermal stability improvement becomes an important factor in providing driving stability to a device.

The compound represented by Chemical Formula 1 may be prepared based on the preparation examples described later.

The compound represented by Chemical Formula 1 may be prepared by reacting a structure including X1 to X3, including L1, and substituted with a dioxoborolane group with naphthalene substituted with a halogen group on one side and substituted with a hydroxyl group on the other side, and after the reaction, by reacting 1,1,2,2,3,3,4,4,4-nonafluorobutane-1-sulfonyl fluoride ($C_4F_{10}O_2S$) therewith, and then reacting a structure including Ar1 and L2, and substituted with a dioxoborolane group therewith.

Alternatively, the compound may be prepared by reacting benzamidine hydrochloride with naphthalene substituted with a halogen group on one side and substituted with an aldehyde group on the other side, and then reacting a structure including Ar1 and L2, and substituted with dioxoborolane group or dioxolane group therewith.

The hetero-cyclic compound represented by Chemical Formula 1 as well as Chemical Formulae 1-1 to 1-14 may be prepared using the methods described above by modifying the substitution position of a halogen group, a hydroxyl group or an aldehyde group.

The hetero-cyclic compound represented by Chemical Formula 1 as well as Chemical Formulae 1-1 to 1-8 may be prepared by modifying the number of heteroatoms in X1 to X3, and modifying Ar2, Ar3 and Lx.

In Lx, x is an integer of 1 or 2.

In addition, the present specification provides an organic light emitting device including the hetero-cyclic compound represented by Chemical Formula 1.

In one embodiment of the present specification, an organic light emitting device including a first electrode; a second electrode provided opposite to the first electrode; and one or more organic material layers provided between the first electrode and the second electrode, wherein one or more layers of the organic material layers include the hetero-cyclic compound represented by Chemical Formula 1.

In the present specification, when describing that a certain member is located "on" another member, this includes not only a case in which the certain member adjoins another member but also a case in which a different another member is present between the two members.

In the present specification, when describing that a certain part "includes" certain constitutions, this means that the part is capable of including other constitutions, not excluding other constitutions, unless particularly described otherwise.

The organic material layer of an organic light emitting device in the present specification may be formed as a monolayer structure, but may also be formed as a multilayer structure in which two or more organic material layers are laminated. For example, an organic light emitting device of the present invention may have a structure that includes a hole injection layer, a hole transfer layer, a light emitting layer, an electron transfer layer, an electron injection layer and the like as the organic material layer. However, the structure of an organic light emitting device is not limited thereto, and may include less numbers of organic material layers.

In one embodiment of the present specification, the organic material layer includes a hole injection layer or a hole transfer layer, and the hole injection layer or the hole transfer layer includes the hetero-cyclic compound.

In another embodiment, the organic material layer includes a light emitting layer, and the light emitting layer includes the hetero-cyclic compound as the host of the light emitting layer.

In one embodiment of the present specification, the organic material layer includes an electron transfer layer or an electron injection layer, and the electron transfer layer or the electron injection layer includes the hetero-cyclic compound.

In one embodiment of the present specification, the electron transfer layer, the electron injection layer, or the layer carrying out electron transfer and electron injection at the same time includes the hetero-cyclic compound only.

In one embodiment of the present specification, the organic material layer further includes a hole injection layer or a hole transfer layer including a compound that includes an arylamino group, a carbazole group or a benzocarbazole group, in addition to the organic material layer including the hetero-cyclic compound.

In one embodiment of the present specification, the organic material layer including the hetero-cyclic compound includes the hetero-cyclic compound as a host, and includes other organic compounds, metals or metal compounds as a dopant.

In another embodiment, the organic light emitting device may be an organic light emitting device having a structure in which an anode, one or more organic material layers and a cathode are laminated in consecutive order on a substrate (normal type).

In another embodiment, the organic light emitting device may be an organic light emitting device having a structure in which a cathode, one or more organic material layers and an anode are laminated in consecutive order on a substrate (inverted type).

For example, the structures of an organic light emitting device according to one embodiment of the present specification are illustrated in FIGS. 1 and 2.

FIG. 1 illustrates the structure of an organic electronic device in which a substrate (1), an anode (2), a light emitting layer (3) and a cathode (4) are laminated in consecutive order. In the structure such as this, the hetero-cyclic compound may be included in the light emitting layer (3).

FIG. 2 illustrates the structure of an organic electronic device in which a substrate (1), an anode (2), a hole injection layer (5), a hole transfer layer (6), a light emitting layer (3), an electron transfer layer (7) and a cathode (4) are laminated in consecutive order. In the structure such as this, the hetero-cyclic compound may be included in one or more layers of the hole injection layer (5), the hole transfer layer (6), the light emitting layer (3) and the electron transfer layer (7).

In the structure such as this, the compound may be included in one or more layers of the hole injection layer, the hole transfer layer, the light emitting layer and the electron transfer layer.

The organic light emitting device of the present specification may be prepared using materials and methods known in the related art, except that one or more layers of the organic material layers include the compound of the present specification, that is, the hetero-cyclic compound.

When the organic light emitting device includes a plurality of organic material layers, the organic material layers may be formed with an identical material or different materials.

The organic light emitting device of the present specification may be prepared using materials and methods known in the related art, except that one or more layers of the organic material layers include the hetero-cyclic compound, that is, the compound represented by Chemical Formula 1.

For example, the organic light emitting device of the present specification may be prepared by laminating a first electrode, an organic material layer and a second electrode in consecutive order on a substrate. Herein, the anode is formed on the substrate by depositing a metal, a metal oxide having conductivity, or alloys thereof using a physical vapor deposition (PVD) method such as a sputtering method or an e-beam evaporation method, and after the organic material layer including a hole injection layer, a hole transfer layer, a light emitting layer and an electron transfer layer is formed thereon, a material capable of being used as the cathode is deposited thereon, and as a result, the organic light emitting device may be prepared. In addition to this method, the organic light emitting device may be prepared by depositing a cathode material, an organic material layer and an anode material in consecutive order on a substrate.

In addition, when the organic light emitting device is prepared, the compound of Chemical Formula 1 may be formed as the organic material layer using a solution coating method as well as a vacuum deposition method. Herein, the solution coating method means spin coating, dip coating, doctor blading, ink jet printing, screen printing, a spray method, roll coating or the like, but is not limited thereto.

In addition to these methods, the organic light emitting device may also be prepared by depositing a cathode material, an organic material layer and an anode material on a substrate in consecutive order (International Patent Publication No. 2003/012890). However, the preparation method is not limited thereto.

In one embodiment of the present specification, the first electrode is an anode, and the second electrode is a cathode.

In another embodiment, the first electrode is a cathode, and the second electrode is an anode.

As the anode material, a material having large work function is normally preferable so that hole injection to the organic material layer is smooth. Specific examples of the anode material capable of being used in the present invention include metals such as vanadium, chromium, copper, zinc or gold, or alloys thereof; metal oxides such as zinc oxides, indium oxides, indium tin oxides (ITO) or indium zinc oxide (IZO); and combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, a material having small work function is normally preferable so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer that injects holes from an electrode, and a hole injection material is preferably a compound that has an ability to transfer holes, therefore, has a hole injection effect in an anode, has an excellent hole injection effect for a light emitting layer or a light emitting material, prevents the movement of excitons, which are generated in the light emitting layer, to an electron injection layer or an electron injection material, and in addition, has an excellent thin film forming ability. The highest occupied molecular orbital (HOMO) of the hole injection material is preferably between the work function of an anode material and the HOMO of surrounding organic material layers. Specific examples of the hole injection material include a metal porphyrin, oligothiophene, an arylamine-based organic material, a hexanitrile hexaazatriphenylene-based organic material, a quinacridone-based organic material, a perylene-based organic material, anthraquinone, and a polyaniline- and polythiophene-based conductive polymer, and the like, but are not limited thereto.

The hole transfer layer is a layer that receives holes from a hole injection layer and transfers the holes to a light emitting layer, and as the hole transfer material, a material capable of receiving the holes from an anode or a hole injection layer, move the holes to a light emitting layer, and has high mobility for the holes is suitable. Specific examples thereof include an arylamine-based organic material, a conductive polymer, a block copolymer having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxy-quinoline aluminum complex (Alq$_3$); a carbazole-based compound; a dimerized styryl compound; BAlq; a 10-hydroxybenzo quinoline-metal compound; a benzoxazole-, a benzthiazole- and a benzimidazole-based compound; a poly(p-phenylenevinylene) (PPV)-based polymer; a spiro compound; polyfluorene, rubrene or the like, but are not limited thereto.

The light emitting layer may include a host material and a dopant material. The host material includes a fused aromatic ring derivative, a heteroring-containing compound, or the like. Specifically, the fused aromatic ring derivative includes an anthracene derivative, a pyrene derivative, a naphthalene derivative, a pentacene derivative, a phenanthrene compound, a fluoranthene compound and the like, and the heteroring-containing compound includes a carbazole derivative, a dibenzofuran derivative, a ladder-type furan compound, a pyrimidine derivative and the like, but the material is not limited thereto.

The dopant material includes an aromatic amine derivative, a styrylamine compound, a boron complex, a fluoranthene compound, a metal complex, and the like. Specifically, the aromatic amine derivative includes arylamino-including pyrene, anthracene, crycene and Periflanthene as the fused aromatic derivative having a substituted or unsubstituted arylamino group, and the styrylamine compound includes a compound in which a substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine and the like is included, but the styrylamine compound is not limited thereto. In addition, the metal complex includes an iridium complex, a platinum complex or the like, but is not limited thereto.

The electron transfer layer is a layer that receives electrons from an electron injection layer and transfers the electrons to a light emitting layer, and as the electron transfer material, a material capable of receiving the electrons from a cathode, move the electrons to a light emitting layer, and has high mobility for the electrons is suitable. Specific examples thereof include an Al complex of 8-hydroxyquinoline; a complex including Alq3; an organic radical compound; a hydroxyflavone-metal complex and the like, but are not limited thereto. The electron transfer layer may be used together with any desired cathode material as used according to existing technologies. Particularly, examples of the suitable cathode material include common materials that have small work function, and in which an aluminum layer or a silver layer follows. Specifically the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect in a cathode and has an excellent electron injection effect for a light emitting layer or a light emitting material, prevents the movement of excitons generated in the light emitting layer to the electron injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, a metal complex compound, a nitrogen-containing 5-membered ring derivative, and the like, but are not limited thereto.

The metal complex compound may include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)berylium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium and the like, but is not limited thereto.

The organic light emitting device according to the present specification may be a top-emission type, a bottom-emission type or a dual-emission type depending on the materials used.

In one embodiment of the present specification, the hetero-cyclic compound may be included in an organic solar cell or an organic transistor in addition to an organic light emitting device.

Hereinafter, the hetero-cyclic compound represented by Chemical Formula 1 and the manufacture of an organic light emitting device including the same will be described in detail with reference to examples. However, the following examples are for illustrative purposes only, and the scope of the present specification is not limited thereto.

<Synthesis Example 1> Preparation of Compound Represented by Chemical Formula 2-1-1

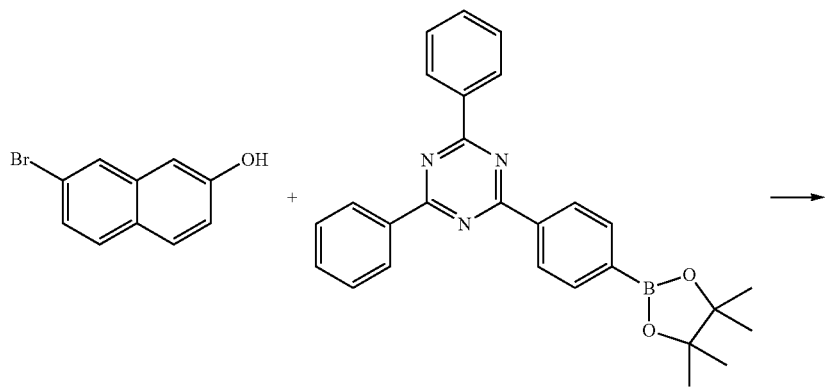

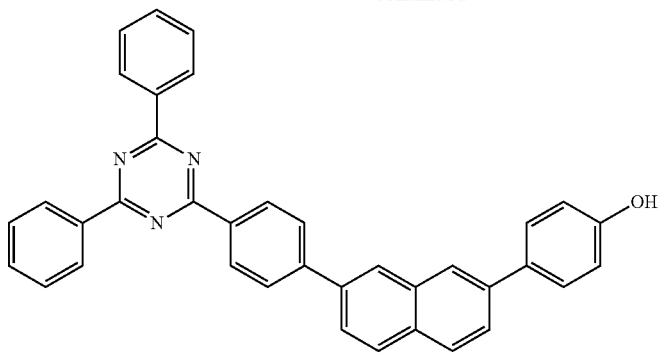
[Chemical Formula 1A]
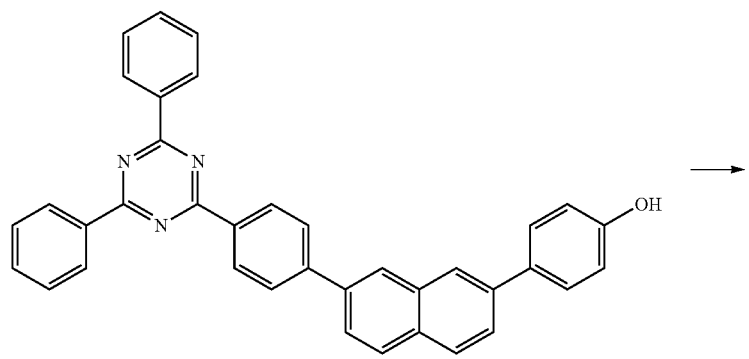
[Chemical Formula 1A]
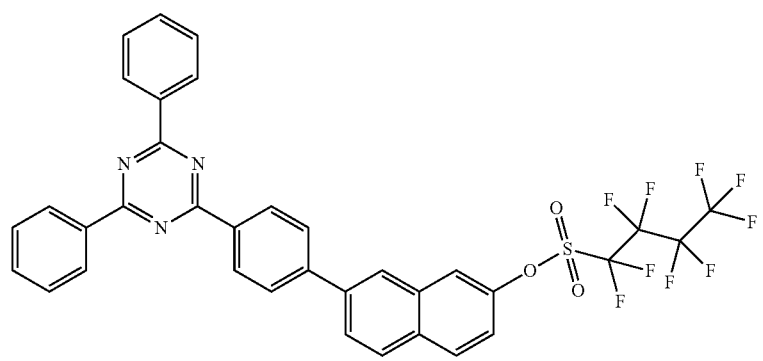
[Chemical Formula 1B]

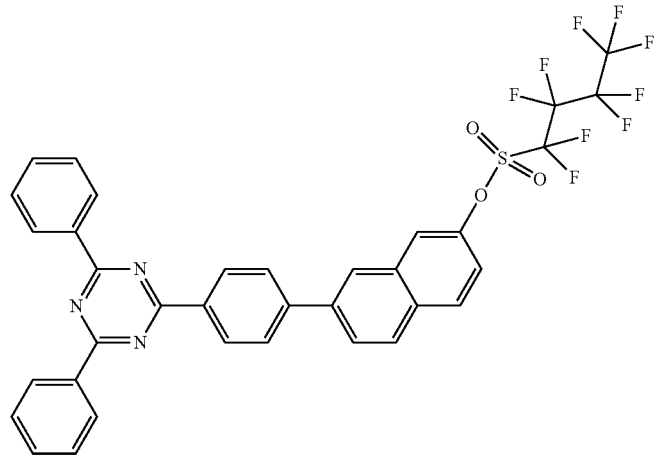

[Chemical Formula 1B]

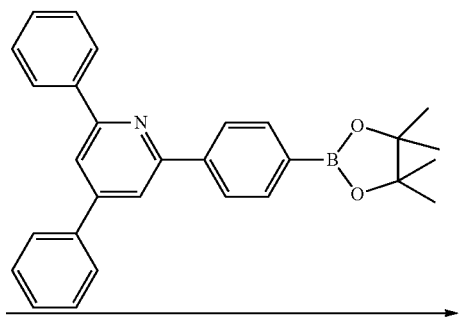

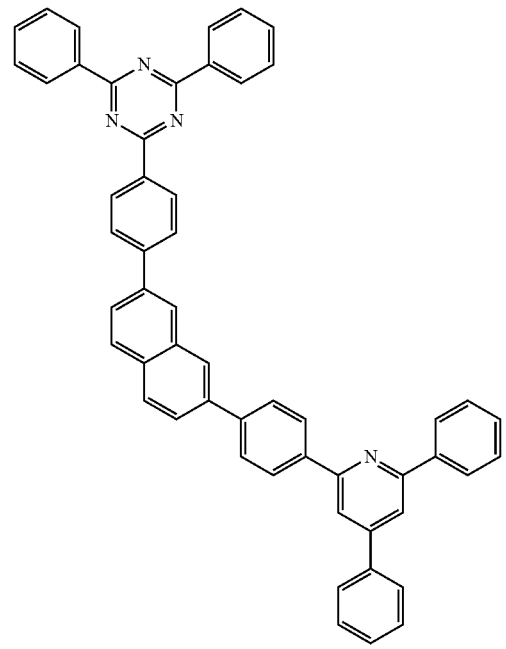

[Chemical Formula 2-1-1]

(1) Preparation of Preparation of Chemical Formula 1A 7-bromo-2-naphthol (21 g, 94.1 mmol), triazine dioxoborolane (50 g, 114.9 mmol) and potassium carbonate ($K_2CO_3$) (39 g, 282 mmol) were dissolved in tetrahydrofuran (THF) (300 mL) and $H_2O$ (100 ml), and the mixture was heated to 90° C. Tetrakis(triphenylphosphine) palladium (Pd(PPh$_3$)$_4$) (2.17 g, 1.88 mmol) was added thereto, and the result was refluxed for 1 hour. The result was cooled to room temperature, and the aqueous layer was removed. Magnesium sulfate (MgSO$_4$) was placed in the organic layer and was filtered off. The filtrate was concentrated and then purified using column chromatography to obtain Chemical Formula 1A (30 g, yield 71%).

MS: [M+H]$^+$=452

(2) Preparation of Chemical Formula 1B

Chemical Formula 1A (22 g, 48.8 mmol), $C_4F_{10}O_2S$ (10.5 ml, 58.4 mmol) and potassium carbonate ($K_2CO_3$) (20 g, 145 mmol) were dissolved in acetonitrile (300 mL), and the mixture was heated to 50° C. After refluxing for 12 hours, the result was cooled to room temperature and then filtered. Chemical Formula 1B (30 g, yield 84%) was obtained.

MS: [M+H]$^+$=734

(3) Preparation of Chemical Formula 2-1-1

Chemical Formula 1B (16 g, 21.8 mmol), diphenylpyridine dioxoborolane (10.4 g, 24 mmol) and potassium carbonate ($K_2CO_3$) (9 g, 65.2 mmol) were dissolved in tetrahydrofuran (THF) (300 mL) and $H_2O$ (100 ml), and the mixture was heated to 90° C. Tetrakis(triphenylphosphine) palladium (Pd(PPh$_3$)$_4$) (0.5 g, 0.43 mmol) was added thereto, and the result was refluxed for 4 hours. After the result was cooled to room temperature, the aqueous layer was removed. Magnesium sulfate (MgSO$_4$) was placed in the organic layer and was filtered off. The filtrate was concentrated and then purified using column chromatography to obtain Chemical Formula 2-1-1 (11 g, yield 68%).

MS: [M+1-1]$^+$=741

<Synthesis Example 2> Preparation of Compound Represented by Chemical Formula 2-1-2

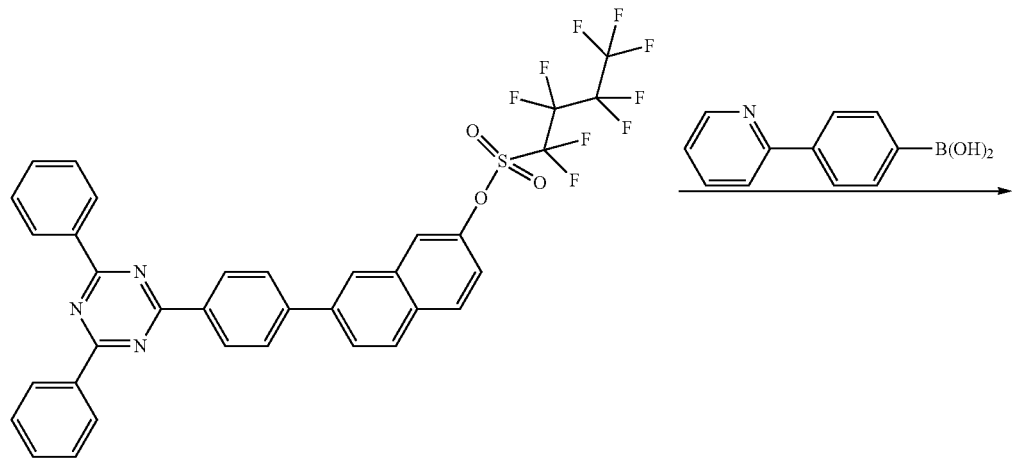

[Chemical Formula 1B]

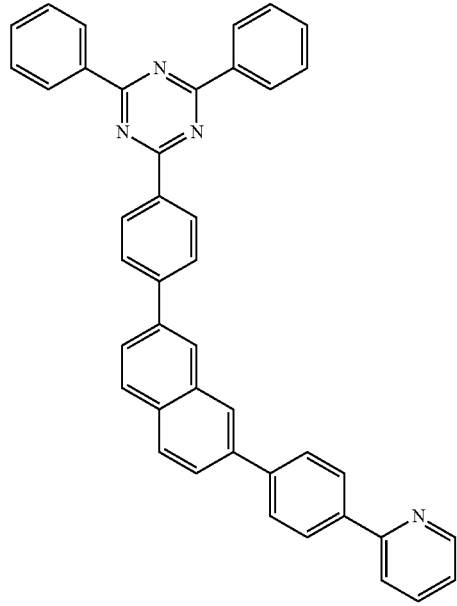

[Chemical Formula 2-1-2]

(1) Preparation of Chemical Formula 2-1-2

Chemical Formula 2-1-2 (20 g, yield 78%) was prepared in the same manner as in the preparation of Chemical Formula 2-1-1 of Synthesis Example 1, except that pyridinephenylboronic acid (9.6 g, 48 mmol) was used instead of diphenylpyridine dioxoborolane.

MS: [M+H]$^+$=589

<Synthesis Example 3> Preparation of Compound Represented by Chemical Formula 2-8-1
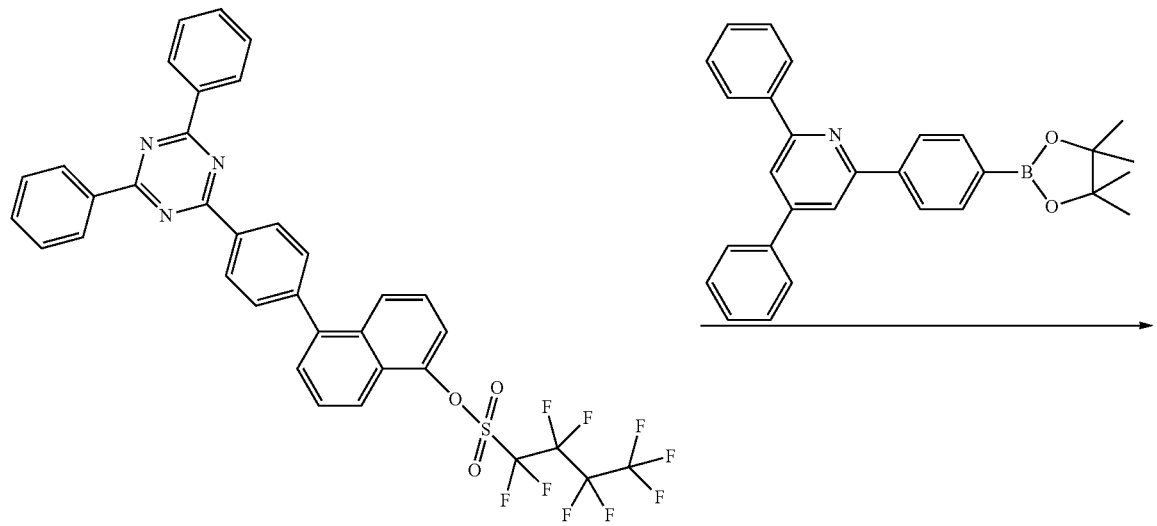
[Chemical Formula 2B]
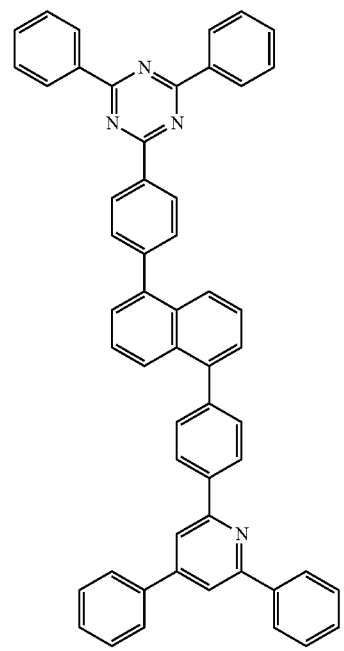
[Chemical Formula 2-8-1]
(1) Preparation of Chemical Formula 2-8-1
Chemical Formula 2-8-1 (10 g, yield 62%) was prepared in the same manner as in the preparation of Chemical Formula 2-1-1 of Synthesis Example 1, except that Chemical Formula 2B (16 g, 21.8 mmol) was used instead of Chemical Formula 1B.
MS: $[M+H]^+=741$ <Synthesis Example 4> Preparation of Compound Represented by Chemical Formula 2-8-2

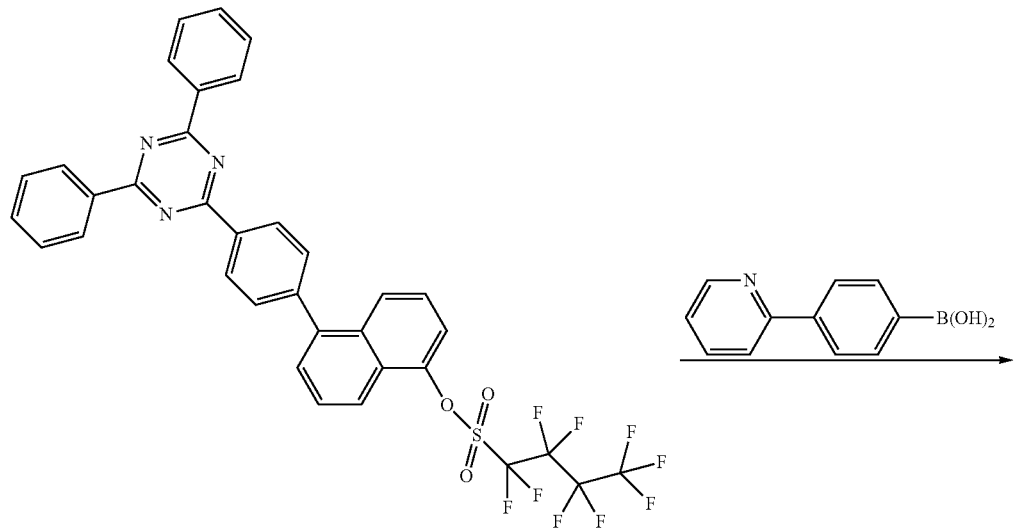

[Chemical Formula 2B]

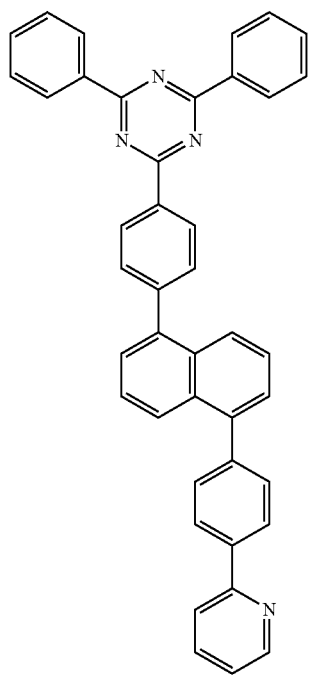

[Chemical Formula 2-8-2]

(1) Preparation of Chemical Formula 2-8-2

Chemical Formula 2-8-2 (19 g, yield 74%) was prepared in the same manner as in the preparation of Chemical Formula 2-8-1 of Synthesis Example 3, except that pyridinephenyl boronic acid (9.6 g, 48 mmol) was used instead of diphenylpyridine dioxoborolane.

MS: $[M+H]^+=589$

<Synthesis Example 5> Preparation of Compound Represented by Chemical Formula 2-12-1
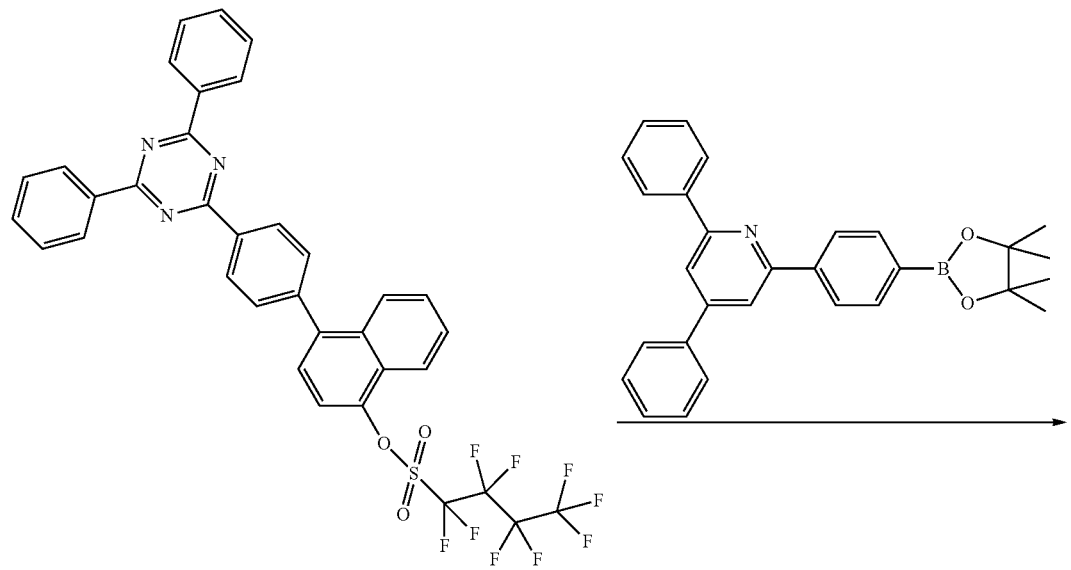
[Chemical Formula 3B]
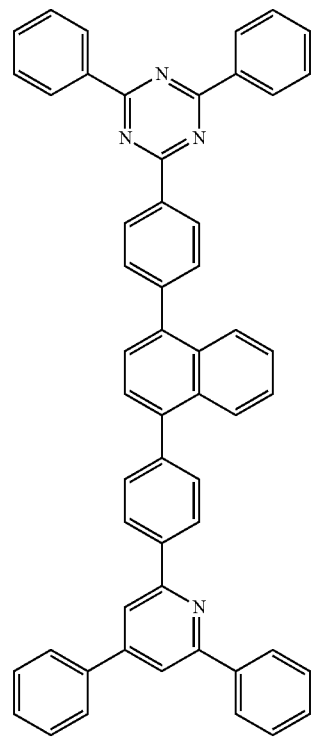
[Chemical Formula 2-12-1]
(1) Preparation of Chemical Formula 2-12-1
Chemical Formula 2-12-1 (13 g, yield 80.7%) was prepared in the same manner as in the preparation of Chemical Formula 2-1-1 of Synthesis Example 1, except that Chemical Formula 3B (16 g, 21.8 mmol) was used instead of Chemical Formula 1B.
MS: $[M+H]^+$=741

<Synthesis Example 6> Preparation of Compound Represented by Chemical Formula 2-12-2

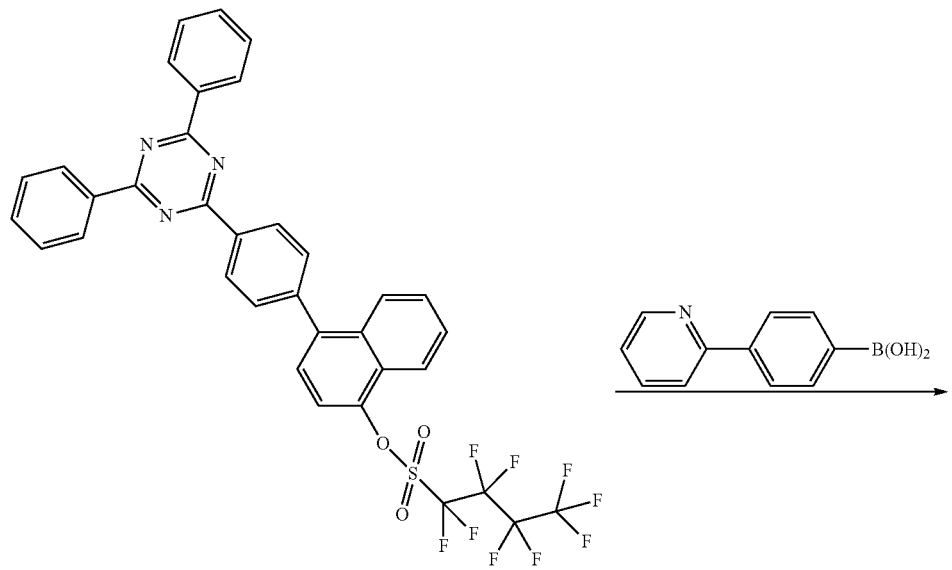

[Chemical Formula 3B]

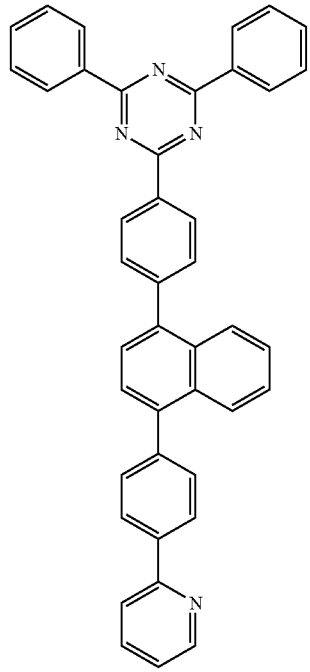

[Chemical Formula 2-12-2]

(1) Preparation of Chemical Formula 2-12-2

Chemical Formula 2-12-2 (21 g, yield 82%) was prepared in the same manner as in the preparation of Chemical Formula 2-12-1 of Synthesis Example 5, except that pyridinephenylboronic acid (9.6 g, 48 mmol) was used instead of diphenylpyridine dioxoborolane.

MS: $[M+H]^+$=589

<Synthesis Example 7> Preparation of Compound Represented by Chemical Formula 3-1-1

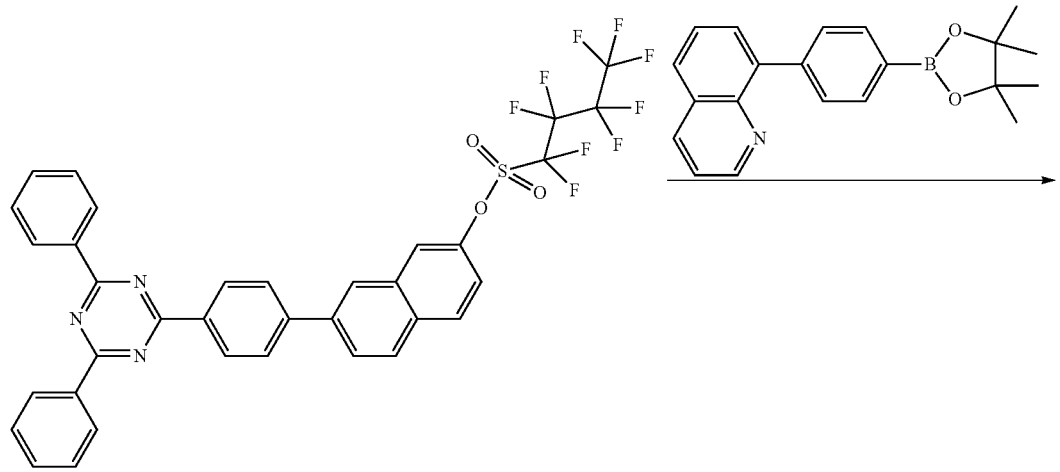

[Chemical Formula 1B]

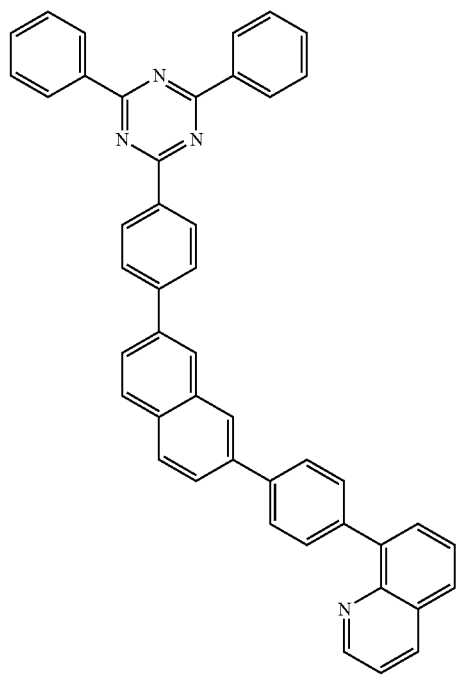

[Chemical Formula 3-1-1]

(1) Preparation of Chemical Formula 3-1-1

Chemical Formula 3-1-1 (11 g, yield 79%) was prepared in the same manner as in the preparation of Chemical Formula 2-1-1 of Synthesis Example 1, except that quinolinephenyl dioxoborolane (7.9 g, 24 mmol) was used instead of diphenylpyridine dioxoborolane.

MS: $[M+H]^+$=639

<Synthesis Example 8> Preparation of Compound Represented by Chemical Formula 3-1-3
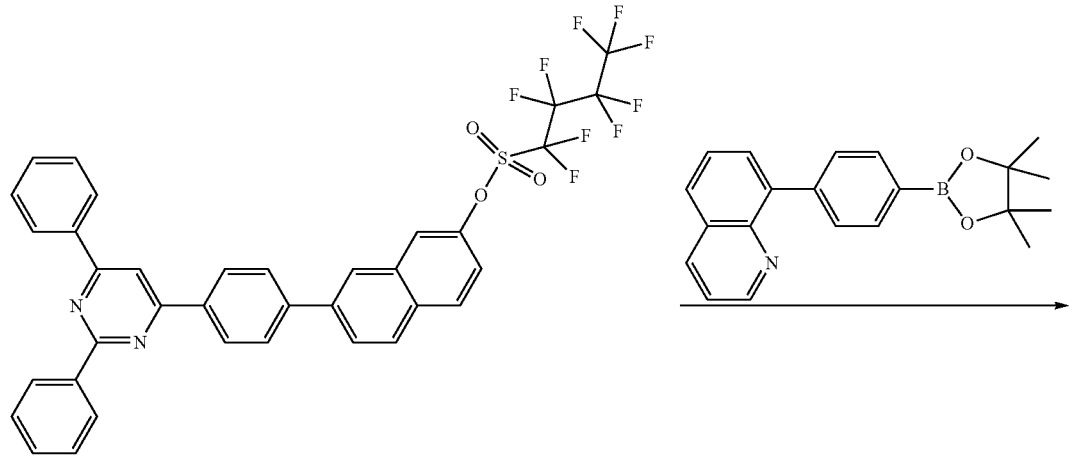
[Chemical Formula 4B]
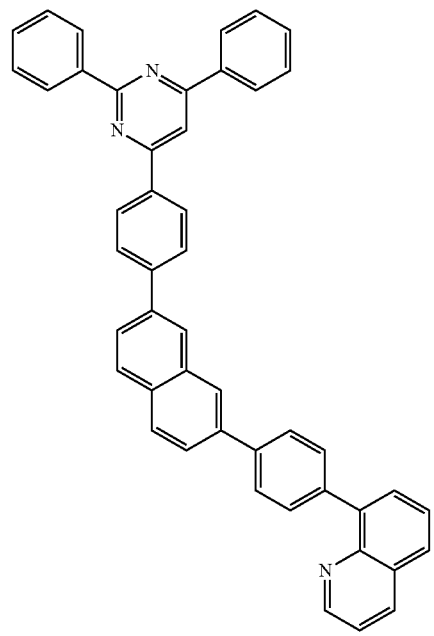
[Chemical Formula 3-1-3]
(1) Preparation of Chemical Formula 3-1-3
Chemical Formula 3-1-3 (9 g, yield 65%) was prepared in the same manner as in the preparation of Chemical Formula 3-1-1 of Synthesis Example 7, except that Chemical Formula 4B (16 g, 21.8 mmol) was used instead of Chemical Formula 1B.
MS: $[M+H]^+ = 638$ <Synthesis Example 9> Preparation of Compound Represented by Chemical Formula 3-1-5
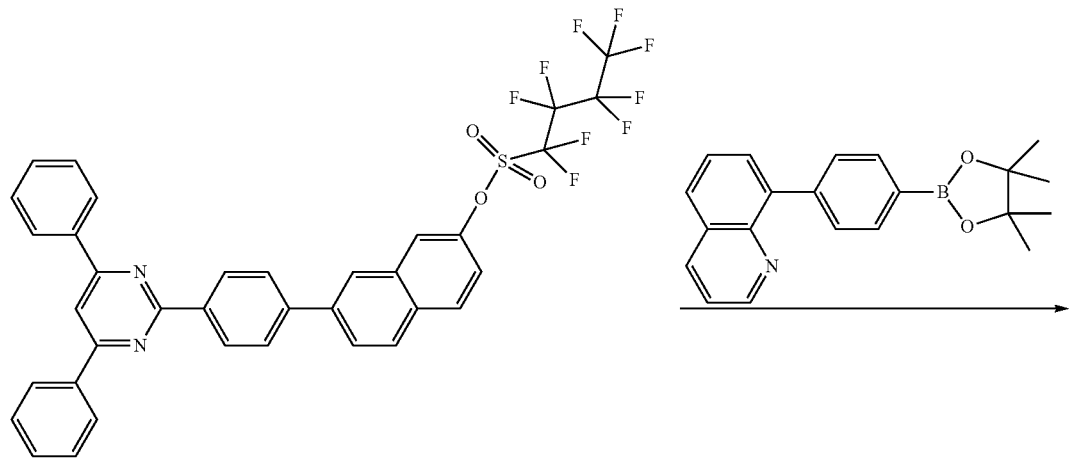
[Chemical Formula 5B]
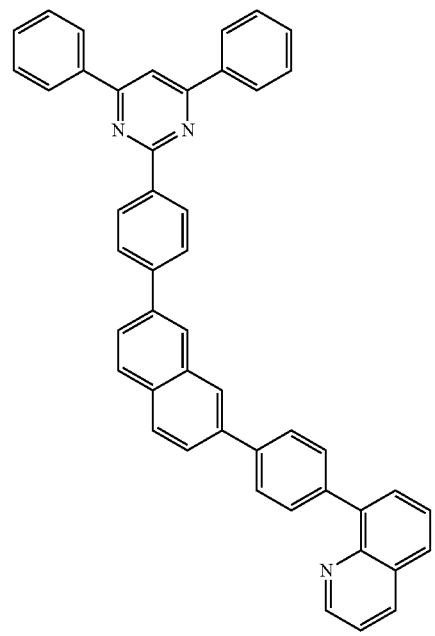
[Chemical Formula 3-1-5]
(1) Preparation of Chemical Formula 3-1-5
Chemical Formula 3-1-5 (11 g, yield 80%) was prepared in the same manner as in the preparation of Chemical Formula 3-1-1 of Synthesis Example 7, except that Chemical Formula 5B (16 g, 21.8 mmol) was used instead of Chemical Formula 1B.
MS: $[M+H]^+=638$ <Synthesis Example 10> Preparation of Compound Represented by Chemical Formula 3-8-1
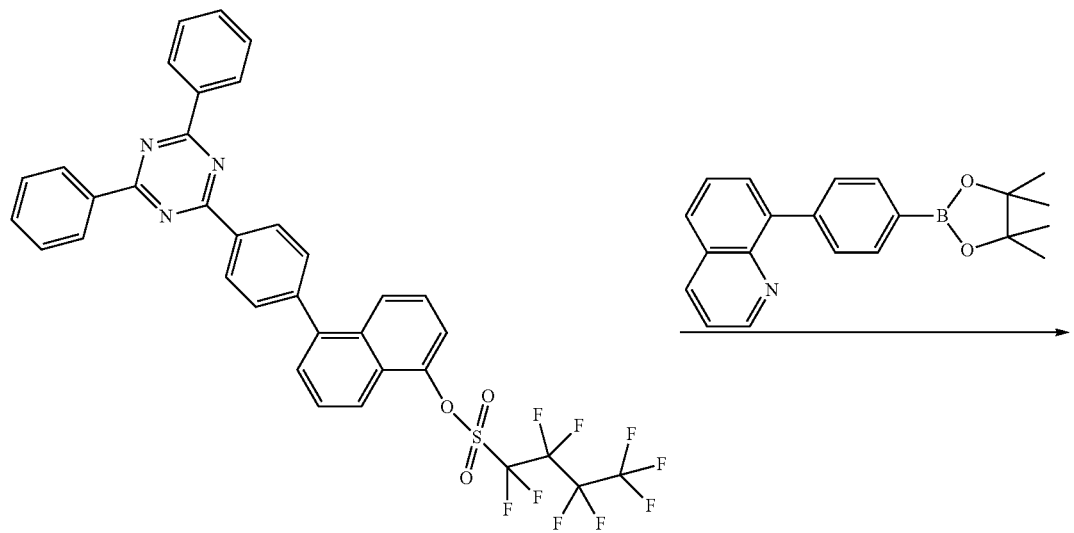
[Chemical Formula 2B]
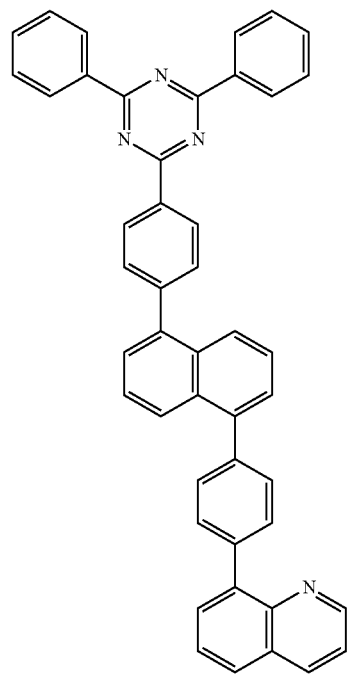
[Chemical Formula 3-8-1]
(1) Preparation of Chemical Formula 3-8-1
Chemical Formula 3-8-1 (7.5 g, yield 54%) was prepared in the same manner as in the preparation of Chemical Formula 3-1-1 of Synthesis Example 7, except that Chemical Formula 3B (16 g, 21.8 mmol) was used instead of Chemical Formula 1B.
MS: $[M+H]^+=639$ <Synthesis Example 11> Preparation of Compound Represented by Chemical Formula 3-12-1
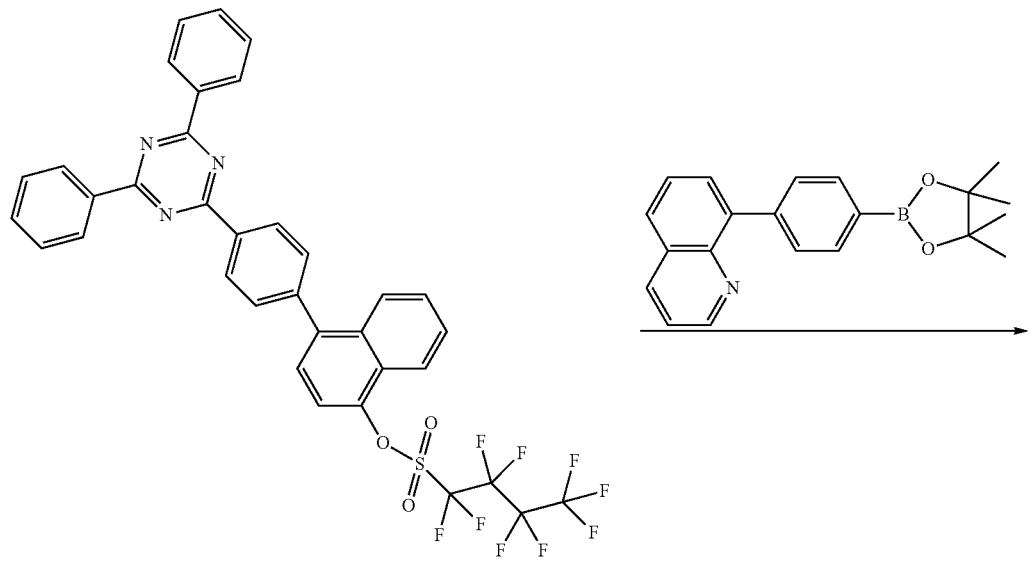
[Chemical Formula 3B]
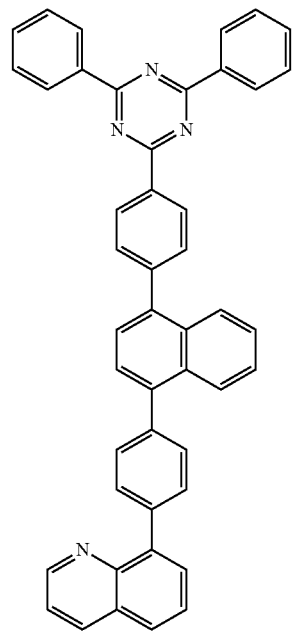
[Chemical Formula 3-12-1]
(1) Preparation of Chemical Formula 3-12-1
Chemical Formula 3-12-1 (8 g, yield 56%) was prepared in the same manner as in the preparation of Chemical Formula 3-1-1 of Synthesis Example 7, except that Chemical Formula 3B (16 g, 21.8 mmol) was used instead of Chemical Formula 1B.
MS: $[M+H]^+=639$ <Synthesis Example 12> Preparation of Compound Represented by Chemical Formula 3-8-3
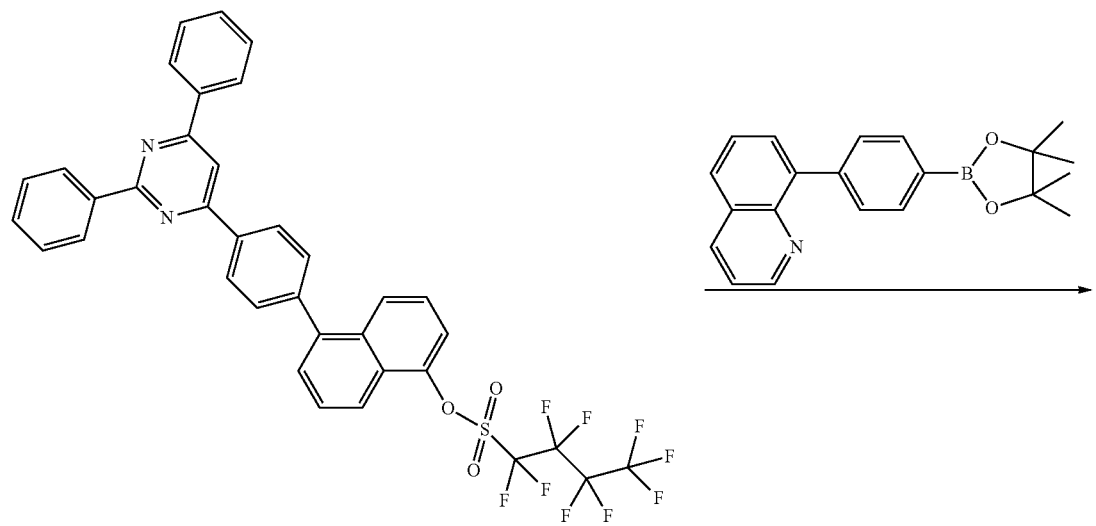
[Chemical Formula 6B]
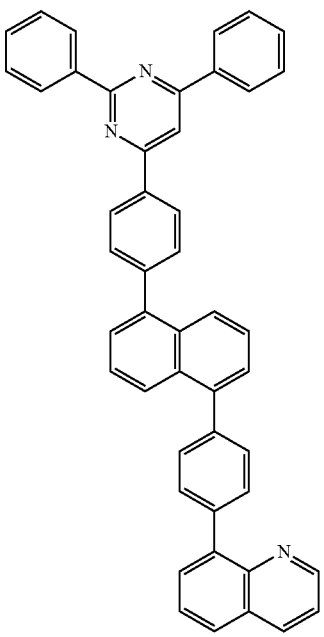
[Chemical Formula 3-8-3]
(1) Preparation of Chemical Formula 3-8-3
Chemical Formula 3-8-3 (13 g, yield 86%) was prepared in the same manner as in the preparation of Chemical Formula 3-1-1 of Synthesis Example 7, except that Chemical Formula 6B (16 g, 21.8 mmol) was used instead of Chemical Formula 1B.
MS: $[M+H]^+=638$ <Synthesis Example 13> Preparation of Compound Represented by Chemical Formula 3-12-3
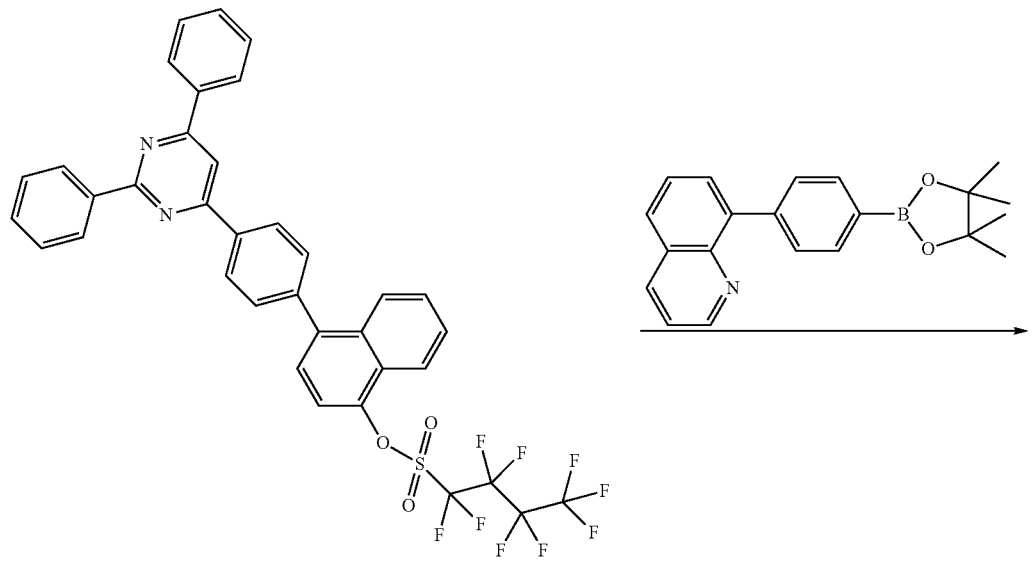
[Chemical Formula 7B]
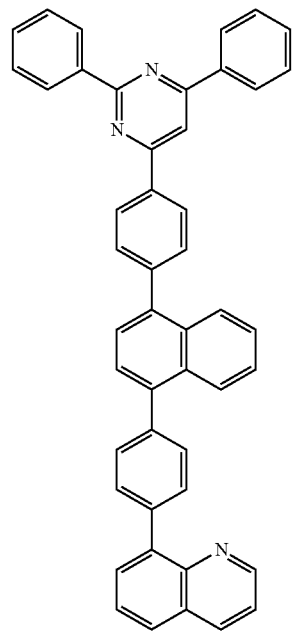
[Chemical Formula 3-12-3]
(1) Preparation of Chemical Formula 3-12-3
Chemical Formula 3-12-3 (11 g, yield 79%) was prepared in the same manner as in the preparation of Chemical Formula 3-1-1 of Synthesis Example 7, except that Chemical Formula 7B (16 g, 21.8 mmol) was used instead of Chemical Formula 1B.
MS: $[M+H]^+=638$ <Synthesis Example 14> Preparation of Compound Represented by Chemical Formula 3-8-5
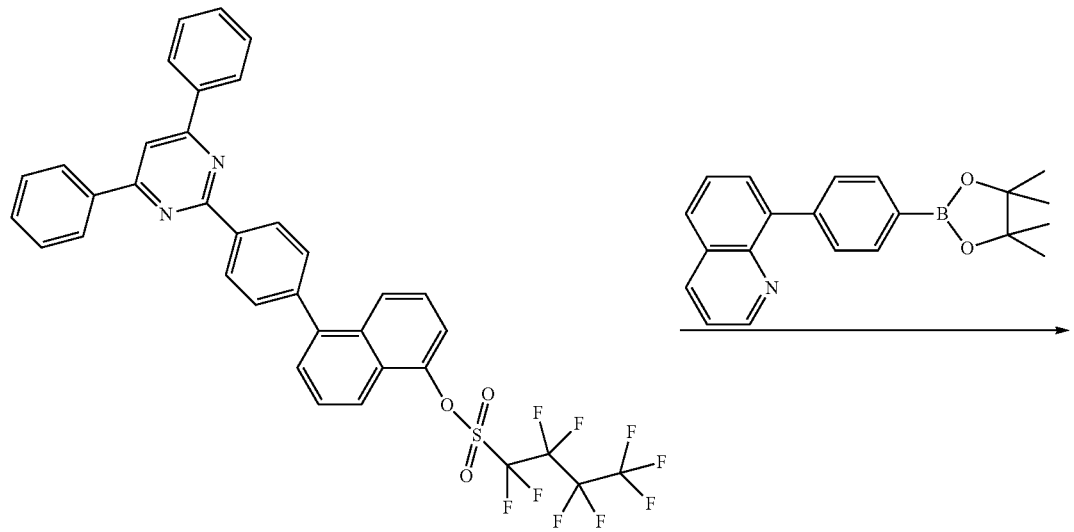
[Chemical Formula 8B]
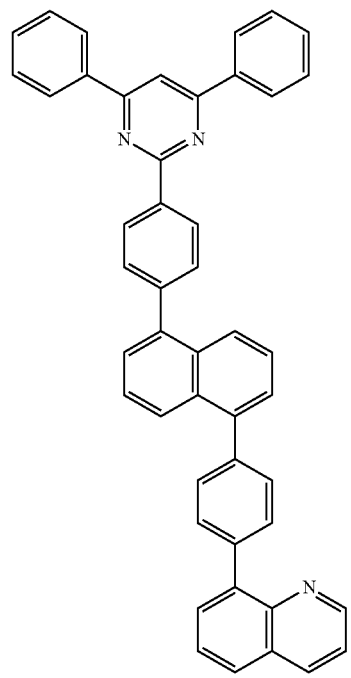
[Chemical Formula 3-8-5]
(1) Preparation of Chemical Formula 3-8-5
Chemical Formula 3-8-5 (9 g, yield 65%) was prepared in the same manner as in the preparation of Chemical Formula 3-1-1 of Synthesis Example 7, except that Chemical Formula 8B (16 g, 21.8 mmol) was used instead of Chemical Formula 1B.
MS: $[M+H]^+=638$ <Synthesis Example 15> Preparation of Compound Represented by Chemical Formula 3-12-5
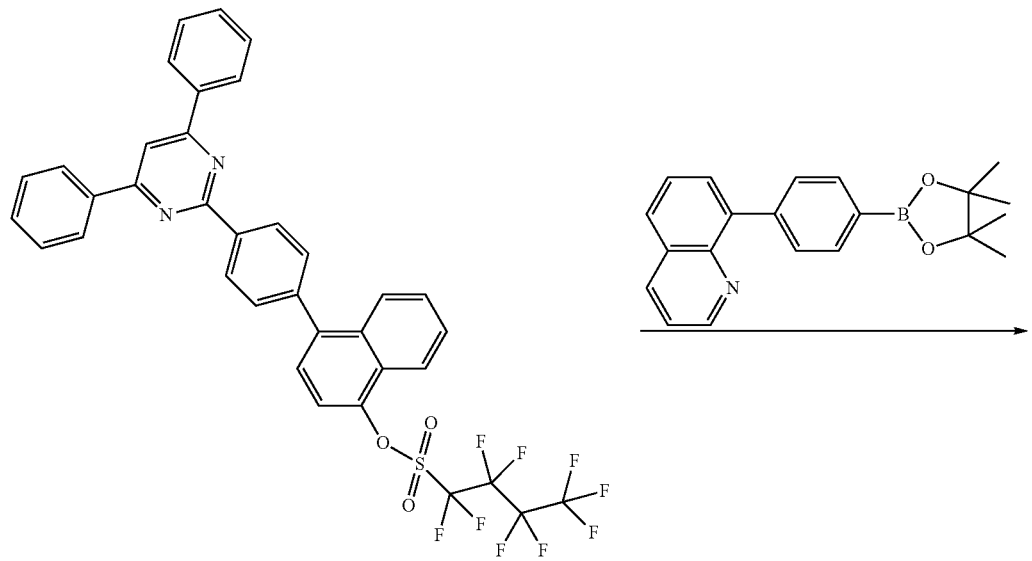
[Chemical Formula 9B]
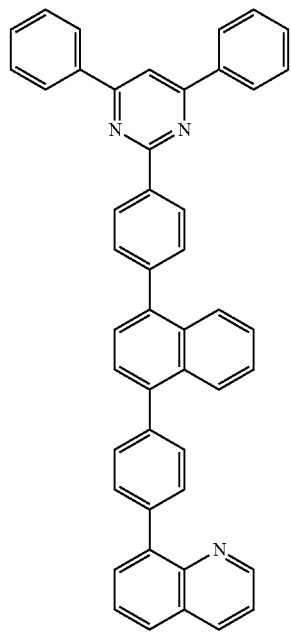
[Chemical Formula 3-12-5]
(1) Preparation of Chemical Formula 3-12-5
Chemical Formula 3-12-5 (10 g, yield 72%) was prepared in the same manner as in the preparation of Chemical Formula 3-1-1 of Synthesis Example 7, except that Chemical Formula 9B (16 g, 21.8 mmol) was used instead of Chemical Formula 1B.
MS: $[M+H]^+=638$ <Synthesis Example 16> Preparation of Compound Represented by Chemical Formula 2-2-1
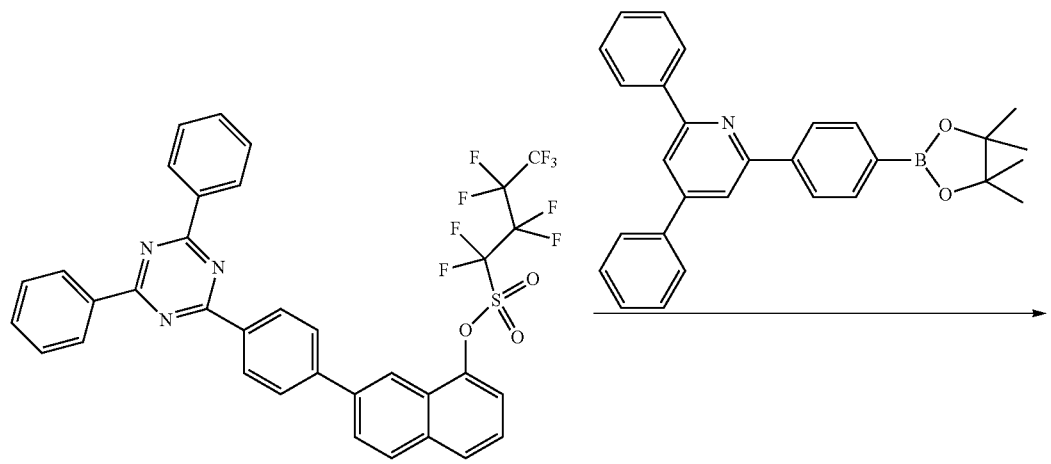
[Chemical Formula 10B]
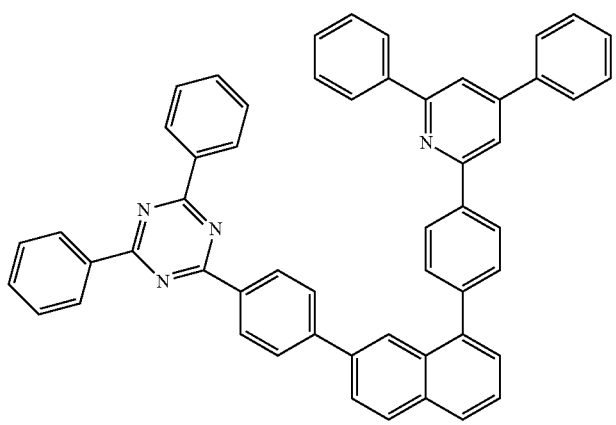
[Chemical Formula 2-2-1]
Chemical Formula 2-2-1 (9 g, yield 69%) was prepared in the same manner as in the preparation of Chemical Formula 2-1-1 of Synthesis Example 1, except that Chemical Formula 10B (13 g, 17.7 mmol) was used instead of Chemical Formula 1B.
MS: $[M+H]^+=741$ <Synthesis Example 17> Preparation of Compound Represented by Chemical Formula 2-3-1
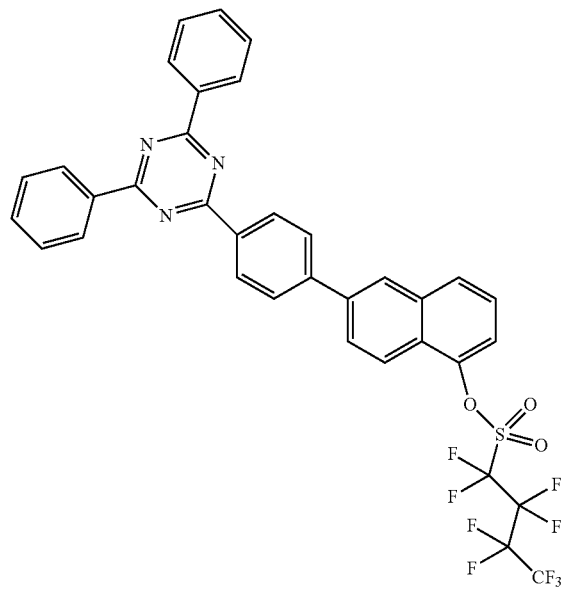
[Chemical Formula 11B]
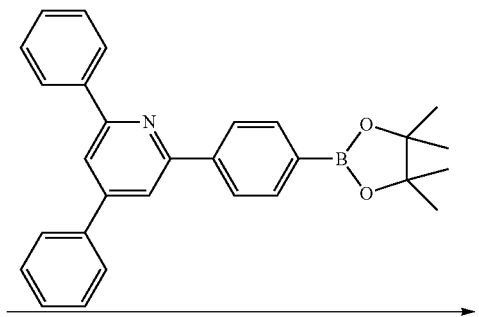
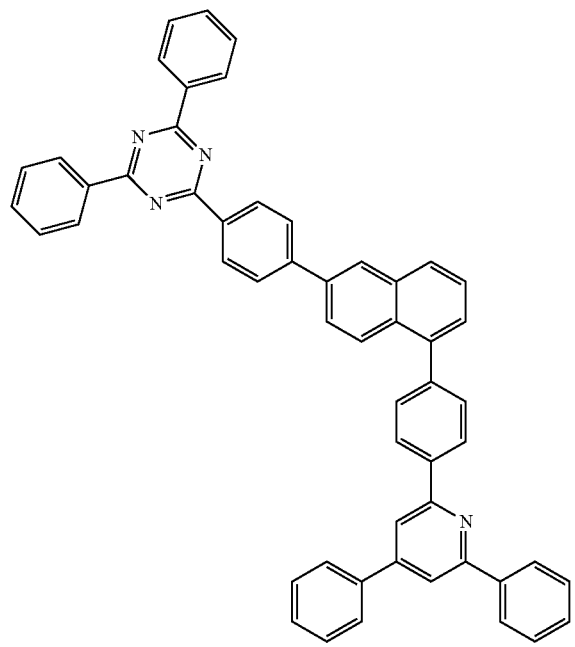
[Chemical Formula 2-3-1]
Chemical Formula 2-3-1 (10 g, yield 66%) was prepared in the same manner as in the preparation of Chemical Formula 2-1-1 of Synthesis Example 1, except that Chemical Formula 11B (15 g, 20.4 mmol) was used instead of Chemical Formula 1B.
MS: $[M+H]^+=741$ <Synthesis Example 18> Preparation of Compound Represented by Chemical Formula 2-4-1
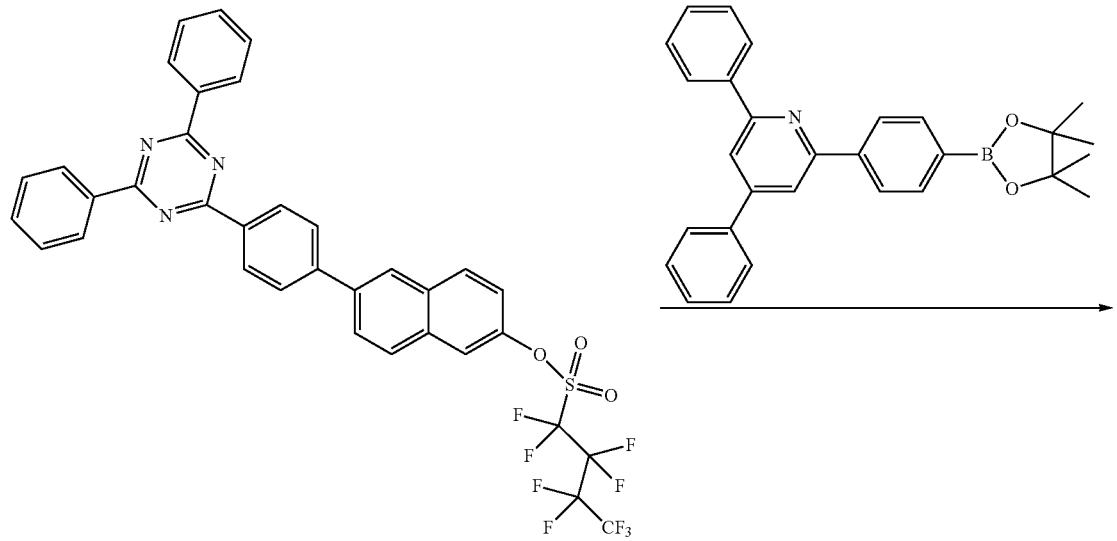
[Chemical Formula 12B]
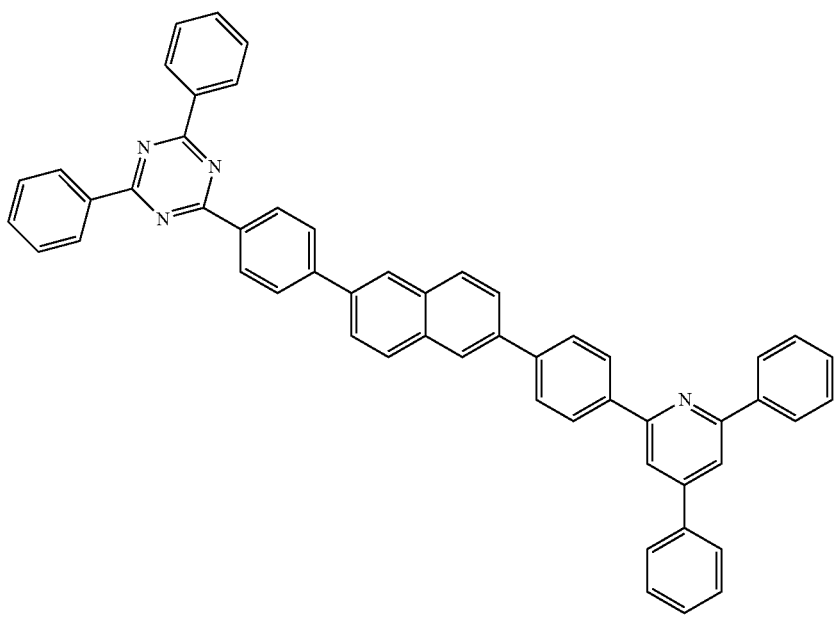
[Chemical Formula 2-4-1]
Chemical Formula 2-4-1 (7 g, yield 63%) was prepared in the same manner as in the preparation of Chemical Formula 2-1-1 of Synthesis Example 1, except that Chemical Formula 12B (11 g, 15.0 mmol) was used instead of Chemical Formula 1B.
MS: $[M+H]^+$=741

<Synthesis Example 19> Preparation of Compound Represented by Chemical Formula 2-5-1

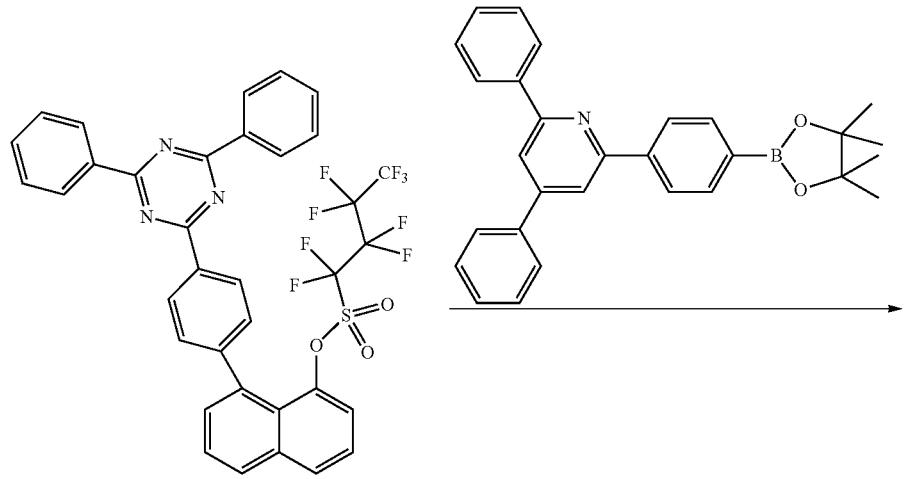

[Chemical Formula 13B]

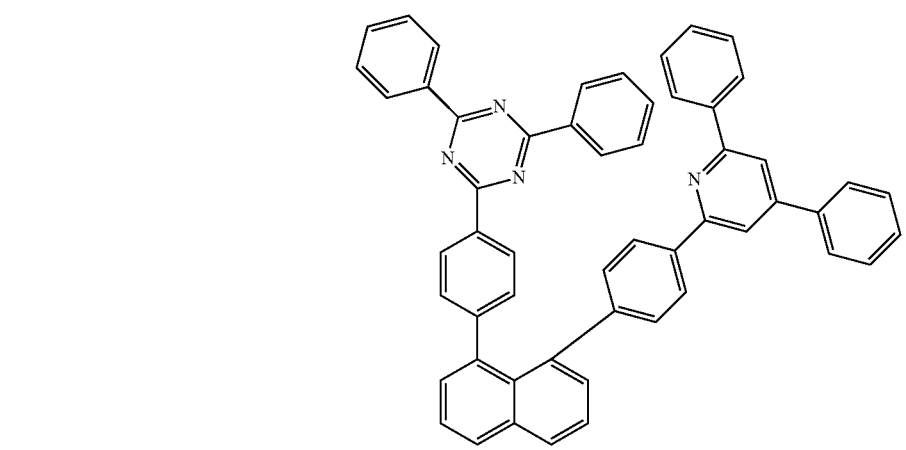

[Chemical Formula 2-5-1]

Chemical Formula 2-5-1 (12 g, yield 75%) was prepared in the same manner as in the preparation of Chemical Formula 2-1-1 of Synthesis Example 1, except that Chemical Formula 13B (16 g, 21.8 mmol) was used instead of Chemical Formula 1B.

MS: [M+H]$^+$=741

<Synthesis Example 20> Preparation of Compound Represented by Chemical Formula 5-11-1

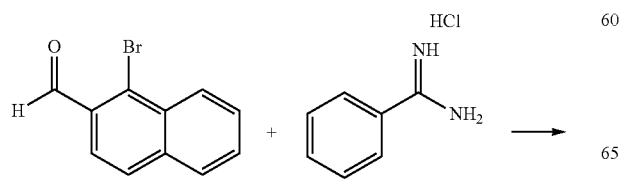

-continued

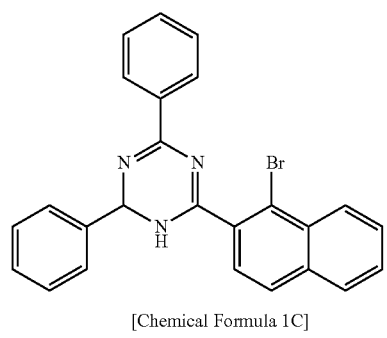

[Chemical Formula 1C]

-continued

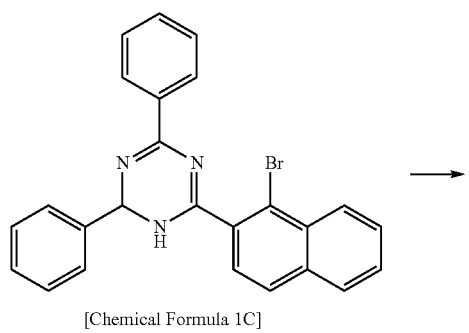

[Chemical Formula 1C]

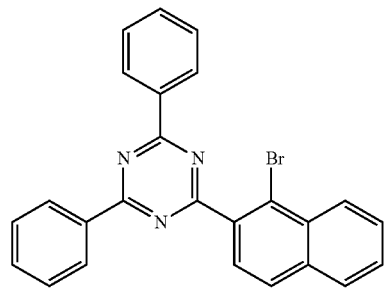

[Chemical Formula 1D]

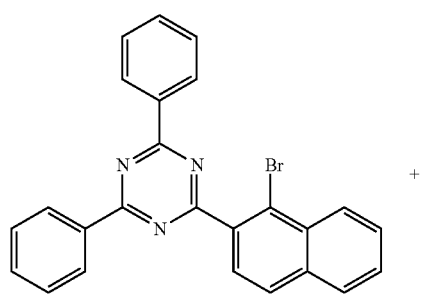

[Chemical Formula 1D]

+

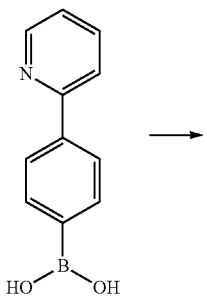

-continued

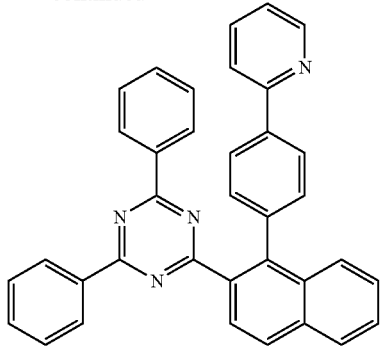

[Chemical Formula 5-11-1]

(1) Preparation of Chemical Formula 1C 1-bromo-2-naphthaldehyde (50 g, 212.7 mmol), benzamidine hydrochloride (100 g, 638.1 mmol) and potassium phosphate ($K_3PO_4$) (90.3 g, 425.3 mmol) were dissolved in dimethyl sulfoxide (DMSO) (500 ml), and the mixture was heated to 90° C. for 24 hours. The result was cooled to room temperature, and then filtered while washing with tetrahydrofuran (THF). The result was concentrated and purified using column chromatography to obtain Chemical Formula 1C (56 g, yield 60%).

MS: $[M+H]^+=439$ (2) Preparation of Chemical Formula 1D

After Chemical Formula 1C (50 g, 113.5 mmol) was dissolved in tetrahydrofuran (THF) (500 ml), the mixture was stirred while adding 2,3-dichloro-5,6-dicyano-1,4-benzoquinone (DDQ) (25.8 g, 113.5 mmol) thereto. After 3 hours, the result was concentrated and only the organic layer was extracted with chloroform and water. After the organic layer was concentrated, ethanol was added thereto to solidify, and the result was filtered to obtain Chemical Formula 1D (40 g, yield 80%).

MS: $[M+H]^+=437$ (3) Preparation of Chemical Formula 5-11-1

Chemical Formula 1D (10 g, 22.8 mmol), phenylpyridine boronic acid (4.5 g, 22.8 mmol) and potassium carbonate ($K_2CO_3$) (9.5 g, 68.4 mmol) were dissolved in tetrahydrofuran (THF) (200 mL) and $H_2O$ (70 ml), and the mixture was heated to 90° C. Tetrakis(triphenylphosphine) palladium ($Pd(PPh_3)_4$) (0.8 g, 0.68 mmol) was added thereto, and the result was refluxed for 4 hours. The result was cooled to room temperature, and the aqueous layer was removed. Magnesium sulfate ($MgSO_4$) was placed in the organic layer and was filtered off. The filtrate was concentrated and then purified using column chromatography to obtain Chemical Formula 5-11-1 (8 g, yield 68%).

MS: $[M+H]^+=512$

<Synthesis Example 21> Preparation of Compound Represented by Chemical Formula 6-11-1

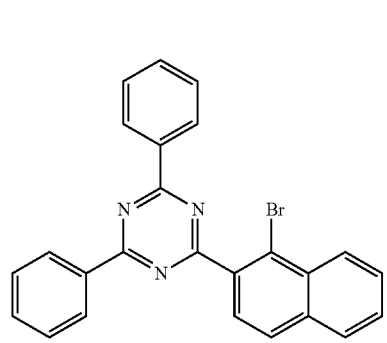

[Chemical Formula 1D]

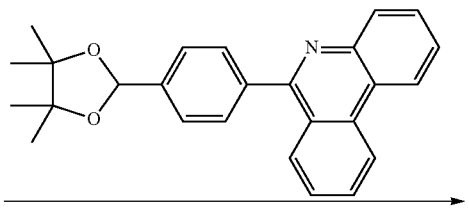

[Chemical Formula 6-11-1]

(1) Preparation of Chemical Formula 6-11-1

Chemical Formula 6-11-1 (10 g, yield 72%) was prepared in the same manner as in the preparation of Chemical Formula 5-11-1 of Synthesis Example 20, except that 6-(4-(4,4,5,5-tetramethyl-1,3-dioxolan-2-yl)phenyl)phenanthridine (8.7 g, 22.8 mmol) was used instead of phenylpyridine boronic acid.

MS: [M+H]⁺=612

<Synthesis Example 22> Preparation of Compound Represented by Chemical Formula 5-14-1

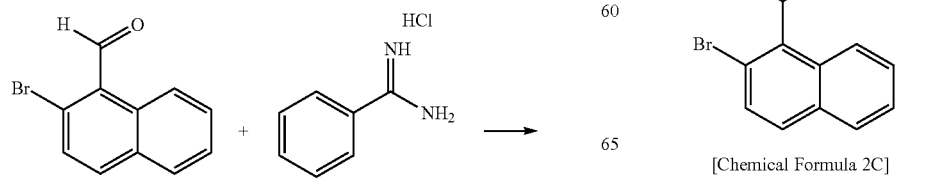

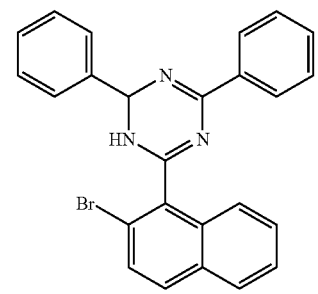

[Chemical Formula 2C]

[Chemical Formula 2C]

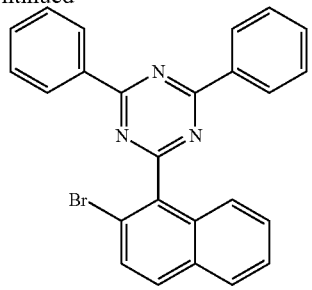

[Chemical Formula 2D]

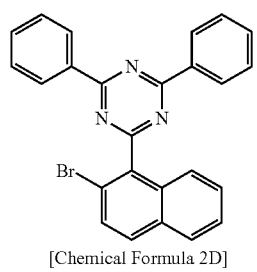

[Chemical Formula 2D]

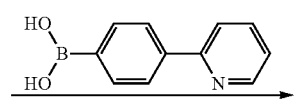

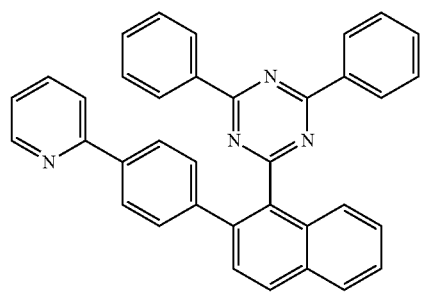

[Chemical Formula 5-14-1]

(1) Preparation of Chemical Formula 2C

Chemical Formula 2C (65.5 g, yield 70%) was prepared in the same manner as in the preparation of Chemical Formula 1C of Synthesis Example 20, except that 2-bromo-1-naphthaldehyde (50 g, 212.7 mmol) was used instead of 1-bromo-2-naphthaldehyde.

MS: [M+H]$^+$=439

(2) Preparation of Chemical Formula 2D

Chemical Formula 2D (42 g, yield 84%) was prepared in the same manner as in the preparation of Chemical Formula 1D of Synthesis Example 20, except that Chemical Formula 2C (50 g, 113.5 mmol) was used instead of Chemical Formula 10.

MS: [M+H]$^+$=437

(3) Preparation of Chemical Formula 5-14-1

Chemical Formula 5-14-1 (8.6 g, yield 67%) was prepared in the same manner as in the preparation of Chemical Formula 5-11-1 of Synthesis Example 20, except that Chemical Formula 2D (11 g, 25.1 mmol) was used instead of Chemical Formula 1D.

MS: [M+H]$^+$=512

<Synthesis Example 23> Preparation of Compound Represented by Chemical Formula 6-14-1

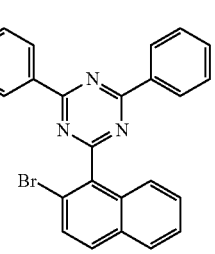
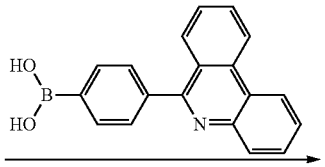

[Chemical Formula 2D]

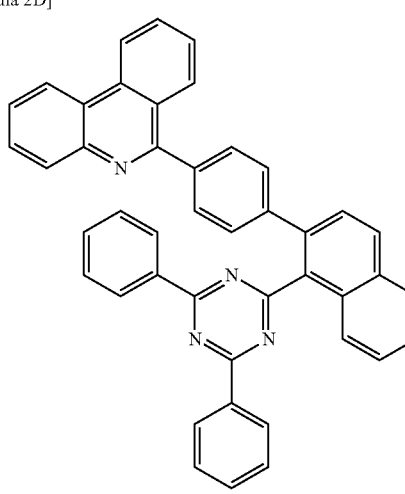

[Chemical Formula 6-14-1]

(1) Preparation of Chemical Formula 6-14-1

Chemical Formula 6-14-1 (9.5 g, yield 68%) was prepared in the same manner as in the preparation of Chemical Formula 5-14-1 of Synthesis Example 22, except that 6-(4-(4,4,5,5-tetramethyl-1,3-dioxolan-2-yl)phenyl)phenanthridine (8.7 g, 22.8 mmol) was used instead of diphenylpyridine boronic acid.

MS: [M+H]$^+$=612

Example 1

A glass substrate (corning 7059 glass) on which indium tin oxide (ITO) was coated as a thin film to a thickness of 1,000 Å was placed in distilled water, in which a dispersant is dissolved, and ultrasonic cleaned. As a detergent, a product of Fischer Corporation was used, and as the distilled water, distilled water filtered twice with a filter manufactured by Millipore Corporation was used. After the ITO was cleaned for minutes, ultrasonic cleaning was repeated twice for 10 minutes using distilled water. After the cleaning with distilled water was finished, ultrasonic cleaning was performed with isopropyl alcohol, acetone and methanol solvents in this order, and the substrate was dried.

On the transparent ITO electrode prepared as above, a hole injection layer was formed to a thickness of 500 Å by thermal vacuum depositing hexanitrile hexazatriphenylene. HT1 (400 Å), which is a hole transfer material, was vacuum deposited on the hole injection layer, and then a host H1 compound and a dopant D1 compound were vacuum deposited to a thickness of 300 Å as a light emitting layer. On the light emitting layer, an electron injection and transfer layer was formed to a thickness of 350 Å by vacuum depositing Chemical Formula 2-1-1 and a lithium quinolate (LiQ) compound prepared in Preparation Example 1 in the weight ratio of 1:1. A cathode was formed on the electron injection and transfer layer by depositing lithium fluoride (LiF) to a thickness of 12 Å and aluminum to a thickness of 2,000 Å in consecutive order. As a result, the organic light emitting device was manufactured.

In the above process, the deposition rate of the organic material was maintained at 0.4 to 0.7 Å/sec, the deposition rate of lithium fluoride of the cathode at 0.3 Å/sec, and the deposition rate of aluminum at 2 Å/sec, and the degree of vacuum when being deposited was maintained at $2 \times 10^{-7}$ to $5 \times 10^{-6}$ torr, and as a result, the organic light emitting device was manufactured.

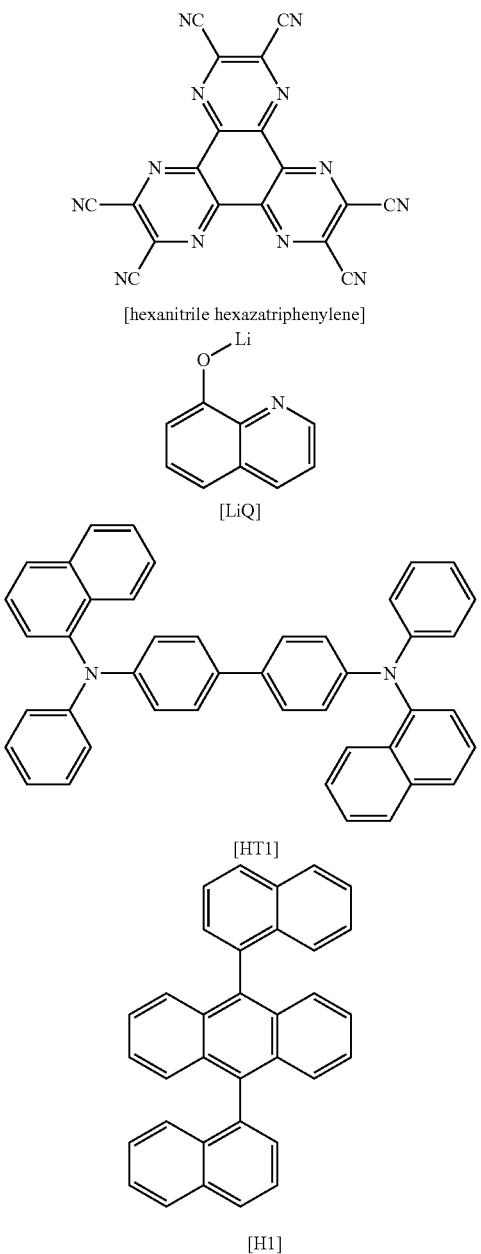

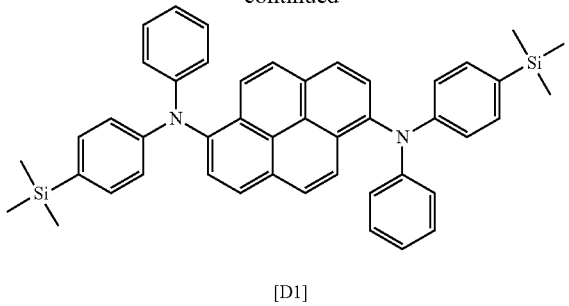

[D1]

Example 2

The experiment was carried out in the same manner as in Example 1 except that Chemical Formula 2-1-2 was used instead of Chemical Formula 2-1-1 as the electron transfer layer.

Example 3

The experiment was carried out in the same manner as in Example 1 except that Chemical Formula 2-8-1 was used instead of Chemical Formula 2-1-1 as the electron transfer layer.

Example 4

The experiment was carried out in the same manner as in Example 1 except that Chemical Formula 2-8-2 was used instead of Chemical Formula 2-1-1 as the electron transfer layer.

Example 5

The experiment was carried out in the same manner as in Example 1 except that Chemical Formula 2-12-1 was used instead of Chemical Formula 2-1-1 as the electron transfer layer.

Example 6

The experiment was carried out in the same manner as in Example 1 except that Chemical Formula 2-12-2 was used instead of Chemical Formula 2-1-1 as the electron transfer layer.

Example 7

The experiment was carried out in the same manner as in Example 1 except that Chemical Formula 3-1-1 was used instead of Chemical Formula 2-1-1 as the electron transfer layer.

Example 8

The experiment was carried out in the same manner as in Example 1 except that Chemical Formula 3-1-3 was used instead of Chemical Formula 2-1-1 as the electron transfer layer.

Example 9

The experiment was carried out in the same manner as in Example 1 except that Chemical Formula 3-1-5 was used instead of Chemical Formula 2-1-1 as the electron transfer layer.

Example 10

The experiment was carried out in the same manner as in Example 1 except that Chemical Formula 3-8-1 was used instead of Chemical Formula 2-1-1 as the electron transfer layer.

Example 11

The experiment was carried out in the same manner as in Example 1 except that Chemical Formula 3-12-1 was used instead of Chemical Formula 2-1-1 as the electron transfer layer.

Example 12

The experiment was carried out in the same manner as in Example 1 except that Chemical Formula 3-8-3 was used instead of Chemical Formula 2-1-1 as the electron transfer layer.

Example 13

The experiment was carried out in the same manner as in Example 1 except that Chemical Formula 3-12-3 was used instead of Chemical Formula 2-1-1 as the electron transfer layer.

Example 14

The experiment was carried out in the same manner as in Example 1 except that Chemical Formula 3-8-5 was used instead of Chemical Formula 2-1-1 as the electron transfer layer.

Example 15

The experiment was carried out in the same manner as in Example 1 except that Chemical Formula 3-12-5 was used instead of Chemical Formula 2-1-1 as the electron transfer layer.

Example 16

The experiment was carried out in the same manner as in Example 1 except that Chemical Formula 2-2-1 was used instead of Chemical Formula 2-1-1 as the electron transfer layer.

Example 17

The experiment was carried out in the same manner as in Example 1 except that Chemical Formula 2-3-1 was used instead of Chemical Formula 2-1-1 as the electron transfer layer.

Example 18

The experiment was carried out in the same manner as in Example 1 except that Chemical Formula 2-4-1 was used instead of Chemical Formula 2-1-1 as the electron transfer layer.

Example 19

The experiment was carried out in the same manner as in Example 1 except that Chemical Formula 2-5-1 was used instead of Chemical Formula 2-1-1 as the electron transfer layer.

Example 20

The experiment was carried out in the same manner as in Example 1 except that Chemical Formula 5-11-1 was used instead of Chemical Formula 2-1-1 as the electron transfer layer.

Example 21

The experiment was carried out in the same manner as in Example 1 except that Chemical Formula 5-14-1 was used instead of Chemical Formula 2-1-1 as the electron transfer layer.

Example 22

The experiment was carried out in the same manner as in Example 1 except that Chemical Formula 6-11-1 was used instead of Chemical Formula 2-1-1 as the electron transfer layer.

Example 23

The experiment was carried out in the same manner as in Example 1 except that Chemical Formula 6-14-1 was used instead of Chemical Formula 2-1-1 as the electron transfer layer.

Comparative Example 1

The organic light emitting device was manufactured in the same manner as in Example 1, except that the following ET1 compound was used instead of Chemical Formula 2-1-1.

[ET1]

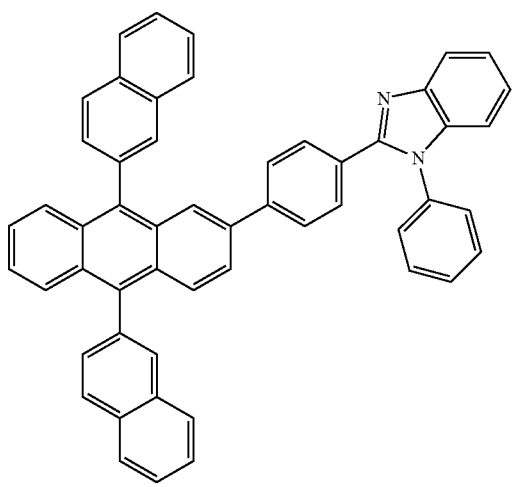

Comparative Example 2

The organic light emitting device was manufactured in the same manner as in Example 1, except that the following ET2 compound was used instead of Chemical Formula 2-1-1.

[ET2]

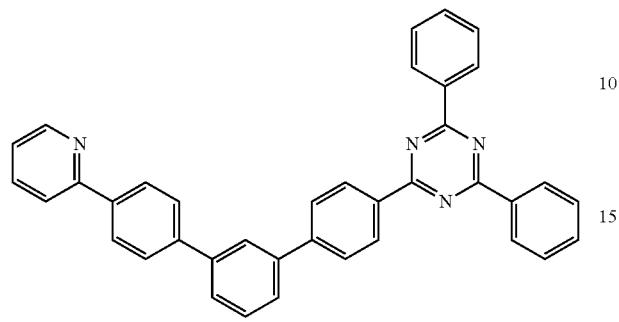

Comparative Example 3

The organic light emitting device was manufactured in the same manner as in Example 1, except that the following ET3 compound was used instead of Chemical Formula 2-1-1.

[ET3]

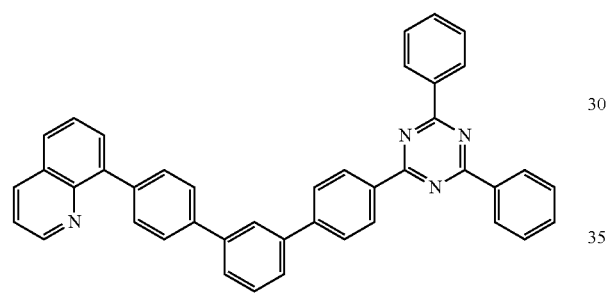

Comparative Example 4

The organic light emitting device was manufactured in the same manner as in Example 1, except that the following ET4 compound was used instead of Chemical Formula 2-1-1.

[ET4]

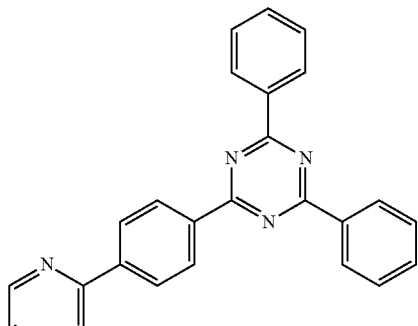

Comparative Example 5

The organic light emitting device was manufactured in the same manner as in Example 1, except that the following ET5 compound was used instead of Chemical Formula 2-1-1.

[ET5]

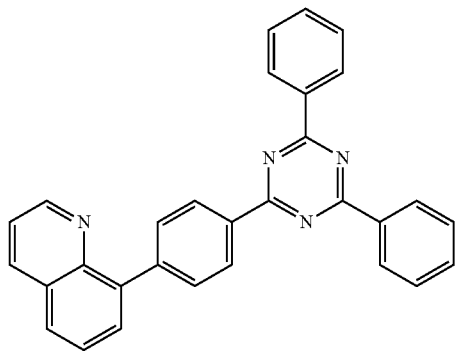

Comparative Example 6

The organic light emitting device was manufactured in the same manner as in Example 1, except that the following ET6 compound was used instead of Chemical Formula 2-1-1.

[ET6]

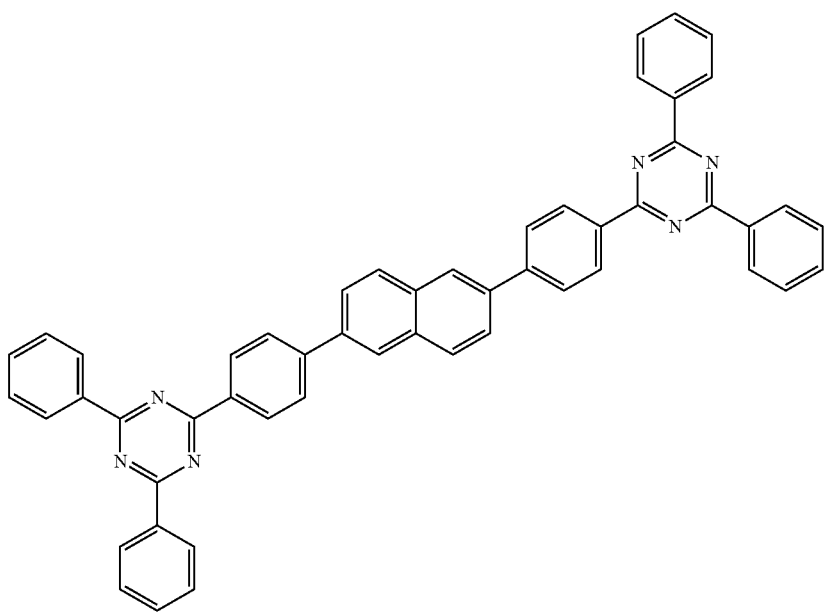

The results of the experiments carried out on the organic light emitting devices prepared using each compound as an electron transfer layer material, as in Examples 1 to 15 and Comparative Examples 1 to Comparative Example 6, are shown in Table 1.

TABLE 1

| Example 10 mA/cm$^2$ | Compound | Voltage (V) | Current Efficiency (cd/A) | Color Coordinate (x, y) |
|---|---|---|---|---|
| Example 1 | Chemical Formula 2-1-1 | 3.71 | 5.27 | (0.137, 0.124) |
| Example 2 | Chemical Formula 2-1-2 | 3.99 | 5.41 | (0.139, 0.124) |
| Example 3 | Chemical Formula 2-8-1 | 4.01 | 5.47 | (0.138, 0.127) |
| Example 4 | Chemical Formula 2-8-2 | 3.90 | 5.35 | (0.138, 0.129) |
| Example 5 | Chemical Formula 2-12-1 | 3.75 | 5.24 | (0.137, 0.126) |
| Example 6 | Chemical Formula 2-12-2 | 3.88 | 5.30 | (0.137, 0.124) |
| Example 7 | Chemical Formula 3-1-1 | 3.98 | 5.24 | (0.137, 0.126) |
| Example 8 | Chemical Formula 3-1-3 | 4.10 | 5.55 | (0.137, 0.126) |
| Example 9 | Chemical Formula 3-1-5 | 4.05 | 5.58 | (0.137, 0.126) |
| Example 10 | Chemical Formula 3-8-1 | 3.71 | 5.44 | (0.137, 0.126) |
| Example 11 | Chemical Formula 3-12-1 | 3.98 | 5.20 | (0.137, 0.126) |
| Example 12 | Chemical Formula 3-8-3 | 4.02 | 5.51 | (0.137, 0.126) |
| Example 13 | Chemical Formula 3-12-3 | 4.11 | 5.60 | (0.137, 0.126) |
| Example 14 | Chemical Formula 3-8-5 | 4.05 | 5.48 | (0.137, 0.126) |
| Example 15 | Chemical Formula 3-12-5 | 4.07 | 5.61 | (0.137, 0.126) |
| Example 16 | Chemical Formula 2-2-1 | 3.87 | 5.49 | (0.138, 0.129) |
| Example 17 | Chemical Formula 2-3-1 | 3.99 | 5.21 | (0.137, 0.126) |
| Example 18 | Chemical Formula 2-4-1 | 4.05 | 5.38 | (0.137, 0.124) |
| Example 19 | Chemical Formula 2-5-1 | 3.92 | 5.26 | (0.137, 0.126) |
| Example 20 | Chemical Formula 5-11-1 | 3.97 | 5.50 | (0.137, 0.126) |
| Example 21 | Chemical Formula 5-14-1 | 4.03 | 5.48 | (0.137, 0.126) |
| Example 22 | Chemical Formula 6-11-1 | 3.98 | 5.52 | (0.137, 0.126) |
| Example 23 | Chemical Formula 6-14-1 | 4.01 | 5.47 | (0.137, 0.126) |
| Comparative Example 1 | ET1 | 4.00 | 5.01 | (0.140, 0.129) |
| Comparative Example 2 | ET2 | 4.01 | 5.13 | (0.140, 0.129) |
| Comparative Example 3 | ET3 | 4.21 | 5.22 | (0.139, 0.129) |
| Comparative Example 4 | ET4 | 3.95 | 4.7 | (0.137, 0.126) |
| Comparative Example 5 | ET5 | 4.1 | 5.10 | (0.140, 0.126) |
| Comparative Example 6 | ET6 | 4.20 | 5.01 | (0.139, 0.127) |

As seen from Table 1, the organic light emitting device prepared using the compound of the present specification as an electron transfer layer has superior properties in efficiency, driving voltage, and stability when compared to cases using existing materials.

When comparing Examples 1 to 15 and Comparative Examples 2 to 3 of Table 1, it is verified that an organic light emitting device having low voltage and/or high efficiency is provided when a naphthyl group is included as a linker of Ar1 and a nitrogen-containing ring group including X1 to X3 compared to when a monocyclic aromatic hydrocarbon group such as a phenyl group is included. When a naphthyl group is included as a linker of Ar1 and a nitrogen-containing ring group including X1 to X3, the LUMO orbital distribution is wider compared to a case including a monocyclic aromatic hydrocarbon ring such as phenyl, which leads to the lowering of an LUMO energy level, and as a result, electron transfer and injection abilities are superior. In addition, abundant pi-conjugated electrons of a naphthyl group itself may contribute to the increase of charge mobility of materials.

In addition, as seen in Table 1, it is verified that Examples 1 to 15, in which Ar1 and a nitrogen-containing ring group including X1 to X3 are different from each other, and a triazine group is a symmetric skeleton, exhibit low voltage and/or high efficiency, compared to Comparative Example 6 in which a nitrogen-containing ring group including X1 to X3 and Ar1 are the same as each other. This basically shows that an asymmetric structure is capable of forming a uniform thin film in a deposition process compared to a symmetric structure. Therefore, a device including the hetero-cyclic compound according to one embodiment of the present specification has excellent charge mobility. Furthermore, the hetero-cyclic compound according to one embodiment of the present specification has a high dipole moment value due to electrophysical asymmetry. It may be analyzed such that the hetero-cyclic compound according to one embodiment having a high dipole moment value has properties improving high electron transfer abilities in a device.

In addition, when comparing Examples 1 to 15 and Comparative Examples 4 to 5 of Table 1, it is observed that when two or more linkers including divalent naphthalene is included between Ar1 and a nitrogen-containing ring group including X1 to X3, efficiency increases compared to cases including one linker. When one linker is included between Ar1 and a nitrogen-containing ring group including X1 to X3, the LUMO energy level becomes too low due to the short distance between the two nitrogen-containing ring groups, therefore, the energy barrier between an electron transfer layer and a light emitting layer becomes large, which eventually leads to efficiency decrease. Therefore, according to one embodiment of the present invention, efficiency increase may be induced by lowering the energy barrier between an electron transfer layer and a light emitting layer when two or more linkers including divalent naphthalene are included.

Consequently, when two or more linkers including a naphthyl group are included between Ar1 and a nitrogen-containing ring group including X1 to X3, the LUMO energy level becoming too low due to the short distance between the two nitrogen-containing ring groups may be prevented. In this case, efficiency may be increased by lowering the energy barrier between an electron transfer layer and a light emitting layer.

The invention claimed is:

1. A hetero-cyclic compound represented by the following Chemical Formula 1:

[Chemical Formula 1]

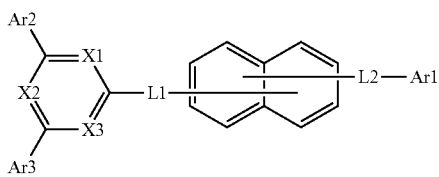

wherein, in Chemical Formula 1,

L1 is a substituted or unsubstituted arylene group; or a substituted or unsubstituted alkenylene group, L2 is a substituted or unsubstituted arylene group; or a substituted or unsubstituted alkenylene group, and when L1 or L2 is a phenylene group, L1 or L2 is a para-phenylene group;

X1 to X3 are the same as or different from each other, and each independently N or CH, and at least one of X1 to X3 is N;

Ar2 and Ar3 are the same as or different from each other and each independently a substituted or unsubstituted aryl group; or a substituted or unsubstituted heteroring group;

Ar1 is represented by any one of the following Chemical Formula 3 to Chemical Formula 4,

[Chemical Formula 3]

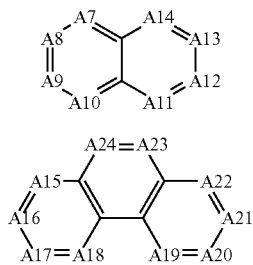

[Chemical Formula 4]

wherein, in Chemical Formula 3 to 4, at least one of A7 to A14 is N, another is a carbon atom linking to L2, and the rest is CR;

at least one of A15 to A24 is N, another is a carbon atom linking to L2, and the rest is CR;

CRs that are not N or a carbon atom linking to L2 among A7 to A24 are the same as or different from each other;

R is hydrogen; a substituted or unsubstituted aryl group; or a substituted or unsubstituted heteroring group; and

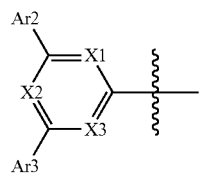

and Ar1 are different from each other.

2. The hetero-cyclic compound of claim 1, wherein the compound represented by Chemical Formula 1 is represented by any one of the following Chemical Formulae 1-1 to 1-8:

[Chemical Formula 1-1]

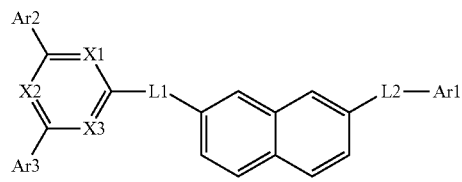

[Chemical Formula 1-2]

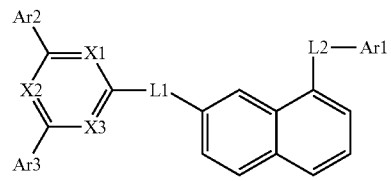

[Chemical Formula 1-3]

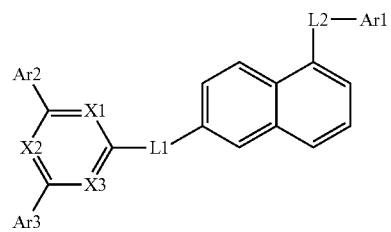

[Chemical Formula 1-4]

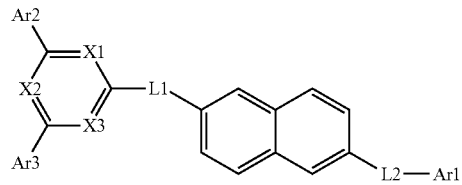

[Chemical Formula 1-5]

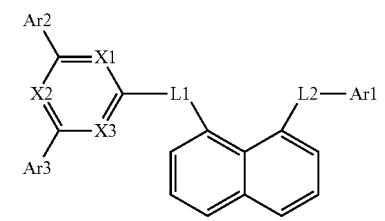

[Chemical Formula 1-6]

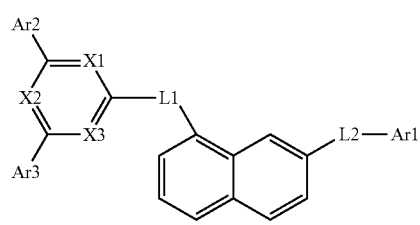

[Chemical Formula 1-7]

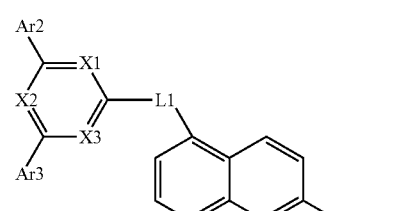

[Chemical Formula 1-8]

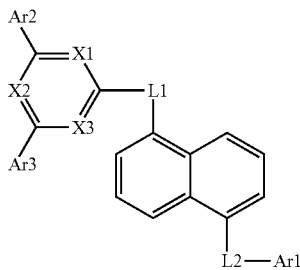

wherein, in Chemical Formulae 1-1 to 1-8, Ar1, Ar2, Ar3, X1 to X3, and L1 and L2 are the same as those defined in Chemical Formula 1.

3. The hetero-cyclic compound of claim 1, wherein the hetero-cyclic compound represented by Chemical Formula 1 is represented by any one of the following Chemical Formulae 1-9 to 1-14:

[Chemical Formula 1-9]

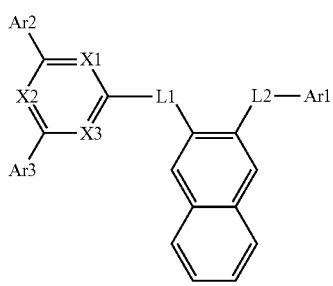

[Chemical Formula 1-10]

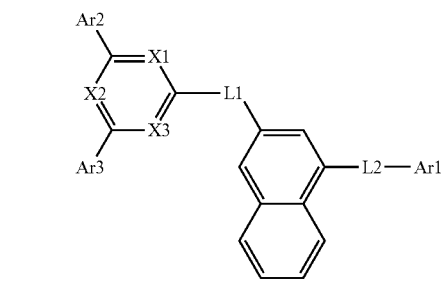

[Chemical Formula 1-11]

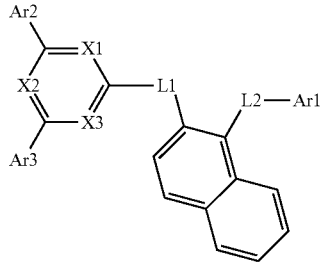

[Chemical Formula 1-12]

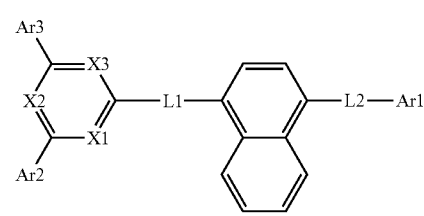

[Chemical Formula 1-13]

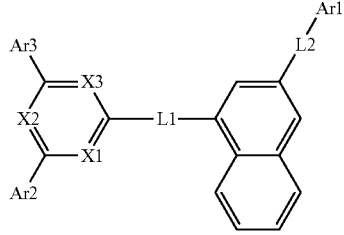

[Chemical Formula 1-14]

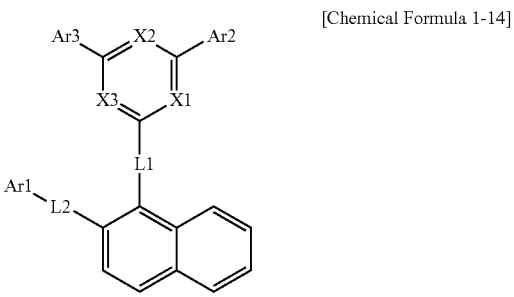

wherein, in Chemical Formulae 1-9 to 1-14, Ar1, Ar2, Ar3, X1 to X3, and L1 and L2 are the same as those defined in Chemical Formula 1.

4. The hetero-cyclic compound of claim 1, wherein Ar1 is any one of the following structures:

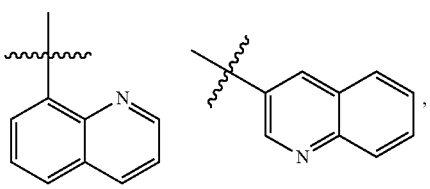 [SMILES: *c1cccc2cccnc12 ; *c1cnc2ccccc2c1]

wherein the structure is unsubstituted or substituted with one, two or more substituents selected from the group consisting of a substituted or unsubstituted aryl group; and a substituted or unsubstituted heteroring group.

5. The hetero-cyclic compound of claim 1, wherein Ar1 is the following structure:

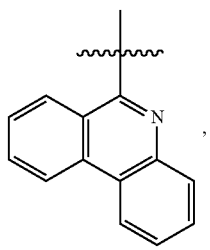 [SMILES: *c1nc2ccccc2c2ccccc12]

wherein the structure is unsubstituted or substituted with one, two or more substituents selected from the group consisting of a substituted or unsubstituted aryl group; and a substituted or unsubstituted heteroring group.

6. The hetero-cyclic compound of claim 1, wherein L1 and L2 are the same as or different from each other, and each independently a substituted or unsubstituted arylene group.

7. The hetero-cyclic compound of claim 1, wherein L1 is a direct bond, and L2 is a substituted or unsubstituted arylene group.

8. The hetero-cyclic compound of claim 1, wherein Ar2 and Ar3 are the same as or different from each other, and each independently a substituted or unsubstituted phenyl group; a substituted or unsubstituted biphenyl group; or a substituted or unsubstituted naphthyl group.

9. The hetero-cyclic compound of claim 1, wherein R is hydrogen; or a substituted or unsubstituted aryl group.

10. A hetero-cyclic compound represented by any one of the following formulae:

[formula 3-1-1]

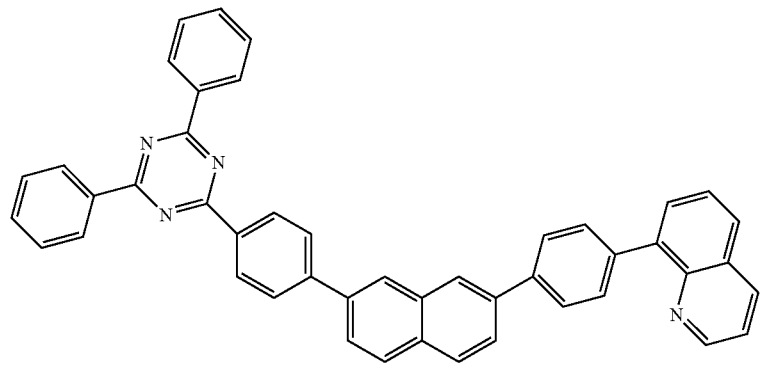

[formula 3-1-2]

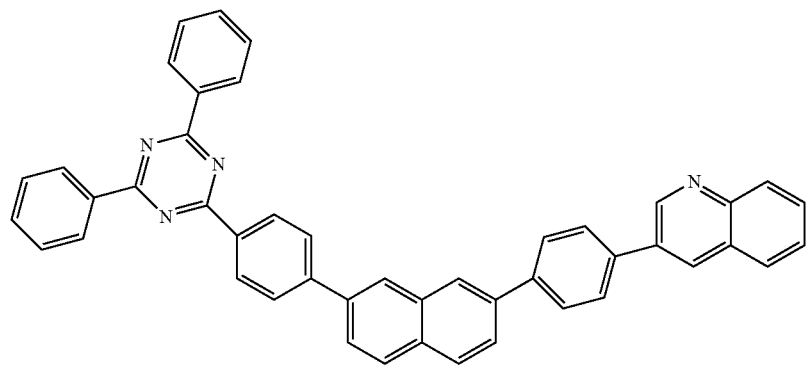

[formula 3-1-3]

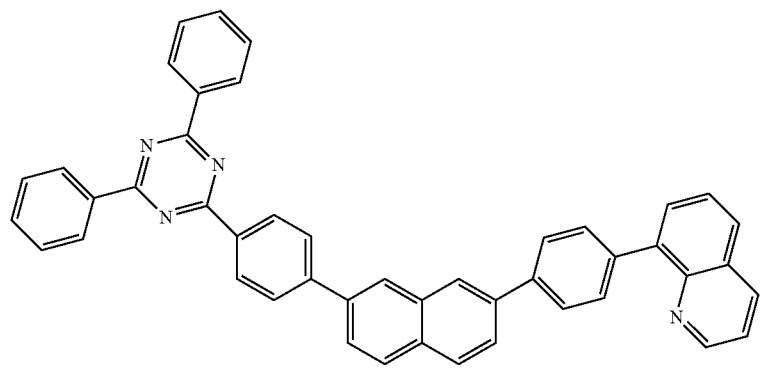

[formula 3-1-4]

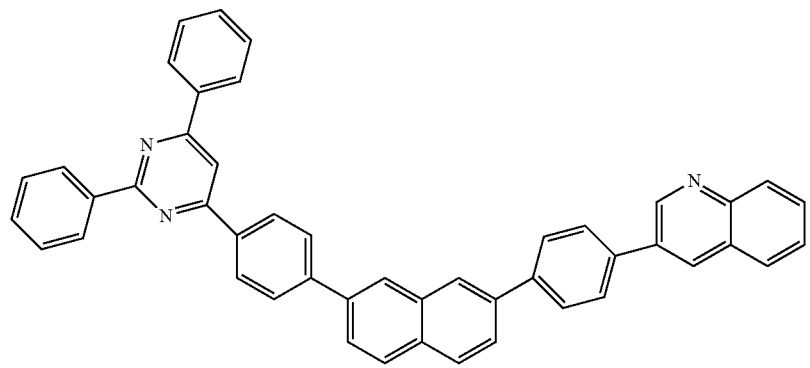

[formula 3-1-5]
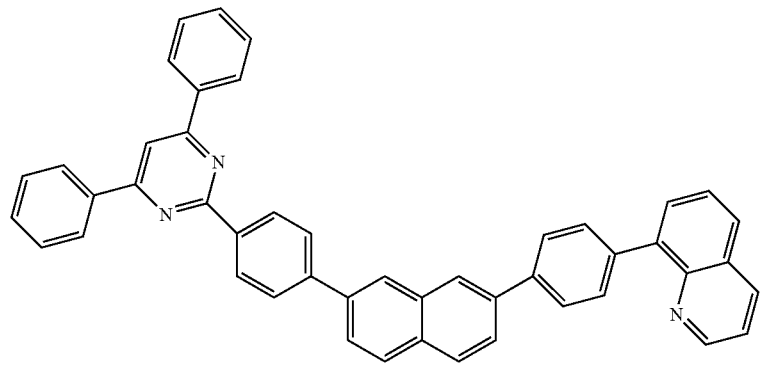
[formula 3-1-6]
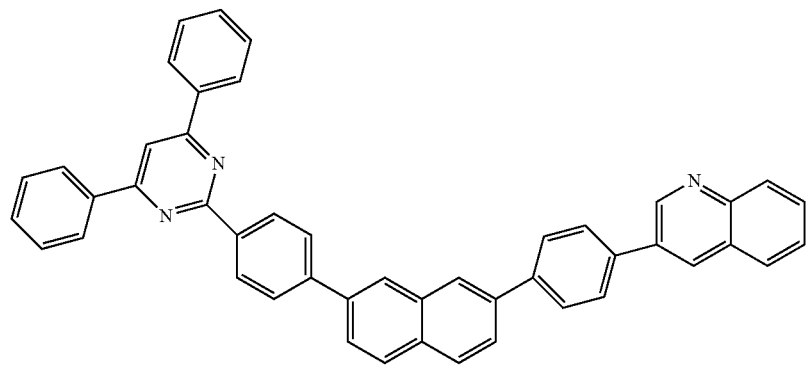
[formula 3-2-1]
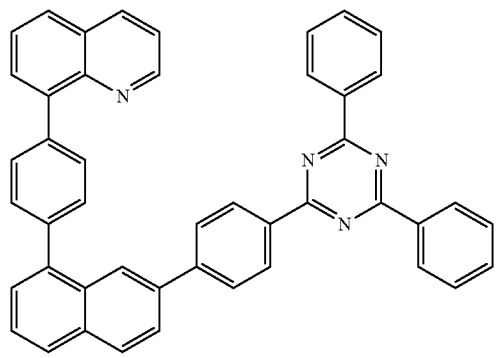
[formula 3-2-2]
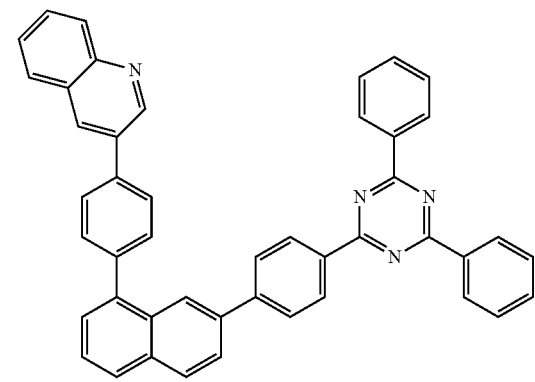
[formula 3-2-3]
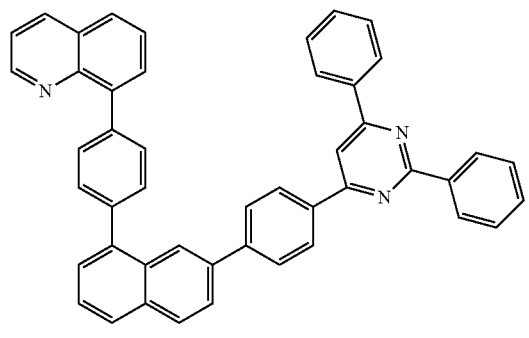
[formula 3-2-4]
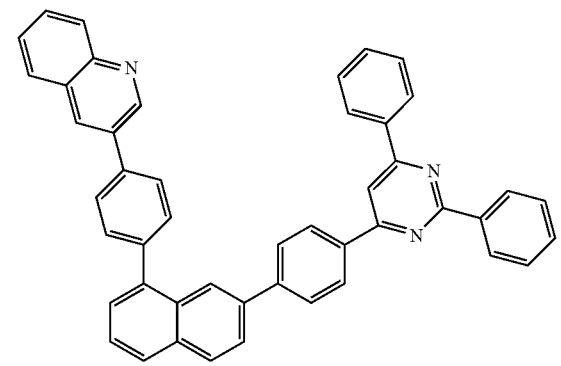

[formula 3-2-5]
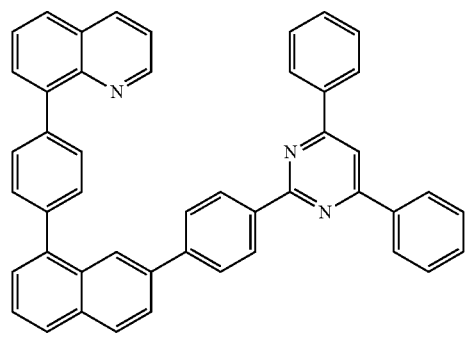
[formula 3-2-6]
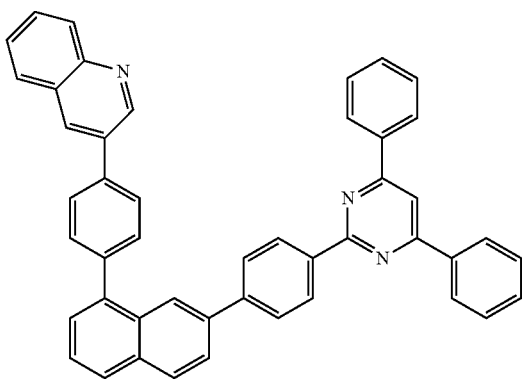
[formula 3-3-1]
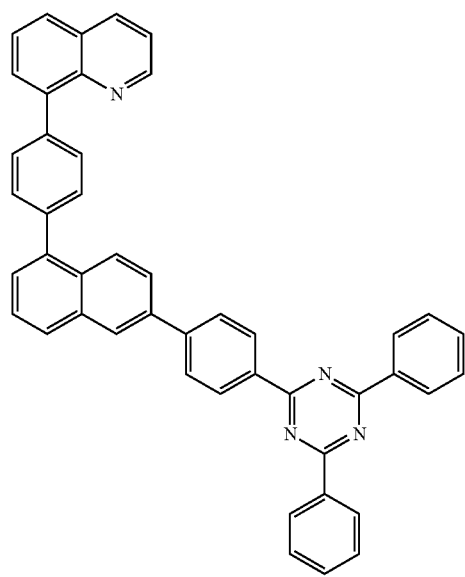
[formula 3-3-2]
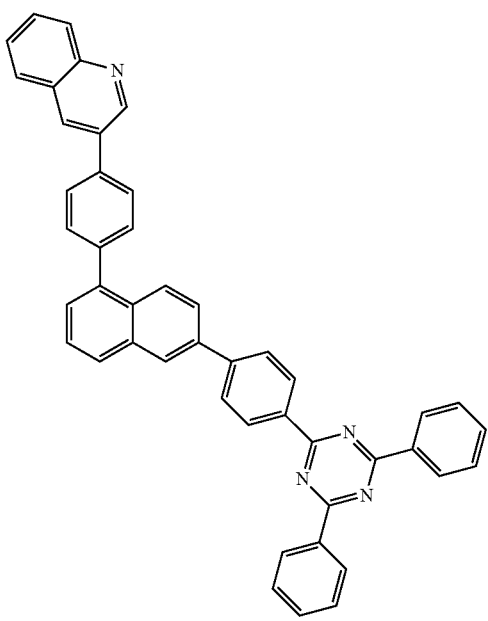

[formula 3-3-3]
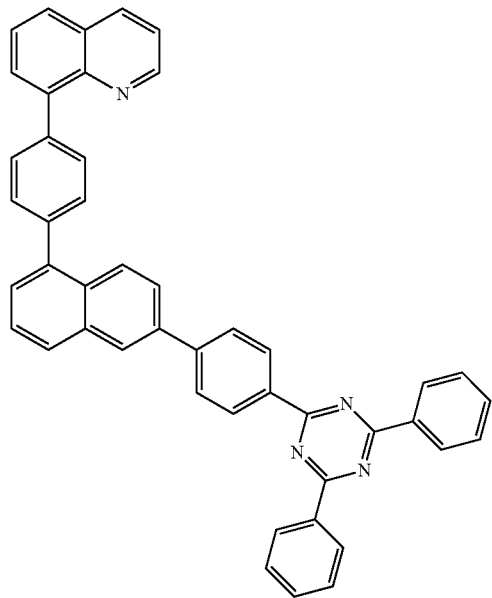
[formula 3-3-4]
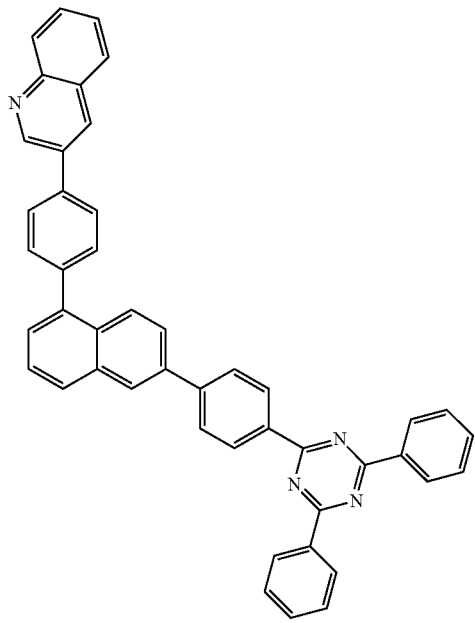
[formula 3-3-5]
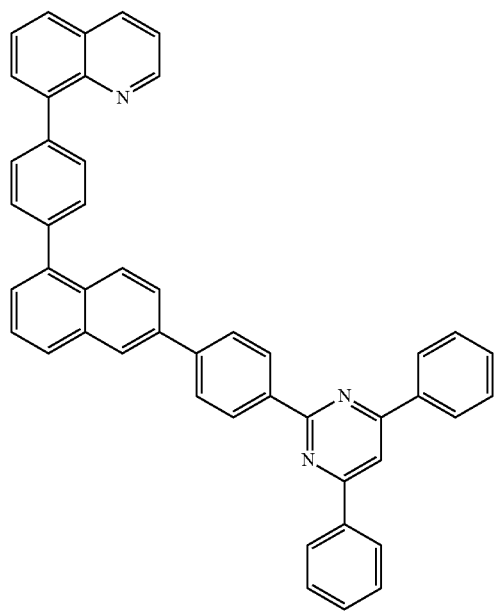
[formula 3-3-6]
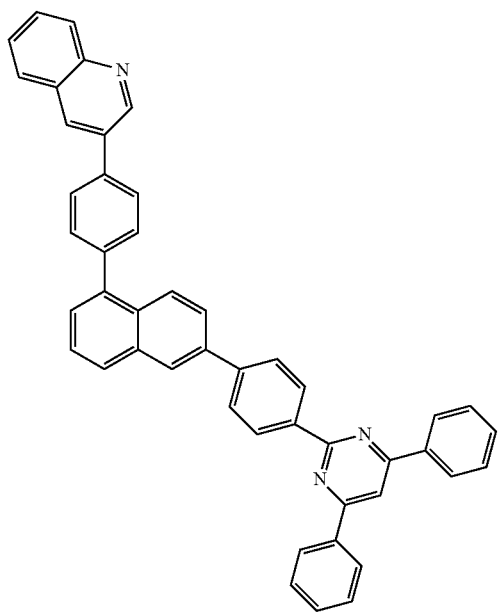

-continued
[formula 3-4-1]
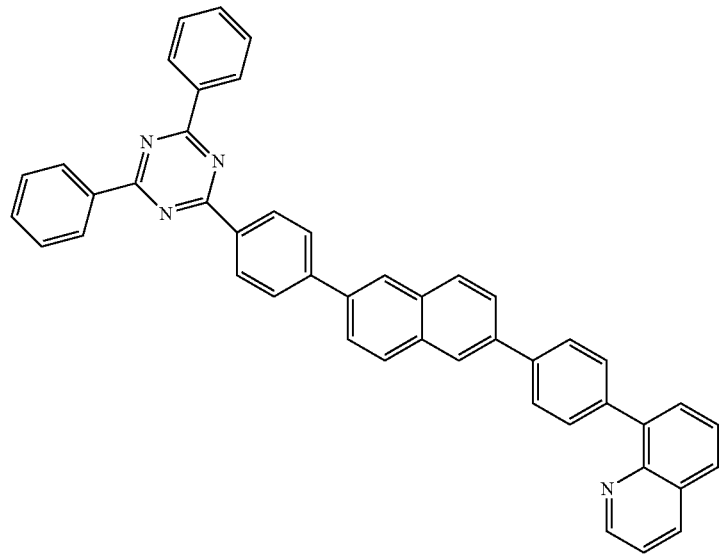
[formula 3-4-1]
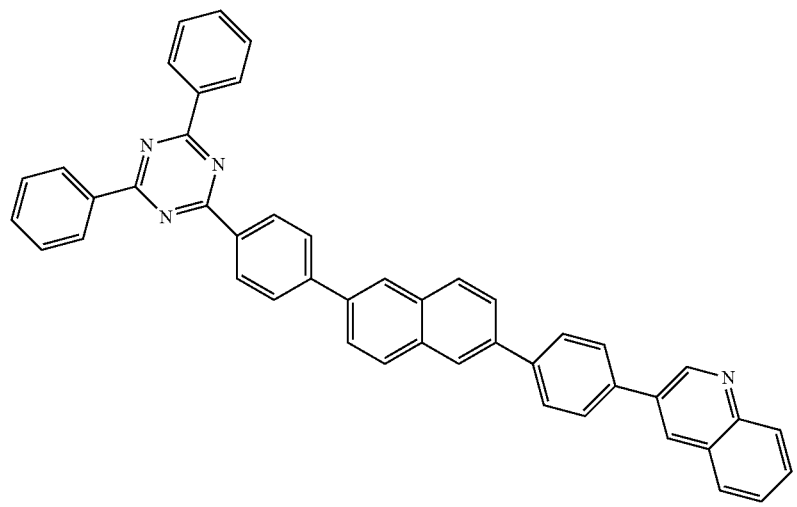
[formula 3-4-3]
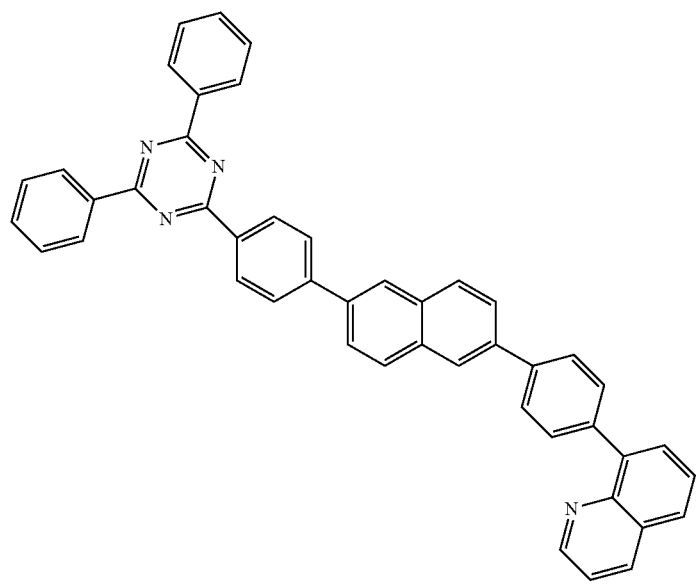

[formula 3-4-4]
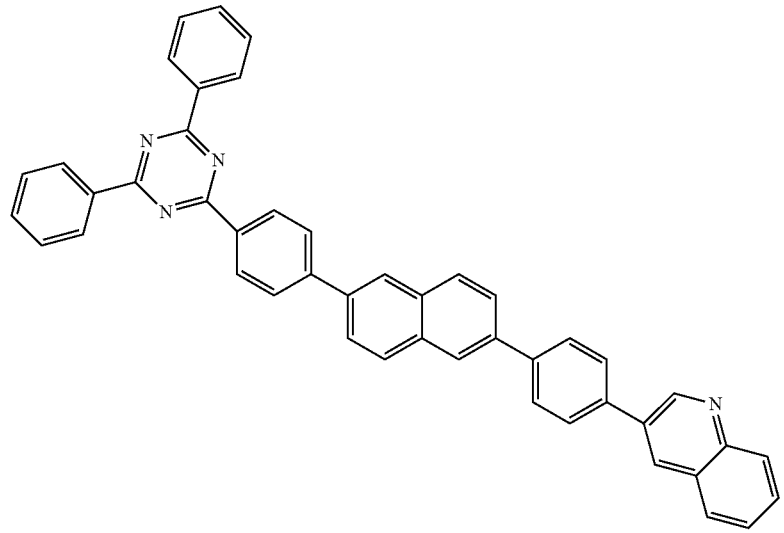
[formula 3-4-5]
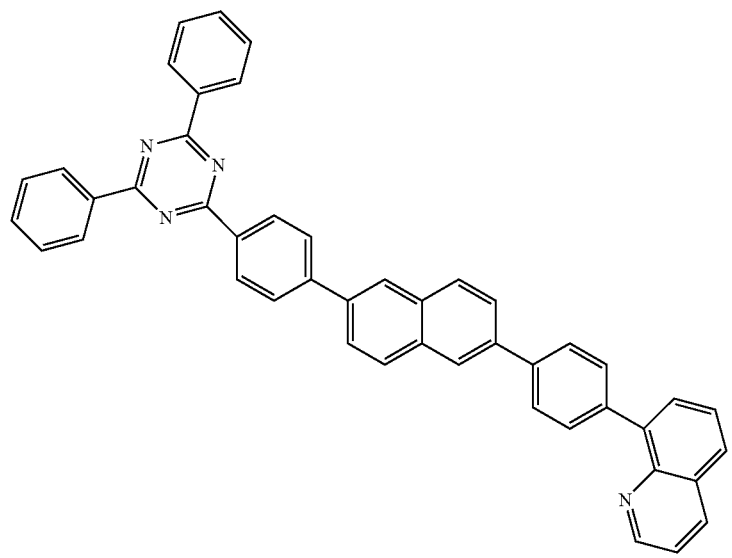
[formula 3-4-6]
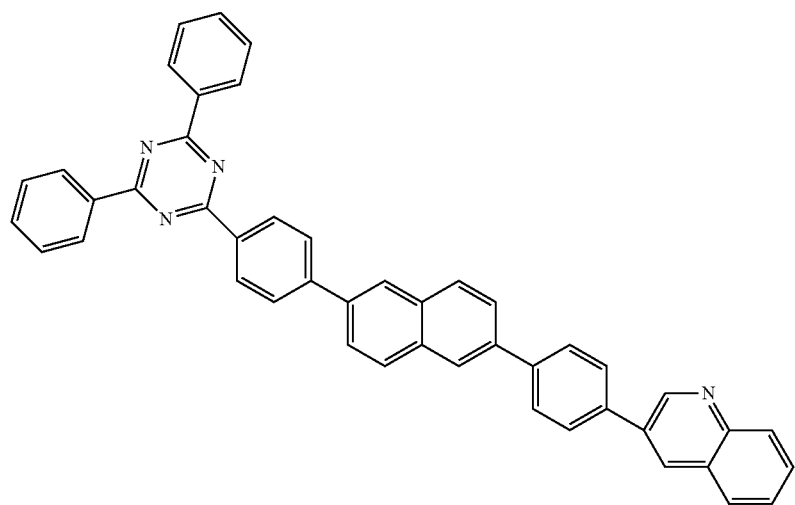

-continued
[formula 3-5-1]
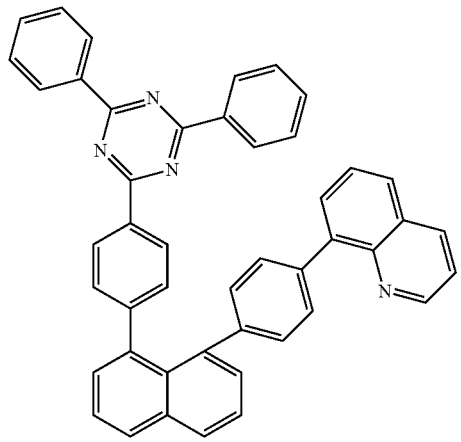
[formula 3-5-2]
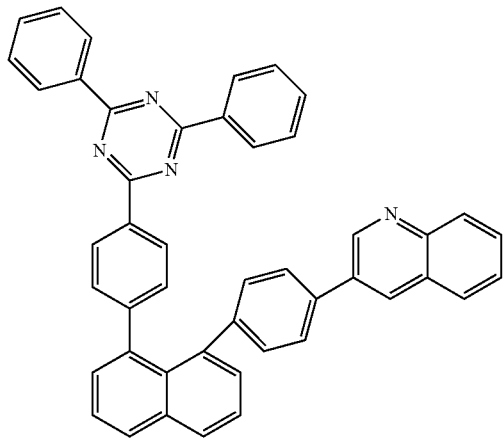
[formula 3-5-3]
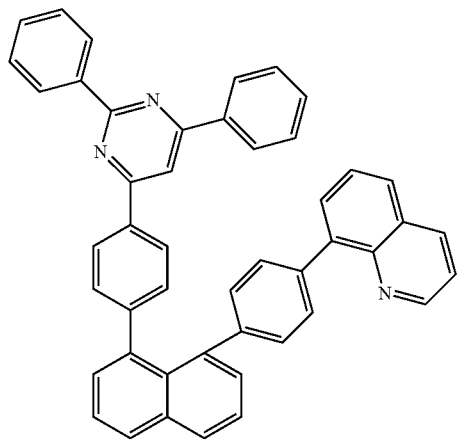
[formula 3-5-4]
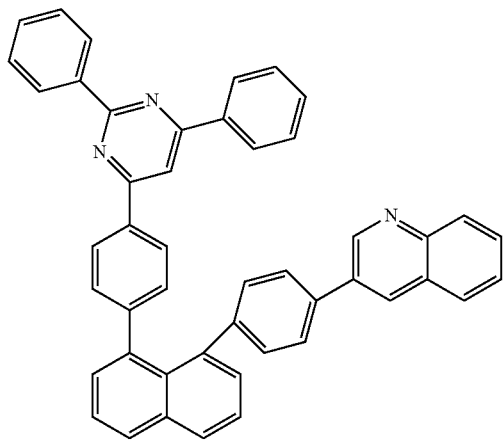
[formula 3-5-5]
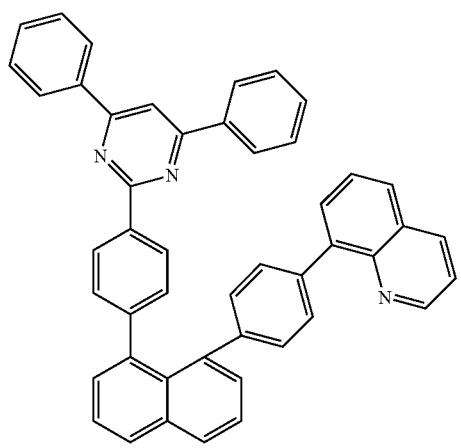
[formula 3-5-6]
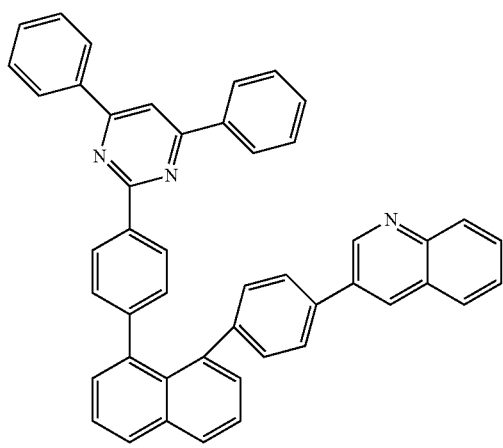

-continued
[formula 3-6-1]
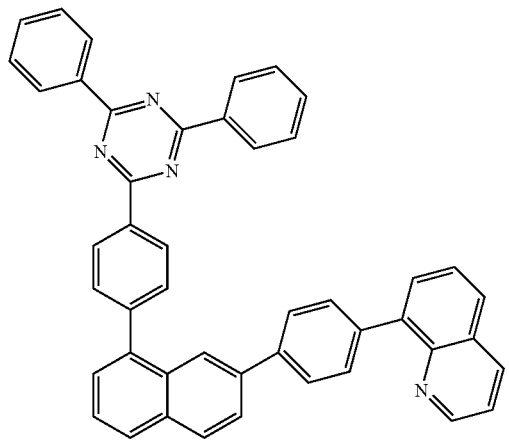
[formula 3-6-2]
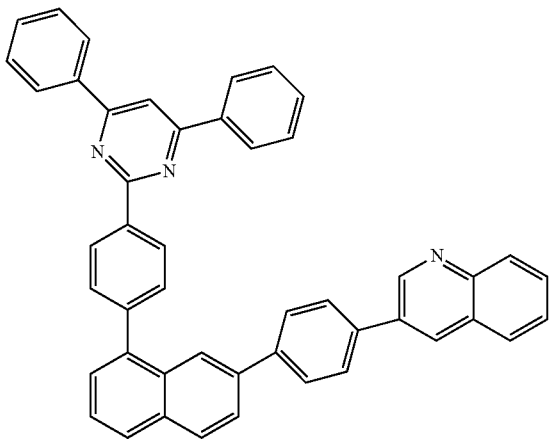
[formula 3-6-3]
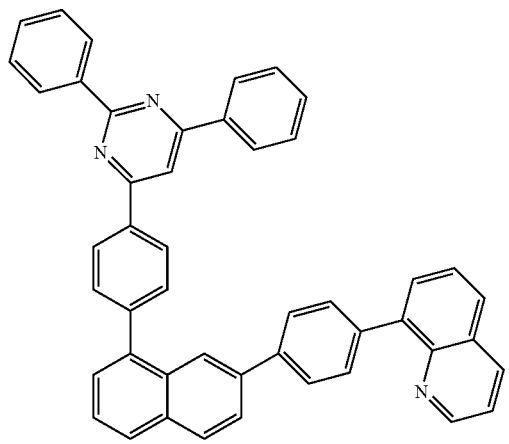
[formula 3-6-4]
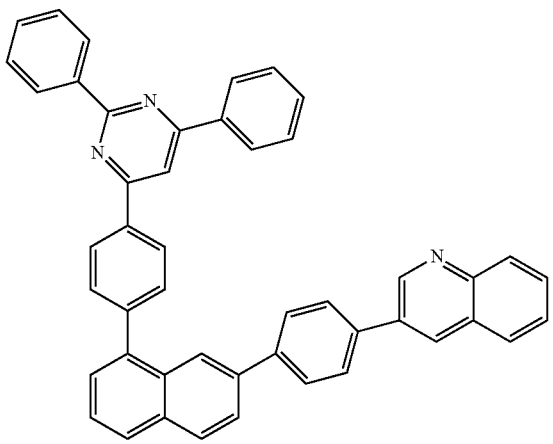
[formula 3-6-5]
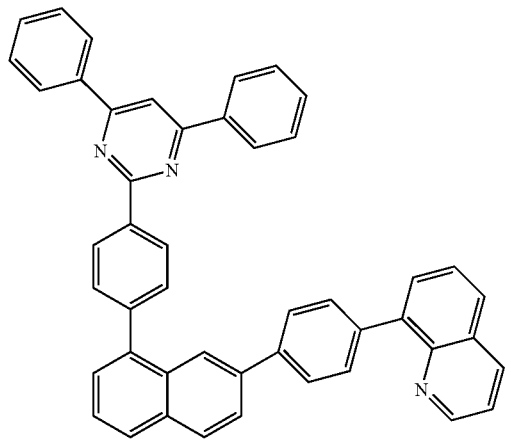
[formula 3-6-6]
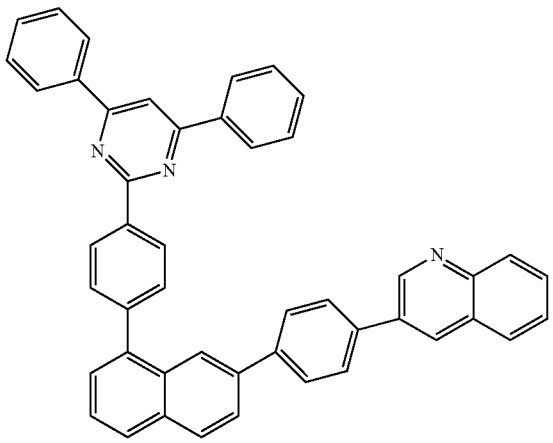

-continued
[formula 3-7-1]
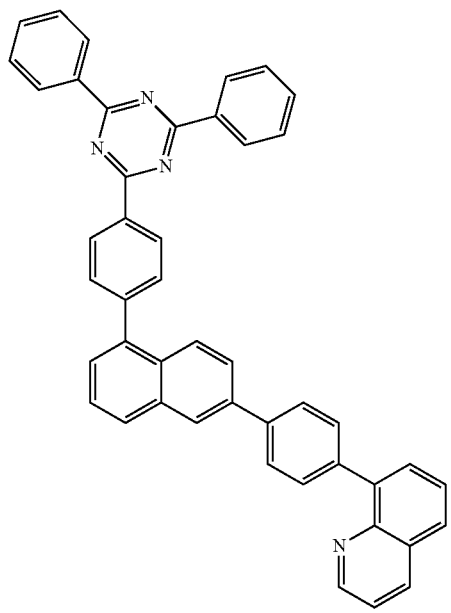
[formula 3-7-2]
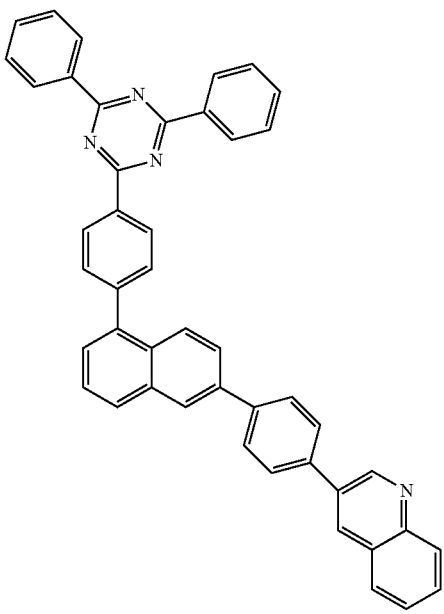
[formula 3-7-3]
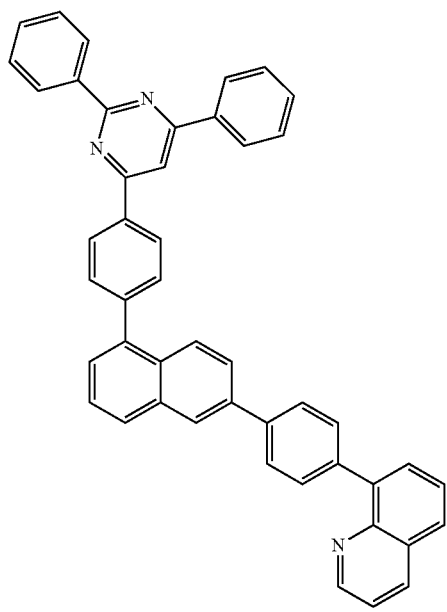
[formula 3-7-4]

[formula 3-7-5]
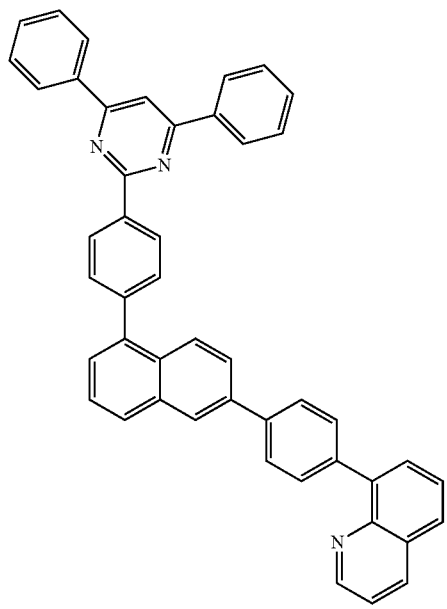
[formula 3-7-6]
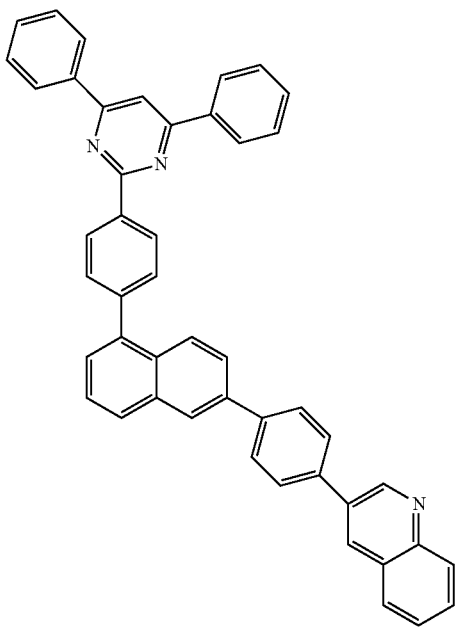
[formula 3-8-1]
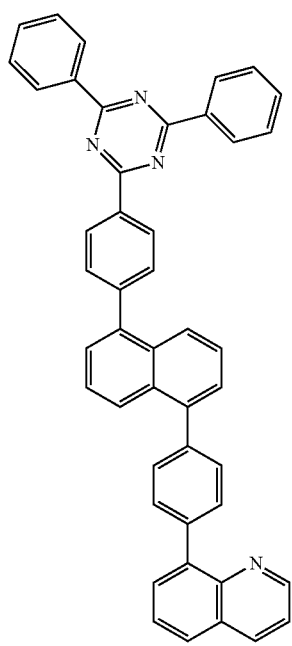
[formula 3-8-2]
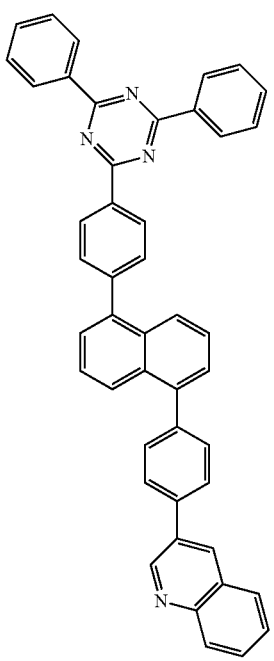

[formula 3-8-3]
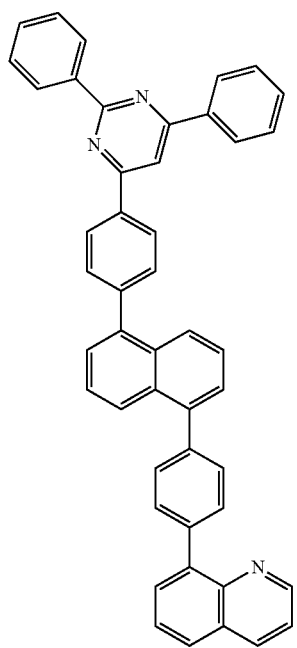
[formula 3-8-4]
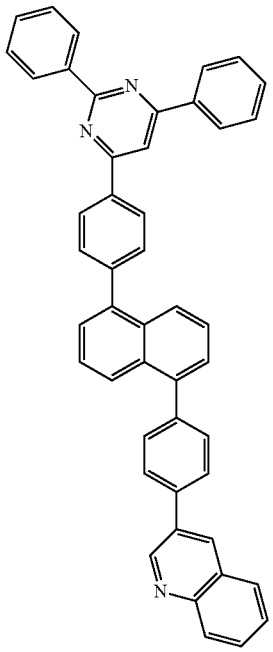
[formula 3-8-5]
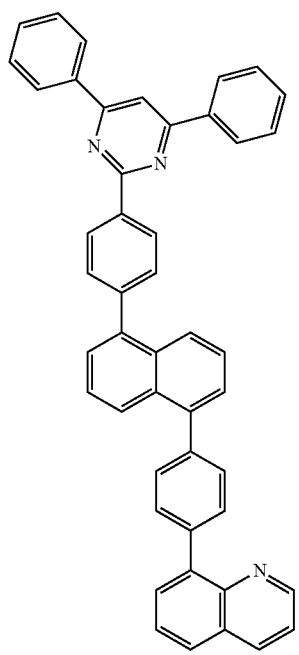
[formula 3-8-6]
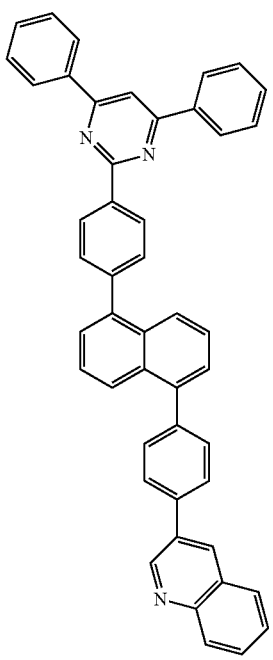

-continued
[formula 3-9-1]
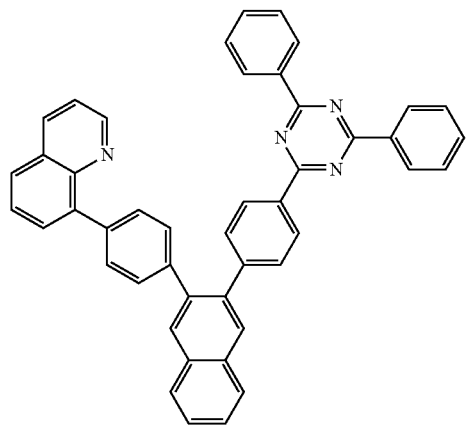
[formula 3-9-2]
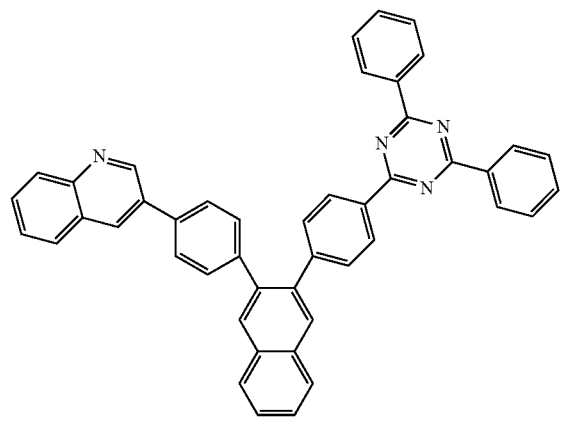
[formula 3-9-3]
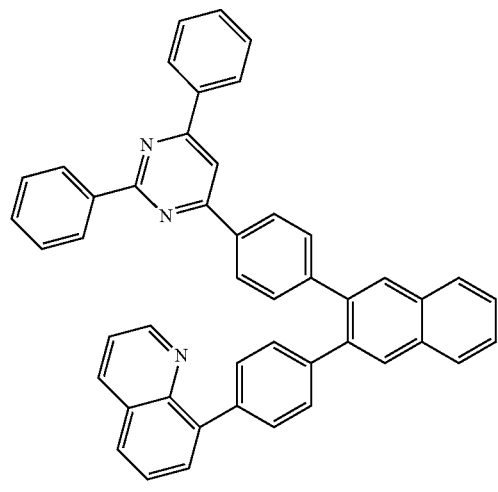
[formula 3-9-4]
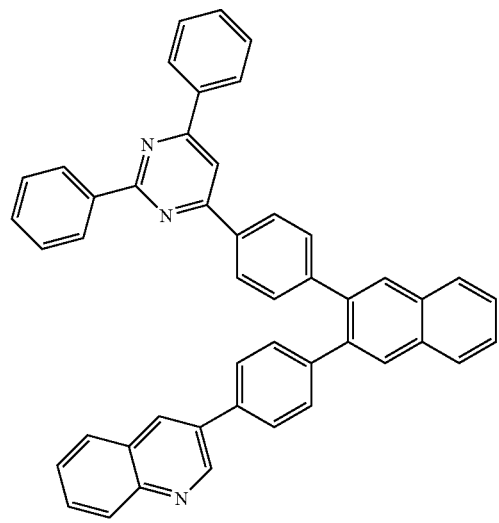
[formula 3-9-5]
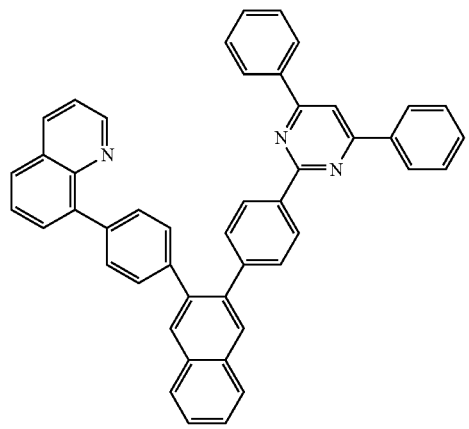
[formula 3-9-6]
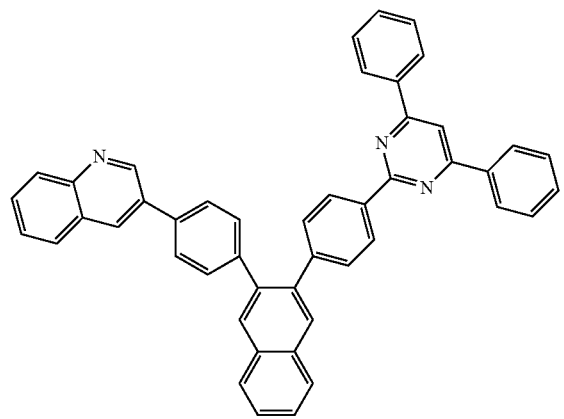

-continued
[formula 3-10-1]
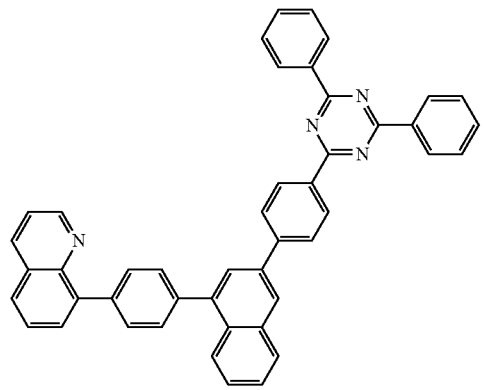
[formula 3-10-2]
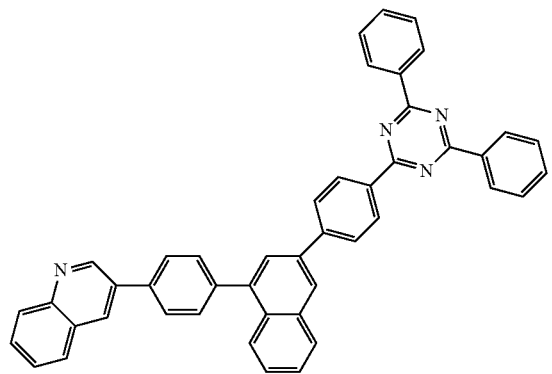
[formula 3-10-3]
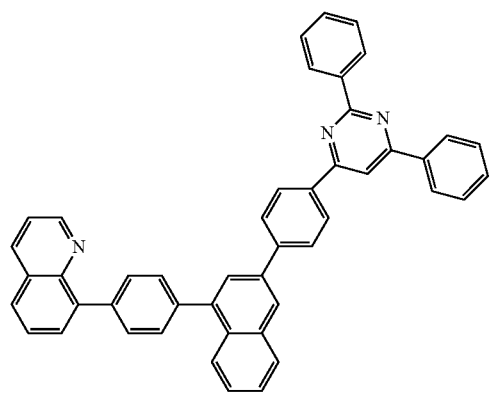
[formula 3-10-4]
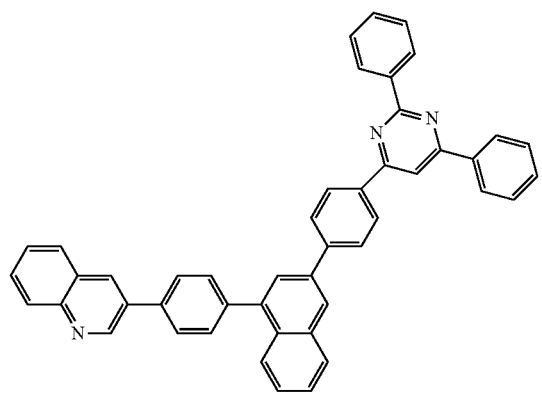
[formula 3-10-5]
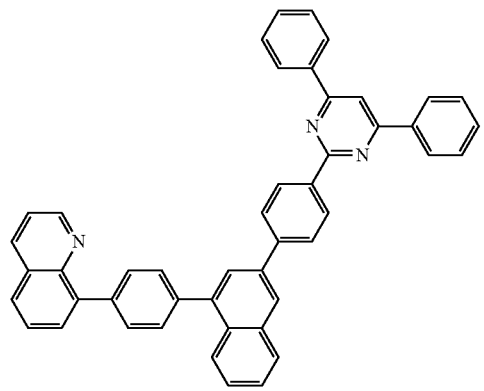
[formula 3-10-6]
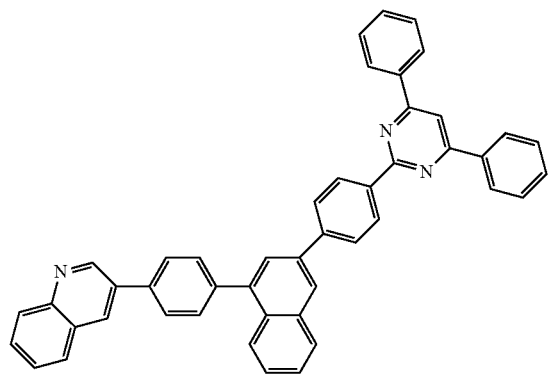

-continued
[formula 3-11-1]
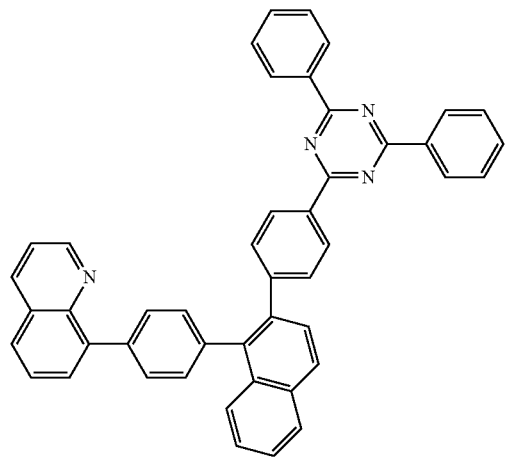
[formula 3-11-2]
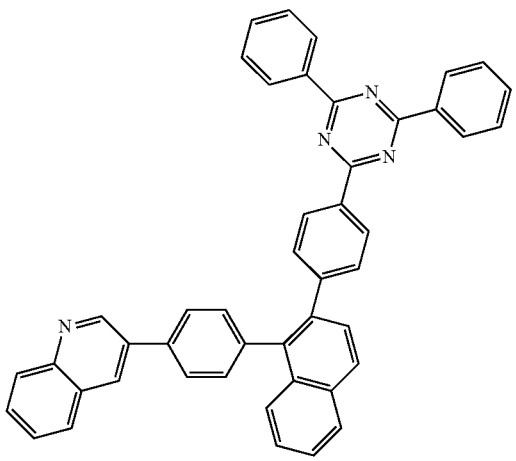
[formula 3-11-3]
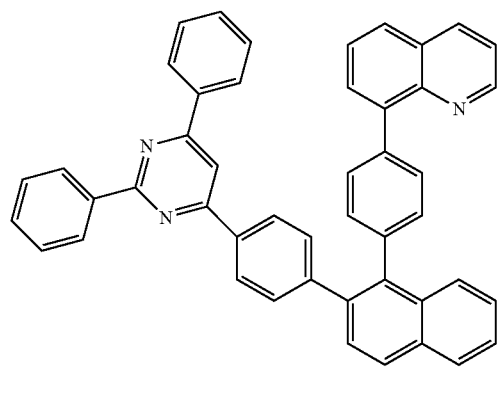
[formula 3-11-4]
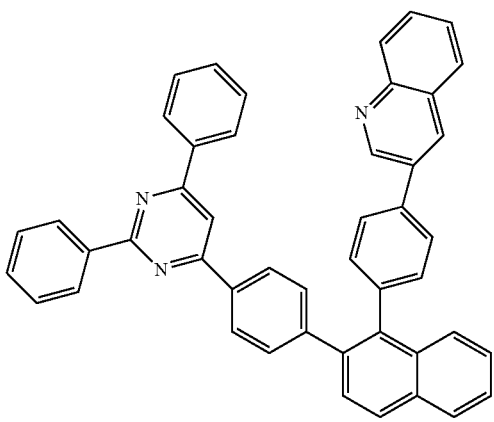
[formula 3-11-5]
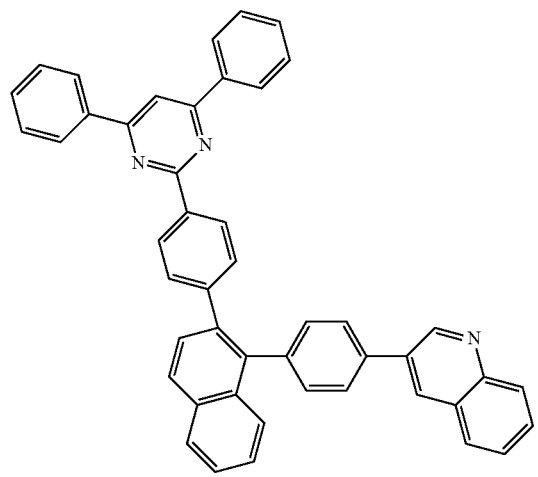
[formula 3-11-6]
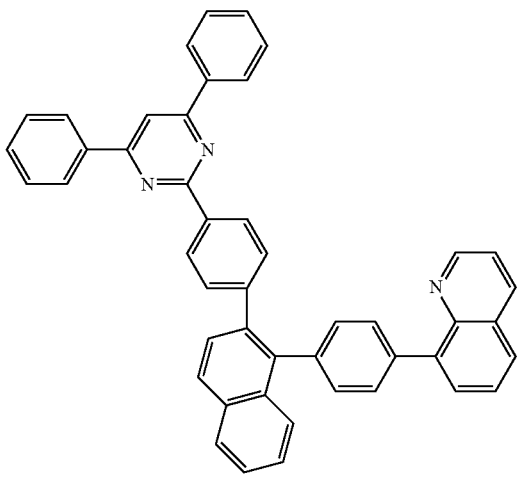

[formula 3-12-1]
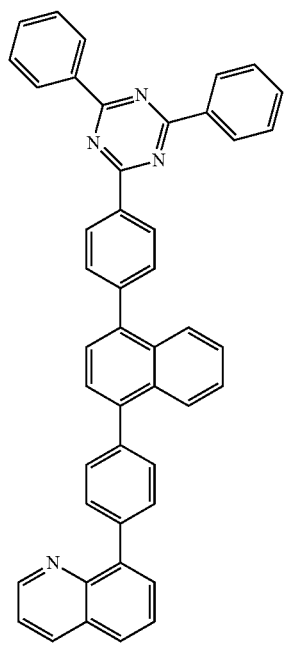
[formula 3-12-2]
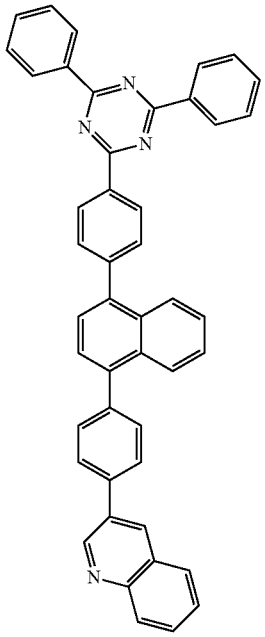
[formula 3-12-3]
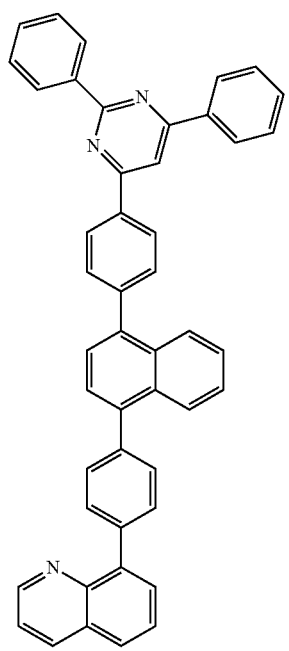
[formula 3-12-4]
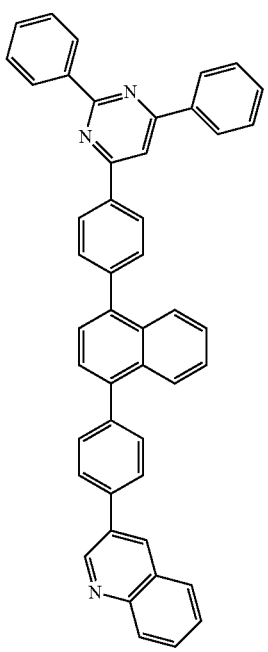

-continued
[formula 3-12-5]
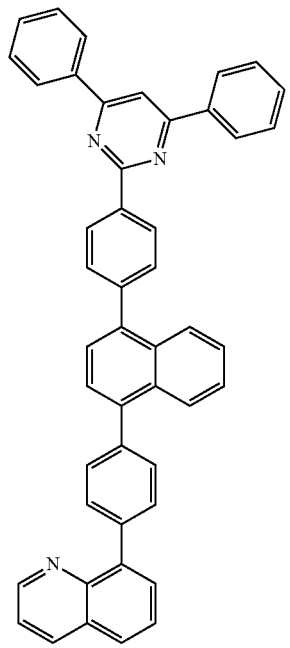
[formula 3-12-6]
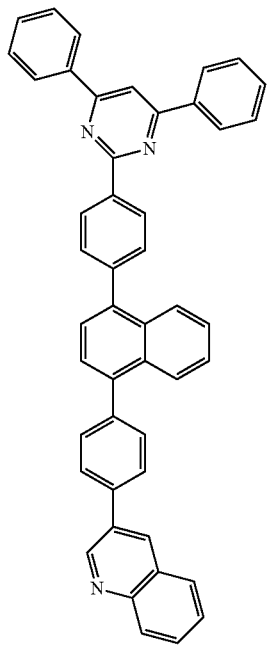
[formula 3-13-1]
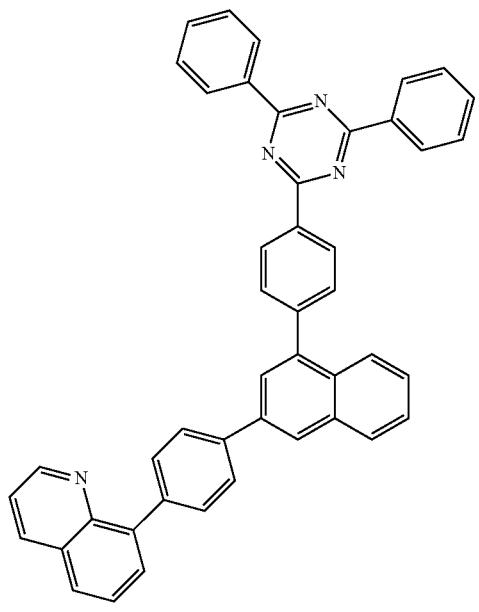
[formula 3-13-2]
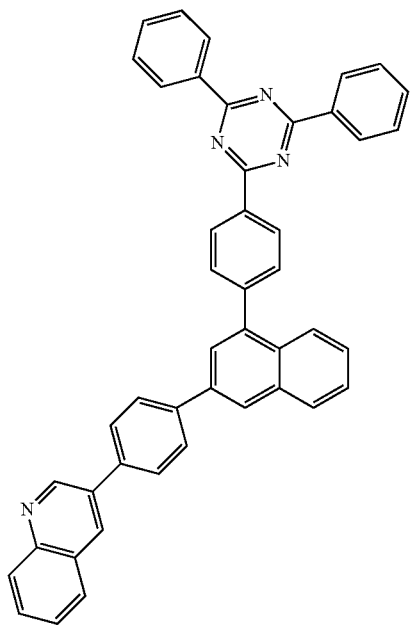

213
214
[formula 3-13-3]
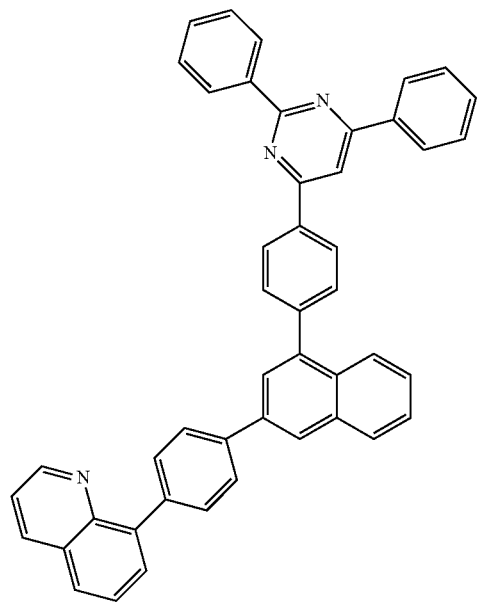
[formula 3-13-4]
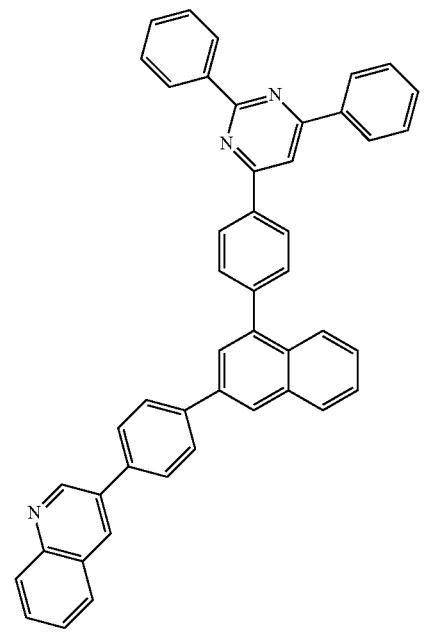
[formula 3-13-5]
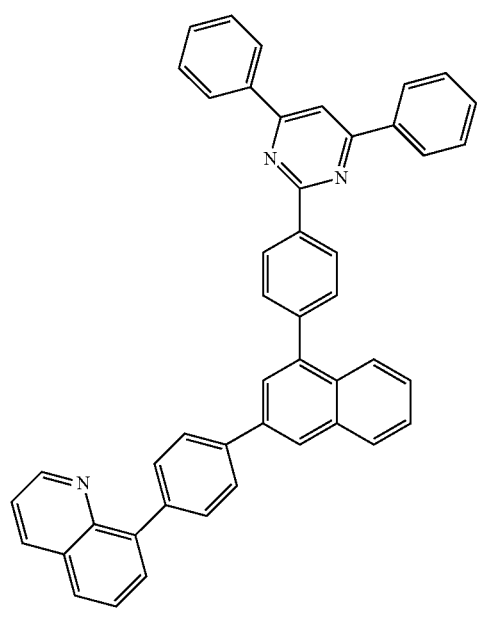
[formula 3-13-6]
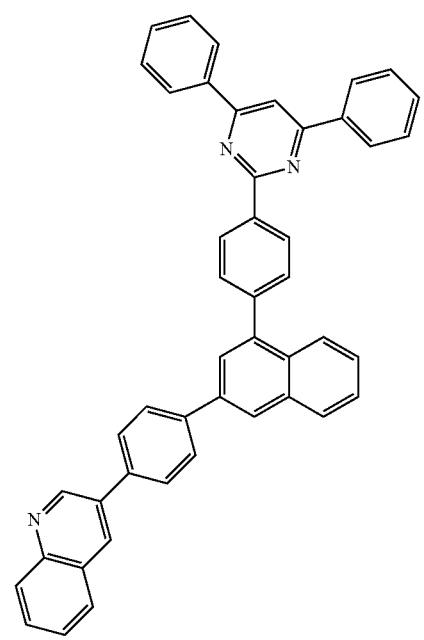

-continued
[formula 3-14-1]
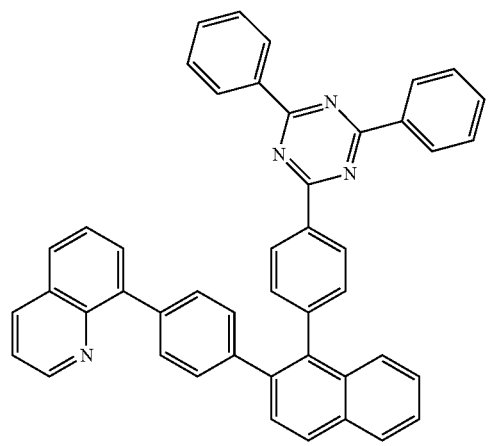
[formula 3-14-2]
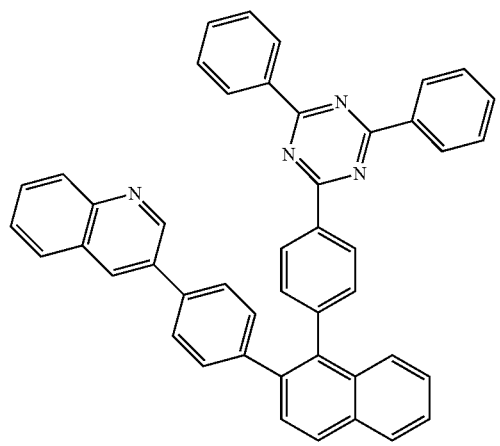
[formula 3-14-3]
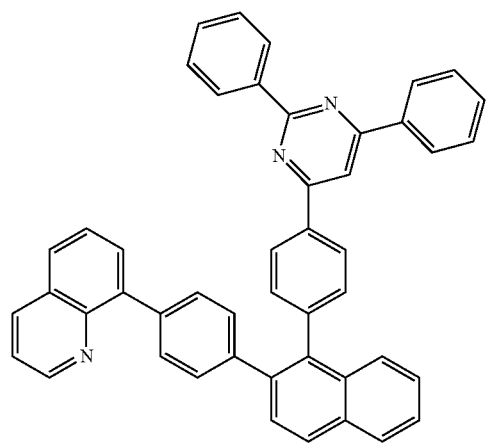
[formula 3-14-4]
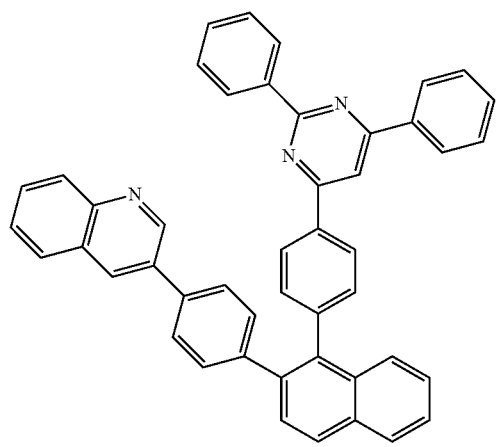
[formula 3-14-5]
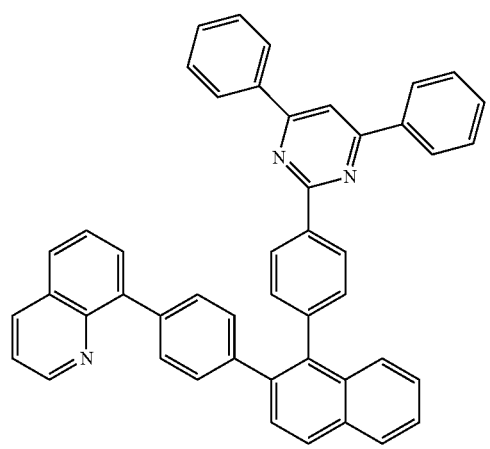
[formula 3-14-6]
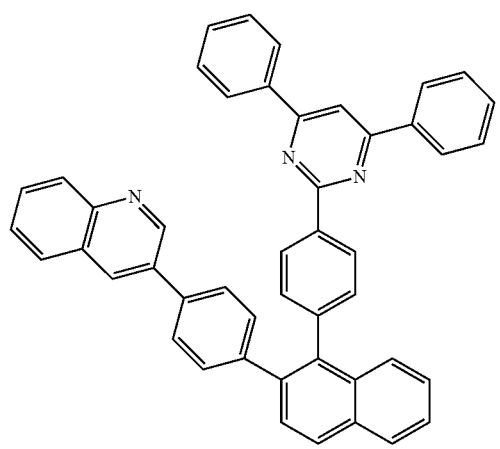

[formula 4-1-1]
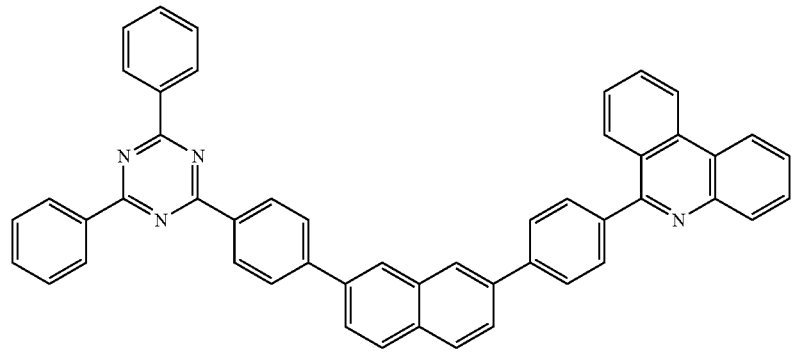
[formula 4-2-1]
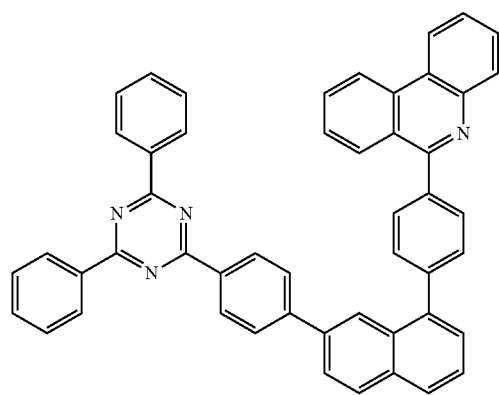
[formula 4-3-1]
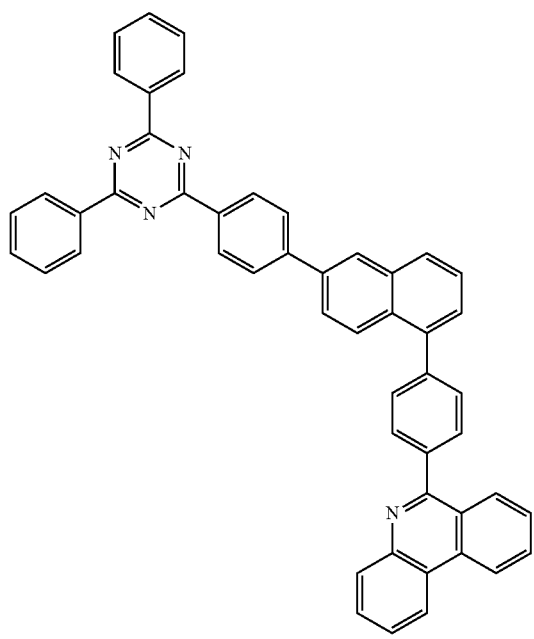
[formula 4-4-1]
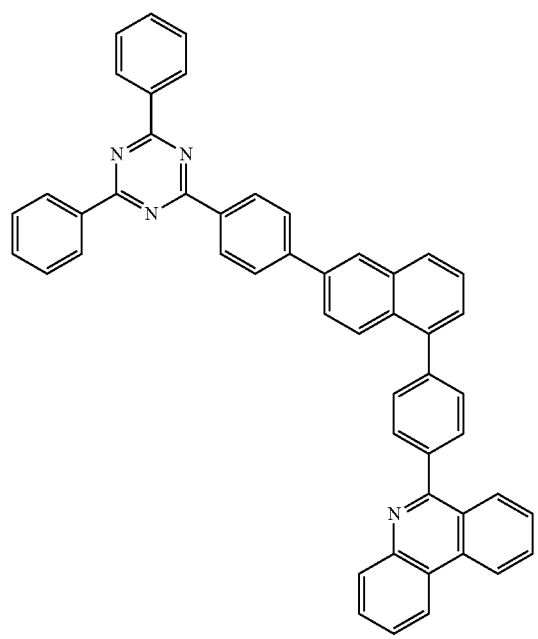
[formula 4-5-1]
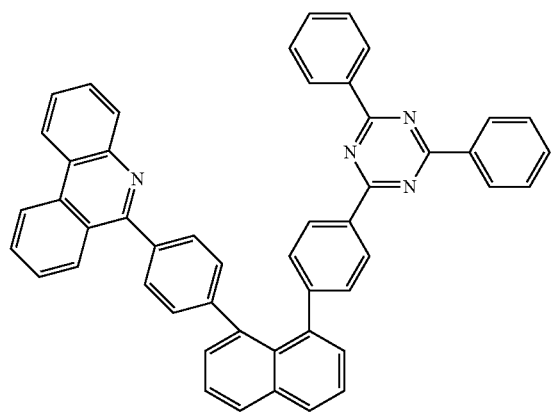

-continued
[formula 4-6-1]
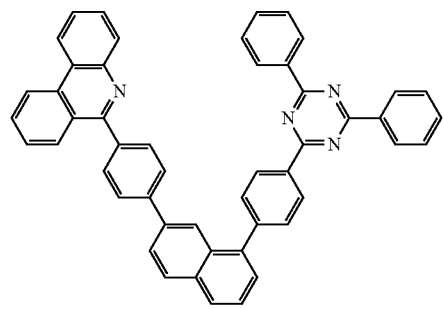
[formula 4-7-1]
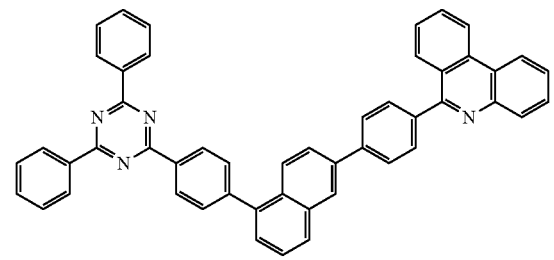
[formula 4-8-1]
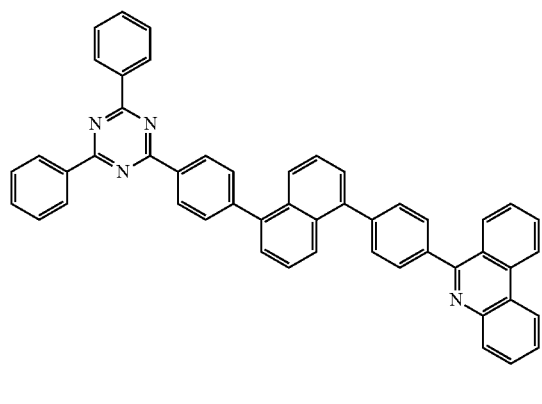
[formula 4-9-1]
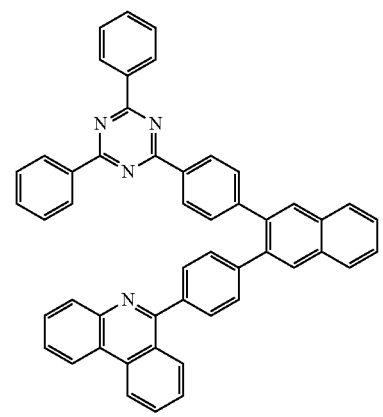
[formula 4-10-1]
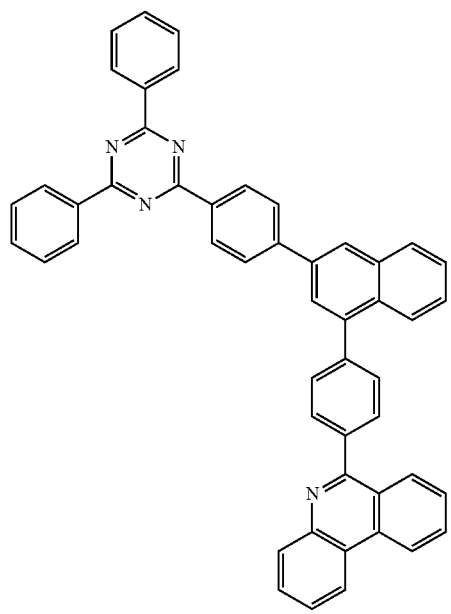
[formula 4-11-1]
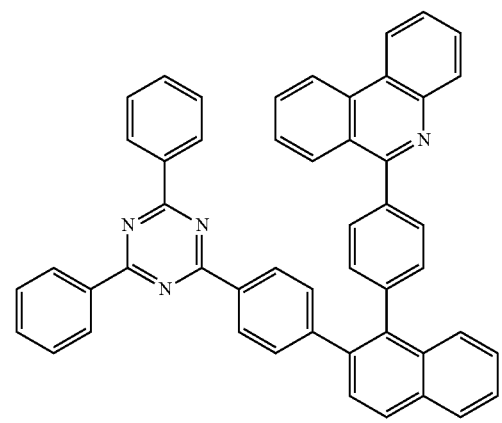

-continued
[formula 4-12-1]
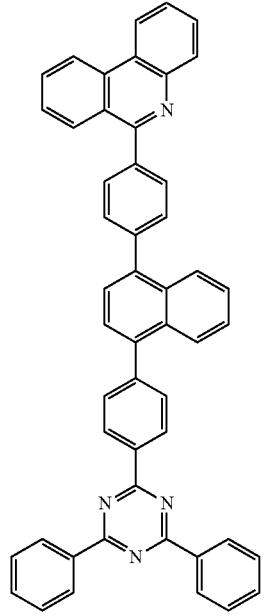
[formula 4-13-1]
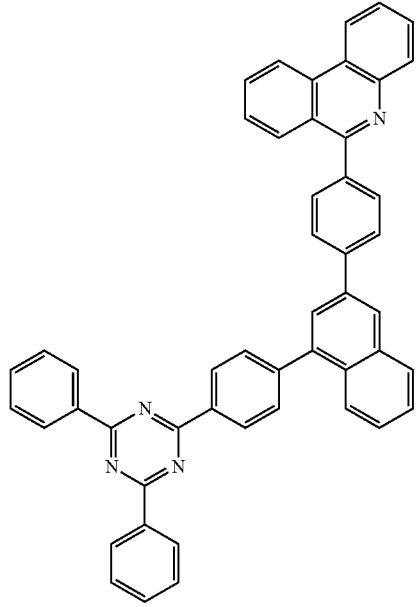
[formula 4-14-1]
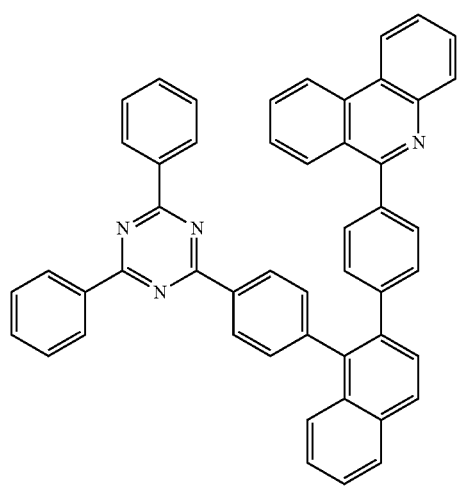
[formula 6-1-1]
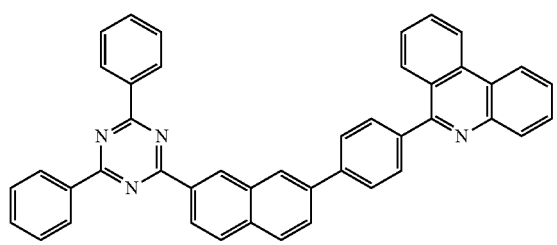

[formula 6-2-1]
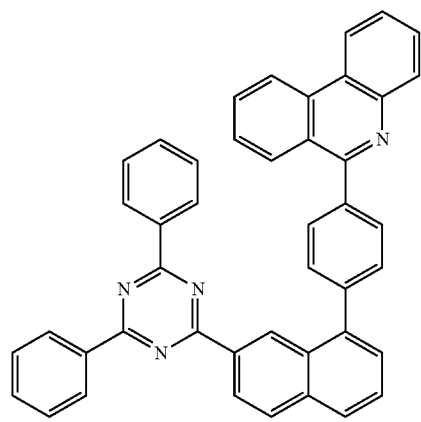
[formula 6-3-1]
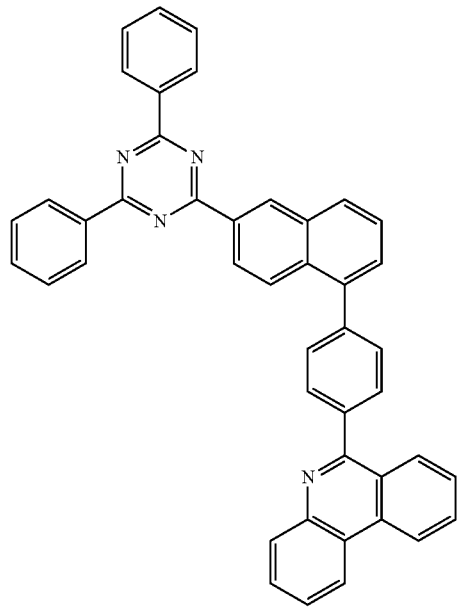
[formula 6-4-1]
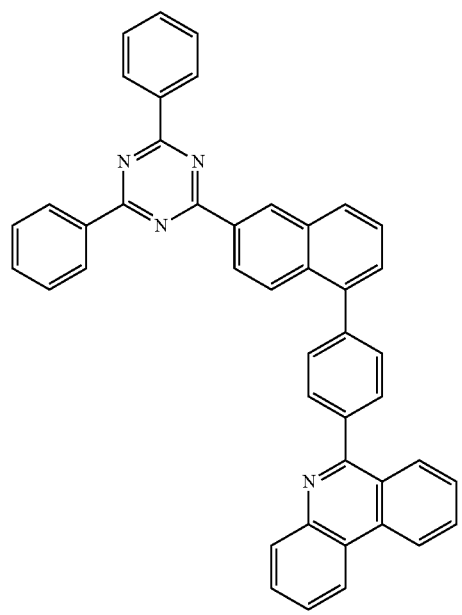
[formula 6-5-1]
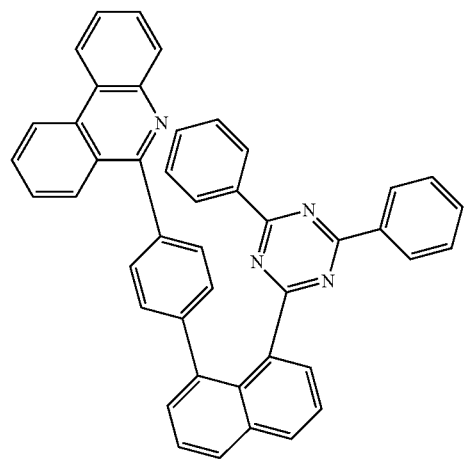

-continued
[formula 6-6-1]
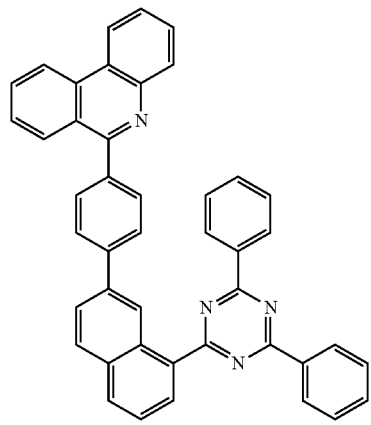
[formula 6-7-1]
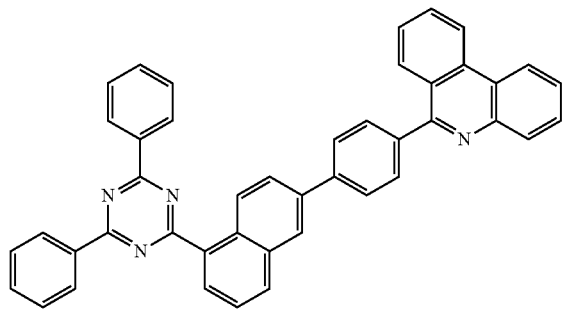
[formula 6-8-1]
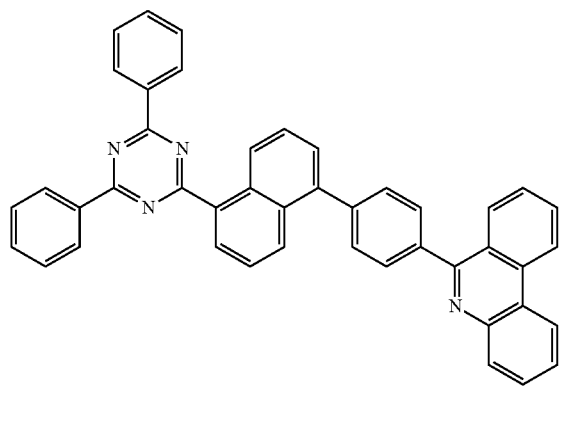
[formula 6-9-1]
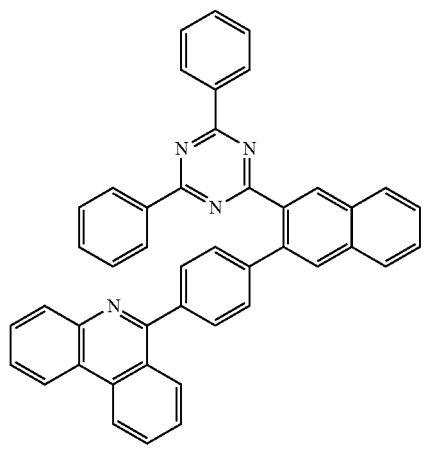
[formula 6-10-1]
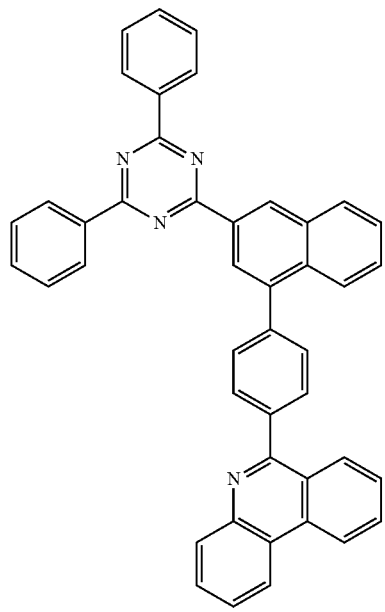
[formula 6-11-1]
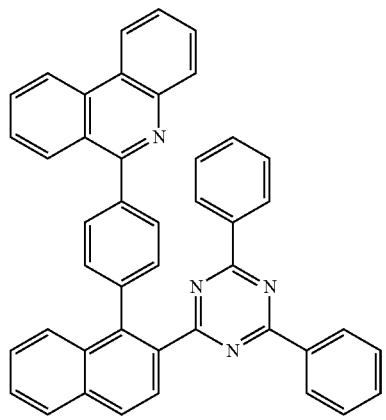

[formula 6-12-1]

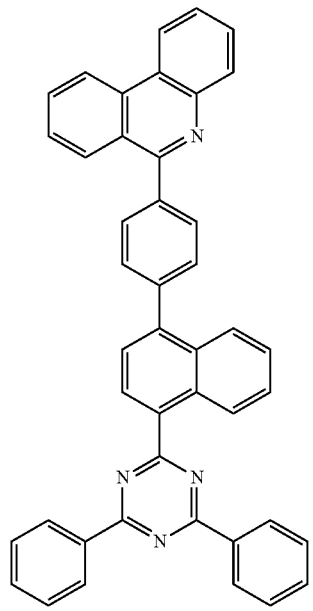

[formula 6-13-1]

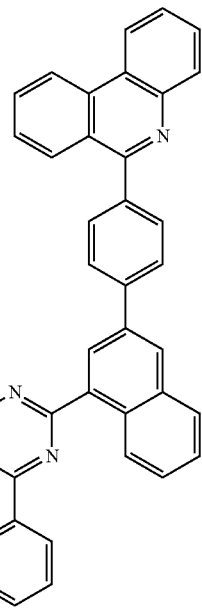

[formula 6-14-1]

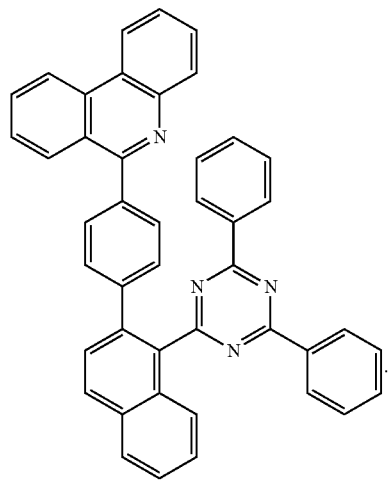

11. An organic light emitting device comprising:
a first electrode;
a second electrode provided opposite to the first electrode; and
one or more organic material layers provided between the first electrode and the second electrode,
wherein one or more layers of the organic material layers include the hetero-cyclic compound of claim 1.

12. The organic light emitting device of claim 11, wherein the organic material layer includes a hole injection layer or a hole transfer layer, and the hole injection layer or the hole transfer layer includes the hetero-cyclic compound.

13. The organic light emitting device of claim 11, wherein the organic material layer includes a light emitting layer, and the light emitting layer includes the hetero-cyclic compound as a host of the light emitting layer.

14. The organic light emitting device of claim 11, wherein the organic material layer includes an electron transfer layer or an electron injection layer, and the electron transfer layer or the electron injection layer includes the hetero-cyclic compound.

* * * * *